US007977462B2

(12) United States Patent  
Hornbeck et al.

(10) Patent No.: US 7,977,462 B2  
(45) Date of Patent: Jul. 12, 2011

(54) TYROSINE PHOSPHORYLATION SITES

(75) Inventors: Peter Hornbeck, Magnolia, MA (US); Ailan Guo, Burlington, MA (US); Ting-Lei Gu, Woburn, MA (US); Klarisa Rikova, Reading, MA (US); Albrecht Moritz, Salem, MA (US); Charles Farnsworth, Concord, MA (US); Matthew Stokes, Beverly, MA (US); Jian Yu, Hamilton, MA (US); Erik Spek, Cambridge, MA (US); Yu Li, Andover, MA (US); Anthony Possemato, Framingham, MA (US); Jessica Cherry, Durham, NH (US); Valerie Goss, Seabrook, NH (US); Jeffrey Mitchell, Nashua, NH (US); John Rush, Beverly, MA (US); Corinne Michaud, Salem, MA (US)

(73) Assignee: Cell Signaling Technology, Inc., Danvers, MA (US)

( * ) Notice: Subject to any disclaimer, the term of this patent is extended or adjusted under 35 U.S.C. 154(b) by 0 days.

(21) Appl. No.: 12/148,547

(22) Filed: Apr. 18, 2008

(65) Prior Publication Data

US 2009/0098581 A1 Apr. 16, 2009

Related U.S. Application Data

(60) Provisional application No. 60/925,253, filed on Apr. 19, 2007.

(51) Int. Cl.  
*C07K 16/00* (2006.01)  
*C12P 21/08* (2006.01)

(52) U.S. Cl. ............... 530/387.1; 530/387.7; 530/387.9; 530/388.1; 530/388.8; 530/388.85; 530/389.1; 530/389.7

(58) Field of Classification Search .................. None  
See application file for complete search history.

(56) References Cited

U.S. PATENT DOCUMENTS

| | | |
|---|---|---|
| 3,940,475 A | 2/1976 | Gross et al. |
| 4,289,747 A | 9/1981 | Chu et al. |
| 4,349,893 A | 9/1982 | Wiegman et al. |
| 4,376,110 A | 3/1983 | David et al. |
| 4,474,893 A | 10/1984 | Reading et al. |
| 4,634,664 A | 1/1987 | Oestberg et al. |
| 4,634,666 A | 1/1987 | Engleman et al. |
| 4,659,678 A | 4/1987 | Forrest et al. |
| 4,676,980 A | 6/1987 | Segal et al. |
| 4,727,022 A | 2/1988 | Skold et al. |
| 4,816,397 A | 3/1989 | Boss et al. |
| 4,816,567 A | 3/1989 | Cabilly et al. |
| 4,946,778 A | 8/1990 | Ladner et al. |
| 5,004,692 A | 4/1991 | Tso et al. |
| 5,092,885 A | 3/1992 | Yamada et al. |
| 5,112,946 A | 5/1992 | Maione et al. |
| 5,192,744 A | 3/1993 | Bouck et al. |
| 5,202,352 A | 4/1993 | Okada et al. |
| 5,225,539 A | 7/1993 | Winter et al. |
| 5,260,203 A | 11/1993 | Ladner et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,585,089 A | 12/1996 | Queen et al. |
| 5,675,063 A | 10/1997 | Knight et al. |
| 5,677,427 A | 10/1997 | Goldenberg et al. |
| 5,693,761 A | 12/1997 | Queen et al. |
| 5,693,762 A | 12/1997 | Queen et al. |
| 5,789,208 A | 8/1998 | Sharon et al. |
| 5,969,108 A | 10/1999 | McCafferty et al. |
| 6,103,889 A | 8/2000 | Whitlow et al. |
| 6,120,767 A | 9/2000 | Robinson et al. |
| 6,150,584 A | 11/2000 | Kucherlapati et al. |
| 6,180,370 B1 | 1/2001 | Queen et al. |
| 6,329,508 B1 | 12/2001 | Friden et al. |
| 6,331,415 B1 | 12/2001 | Cabilly et al. |
| 6,335,163 B1 | 1/2002 | Sharon et al. |
| 6,355,245 B1 | 3/2002 | Evans et al. |
| 6,395,718 B1 | 5/2002 | Slusher et al. |
| 6,407,213 B1 | 6/2002 | Carter et al. |
| 6,441,140 B1 | 8/2002 | Comb et al. |
| 6,462,075 B1 | 10/2002 | Bowen et al. |
| 6,465,431 B1 | 10/2002 | Thorn et al. |
| 6,475,784 B1 | 11/2002 | Papkoff et al. |
| 6,482,802 B1 | 11/2002 | Hu et al. |
| 6,482,810 B1 | 11/2002 | Brem et al. |
| 6,500,431 B1 | 12/2002 | Gill et al. |
| 6,500,924 B1 | 12/2002 | Brooks et al. |
| 6,518,298 B2 | 2/2003 | Green et al. |
| 6,521,439 B2 | 2/2003 | Folkman et al. |
| 6,525,019 B2 | 2/2003 | D'Amato et al. |
| 6,538,103 B1 | 3/2003 | Ji et al. |

(Continued)

FOREIGN PATENT DOCUMENTS

EP 0120694 3/1984

(Continued)

OTHER PUBLICATIONS

Andreev et al. (Mol. Cell. Biol. Mar. 1999 19: 2338-2350).* U.S. Appl. No. 10/634,581, filed May 8, 2003, Johnson et al.  
Abu-Duhier et al., "Identification of novel FLT-3 Asp835 mutations in adult acute myeloid leukemia," Br. J. Haematol. 113: 983-988 (2001).  
Hardy, et al., "Clinical and Molecular Genetic Analysis of 19 Wolfram Syndrome Kindreds Demonstrating a Wide Spectrum of Mutations in WFS1," Am. J. Hum. Genet. 65:1279-1290 (1999).  
Dessein, et al., "Severe Hepatic Fibrosis in *Schistoma mansoni* Infection Is Controlled by a Major Locus That Is Closely Linked to the Interferon-y Receptor Gene," Am. J. Hum. Genet. 65: 709-721 (1999).

(Continued)

*Primary Examiner* — Peter J Reddig  
(74) *Attorney, Agent, or Firm* — Nancy Chiu Wilker

(57) ABSTRACT

The invention discloses 482 novel phosphorylation sites identified in carcinoma and/or leukemia, peptides (including AQUA peptides) comprising a phosphorylation site of the invention, antibodies specifically bind to a novel phosphorylation site of the invention, and diagnostic and therapeutic uses of the above.

2 Claims, 31 Drawing Sheets

U.S. PATENT DOCUMENTS

| | | | |
|---|---|---|---|
| 6,544,758 | B2 | 4/2003 | O'Reilly et al. |
| 6,544,947 | B2 | 4/2003 | Holaday et al. |
| 6,548,477 | B1 | 4/2003 | Olson et al. |
| 6,548,640 | B1 | 4/2003 | Winter et al. |
| 6,559,126 | B2 | 5/2003 | Tournaire et al. |
| 6,569,845 | B1 | 5/2003 | Futamura et al. |
| 6,573,256 | B2 | 6/2003 | Bishop et al. |
| 6,783,961 | B1 | 8/2004 | Edwards et al. |
| 6,867,007 | B2 | 3/2005 | Kauvar et al. |
| 6,884,869 | B2 | 4/2005 | Senter et al. |
| 6,979,557 | B2 | 12/2005 | Isogai et al. |
| 7,109,000 | B2 | 9/2006 | Edinger et al. |
| 7,198,896 | B2 | 4/2007 | Rush et al. |
| 7,300,753 | B2 | 11/2007 | Rush et al. |

FOREIGN PATENT DOCUMENTS

| | | |
|---|---|---|
| EP | 1184665 | 9/1986 |
| EP | 0239400 | 9/1987 |
| EP | 0404097 | 12/1990 |
| WO | WO 84/03508 | 9/1984 |
| WO | WO 85/03508 | 8/1985 |
| WO | WO 86/01533 | 3/1986 |
| WO | WO 91/10741 | 7/1991 |
| WO | WO 91/17271 | 11/1991 |
| WO | WO 92/01047 | 1/1992 |
| WO | WO 93/11161 | 6/1993 |
| WO | WO 93/12227 | 6/1993 |
| WO | WO 95/20401 | 8/1995 |
| WO | WO 96/27011 | 6/1996 |
| WO | WO 00/49144 A2 * | 8/2000 |
| WO | WO 02/00729 | 3/2002 |
| WO | WO 03/016861 | 2/2003 |
| WO | WO 03/089474 | 10/2003 |
| WO | WO 03/106644 | 12/2003 |
| WO | WO 2004/009618 | 1/2004 |
| WO | WO 2004/039963 | 5/2004 |
| WO | WO 2004/066957 | 8/2004 |
| WO | WO 2004/091658 | 10/2004 |
| WO | WO 2005/056825 | 6/2005 |
| WO | WO 2005/083444 | 9/2005 |

OTHER PUBLICATIONS

Di Barletta, et al., "Different Mutations in the LMNA Gene Cause Autosomal Dominant and Autosomal Recessive Emery-Dreifuss Muscular Dystrophy," Am. J. Hum. Genet. 66:1407-1412 (2000).

Ebrahimi, et al., "Murine Gammaherpesvirus-68 Infection Causes Multi-Organ Fibrosis and Alters Leukocyte Trafficking in Interferon-y Receptor Knockout Mice," American Journal of Pathology, 158(6): 2117-2125 (Jun. 2001).

Jemal, et al., "Cancer Statistics 2005," CA: A Cancer Journal for Clinicians, 55(1): 10-30 (Jan./Feb. 2005).

Pollard, et al., "Using Single-Gene Deletions to Identify Checkpoints in the Progression of Systemic Autoimmunity," Annals of the New York Academy of Sciences 987: 236-239 (Apr. 2003).

Jaskiewicz, et al., "Expression of p53 Tumor Suppressor Gene, Oncoprotein c-erbB-2, Cellular Proliferation and Differentiation n Malignant and Benign Pancreatic Lesions," Anticancer Research 14: 1919-1922 (1994).

Agarwal, et al., "Inositol Hexaphosphate Inhibits Constitutive Activation of NF-xB in Androgen-independent Human Prostate Carcinoma DU145 Cells," Anticancer Research 23: 3855-3862 (2003).

Arias-Romero, et al., "A tale of two Paks," Biol. Cell 100: 97-108 (2008).

Bache, et al., "Phosphorylation of Hrs downstream of the epidermal growth factor receptor," Eur. J. Biochem 269: 3881-3881 (2002).

Belsches, et al., "Role of c-Src Tyrosine Kinase in EEGF-Induced Mitogenesis," Frontiers in Bioscience 269: 3881-3887 (Oct. 15, 1997).

G-Amlak, et al., "Reguation of myeloma cell growth through Akt/Gsk3/forkhead signaling pathway," Biochemical and Biophysical Research Sommunications 297: 760-764 (2002).

Radaeva, et al., "Interferon-y inhibits interferon-a signalling in hepatic cells: evidence for the involvement of STAT1 induction and hyperexpression of STAT1 in chronic hepatitis C," Biochem J. 379: 199-208 (2004).

Awasthi, et al., "Novel Function of Human RLIP76: ATP-Dependent Transport of Glutathione Conjugates and Doxorubicin", Biochemistry 39: 9327-9334 (2000).

Jagani, et al., "Foxe tumor suppressors and BCR-ABL-induced leukemia: A matter of evasion of apoptosis," Biochimica et Biophysica Acta 1785: 63-84 (2008).

Hashimoto, et al., "The Breakpoint Cluster Region Gene on Chromosome 22q11 Is Associated with Bipolar Disorder," Biol Psychiatry 57(10): 1097-1102 (May 15, 2005).

Bird, et al., "Single-Chain Antigen-Binding Proteins," Science 242: 423-426 (Oct. 21, 1988).

Blood, et al., "Tumor interactions with the vasculature: angiogenesis and tumor metastasis," Biochemica et Biophysica Acta 1032: 89-118 (1990).

Awasthi, et al., "RLIP76, a non-ABC transporter, and drug resistance in epilepsy," BMC Neuroscience 6(61): 1-11 (2005).

Boder, et al., "Yeast surface display for screening combinatorial polypeptide libraries", Nature Biotechnology 15: 553-557 (Jun. 1997).

Bordin, et al., "Band 3 is an anchor protein and a target for SHP-2 tyrosine phosphatase in human erythrocytes," Blood 100(1): 276-282 (Jul. 1, 2002).

Brand, et al., "Fluorescence Probes for Structure1," Annu.Rev. Biochem. 41:843-868 (1972).

Brennan, et al., "Preparation of Bispecific Antibodies by Chemical Recombination of Monoclonal Immunoglobulin G1 Fragments," Science 229: 81-83 (Jul. 5, 1985).

Byers et al., "Rationale for clinical use of immunotoxins in cancer and autoimmune disease," Seminars in Cell Biology 2:59-70 (1991).

Calalb, et al.,"Tyrosine Phosphorylation of Focal Adhesion Kinase at Sites in the Catalytic Domain Regulates Kinase Activity: a Role for Src Family Kinases," Molecular and Cellular Biology 15(2): 954-963 (Feb. 1995).

Grand, et al., "p53-Binding Protein 1 Is Fused to the Platelet-Derived Growth Factor Receptor B in a Patient with a t(5;15)(q33;q22) and a Imagine-Responsive Eosinophilic Myeloproliferative Disorder," Cancer Research 64: 7216-7219 (Oct. 15, 2004).

Carr, et al., "The Need for Guidelines in Publication of Peptide and Protein Identification Data," Molecular & Cellular Proteomics 3(6): 531-533 (2004).

Cell Signaling Technology, "Phospho-PLCgammal (Tyr783) Antibody," 2007 Cell Signaling Technology, Inc., Jul. 2000, 1-3.

Accili et al., "FoxOs at the Crossroads of Cellular Metabolism, Differentiation, and Transformation," Cell 117: 421-426 (May 14, 2004).

Chow et al., "Measurement of MAP Kinase Activation by Flow Cytometry Using Phospho-Specific Antibodies to MEK and ERK: Potential for Pharmacodynamic Monitoring of Signal Transduction Inhibitors", Cytometry (Communications in Clinical Cytometry) 46: 72-78 (2001).

Coia, et al., "Panning and selection of proteins using ribosome display", Journal of Immunological Methods 254: 191-197 (2001).

Crook, et al.,"Repressed by a NuRD", Nature Cel Biology 8(3): 212-214 (Mar. 2006).

Cross, et al.,"Serine/Threonine Protein Kinases and Apoptosis", Experimental Cell Research 256: 34-41 (2000).

Czernik, et al.,"Production of Phosphorylation State-Specific Antibodies", Methods in Enzymology 201: 264-283 (1991).

Daley, et al, "Induction of Chronic Myelogenous Leukemia in Mice by the P210bcr/abl Gene of the Philadelphia Chromosome," Science 247: 824-830 (1990).

Denslow, et al., "The human Mi-2/NuRD complex and gene regulation", Oncogene 26: 5433-5438 (2007).

Dorahy, et al., "Capture by chemical crosslinkers provides evidence that integrin allbfl3 forms complex with protein tyrosine kinases in intact platelets" Biochem J. 389: 481-490 (1995).

Druker, et al., "Imatinib as a Paradigm of Targeted Therapies," Adv. Cancer Res. 91: 1-30 (2004).

Edgar, et al., "Flotillin-1: gene structure c DNA cloning from human lung and the identification of alternative polyadenylation signals," The international Journal of Biochemisty & Cell Biology 33: 53-64 (2001).

Blanton, et al., "Schistosomal hepatic fibrosis and the interferon gamma receptor: a linkage analysis using single-nucleotide polymorphic markers", European Journal of Human Genetics 13: 660-668 (2005).

Song, et at., "Lamin A/C mutations associated with familial and sporadic cases of dilated cardiomyopathy in Koreans", Experimental and Molecular Medicine 39( 1): 114-120 (Feb. 2007).

Fanger, et al., "Bispecific antibodies and targeted cellular cytotoxicity", Immunol Today 12(2): 51-4 (Feb. 1991).

Vadlamudi, et al., "Heregulin and HER2 signaling selectively activates c-Src phosphorylation at tyrosine 215" FEBS Letters 543:76-80 (2003).

Yang, et al "ERK promotes tumorigenesis by inhibiting FOXO3a via MDM2-mediated degradation." Nat Cell Biol. 10(2):138-48 (Feb. 2008).

Fujita N. et al., "MTA3 and the Mi-2/NuRD complex regulate cell fate during B lymphocyte differentiation." Cell 119: 75-86 (2004).

Fujita N. et al., "MTA3; a Mi-2/NuRD Complex Subunit, Regulates an Invasive Growth Pathway in Breast Cancer." Cell 113: 207-19 (Apr. 18, 2003).

Meinhart, et al "A Structural Perspective of CTD Function." Genes and Development 19: 1401-1415 (2005).

Gerber et al., "Absolute quantification of proteins and phosphoproteins from cell lysates by tandem MS," PNAS 100(12): 6940-6945 (Jun. 10, 2003).

Graves et al. "Protein phosphorylation and signal transduction," Pharmacol. Ther. 82(2-3): 111-121 (1999).

Griffiths et al. "Human anti-self antibodies with high specificity from phage display libraries." EMBO Journal. 129(2): 725-734 (1993).

Griffiths et al. "Isolation of high affinity human antibodies directly from large synthetic repertoires," EMBO J. 13(14): 3245-3260 (1994).

Gruber et al. "Efficient tumor cell lysis mediated by a bispecific single chain antibody expressed in *Escherichia coli*." J. Immunol., 152: 5368-5374 (1994).

Gu et al. "Phosphotyrosine profiling identifies the KG-1 cell line as a model for the study of FGFR1 fusions in acute myeloid leukemia." Blood, 108(13): 4202-4204, supplemental table 1 (Dec. 15, 2006).

Hanes J. et al. "Picomolar affinity antibodies from a fully synthetic naive library selected and evolved by ribosome display." Nat. Biotechnol. 18:1287-92 (Dec. 2000).

Heessen S., Fornerod M., "The inner nuclear envelope as a transcription factor resting place," EMBO Rep. 8(10): 914-918 (2007).

Kakumu, et al "Interferon-gamma receptors on T cells in patients with chronic liver disease." Hepatogastroenterology 35: 158-61 (Aug. 1988).

Hollinger et al., "Diabodies: small bivalent and bispecific antibody fragments." Proc. Natl. Acaf. Sci. USA, 90: 6444-6448 (1993).

Burwinkel et al "Phosphorylase-kinase-deficient liver glycogenosis with an unusual biochemical phenotype in blood cells associated with a missense mutation in the beta subunit gene (PHKB)." Hum Genet. 101: 170-174 (Dec. 1997).

Blume-Jensen et al., "Oncogenic kinase signalling." Nature 411: 355-65 (May 2001).

Huse w. "Generation of a Large Combinatorial Library of the Immunoglobulin Repertoire in Phage Lambda." Science 246: 1275-1281 (1989).

Ingber et al., "Inhibition of Angiogenesis Through Modulation of Collagen Metabolism," Lab. Invest. 59: 44-51 (1988).

Htun Van Der Horst, et al "Tyrosine phosphorylation of PYK2 mediates heregulin-induced glioma invasion: novel heregulin/HER3-stimulated signaling pathway in glioma." Int. J Cancer 113(5): 689-98 (Feb. 20, 2005).

Irby et al., "Role of Src expression and activation in human cancer." Oncogene 16: 5636-642 (2000).

Jullien-Flores "Bridging Ral GTPase to Rho pathways" RLIP76, a Ral effector with CDC42/Rac GTPase-activating protein activity. J Cell Chem 270(38): 22473-22477 (Sep. 22, 1995).

Hu, et al "HSF-1 interacts with Ral-binding protein 1 in a stress-responsive, multiprotein complex with HSP90 in vivo" J Cell Chem. 278(19): 17299-17306 (May 9, 2003).

Birkenkamp, et al "FOXO3a induces differentiation of Bcr-Abl-transformed cells through transcriptional down-regulation of Id1." J'Biol. Chem. 282(4): 2211-2220 (Jan. 26, 2007).

Goldfinger, et al "RLIP76 (Ra1BP1) is an R-Ras effector that mediates adhesion-dependent Rac activation and cell migration." J Cell Biol. 174(6):877-88 (Sep. 11, 2006).

Dorman, et al "Viral infections in interferon-gamma receptor deficiency." The Journal of Pediatrics 135(5):640-643 ( Nov. 2006).

Kim H. et al., "Epidermal growth factor-dependent association of phosphatidylinositol 3-kinase with the erbB3 gene product" J Biol. Chem. 269(40): 24747-24755 (1994).

Kohler, et al "Derivation of specific antibody-producing tissue culture and tumor lines by cell fusion." Eur. J. Immunol. 6(7): 511-519 (1976).

Kostelny et al., "Formation of a Bispecific Antibody by the Use of Leucine Zippers." J. Immunol., 148(5): 1547-1557 (1992).

Dorman, et al "Clinical features of dominant and recessive interferon gamma receptor 1 deficiencies." Lancet 364(9451): 2113-2121 (Dec. 2004).

Merrifield "Solid Phase Peptide Synthesis I, The Synthesis of a Tetrapeptide." J. Am. Chem. Soc. 85:21-49 (1962).

Milstein and Cuello "Hybrid hybridomas and their use in immunohistochemistry." Nature, 305:537-540 (1983).

Radziwill, et al "The Bcr kinase downregulates Ras signaling by phosphorylating AF-6 and binding to its PDZ domain." Mol. Cell Biol. (13): 4663-4642 (Jul. 23, 2003).

Morrison et al., "Chimeric human antibody molecules: Mouse antigen-binding domains with human constant region domains." Proc. Nat'l Acad. Sci. 81: 6851-6855 (1984).

Moses et al., "Identification of an Inhibitor of Neovascularization from cartilage." Science, 248:1408-1410 (1990).

Mullinax et al., "Identification of human antibody fragment clones specific for tetanus toxoid in a bacteriophage gamma immunoexpression library." Proc. Nat'l Acad. Sci. 87: 8095-8099 (Oct. 1990).

Nakamura, Y., "Codon usage tabulated from international DNA sequence databases: status for the year 2000." Nucleic Acids Res. 28(1): 292 (Jan. 2000).

Nardi, et al., "Mechanisms and implications of imatinib resistance mutations in BCR-ABL." Curr. Opin. Hematol. 11: 35-43 (2003).

Shackleton, et al "LMNA, encoding lamin A/C, is mutated in partial lipodystrophy." Nat. Genet. (2):153-156 (Feb. 24, 2000).

Shankaran, et al "IFN gamma and lymphocytes prevent primary tumour development and shape tumour immunogenicity." Nature 410: 1107-1111 (Apr. 26, 2001).

Feske, et al "A mutation in Orai1 causes immune deficiency by abrogating CRAC channel function." Nature 441: 179-85 (May 11, 2006).

Neuberger, et al "Recombinant antibodies possessing novel effector functions." Nature. 312(5995): 604-608 (Dec. 1984).

Newman et al., "Primatization of Recombinant Antibodies for Immunotherapy of human Diseases: A Macaque/Human Chimeric Antibody Against Human CD4." BioTechnology 10: 1455-1460 (1992).

Nissim et al., "Antibody fragments from a 'single pot' phage display library as immunochemical reagents." EMBO J. 13(3):692-698 (Feb. 1994).

Ostberg, et al.,"Human x (Mouse x Human) Hybridomas Stably Producing Human Antibodies", Hybridoma 2(4): 361-367 (1983).

Olayioye, et al.,"The ErbB signaling network: receptor heterodimerization in development and cancer", The EMBO Journal 19(13): 3159-3167 (2000).

Liu, et al., "Induction of prosurvival molecules by apoptotic stimuli: involvement of FOX03a AND ROS", Oncogene 24: 2020-2031 (2005).

Order, et al., "Analysis, Results, and Future Prospective of the Therapeutic Use of Radiolabeled Antibody in Cancer Therapy", Monoclonal Antibodies for Cancer Detection and Therapy, Baldwin et al. (eds.), pp. 303-316 (Academic Press 1985).

Paweletz, et al., "Reverse phase protein microarrays which capture disease progression show activation of pro-survival pathways at the cancer invasion front", Oncogene 20: 1981-1989 (2001).

Pluckthun et al., "Antibodies from *Escherichia coli*" The Pharmacology of Monoclonal Antibodies, vol. 113, Rosenburg and Moore, eds. (Springer-Verlag: New York, 1994), pp. 269-315.

Prigent, et al., "Identification of c-erbB-3 binding sites for phosphatidylinositol 3'-kinase and SHC using an EGF receptor/c-erbB-3 chimera" The EMBO Journal 13(12): 2831-2841 (1994).

Cao, Kan "A lamin A protein isoform over expressed in Hutchinson-Gilford progeria syndrome interferes with mitosis in progeria and normal cells" Proc. Natl. Acad. Sci U S A. 104(12): 4949-4954 (Mar. 2007).

Dechat, H. "Alterations in mitosis and cell cycle progression caused by a mutant lamin A known to accelerate human aging." Proc. Natl. Acad. Sci U S A. 104(12): 4955-60 (Mar. 20, 2007).

Hanes, J. "In vitro selection and evolution of functional proteins by using ribosome display" Proc. Natl. Acad. Sci. U. S. A. 94(10): 4937-4342 (1997).

Hanes, J. "Ribosome display efficiently selects and evolves high-affinity antibodies in vitro from immune libraries." Proc. Natl. Acad. Sci. U. S. A. 95(24): 14130-14135 (1998).

Masui, et al., "A possible association between missense polymorphism of the breakpoint cluser region gene and lithium prophylaxis in bipolar disorder", Progress in Neuro-Psychopharmacogy & Biological Psychiatry 32: 204-208 (2008).

Reddy, et al., "Transcriptional repression mediated by repositioning of genes to the nuclear lamina," Nature 452: 243-247 (Mar. 13, 2008).

Rosnet, et al.,"Hematopoietic Receptors of Class III Receptor-type Tyrosine Kinases", Critical Reviews in Ontogenesis, 4(6): 595-613 (1993).

Rush, et al., "Immunoaffinity Profiling of Tyrosine Phosphorylation in Cancer Cells," Nature Biotechnology, 23(1): 94-101 (2005).

Schaller, et al.,"Autophosphorylation of the Focal Adhesion Kinase, pp125FAK Directs SH2-Dependent Binding of pp60src", Molecular and Cellular Biology, 14(3): 1680-1688 (Mar. 1994).

Schindler, et al., "Structural Mechanism for STI-571 Inhibition of Abelson Tyrosine Kinase", Science 289: 1938-1942 (2000).

Schreiber, et al., "Target-Oriented and Diversity-Oriented Organic Synthesis in Drug Discovery", Science 287, 1964-1969 (2000).

Castrillon, et al., "Suppression of Ovarian Follicle Activation in Mice by the Transcription Factor Foxo3a", Science 301: 215-218 (2003).

Shalaby, et al., "Development of Humanized Bispecitic Antibodies Reactive with Cytotoxic Lymphocytes and Tumor Cells Overexpressing the HER2 Protoongocene", J. Exp. Med., 175: 217-225 (Jan. 1992).

Shen, et al.,"Evidence for SH3 domain directed binding and phosphorylation of Sam68 by Src", Oncogene 18 4647-4653 (1999).

Spira, et al.,"The identification of monoclonal class switch variants by Sib Selection and an ELISA Assay", Journal of Immunological Methods, 74 (1984) 307-315.

Steplewski, et al., "Isolation and characterization of anti-monosialoganglioside monoclonal antibody 19-9 class-switch variants", Proc. Nat'l. Acad. Sci., USA vol. 82 pp. 8653-8657, Dec. 1985.

Stryer, et al., "Fluorescence Spectroscopy of Proteins" Science, 162: 526-533 (1986).

Suresh, et al., "Bispecific monoclonal antibodies from hybrid hybridomas" Methods in Enzymology, vol. 121, 210-228 (1986).

Tutt, et al., "Trispecific F(ab'), Derivatives That Use Cooperative Signaling Via the TCR/CD3 Complex and CD2 to Activate and Redirect Resting Cytotoxic T Cells" The Jouhnal of Immunology 147(1):60-9 (1991).

Upstate, et al., "Antibodies for Phosphorylation & Beyond", Internet Article, Jun. 2004, 1-5.

Vijapurkar, et al.,"Roles of mitogen-activated protein kinase and phosphoinositide 3'kinase in ErbB2/ErbB3 coreceptor-mediated heregulin signaling" Experimental Cell Research 284, 291-302 (2003).

Walker. et al., "Interaction of Human IgG Chimeric Antibodies With the Human FcRII Receptors: Requirements for Antibody-Mediated Host Cell-Target Cell Interaction" Molecular Immunology , vol. 26 No. 4, pp. 403-411 (1989).

Wetzel, et al., Evaluation of CML model cell lines ad imatinib mesylate response: Determinants of signaling profiles. Journal of Immunological Methods, 305: 59-66 (2005).

Yamamoto, et al., "Activating mutation of D835 within the activation loop of FLT3 in human hematologic malignancies" Blood, vol. 97, No. 8 2434-2439 (Apr. 15, 2001).

Yang, et al., "Lysine acetylation and the bromodomian: a new partnership for signaling", BioEssays, vol. 26, Iss 10, 1076-1087 (2004).

Yeatman, et at, "A Renaissance for SRC", Nature Rev. Cancer 4(6):470-480 (Jun. 2004).

Yeung, et al., "Quantitative Screening of Yeast Surface-Displayed Polypeptide Libraries by Magnetic Bead Capture" Biotechnol. Prog. 18(2): 212-20 (2002).

Yokota, et al., "Internal tandem duplication of the FLT3 gene is preferentially seen in acute myeloid leukemia and myelodysplastic syndrome among various hematological malignancies. A study on a large series of patients and cell lines", Leukemia 11: 1605-1609 (1997).

Zapata, et al., "Engineering linear F (ab')2 fragments for efficient production in *Escherichia coli* and enhanced antiproliferative activity" Protein Engineering vol. 8 No. 10 pp. 1057-1062, 1995.

Zhang, et al., "Phosphoprotein Analysis Using Antibodies Broadly Reactive against Phosphorylated Motifs" Journal of Biological Chemistry, vol. 227 (42) 39379-39387 (2002).

Roof, et al., "Molecular Characterization of abLIM, a Novel Actin-binding and Double Zinc Finger Protein" Journal of Cell Biology, vol. 138 (3) 575-588 (Aug. 11, 1997).

Mustelin, et al., "Positive and negative regulation of T-cell activation through kinases and phosphates" Biochemical Journal, vol. 371 (1) 15-27 (Apr. 1, 2003).

Lucas, et al., "Regulation of Synthesis and Activity of the PLSTIRE Protein (Cyclin-Dependent Kinase 6 (cdk6)), a Major Cyclin D-Associated cdk4 Homologue in Normal Human T Lymphocytes" Journal of Immunology vol. 154 (12) 6275-6284 (1995).

Meyrson et al., "A family of human cc2-related protein kinases" EMBO Journal vol. 11 (8) 2909-2917 (1992).

Nagasawa et al., "Rapid Nuclear Translocation and Increases Activity of Cyclin Dependent Kinase 6 After T Cell Activation" Journal of Immunology vol. 158 (11) 5146-5154 (1997).

Cell Signaling Technology, "Phospho-LAT (Tyr191) Antibody" 1-3 (May 2002).

Iavarone et al., "Repression of the CDK activator Cdc25A and cell cycle arrest by cytokine TGF-beta in cells lacking the CDK inhibitor p15" Nature vol. 387 (6631) 417-422 (1997).

\* cited by examiner

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 2 | Cbl | NP_005179.2 | Adaptor/scaffold | Y141 | MyEENSQPR | cancer, esophageal | Kyse270 | SEQ ID NO: 1 |
| 3 | Cbl-b | NP_733762.2 | Adaptor/scaffold | Y337 | SyNPDLTGLCEPTPHDHIK | cancer, lymphoma, Hodgkin's disease | L540 | SEQ ID NO: 2 |
| 4 | CNKSR2 | NP_055742.2 | Adaptor/scaffold | Y671 | INMLTAGyAER | | brain | SEQ ID NO: 3 |
| 5 | CSDE1 | NP_001007554.1 | Adaptor/scaffold | Y138 | VFyLTYTPEDVE | cancer, leukemia | Jurkat | SEQ ID NO: 4 |
| 6 | CSDE1 | NP_001007554.1 | Adaptor/scaffold | Y141 | VFYLTyTPEDVE | cancer, leukemia | Jurkat | SEQ ID NO: 5 |
| 7 | CTNND1 | NP_001322.1 | Adaptor/scaffold | Y208 | NFHyPPDGYSR | cancer, gastric | KATO III | SEQ ID NO: 6 |
| 8 | DLG3 | NP_066943.2 | Adaptor/scaffold | Y808 | QIIEDQSGHyIWVPSPEKL | cancer, gastric; cancer, lung; cancer, lung, non-small cell | H3255; KATO III; MKN-45; N06CS97; N06bj594(14); SNU-16; SNU-5 | SEQ ID NO: 7 |
| 9 | DNMBP | NP_056036.1 | Adaptor/scaffold | Y430 | SQYySTVGGSHPHSEQYPDLLPLEAR | cancer, leukemia | Jurkat | SEQ ID NO: 8 |
| 10 | Dok4 | NP_060580.2 | Adaptor/scaffold | Y165 | LQITHENIyLWDIHNPR | cancer, colorectal | NCI-H716 | SEQ ID NO: 9 |
| 11 | Dok4 | NP_060580.2 | Adaptor/scaffold | Y220 | MCDAGEGLYTFQTQEGEQIyQR | cancer, gastric | SNU-5 | SEQ ID NO: 10 |
| 12 | ENTH | NP_055481.1 | Adaptor/scaffold | Y172 | ySERYDPEPK | cancer, leukemia | Jurkat | SEQ ID NO: 11 |
| 13 | ENTH | NP_055481.1 | Adaptor/scaffold | Y176 | YSERyDPEPK | cancer, leukemia | Jurkat | SEQ ID NO: 12 |
| 14 | EPB41L1 | NP_036288.2 | Adaptor/scaffold | Y68 | MEEKDySEADGLSER | cancer, leukemia | Jurkat | SEQ ID NO: 13 |
| 15 | FAM125A | NP_612410.1 | Adaptor/scaffold | Y210 | RNDSIYEASSLyGISAMDGVPFTLHPR | cancer, lung, non-small cell | csC66 | SEQ ID NO: 14 |
| 16 | FAM125A | NP_612410.1 | Adaptor/scaffold | Y254 | SLADIEEEyNYGFVVEK | cancer, leukemia | Jurkat | SEQ ID NO: 15 |
| 17 | FAM125A | NP_612410.1 | Adaptor/scaffold | Y256 | SLADIEEEYNyGFVVEK | cancer, leukemia | Jurkat | SEQ ID NO: 16 |
| 18 | FCHSD2 | NP_055639.1 | Adaptor/scaffold | Y603 | PHASLPPLPLyDQPPSSPYPSPDKR | cancer, lung, non-small cell | H2052 | SEQ ID NO: 17 |
| 19 | FNBP1L | NP_060207.2 | Adaptor/scaffold | Y291 | SGFEPPGDFPFEDYSQHIyR | cancer, gastric | KATO III | SEQ ID NO: 18 |
| 20 | FRS2 | NP_006645.3 | Adaptor/scaffold | Y150 | TPTTPGFAAQNLPNGyPR | cancer, breast | EVSA-T | SEQ ID NO: 19 |
| 21 | FRS2 | NP_006645.3 | Adaptor/scaffold | Y59 | RDSVKWHyLCLR | | 101206 | SEQ ID NO: 21 |
| 22 | Gab1 | NP_002030.2 | Adaptor/scaffold | Y47 | SGRLTGDPDVLEyYK | cancer, esophageal | Kyse510 | SEQ ID NO: 22 |
| 23 | KPNA3 | NP_002258.2 | Adaptor/scaffold | Y506 | ATQGGTyNFDPTANLQTKE | cancer, leukemia | Jurkat | SEQ ID NO: 25 |
| 24 | KPNA4 | NP_002259.1 | Adaptor/scaffold | Y66 | DSDIDGDyRVQNTSLE | cancer, leukemia | Jurkat | SEQ ID NO: 26 |
| 25 | MACF1 | NP_149033.2 | Adaptor/scaffold | Y2230 | GALDTTDGyMGVNQAPEKLDK | cancer, lymphoma, Hodgkin's disease | 639L | SEQ ID NO: 27 |
| 26 | P130Cas | NP_055382.2 | Adaptor/scaffold | Y653 | FTSQDSPDGQyENSEGGWMEDYDYVHLQGK | | CAKI-2 | SEQ ID NO: 29 |
| 27 | PAR3-beta | NP_689739.4 | Adaptor/scaffold | Y1034 | GGPADPVDyLPAAPR | cancer, lung, non-small cell | H2342 | SEQ ID NO: 30 |
| 28 | PEX14 | NP_004556.1 | Adaptor/scaffold | Y290 | GSTVTyHLLGPQEE | cancer, leukemia | Jurkat | SEQ ID NO: 31 |
| 29 | PSD-93 | NP_001355.2 | Adaptor/scaffold | Y223 | GLGFSIAGGVGNQHIPGDNSIyVTK | | brain | SEQ ID NO: 32 |
| 30 | PSD-93 | NP_001355.2 | Adaptor/scaffold | Y750 | FIEAGQyNDNLYGTSVQSVR | | brain | SEQ ID NO: 33 |
| 31 | PSD-95 | NP_001356.1 | Adaptor/scaffold | Y233 | GLGFSIAGGVGNQHIPGDNSIyVTK | | brain | SEQ ID NO: 34 |
| 32 | PSD-95 | NP_001356.1 | Adaptor/scaffold | Y576 | EDSVLSYETVTQMEVHyARPIIILGPTK | | brain | SEQ ID NO: 35 |
| 33 | SAPAP3 | NP_001073887.1 | Adaptor/scaffold | Y823 | EAEDyELPEEILEK | | brain | SEQ ID NO: 36 |
| 34 | SHANK1 | NP_057232.2 | Adaptor/scaffold | Y186 | FLEyVQLGTSDK | | brain | SEQ ID NO: 37 |
| 35 | SHANK3 | XP_037493.7 | Adaptor/scaffold | Y122 | FMDyVQLHSTDK | cancer, leukemia, acute myelogenous (AML) | B18_AML | SEQ ID NO: 38 |
| 36 | Shc2 | XP_944665.2 | Adaptor/scaffold | Y412 | GPPDHEEHLyVNTQGLDAPEPEDSPK | cancer, brain | BT2 | SEQ ID NO: 39 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 37 | SHD | NP_064594.2 | Adaptor/scaffold | Y144 | GVQLyDTPYEEQDPETADGPPSGQKPR | cancer, brain, neuroblastoma; cancer, nerve tissue, | CHP-212; LAN-5; SK-N-DZ | SEQ ID NO: 40 |
| 38 | SNCG | NP_003078.1 | Adaptor/scaffold | Y39 | EGVMyVGAK | cancer, leukemia, chronic myelogenous | K562 | SEQ ID NO: 41 |
| 39 | syntenin | NP_001007068.1 | Adaptor/scaffold | Y50 | SANPANPAILSEASAPIPHDGNLYPRLyPELSQY | cancer, gastric | Hs746T | SEQ ID NO: 42 |
| 40 | CDH1 | NP_004351.1 | Adhesion or extracellular matrix protein | Y876 | KLADMyGGGEDD | cancer, colorectal carcinoma; cancer, gastric; cancer, kidney/renal cell carcinoma/renal | 23132/87; CAL-29; HT29; SNU-16 | SEQ ID NO: 43 |
| 41 | CDH11 | NP_001788.2 | Adhesion or extracellular matrix protein | Y702 | KDIKPEYQyMPR | cancer, lung, non-small cell | h2073 | SEQ ID NO: 44 |
| 42 | CDH23 | NP_071407.2 | Adhesion or extracellular matrix protein | Y1672 | ITIQALDLDEGPNGTVTy | cancer, colorectal carcinoma | HCT 116 | SEQ ID NO: 45 |
| 43 | CGNL1 | NP_116255.2 | Adhesion or extracellular matrix protein | Y108 | ENSEELQLPENPyAQPSPIR | cancer, breast | CAL-51 | SEQ ID NO: 46 |
| 44 | claudin 18 | NP_057453.1 | Adhesion or extracellular matrix protein | Y254 | TEDEVQSyPSKHDYV | cancer, gastric | KATO III | SEQ ID NO: 47 |
| 45 | CNTN6 | NP_055276.1 | Adhesion or extracellular matrix protein | Y225 | TDGVMGEyEPK | cancer, lung, non-small cell | HL234A | SEQ ID NO: 48 |
| 46 | COL17A1 | NP_000485.3 | Adhesion or extracellular matrix protein | Y40 | LTSLPPKGGTSNGyAK | cancer, gastric | SNU-5 | SEQ ID NO: 49 |
| 47 | DCBLD2 | NP_563615.3 | Adhesion or extracellular matrix protein | Y569 | TEGTYDLPyWDR | cancer, gastric; cancer, lung, non-small cell | KATO III; h2073 | SEQ ID NO: 50 |
| 48 | DCBLD2 | NP_563615.3 | Adhesion or extracellular matrix protein | Y649 | KPEEGKEAGyADLDPY | cancer, gastric | Hs746T | SEQ ID NO: 51 |
| 49 | DSC2 | NP_077740.1 | Adhesion or extracellular matrix protein | Y839 | LGEKVyLCNQDENHK | cancer, lung | N06CS23 | SEQ ID NO: 52 |
| 50 | Erbin | NP_061165.1 | Adhesion or extracellular matrix protein | Y425 | VLTNyMFPQQPR | | brain | SEQ ID NO: 53 |
| 51 | FN1 | NP_002017.1 | Adhesion or extracellular matrix protein | Y2319 | RPGGEPSPEGTTGQSyNQYSQR | cancer, breast | BC007 | SEQ ID NO: 54 |
| 52 | FN1 | NP_002017.1 | Adhesion or extracellular matrix protein | Y2322 | RPGGEPSPEGTTGQSYNQySQR | cancer, breast | BC007 | SEQ ID NO: 55 |
| 53 | FRAS1 | NP_079350.4 | Adhesion or extracellular matrix protein | Y3985 | NVNILSEPEAAyTFK | cancer, colorectal | sw48 | SEQ ID NO: 56 |
| 54 | laminin receptor 1 | NP_001005472.1 | Adhesion or extracellular matrix protein | Y39 | FLAAGTHLGGTNLDFQMEQYIyKR | cancer, lymphoma, Hodgkin's disease | L540 | SEQ ID NO: 57 |
| 55 | LRRC7 | NP_065845.1 | Adhesion or extracellular matrix protein | Y425 | VLTNyMFPQQPR | | brain | SEQ ID NO: 58 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 56 | occludin | NP_002529.1 | Adhesion or extracellular matrix protein | Y337 | FyPESSYK | cancer, gastric | SNU-16 | SEQ ID NO: 59 |
| 57 | occludin | NP_002529.1 | Adhesion or extracellular matrix protein | Y342 | FYPESSyK | cancer, gastric | SNU-16 | SEQ ID NO: 60 |
| 58 | PVRL3 | NP_056295.1 | Adhesion or extracellular matrix protein | Y510 | FERPMDyYEDLK | cancer, gastric; cancer, lung, non-small cell; cancer, nerve tissue, neuroblastoma | DV-90; KATO III; LCLC-103H; SK-N-FI | SEQ ID NO: 61 |
| 59 | SEMA4F | NP_004254.2 | Adhesion or extracellular matrix protein | Y450 | EyDVLYLGTEDGHLHR | cancer, leukemia; cancer, ovarian | EFO-21; FUOV1; Jurkat | SEQ ID NO: 62 |
| 60 | SEMA4F | NP_004254.2 | Adhesion or extracellular matrix protein | Y454 | EYDVLyLGTEDGHLHR | cancer, leukemia; cancer, ovarian | EFO-21; FUOV1; Jurkat | SEQ ID NO: 63 |
| 61 | BNIP3L | NP_004322.1 | Apoptosis | Y219 | LSTPSASTy | | A498 | SEQ ID NO: 64 |
| 62 | catalase | NP_001743.1 | Apoptosis | Y379 | LGPNYLHIPVNCPyR | cancer, leukemia, acute myelogenous (AML) | AML-30410 | SEQ ID NO: 65 |
| 63 | CYCS | NP_061820.1 | Apoptosis | Y49 | TGQAPGYSyTAANK | cancer, gastric | KATO III | SEQ ID NO: 66 |
| 64 | FAIM3 | NP_005440.1 | Apoptosis | Y315 | SQNNIySACPR | cancer, leukemia; cancer, leukemia, acute lymphocytic (ALL); cancer, leukemia, acute myelogenous (AML); cancer, lung, non-small | HL226B; HL98A; Jurkat; MV4-11; Molm 14; N06bj523(3); SEM | SEQ ID NO: 67 |
| 65 | CALB2 | NP_001731.1 | Calcium-binding protein | Y126 | SGyIEANELK | cancer, gastric | SNU-5 | SEQ ID NO: 68 |
| 66 | CALB2 | NP_001731.1 | Calcium-binding protein | Y35 | HFDADGNGyIEGK | cancer, gastric | KATO III | SEQ ID NO: 69 |
| 67 | CALCOCO2 | NP_005822.1 | Calcium-binding protein | Y376 | GGARQNPGLAyGNPYSGIQE | cancer, leukemia | Jurkat | SEQ ID NO: 70 |
| 68 | CALCOCO2 | NP_005822.1 | Calcium-binding protein | Y380 | GGARQNPGLAYGNPySGIQE | cancer, leukemia | Jurkat | SEQ ID NO: 71 |
| 69 | calsequestrin 2 | NP_001223.2 | Calcium-binding protein | Y178 | SEDSEyYKAFEEAAEHFQPYIK | cancer, laryngeal | ENT15 | SEQ ID NO: 72 |
| 70 | FREQ | NP_055101.2 | Calcium-binding protein | Y115 | LYDLDNDGyITR | cancer, gastric; cancer, kidney/renal cell carcinoma/renal adenocarcinoma; cancer, lung; cancer, lung, non-small cell | A498; CAKI-2; H28; HCC827; LCLC-103H; MKN-45; N06CS107; SNU-5; SW1710; | SEQ ID NO: 73 |
| 71 | Cdc27 | NP_001247.2 | Cell cycle regulation | Y740 | ESLVyFLIGK | cancer, gastric | MKN-45 | SEQ ID NO: 74 |
| 72 | CEP350 | NP_055625.3 | Cell cycle regulation | Y2612 | EKDVSEYFyEK | cancer, leukemia | Jurkat | SEQ ID NO: 75 |
| 73 | CEP350 | NP_055625.3 | Cell cycle regulation | Y337 | KVATAPPAPAyK | cancer, nerve tissue, neuroblastoma | IMR32 | SEQ ID NO: 76 |
| 74 | ch-TOG | NP_055571.2 | Cell cycle regulation | Y268 | LEQQQSAGGDAEGGGDDGDEVPQIDAyELLEAVEILSK | cancer, leukemia | Jurkat | SEQ ID NO: 77 |
| 75 | HCAP-G | NP_071741.2 | Cell cycle regulation | Y929 | GNKEFGDQAEAAQDATLTTTTFQNEDEKNKEVyMTPLR | cancer, leukemia | Jurkat | SEQ ID NO: 78 |
| 76 | SKB1 | NP_006100.2 | Cell cycle regulation | Y283 | EFCSYLQyLEYLSQNR | cancer, lung, non-small cell | H2135 | SEQ ID NO: 79 |
| 77 | CCT6B | NP_006575.2 | Chaperone | Y239 | SLEyEKTEVNSG | cancer, leukemia, acute myelogenous (AML) | UT-7 | SEQ ID NO: 80 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 78 | CCT7 | NP_001009570.1 | Chaperone | Y59 | VHTVEDyQAIVDAEWNILYDKLEK | cancer, leukemia | Jurkat | SEQ ID NO: 81 |
| 79 | CCT-delta | NP_006421.2 | Chaperone | Y269 | TDMDNQIVVSDyAQMDR | cancer, leukemia, acute myelogenous (AML) | EOL-1 | SEQ ID NO: 82 |
| 80 | DNAJB5 | NP_036398.3 | Chaperone | Y52 | EIAEAyDVLSDPK | | brain | SEQ ID NO: 83 |
| 81 | DNAJB6 | NP_490647.1 | Chaperone | Y53 | QVAEAyEVLSDAK | ; cancer, leukemia, chronic myelogenous (CML); cancer, lung | A498; K562; N06CS106 | SEQ ID NO: 84 |
| 82 | ARID1A | NP_006006.3 | Chromatin, DNA-binding, DNA repair or DNA replication | Y762 | NPQMPQySSPQPGSALSPR | cancer, leukemia, acute myelogenous (AML) | MKPL-1 | SEQ ID NO: 85 |
| 83 | C14orf43 | NP_919254.2 | Chromatin, DNA-binding, DNA repair or DNA replication | Y158 | GSPHPGVGVPTyYNHPEALKR | cancer, leukemia, acute myelogenous (AML) | MKPL-1 | SEQ ID NO: 86 |
| 84 | CHD1L | NP_004275.2 | Chromatin, DNA-binding, DNA repair or DNA replication | Y709 | LDyQDPDATSLKYVSGDVTHPQAGAE | cancer, leukemia | Jurkat | SEQ ID NO: 87 |
| 85 | CHD-6 | NP_115597.3 | Chromatin, DNA-binding, DNA repair or DNA replication | Y1640 | LyESLTYSQMSR | cancer, leukemia | Jurkat | SEQ ID NO: 88 |
| 86 | CHD-6 | NP_115597.3 | Chromatin, DNA-binding, DNA repair or DNA replication | Y1645 | LYESLTySQMSR | cancer, leukemia | Jurkat | SEQ ID NO: 89 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 87 | H2BK | NP_542160.1 | Chromatin, DNA-binding, DNA repair or DNA replication protein | Y41 | ESYSVyVYK | cancer, bone, osteosarcoma/malignant fibrous histiocytoma; cancer, brain; cancer, brain, neuroblastoma; cancer, breast; cancer, breast, adenocarcinoma; cancer, breast, ductal carcinoma; cancer, colorectal; cancer, colorectal carcinoma; cancer, esophageal; cancer, esophageal carcinoma; cancer, gastric; cancer, kidney/renal cell carcinoma/renal adenocarcinoma; cancer, laryngeal; cancer, leukemia, acute lymphocytic (ALL); cancer, leukemia, acute myelogenous (AML); cancer, leukemia, chronic myelogenous (CML); cancer, lung; cancer, lung, non-small cell; cancer, lung, non-small-cell, Squmous cell carcinoma; cancer, lung, non-small-cell, large cell carcinoma; cancer, lung, small-cell; cancer, nerve tissue, neuroblastoma; cancer, oropharyngeal squamous cell carcinoma; cancer, ovarian; cancer, ovarian, epithelial carcinoma | 23132/87; 42 MG-BA; 8-MG-BA; A172:; A549; A704; BC007; BT1; BT2; CCF-STTG1; CHP126; CHRF; CMK; COLO-699; Calu-3; Colo680N; DK-MG; DMS 79; Detroit562; ENT05; ES2; GAMG; GMS 10:; H1435; H1437; H1568; H1650; H1651; H1703; H1734; H1781d; H1915; H1975; H2023; H2066:; H2085; H2135; H2172; H2452d; H3255; H358; H446; H4; H520; H524; H810; HCC1143; HCC1395; HCC1428; | SEQ ID NO: 90 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 88 | H2BL | NP_003510.1 | Chromatin, DNA-binding, DNA repair or DNA replication protein | Y41 | ESYSVyVYK | cancer, bone, osteosarcoma/malignant fibrous histiocytoma; cancer, brain; cancer, brain, neuroblastoma; cancer, breast; cancer, breast, adenocarcinoma; cancer, breast, ductal carcinoma; cancer, colorectal; cancer, colorectal carcinoma; cancer, esophageal; cancer, esophageal carcinoma; cancer, gastric; cancer, kidney/renal cell carcinoma/renal adenocarcinoma; cancer, laryngeal; cancer, leukemia, acute lymphocytic (ALL); cancer, leukemia, acute myelogenous (AML); cancer, leukemia, chronic myelogenous (CML); cancer, lung; cancer, lung, non-small cell; cancer, lung, non-small-cell, Squmous cell carcinoma; cancer, lung, non-small-cell, large cell carcinoma; cancer, lung, small-cell; cancer, nerve tissue, neuroblastoma; cancer, oropharyngeal squamous cell carcinoma; cancer, ovarian; cancer, ovarian, epithelial carcinoma | 23132/87; 42 MG-BA; 8-MG-BA; A172; A549; A704; BC007; BT1; BT2; CCF-STTG1; CHP126; CHRF; CMK; COLO-699; Calu-3; Colo680N; DK-MG; DMS 79; Detroit562; ENT05; ES2; GAMG; GMS 10; H1435; H1437; H1568; H1650; H1651; H1703; H1734; H1781; H1915; H1975; H2023; H2066; H2085; H2135; H2172; H2452; H3255; H358; H446; H4; H520; H524; H810; HCC1143; HCC1395; HCC1428; | SEQ ID NO: 91 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 89 | HIST2H2BF | NP_001019770.1 | Chromatin, DNA-binding, DNA repair or DNA replication protein | Y41 | ESYSVyVYK | cancer, bone, osteosarcoma/malignant fibrous histiocytoma; cancer, brain; cancer, brain, neuroblastoma; cancer, breast; cancer, breast, adenocarcinoma; cancer, breast, ductal carcinoma; cancer, colorectal; cancer, colorectal carcinoma; cancer, esophageal; cancer, esophageal carcinoma; cancer, gastric; cancer, kidney/renal cell carcinoma/renal adenocarcinoma; cancer, laryngeal; cancer, leukemia, acute lymphocytic (ALL); cancer, leukemia, acute myelogenous (AML); cancer, leukemia, chronic myelogenous (CML); cancer, lung; cancer, lung, non-small cell; cancer, lung, non-small-cell, Squmous cell carcinoma; cancer, lung, non-small-cell, large cell carcinoma; cancer, lung, small-cell; cancer, nerve tissue, neuroblastoma; cancer, oropharyngeal squamous cell carcinoma; cancer, ovarian; cancer, ovarian, epithelial carcinoma | 23132/87; 42 MG-BA; 8-MG-BA; A172; A549; A704; BC007; BT1; BT2; CCF-STTG1; CHP126; CHRF; CMK; COLO-699; Calu-3; Colo680N; DK-MG; DMS 79; Detroit562; ENT05; ES2; GAMG; GMS 10; H1435; H1437; H1568; H1650; H1651; H1703; H1734; H1781; H1915; H1975; H2023; H2066; H2085; H2135; H2172; H2452; H3255; H358; H446; H4; H520; H524; H810; HCC1143; HCC1395; HCC1428 | SEQ ID NO: 92 |
| 90 | HMGB1 | NP_002119.1 | Chromatin, DNA-binding, DNA repair or DNA replication | Y78 | EMKTyIPPKGETKK | cancer, ovarian | MDAH2774 | SEQ ID NO: 93 |
| 91 | NAP1L1 | NP_004528.1 | Chromatin, DNA-binding, DNA repair or DNA replication | Y377 | GDEENDPDyDPKKDQNPAE | cancer, leukemia | Jurkat | SEQ ID NO: 94 |
| 92 | ARVCF | NP_001661.1 | Cytoskeletal protein | Y201 | DSPSyGSLSR | cancer, gastric; cancer, leukemia, chronic myelogenous (CML); cancer, lung, non-small | H3255; K562; MKN-45 | SEQ ID NO: 95 |
| 93 | calponin 3 | NP_001830.1 | Cytoskeletal protein | Y316 | HGEYQDDyPRDY | cancer, gastric | Hs746T | SEQ ID NO: 96 |
| 94 | CAPZA2 | NP_006127.1 | Cytoskeletal protein | Y198 | IQVHyYEDGNVQLVSHK | cancer, leukemia, chronic myelogenous | KATO III | SEQ ID NO: 97 |
| 95 | CCDC6 | NP_005427.2 | Cytoskeletal protein | Y336 | MDDERyFNE | cancer, leukemia | Jurkat | SEQ ID NO: 98 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 96 | CDK5R AP2 | NP_060719.4 | Cytoskeletal protein | Y1111 | VSVMGTDQSESINTSNETEyLKQK | cancer, leukemia, acute lymphocytic (ALL) | DU.528 | SEQ ID NO: 99 |
| 97 | CLASP2 | NP_055912.1 | Cytoskeletal protein | Y1150 | NMNSEDIySSLRGVTE | cancer, leukemia | Jurkat | SEQ ID NO: 100 |
| 98 | claudin 5 | NP_003268.1 | Cytoskeletal protein | Y212 | RPTATGDyDKKNYV | cancer, lung; cancer, lung, non-small cell; cancer, thyroid, papillary carcinoma | BJ630; ENT01; N06BJ593(13); N06CS02; N06CS06; N06CS22-2; N06CS39; N06CS40; N06CS87; N06CS90; N06CS93-2; N06N102; N06N103; N06N106; N06N121; N06N131; N06N80; N06N90; N06N93; N06bj523(3); N06bj595(15); N06bj667(29); N06cs112; N06cs113; N06cs117; N06cs122; N06cs123(2); N06cs128; | SEQ ID NO: 101 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 99 | claudin 5 | NP_003268.1 | Cytoskeletal protein | Y217 | RPTATGDYDKKNyV | cancer, lung; cancer, lung, non-small cell; cancer, thyroid, papillary carcinoma | BJ630; ENT01; N06BJ593(13); N06CS02; N06CS06; N06CS22-2; N06CS39; N06CS40; N06CS87; N06CS90; N06CS93-2; N06N102; N06N103; N06N106; N06N121; N06N131; N06N80; N06N90; N06N93; N06bj523(3); N06bj595(15); N06bj667(29); N06cs112; N06cs113; N06cs117; N06cs122; N06cs123(2); N06cs128; | SEQ ID NO: 102 |
| 100 | cofilin 1 | NP_005498.1 | Cytoskeletal protein | Y82 | MLPDKDCRyALYDATYETKESK | cancer, esophageal carcinoma; cancer, leukemia | A498; Jurkat | SEQ ID NO: 103 |
| 101 | cofilin 2 | NP_068733.1 | Cytoskeletal protein | Y82 | LLPLNDCRyALYDATYETK | cancer, leukemia | A498; Jurkat | SEQ ID NO: 104 |
| 102 | cordon-bleu | NP_056013.2 | Cytoskeletal protein | Y1143 | LSyTEAEGER | cancer, gastric | KATO III | SEQ ID NO: 105 |
| 103 | cordon-bleu | NP_056013.2 | Cytoskeletal protein | Y652 | VKDKVyGCADGER | cancer, gastric | 23132/87 | SEQ ID NO: 106 |
| 104 | cortactin | NP_005222.2 | Cytoskeletal protein | Y538 | yGLFPANYVELRQ | cancer, lung, non-small cell | H2172 | SEQ ID NO: 107 |
| 105 | COTL1 | NP_066972.1 | Cytoskeletal protein | Y137 | LKKAGGANyDAQTE | cancer, leukemia | Jurkat | SEQ ID NO: 108 |
| 106 | CTNND2 | NP_001323.1 | Cytoskeletal protein | Y1090 | KTDyECTGSNATYHGAK | cancer, breast | KPL-1 | SEQ ID NO: 109 |
| 107 | DBN1 | NP_004386.2 | Cytoskeletal protein | Y32 | SAADWALyTYEDGSDDLKLAASGE | cancer, leukemia | Jurkat | SEQ ID NO: 110 |
| 108 | dystrophin | NP_004014.1 | Cytoskeletal protein | Y894 | MHyPMVEYCTPTTSGEDVR | cancer, colorectal | NCI-H716 | SEQ ID NO: 111 |
| 109 | EB1 | NP_036457.1 | Cytoskeletal protein | Y268 | GFVIPDEGGPQEEQEEy | cancer, leukemia | Jurkat | SEQ ID NO: 112 |
| 110 | EHM2 | NP_061987.3 | Cytoskeletal protein | Y447 | TNPEVHNyQPQYHPNIHPSQPR | cancer, gastric | KATO III | SEQ ID NO: 113 |
| 111 | EHM2 | NP_061987.3 | Cytoskeletal protein | Y451 | TNPEVHNYQPQyHPNIHPSQPR | cancer, gastric | KATO III | SEQ ID NO: 114 |
| 112 | EML4 | NP_061936.2 | Cytoskeletal protein | Y265 | LKLEWAyGYR | cancer, lung, non-small cell | cs110 | SEQ ID NO: 115 |
| 113 | EML4 | NP_061936.2 | Cytoskeletal protein | Y954 | GSGDLGEPLyEEPCNE | cancer, leukemia | Jurkat | SEQ ID NO: 116 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 114 | eplin | NP_057441.1 | Cytoskeletal protein | Y429 | LSLGTyASLHGR | cancer, leukemia, chronic myelogenous | K562 | SEQ ID NO: 117 |
| 115 | EXOC7 | NP_001013861.1 | Cytoskeletal protein | Y90 | TLSCLDHVISyYHVASDTEK | cancer, gastric | KATO III | SEQ ID NO: 118 |
| 116 | ezrin | NP_003370.2 | Cytoskeletal protein | Y499 | SLQDEGAEPTGySAE | cancer, leukemia | Jurkat | SEQ ID NO: 119 |
| 117 | FLNB | NP_001448.2 | Cytoskeletal protein | Y596 | IEyNDQNDGSCDVK | cancer, gastric | 23132/87 | SEQ ID NO: 120 |
| 118 | FLNC | NP_001449.3 | Cytoskeletal protein | Y1303 | VLNPSGAKTDTyVTDNGDGTYR | cancer, gastric | Hs746T | SEQ ID NO: 121 |
| 119 | FLNC | NP_001449.3 | Cytoskeletal protein | Y1312 | VLNPSGAKTDTYVTDNGDGTyR | cancer, gastric | Hs746T | SEQ ID NO: 122 |
| 120 | FNBP1 | NP_055848.1 | Cytoskeletal protein | Y234 | MGESMKTyAEVDR | cancer, lymphoma, Hodgkin's disease | L428 | SEQ ID NO: 123 |
| 121 | FNBP1 | NP_055848.1 | Cytoskeletal protein | Y287 | SGFEPPGDIEFEDyTQPMKR | cancer, leukemia | Jurkat | SEQ ID NO: 124 |
| 122 | INA | NP_116116.1 | Cytoskeletal protein | Y425 | FSTSGLSISGLNPLPNPSyLLPPR | | brain | SEQ ID NO: 125 |
| 123 | K1 | NP_006112.3 | Cytoskeletal protein | Y566 | GSYGSGGSSYGSGGGSyGSGGGGGGHGSYGSGSSSGGYR | cancer, lung | N06CS93-2 | SEQ ID NO: 126 |
| 124 | RP1 | NP_055083.1 | Cytoskeletal protein | Y162 | FYDANyDGKEYDPVEAR | cancer, leukemia | Jurkat | SEQ ID NO: 127 |
| 125 | SAPAP1 | NP_004737.2 | Cytoskeletal protein | Y317 | SCQyLQVPQDEWTGYTPR | | brain | SEQ ID NO: 128 |
| 126 | SHRM | NP_065910.2 | Cytoskeletal protein | Y500 | ESGyIAPQGACNK | cancer, gastric; cancer, lung, non-small cell | H2342; HCC827; MKN-45 | SEQ ID NO: 129 |
| 127 | talin 2 | NP_055874.1 | Cytoskeletal protein | Y1854 | GTFVDyQTTVVK | cancer, nerve tissue, neuroblastoma | GI-CA-N | SEQ ID NO: 130 |
| 128 | talin 2 | NP_055874.1 | Cytoskeletal protein | Y49 | ERVPEAQTGQASDyGLFLSDEDPR | cancer, lymphoma, Hodgkin's disease | HD-MyZ | SEQ ID NO: 131 |
| 129 | OSBPL3 | NP_056365.1 | Endoplasmic reticulum or | Y47 | GEMNyTQEPPVQK | cancer, leukemia | Jurkat | SEQ ID NO: 132 |
| 130 | CA9 | NP_001207.1 | Enzyme, misc. | Y449 | GGVSyRPAEVAETGA | cancer, gastric | SNU-16 | SEQ ID NO: 133 |
| 131 | CCBL1 | NP_004050.3 | Enzyme, misc. | Y15 | MAKQLQARRLDGIDyNPWVEFVK | | 101206 | SEQ ID NO: 134 |
| 132 | CHD2 | NP_001262.3 | Enzyme, misc. | Y596 | LKFNALITTyEILLKDK | cancer, leukemia, chronic myelogenous | K562 | SEQ ID NO: 135 |
| 133 | CNP | NP_149124.3 | Enzyme, misc. | Y373 | LySLGNGR | cancer, brain | BT1 | SEQ ID NO: 136 |
| 134 | CPT1A | NP_001867.2 | Enzyme, misc. | Y514 | GDINPNIPyPTR | cancer, lung | N06CS17 | SEQ ID NO: 138 |
| 135 | CTPS | NP_001896.1 | Enzyme, misc. | Y96 | IYQyVINK | cancer, lymphoma, Hodgkin's disease | L540 | SEQ ID NO: 139 |
| 136 | DDHD1 | NP_085140.1 | Enzyme, misc. | Y89 | GEPGLHLAPGTDDHNHHLALDPCLSDENyDFSSAESGSSLR | cancer, leukemia | Jurkat | SEQ ID NO: 140 |
| 137 | DDX10 | NP_004389.2 | Enzyme, misc. | Y273 | LSLKNPEyVWVHEK | cancer, leukemia, acute myelogenous (AML) | EOL-1 | SEQ ID NO: 141 |
| 138 | DDX42 | NP_031398.2 | Enzyme, misc. | Y160 | GIRDDIEEEDDQEAyFR | cancer, leukemia | Jurkat | SEQ ID NO: 142 |
| 139 | DDX9 | NP_001348.2 | Enzyme, misc. | Y21 | KMTPSyEIR | cancer, lymphoma, Hodgkin's disease | L540 | SEQ ID NO: 143 |
| 140 | DEGS1 | NP_003667.1 | Enzyme, misc. | Y14 | VSREDFEWVyTDQPHADR | cancer, leukemia | Jurkat | SEQ ID NO: 144 |
| 141 | DHCR7 | NP_001351.2 | Enzyme, misc. | Y382 | VIECSyTSADGQR | cancer, esophageal carcinoma; cancer, leukemia, acute myelogenous (AML); cancer, lung, non-small | H1781; Kyse140; MV4-11; Molm 14 | SEQ ID NO: 147 |
| 142 | DHX33 | NP_064547.2 | Enzyme, misc. | Y380 | KyNPDSGLEVLAVQR | cancer, leukemia, chronic myelogenous | K562 | SEQ ID NO: 148 |
| 143 | DHX36 | NP_065916.1 | Enzyme, misc. | Y1006 | NFPPRFQDGyYS | cancer, leukemia | Jurkat | SEQ ID NO: 149 |
| 144 | Diminuto | NP_055577.1 | Enzyme, misc. | Y299 | LNSIGNyYK | cancer, leukemia, acute lymphocytic (ALL) | SEM | SEQ ID NO: 150 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 145 | Diminuto | NP_055577.1 | Enzyme, misc. | Y300 | LNSIGNYyK | cancer, leukemia, acute lymphocytic (ALL) | SEM | SEQ ID NO: 151 |
| 146 | DUS3L | NP_064560.1 | Enzyme, misc. | Y308 | LyLAPLTTCGNLPFR | cancer, lung, small-cell | SCLC T4 | SEQ ID NO: 152 |
| 147 | EPRS | NP_004437.2 | Enzyme, misc. | Y684 | RGFFICDQPyEPVSPYSCK | cancer, lymphoma, Hodgkin's disease | HDLM-2 | SEQ ID NO: 153 |
| 148 | FBPase | NP_000498.2 | Enzyme, misc. | Y259 | TLVyGGIFLYPANK | cancer, lung, non-small | cs110 | SEQ ID NO: 154 |
| 149 | G6PI | NP_000166.2 | Enzyme, misc. | Y92 | MFNGEKINyTEGR | cancer, laryngeal | ENT15; ENT19; ENT7 | SEQ ID NO: 155 |
| 150 | IMPDH2 | NP_000875.2 | Enzyme, misc. | Y459 | FVPyLIAGIQHSCQDIGAK | cancer, lymphoma, Hodgkin's disease | L540 | SEQ ID NO: 156 |
| 151 | LDH-B | NP_002291.1 | Enzyme, misc. | Y173 | FRyLMAEK | cancer, lymphoma, Hodgkin's disease | L540 | SEQ ID NO: 157 |
| 152 | LSD1 | NP_055828.2 | Enzyme, misc. | Y135 | EMDESLANLSEDEyYSEEER | cancer, leukemia, acute myelogenous (AML); cancer, leukemia, chronic myelogenous (CML); cancer, lung, non- | H3255; K562; Molm 14; N06BJ606(19) | SEQ ID NO: 158 |
| 153 | LSD1 | NP_055828.2 | Enzyme, misc. | Y136 | EMDESLANLSEDEYySEEER | cancer, leukemia, acute myelogenous (AML); cancer, leukemia, chronic myelogenous (CML); cancer, lung, non-small cell; cancer, nerve tissue, neuroblastoma | H3255; K562; MHH-NB-11; Molm 14; N06BJ606(19) | SEQ ID NO: 159 |
| 154 | ACSM2A | NP_001010845.1 | Enzyme, misc. | Y303 | FDPLVILKTLSSyPIK | cancer, leukemia | Jurkat | SEQ ID NO: 160 |
| 155 | NTE | NP_006693.3 | Enzyme, misc. | Y431 | EQPAGACEySYCEDESATGGCPFGPYQGR | cancer, leukemia | Jurkat | SEQ ID NO: 161 |
| 156 | PLD1 | NP_002653.1 | Enzyme, misc. | Y42 | ELHFEGEEVDyDVSPSDPK | cancer, leukemia | NALM-19 | SEQ ID NO: 162 |
| 157 | SCLY | NP_057594.2 | Enzyme, misc. | Y280 | GLGEFTPLyPMLFGGGQER | cancer, gastric; cancer, lung, non-small cell | LXF-289; MKN-45 | SEQ ID NO: 163 |
| 158 | Cdc42 | NP_001782.1 | G protein or regulator | Y32 | TTNKFPSEyVPTVF | cancer, gastric | Hs746T | SEQ ID NO: 164 |
| 159 | Cdc42EP1 | NP_689449.1 | G protein or regulator | Y130 | NAISLPQLNQAAyDSLVVGK | cancer, gastric | MKN-45 | SEQ ID NO: 165 |
| 160 | Cdc42EP1 | NP_689449.1 | G protein or regulator | Y331 | HWGAGWDGGHHyPEMDAR | cancer, gastric | SNU-16 | SEQ ID NO: 166 |
| 161 | CENTD1 | NP_056045.2 | G protein or regulator | Y867 | KAGQSLQMEFLyHNK | cancer, leukemia, acute myelogenous (AML) | B13_AML | SEQ ID NO: 167 |
| 162 | CENTD2 | NP_056057.1 | G protein or regulator | Y119 | yFDSNKDAYSK | cancer, lung; cancer, lung, non-small cell | HL233B; N06CS22-1 | SEQ ID NO: 168 |
| 163 | CENTD2 | NP_056057.1 | G protein or regulator | Y127 | YFDSNKDAySK | cancer, lung; cancer, lung, non-small cell | HL233B; N06CS22-1 | SEQ ID NO: 169 |
| 164 | ARHGAP3 | NP_004058.1 | G protein or regulator | Y153 | YISKMTTNPIyE | cancer, leukemia | Jurkat | SEQ ID NO: 170 |
| 165 | ARHGAP3 | NP_004058.1 | G protein or regulator | Y158 | MTTNPIYEHIGyATLLR | cancer, leukemia | Jurkat | SEQ ID NO: 171 |
| 166 | DDEF2 | NP_003878.1 | G protein or regulator | Y724 | EDRPISFyQLGSNQLQSNAVSLAR | cancer, leukemia | Jurkat | SEQ ID NO: 172 |
| 167 | DOCK10 | NP_055504.1 | G protein or regulator | Y1126 | EDQLEyQEELR | cancer, lung, non-small cell | H596 | SEQ ID NO: 173 |
| 168 | DOCK9 | NP_056111.1 | G protein or regulator | Y340 | LFyLDPDAQK | cancer, gastric | KATO III | SEQ ID NO: 174 |
| 169 | ephexin1 | NP_062824.1 | G protein or regulator | Y288 | LVTSEASyYKSLNLLVSHFMENE | cancer, leukemia | Jurkat | SEQ ID NO: 175 |
| 170 | ephexin1 | NP_062824.1 | G protein or regulator | Y289 | LVTSEASYyKSLNLLVSHFMENE | cancer, leukemia | Jurkat | SEQ ID NO: 176 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 171 | ephexin1 | NP_062824.1 | G protein or regulator | Y537 | QIPGDKyQVFDSAPR | cancer, leukemia, chronic myelogenous | CML-06/164 | SEQ ID NO: 177 |
| 172 | EPS8L2 | NP_073609.2 | G protein or regulator | Y678 | VySQLTMQK | cancer, gastric | 23132/87; A498; SNU-5 | SEQ ID NO: 178 |
| 173 | EVI5L | NP_660288.1 | G protein or regulator | Y788 | LAAPySQGLDN | cancer, leukemia | Jurkat | SEQ ID NO: 179 |
| 174 | FGD5 | NP_689749.2 | G protein or regulator | Y603 | QQSADQDAESAyTEPYK | cancer, breast | ZR-75-30 | SEQ ID NO: 180 |
| 175 | G-alpha(z) | NP_002064.1 | G protein or regulator | Y75 | EYKPLIIyNAIDSLTR | | brain | SEQ ID NO: 181 |
| 176 | G-alpha2(i) | NP_002061.1 | G protein or regulator | Y155 | EYQLNDSAAyYLNDLER | | brain | SEQ ID NO: 182 |
| 177 | GPSM3 | NP_071390.1 | G protein or regulator | Y108 | EQLySTILSHQCQR | cancer, leukemia | Jurkat | SEQ ID NO: 183 |
| 178 | IQGAP1 | NP_003861.1 | G protein or regulator | Y1284 | FNVDEySDLVTLTK | cancer, gastric | MKN-45 | SEQ ID NO: 184 |
| 179 | IQGAP1 | NP_003861.1 | G protein or regulator | Y694 | GGyYYYHNLETQEGGWDEPPNFVQNSMQLSR | cancer, multiple myeloma | OPM-1 | SEQ ID NO: 185 |
| 180 | IQGAP1 | NP_003861.1 | G protein or regulator | Y695 | GGYyYYHNLETQEGGWDEPPNFVQNSMQLSR | cancer, multiple myeloma | OPM-1 | SEQ ID NO: 186 |
| 181 | IQGAP1 | NP_003861.1 | G protein or regulator | Y697 | GGYYYyHNLETQEGGWDEPPNFVQNSMQLSR | cancer, gastric | KATO III | SEQ ID NO: 187 |
| 182 | IQGAP2 | AAB37765.1 | G protein or regulator | Y630 | ESSWVTPESCFyKESWLTGK | cancer, leukemia, chronic myelogenous | K562 | SEQ ID NO: 188 |
| 183 | IQGAP3 | NP_839943.2 | G protein or regulator | Y1268 | FAVDEySDMVAVAKPMVYITVGELVNTHR | cancer, gastric | SNU-16 | SEQ ID NO: 189 |
| 184 | RICS | NP_055530.2 | G protein or regulator | Y1424 | GPVMSQyDNMTPAVQDDLGGIYVIHLR | cancer, gastric | MKN-45 | SEQ ID NO: 190 |
| 185 | RRAS2 | NP_036382.2 | G protein or regulator | Y105 | GSFEEIyKFQR | cancer, leukemia, chronic myelogenous | Baf3(FLT3|D835Y) | SEQ ID NO: 191 |
| 186 | SIPA1L3 | NP_055888.1 | G protein or regulator | Y1265 | GEPQySSHSSSNTLSSNASSSHSDDR | cancer, lung, non-small cell | H1781; h2073 | SEQ ID NO: 192 |
| 187 | SIPA1L3 | NP_055888.1 | G protein or regulator | Y1316 | GGSSDSGIDTTLyTSSPSCMSLAK | cancer, leukemia | Jurkat | SEQ ID NO: 193 |
| 188 | SRGAP2 | NP_056141.2 | G protein or regulator | Y699 | GPVYSRGGSMEDyCDSPHGE | cancer, leukemia | Jurkat | SEQ ID NO: 194 |
| 189 | ITIH1 | NP_002206.1 | Inhibitor protein | Y431 | FPLyNLGFGHNVDFNFLEVMSMENNG | cancer, colorectal | NCI-H716 | SEQ ID NO: 195 |
| 190 | EM55 | NP_002427.1 | Kinase (non-protein) | Y316 | FVYPVPyTTRPPRKSEEDGK | cancer, ovarian | CaoV4 | SEQ ID NO: 196 |
| 191 | PIK3CA | NP_006209.2 | Kinase (non-protein) | Y294 | ESLySQLPMDCFTMPSYSR | cancer, leukemia, acute myelogenous (AML) | EOL-1 | SEQ ID NO: 197 |
| 192 | PIK3R1 | NP_852664.1 | Kinase (non-protein) | Y76 | GDFPGTYVEyIGR | cancer, leukemia, acute myelogenous (AML) | EOL-1 | SEQ ID NO: 198 |
| 193 | PIK3R2 | NP_005018.1 | Kinase (non-protein) | Y460 | SREyDQLYEEYTR | cancer, esophageal | Kyse450 | SEQ ID NO: 199 |
| 194 | PIP5K | NP_055855.2 | Kinase (non-protein) | Y154 | GKSQDSDLKQyWMPDSQCKE | cancer, leukemia | Jurkat | SEQ ID NO: 200 |
| 195 | PIP5KG | NP_036530.1 | Kinase (non-protein) | Y354 | ALySTAMESIQGGAAR | | brain | SEQ ID NO: 201 |
| 196 | ephrin-B1 | NP_004420.1 | Ligand, receptor | Y79 | PYEYYKLyLVR | cancer, ovarian | CaoV3 | SEQ ID NO: 202 |
| 197 | FRMD6 | NP_689543.1 | Lipid binding protein | Y262 | QLLyDFPWTNVGK | | brain | SEQ ID NO: 203 |
| 198 | PLEKHA1 | NP_001001974.1 | Lipid binding protein | Y345 | GFyESLAK | cancer, gastric | MKN-45 | SEQ ID NO: 204 |
| 199 | DCTN3 | NP_009165.1 | Motor or contractile protein | Y67 | KIEDLIKyLDPEYIDR | cancer, leukemia, chronic myelogenous (CML) | Baf3(FGFR1 truncation: 10ZF) | SEQ ID NO: 206 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 200 | DNCH1 | NP_001367.2 | Motor or contractile | Y970 | ITNQVlyLNPPIEECR | cancer, leukemia, acute myelogenous (AML) | MKPL-1 | SEQ ID NO: 207 |
| 201 | KIF2A | NP_004511.1 | Motor or contractile | Y168 | KRAQDVDATNPNyE | cancer, leukemia | Jurkat | SEQ ID NO: 208 |
| 202 | KNSL8 | NP_958929.1 | Motor or contractile | Y205 | GQGATAAQQGGyEIPAR | cancer, leukemia | Jurkat | SEQ ID NO: 209 |
| 203 | MRLC2V | NP_000423.2 | Motor or contractile | Y118 | GVLKADyVR | cancer, laryngeal | ENT7 | SEQ ID NO: 210 |
| 204 | MYH1 | NP_005954.3 | Motor or contractile protein | Y1856 | KVKELTyQTEEDRK | cancer, laryngeal; cancer, lung, non-small cell; cancer, pancreatic | ENT02; ENT12; ENT15; ENT19; ENT7; H1650; H1703 | SEQ ID NO: 211 |
| 205 | MYH1 | NP_005954.3 | Motor or contractile protein | Y424 | GQTVQQVyNAVGALAK | cancer, laryngeal; cancer, lung, non-small cell | ENT15; ENT7; N06c78 | SEQ ID NO: 212 |
| 206 | MYH2 | NP_060004.2 | Motor or contractile protein | Y1858 | ELTyQTEEDRKNILR | cancer, laryngeal; cancer, lung, non-small cell; cancer, pancreatic | ENT15; ENT7; HP28; N06c78 | SEQ ID NO: 213 |
| 207 | MYH2 | NP_060004.2 | Motor or contractile protein | Y822 | EAIFCIQyNIR | cancer, laryngeal; cancer, lung, non-small cell | ENT15; ENT19; ENT7; N06c78 | SEQ ID NO: 214 |
| 208 | MYH4 | NP_060003.2 | Motor or contractile protein | Y1856 | ELTyQTEEDRK | cancer, laryngeal; cancer, lung, non-small cell; cancer, pancreatic | ENT15; ENT7; HP28; N06c78 | SEQ ID NO: 215 |
| 209 | MYH4 | NP_060003.2 | Motor or contractile protein | Y424 | GQTVQQVyNAVGALAK | cancer, laryngeal; cancer, lung, non-small cell | ENT15; ENT7; N06c78 | SEQ ID NO: 216 |
| 210 | MYH7 | NP_000248.2 | Motor or contractile protein | Y422 | GQNVQQVIyATGALAK | cancer, laryngeal; cancer, lung, non-small cell | ENT02; ENT10; ENT15; ENT19; ENT7; N06c78 | SEQ ID NO: 217 |
| 211 | MYH8 | NP_002463.1 | Motor or contractile protein | Y424 | GQTVQQVyNAVGALAK | cancer, laryngeal; cancer, lung, non-small cell | ENT15; ENT7; N06c78 | SEQ ID NO: 218 |
| 212 | MYO10 | NP_036466.1 | Motor or contractile | Y585 | FDFIyDLFEHVSSR | cancer, lung, non-small cell | H2052 | SEQ ID NO: 219 |
| 213 | MYO1C | NP_203693.3 | Motor or contractile | Y438 | SEQEEYEAEGIAWEPVQyFNNK | cancer, lymphoma, Hodgkin's disease | KATO III | SEQ ID NO: 220 |
| 214 | MYO1F | NP_036467.2 | Motor or contractile protein | Y438 | WTPIQyFNNK | cancer, kidney/renal cell carcinoma/renal adenocarcinoma | BC-3C | SEQ ID NO: 221 |
| 215 | CD45 | NP_002829.2 | Phosphatase | Y681 | NRyVDILPYDYNR | cancer, leukemia | Jurkat | SEQ ID NO: 222 |
| 216 | DARPP-32 | NP_115568.2 | Phosphatase | Y116 | ELGyPREEDEEEEEDDEEEEEEEDSQAEVLK | cancer, gastric | KATO III | SEQ ID NO: 223 |
| 217 | DUSP3 | NP_004081.1 | Phosphatase | Y23 | LSVQDLNDLLSDGSGCySLPSQPCNE | cancer, leukemia | Jurkat | SEQ ID NO: 224 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 218 | FBP2 | NP_003828.2 | Phosphatase | Y216 | IYSLNEGyAK | cancer, laryngeal; cancer, lung; cancer, lung, non-small cell | BJ629; BJ631; BJ635; BJ665; ENT02; ENT15; ENT7; HL131B; HL183A; HL183B; HL1881; HL25A; N06CS02; N06CS16; N06CS22-1; N06CS22-2; N06CS23; N06bj667(29); N06c144; N06c78; N06cs109; N06cs112; N06cs123; N06cs126; SCLC T1; cs026; cs042; | SEQ ID NO: 225 |
| 219 | FBP2 | NP_003828.2 | Phosphatase | Y259 | TLVyGGIFLYPANQK | cancer, lung, non-small | HL183B | SEQ ID NO: 226 |
| 220 | INPP5F | NP_055752.1 | Phosphatase | Y430 | FENVQTLTDAlyDIILDMK | cancer, gastric | MKN-45 | SEQ ID NO: 227 |
| 221 | PTPN14 | NP_005392.2 | Phosphatase | Y496 | ERHPyTVPYGPQGVYSNK | cancer, kidney; cancer, kidney/renal cell carcinoma/renal adenocarcinoma; cancer, lung, non-small cell | A704; CAKI-2; LCLC-103H | SEQ ID NO: 228 |
| 222 | CMA1 | NP_001827.1 | Protease | Y35 | PyMAYLEIVTSNGPSK | cancer, lung | gz30 | SEQ ID NO: 229 |
| 223 | CMA1 | NP_001827.1 | Protease | Y38 | PYMAyLEIVTSNGPSK | cancer, lung | gz30 | SEQ ID NO: 230 |
| 224 | CNDP2 | NP_060705.1 | Protease | Y311 | WRyPSLSLHGIEGAFSGSGAK | cancer, lymphoma, Hodgkin's disease | L540 | SEQ ID NO: 231 |
| 225 | PSMB4 | NP_002787.2 | Protease | Y75 | FEGGVVIAADMLGSyGSLAR | cancer, lymphoma, Hodgkin's disease | L540 | SEQ ID NO: 232 |
| 226 | DYRK4 | NP_003836.1 | Protein kinase, dual-specificity | Y356 | yPDSKDLTMVLK | cancer, leukemia | Jurkat | SEQ ID NO: 234 |
| 227 | CKS1 | NP_001817.1 | Protein kinase, regulatory | Y12 | QIYYSDKyDDEEFEYR | cancer, leukemia | Jurkat | SEQ ID NO: 235 |
| 228 | CaMK2-delta | NP_001212.2 | Protein kinase, Ser/Thr (non-receptor) | Y14 | FTDEyQLFEELGK | | brain | SEQ ID NO: 236 |
| 229 | CAMKK2 | NP_006540.3 | Protein kinase, Ser/Thr (non-receptor) | Y190 | LAYNENDNTyYAMK | cancer, leukemia, acute myelogenous (AML) | MKPL-1 | SEQ ID NO: 237 |
| 230 | Cdc2 | NP_001777.1 | Protein kinase, Ser/Thr (non-receptor) | Y4 | MEDyTKIEKIGEGTYGVVYK | cancer, esophageal carcinoma | Kyse70 | SEQ ID NO: 238 |
| 231 | CDK9 | NP_001252.1 | Protein kinase, Ser/Thr (non-receptor) | Y287 | LKAYVRDPyALDIDKLLVLDPAQR | cancer, leukemia, chronic myelogenous (CML) | Baf3(Jak2|Jak2|V617F) | SEQ ID NO: 239 |
| 232 | CK2-alpha1 | NP_001886.1 | Protein kinase, Ser/Thr (non-receptor) | Y50 | GKySEVFEAINITNNEK | cancer, lymphoma, Hodgkin's disease | L540 | SEQ ID NO: 240 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 233 | CRIK | NP_009105.1 | Protein kinase, Ser/Thr (non-receptor) | Y1759 | QyTLEEFLDK | cancer, gastric | SNU-5 | SEQ ID NO: 241 |
| 234 | Nek1 | NP_036356.1 | Protein kinase, Ser/Thr (non-receptor) | Y443 | GQyEHYHAIFDQMQQQR | cancer, leukemia, acute lymphocytic (ALL) | SEM | SEQ ID NO: 242 |
| 235 | Nek1 | NP_036356.1 | Protein kinase, Ser/Thr (non-receptor) | Y446 | GQYEHyHAIFDQMQQQR | cancer, leukemia, acute lymphocytic (ALL) | SEM | SEQ ID NO: 243 |
| 236 | PLK2 | NP_006613.2 | Protein kinase, Ser/Thr (non-receptor) | Y297 | EARyTMPSSLLAPAKHLIASMLSK | cancer, esophageal carcinoma | Kyse70 | SEQ ID NO: 244 |
| 237 | ROCK1 | NP_005397.1 | Protein kinase, Ser/Thr (non-receptor) | Y913 | GLLEEQyFELTQESK | cancer, leukemia | Jurkat | SEQ ID NO: 245 |
| 238 | RSK2 | NP_004577.1 | Protein kinase, Ser/Thr (non-receptor) | Y433 | EDIGVGSySVCK | | RSK2-3 | SEQ ID NO: 246 |
| 239 | RSK2 | NP_004577.1 | Protein kinase, Ser/Thr (non-receptor) | Y644 | FSLSGGyWNSVSDTAK | | RSK2-3; RSK2-4 | SEQ ID NO: 247 |
| 240 | RSK3 | NP_001006933.1 | Protein kinase, Ser/Thr (non-receptor) | Y434 | EDIGVGSySVCK | | RSK2-3 | SEQ ID NO: 248 |
| 241 | RSK3 | NP_001006933.1 | Protein kinase, Ser/Thr (non-receptor) | Y707 | GAMAATyFALNR | | RSK2-3 | SEQ ID NO: 249 |
| 242 | RSK4 | NP_055311.1 | Protein kinase, Ser/Thr (non-receptor) | Y437 | EDIGVGSySVCK | | RSK2-3 | SEQ ID NO: 250 |
| 243 | SRPK1 | NP_003128.3 | Protein kinase, Ser/Thr (non-receptor) | Y62 | GSAPHSESDLPEQEEEILGSDDDEQEDPNDyCK | cancer, leukemia, chronic myelogenous (CML) | K562 | SEQ ID NO: 251 |
| 244 | FRK | NP_002022.1 | Protein kinase, Tyr (non-receptor) | Y221 | IQVPAPFDLSyK | cancer, lung, non-small cell | csC66 | SEQ ID NO: 252 |
| 245 | FRK | NP_002022.1 | Protein kinase, Tyr (non-receptor) | Y317 | HGSLQEyLQNDTGSK | cancer, lung, non-small cell | csC66 | SEQ ID NO: 253 |
| 246 | FRK | NP_002022.1 | Protein kinase, Tyr (non-receptor) | Y368 | NVLVGEHNIyKVADFGLAR | cancer, lung, non-small cell | csC66 | SEQ ID NO: 254 |
| 247 | Lyn | NP_002341.1 | Protein kinase, Tyr (non-receptor) | Y321 | EEPIYIITEyMAK | cancer, lymphoma, Hodgkin's disease | HDLM-2 | SEQ ID NO: 255 |
| 248 | EphA2 | NP_004422.2 | Protein kinase, Tyr (receptor) | Y735 | YLANMNyVHR | cancer, gastric | SNU-5 | SEQ ID NO: 256 |
| 249 | EphA3 | NP_005224.2 | Protein kinase, Tyr (receptor) | Y937 | EIFTGVEySSCDTIAK | cancer, ovarian, epithelial carcinoma | TOV112D | SEQ ID NO: 257 |
| 250 | EphA4 | NP_004429.1 | Protein kinase, Tyr (receptor) | Y798 | WTAPEAIAyR | cancer, gastric | KATO III | SEQ ID NO: 259 |
| 251 | EphA6 | XP_114973.6 | Protein kinase, Tyr (receptor) | Y831 | VLEDDPEAAyTTTGGK | | brain | SEQ ID NO: 260 |
| 252 | EphA6 | NP_001073917.2 | Protein kinase, Tyr (receptor) | Y934 | WTAPEAIAyR | cancer, gastric | KATO III | SEQ ID NO: 261 |
| 253 | EphB1 | NP_004432.1 | Protein kinase, Tyr (receptor) | Y575 | EAVySDKLQHYSTGR | cancer, lymphoma, Hodgkin's disease | HDLM-2 | SEQ ID NO: 262 |
| 254 | EphB1 | NP_004432.1 | Protein kinase, Tyr (receptor) | Y582 | EAVYSDKLQHySTGR | cancer, lung, non-small cell | H1703 | SEQ ID NO: 263 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 255 | EphB1 | NP_004432.1 | Protein kinase, Tyr (receptor) | Y798 | WTAPEAIAyR | cancer, gastric | KATO III | SEQ ID NO: 264 |
| 256 | EphB3 | NP_004434.2 | Protein kinase, Tyr (receptor) | Y812 | WTAPEAIAyR | cancer, gastric | KATO III | SEQ ID NO: 265 |
| 257 | FGFR1 | NP_075594.1 | Protein kinase, Tyr (receptor) | Y522 | GMEyLASKK | cancer, colorectal | NCI-H716 | SEQ ID NO: 266 |
| 258 | FGFR2 | NP_000132.1 | Protein kinase, Tyr (receptor) | Y466 | LSSTADTPMLAGVSEyELPEDPKWEFPR | cancer, colorectal; cancer, gastric | KATO III; NCI-H716 | SEQ ID NO: 267 |
| 259 | FGFR2 | NP_000132.1 | Protein kinase, Tyr (receptor) | Y586 | RPPGMEySYDINR | cancer, colorectal; cancer, gastric | KATO III; NCI-H716; SNU-16 | SEQ ID NO: 268 |
| 260 | FGFR2 | NP_000132.1 | Protein kinase, Tyr (receptor) | Y588 | RPPGMEYSyDINR | cancer, gastric | KATO III; SNU-16 | SEQ ID NO: 269 |
| 261 | FGFR2 | NP_000132.1 | Protein kinase, Tyr (receptor) | Y616 | GMEyLASQK | cancer, multiple myeloma | KMS-11 | SEQ ID NO: 270 |
| 262 | FGFR2 | NP_000132.1 | Protein kinase, Tyr (receptor) | Y733 | MDKPANCTNELyMMMR | cancer, colorectal; cancer, gastric | KATO III; NCI-H716 | SEQ ID NO: 271 |
| 263 | FGFR2 | NP_000132.1 | Protein kinase, Tyr (receptor) | Y805 | SSCSSGDDSVFSPDPMPyEPCLPQYPHINGSVK | cancer, gastric | SNU-16 | SEQ ID NO: 272 |
| 264 | FGFR2 | NP_000132.1 | Protein kinase, Tyr (receptor) | Y812 | SSCSSGDDSVFSPDPMPYEPCLPQyPHINGSVK | cancer, gastric | SNU-16 | SEQ ID NO: 273 |
| 265 | FGFR3 | NP_000133.1 | Protein kinase, Tyr (receptor) | Y607 | GMEyLASQK | cancer, multiple myeloma | KMS-11 | SEQ ID NO: 274 |
| 266 | FLT3 | NP_004110.2 | Protein kinase, Tyr (receptor) | Y865 | WMAPESLFEGlyTIK | cancer, leukemia, chronic myelogenous | Baf3(FLT3|K663Q) | SEQ ID NO: 275 |
| 267 | Lmr2 | NP_055731.2 | Protein kinase, Tyr (receptor) | Y500 | GHLDEGLSyTSIFYPVEVFESSLSDPGPGK | cancer, lung, non-small cell | LCLC-103H | SEQ ID NO: 276 |
| 268 | Met | NP_000236.2 | Protein kinase, Tyr (receptor) | Y1194 | GMKyLASKK | cancer, leukemia, chronic myelogenous (CML); cancer, multiple | Baf3(TEL-FGFR3); KMS-11 | SEQ ID NO: 277 |
| 269 | CD229 | NP_002339.2 | Receptor, channel, transporter or cell surface | Y583 | GAGHDPAPEGQADyDPVTPYVTE | cancer, leukemia | Jurkat | SEQ ID NO: 279 |
| 270 | CD229 | NP_002339.2 | Receptor, channel, transporter or cell surface | Y589 | GAGHDPAPEGQADYDPVTPyVTE | cancer, leukemia | Jurkat | SEQ ID NO: 280 |
| 271 | CD82 | NP_002222.1 | Receptor, channel, transporter or cell surface | Y261 | HVHSEDySKVPKY | cancer, leukemia; cancer, lung | Jurkat; N06CS98 | SEQ ID NO: 281 |
| 272 | CD82 | NP_002222.1 | Receptor, channel, transporter or cell surface | Y267 | HVHSEDYSKVPKy | cancer, laryngeal; cancer, lung, non-small cell | BJ630; ENT05 | SEQ ID NO: 282 |
| 273 | CLCC1 | NP_001041675.1 | Receptor, channel, transporter or cell surface | Y412 | GQMGPTEQGPyAK | cancer, leukemia | Jurkat | SEQ ID NO: 283 |
| 274 | CLCC1 | NP_001041675.1 | Receptor, channel, transporter or cell surface | Y531 | SEAAGSPDQGSTySPAR | cancer, gastric; cancer, leukemia; cancer, lung, non-small cell; cancer, ovarian, epithelial | 23132/87; H2085; H2172; Jurkat | SEQ ID NO: 284 |
| 275 | CR2 | NP_001006659.1 | Receptor, channel, transporter or cell surface protein | Y1083 | EVySVDPYNPAS | cancer, breast; cancer, lung; cancer, lung, non-small cell | BC004; BJ630; N06CS107; N06CS94; cs103 | SEQ ID NO: 285 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 276 | Cx43 | NP_000156.1 | Receptor, channel, transporter or cell surface | Y301 | NyNKQASEQNWANYSAEQNR | cancer, esophageal | Kyse410 | SEQ ID NO: 286 |
| 277 | DNAJC1 | NP_071760.2 | Receptor, channel, transporter or cell surface | Y295 | TTyIQSYDHGTSIEE | cancer, leukemia | Jurkat | SEQ ID NO: 287 |
| 278 | DNAJC1 | NP_071760.2 | Receptor, channel, transporter or cell surface | Y299 | TTYIQSyDHGTSIEE | cancer, leukemia | Jurkat | SEQ ID NO: 288 |
| 279 | DNER | NP_620711.3 | Receptor, channel, transporter or cell surface | Y677 | PAyEEFYNCR | cancer, lymphoma, Hodgkin's disease | GAMG | SEQ ID NO: 289 |
| 280 | DNER | NP_620711.3 | Receptor, channel, transporter or cell surface | Y681 | PAYEEFyNCR | cancer, multiple myeloma | KMS-11 | SEQ ID NO: 290 |
| 281 | DNER | NP_620711.3 | Receptor, channel, transporter or cell surface | Y711 | SRPAMyDVSPIAYEDYSPDDKPLVTLIK | cancer, lymphoma, Hodgkin's disease | L428 | SEQ ID NO: 291 |
| 282 | DNER | NP_620711.3 | Receptor, channel, transporter or cell surface | Y718 | SRPAMYDVSPIAyEDYSPDDKPLVTLIK | cancer, lymphoma, Hodgkin's disease | L428 | SEQ ID NO: 292 |
| 283 | DNER | NP_620711.3 | Receptor, channel, transporter or cell surface | Y721 | SRPAMYDVSPIAYEDySPDDKPLVTLIK | cancer, lymphoma, Hodgkin's disease | L428 | SEQ ID NO: 293 |
| 284 | DYSF | NP_003485.1 | Receptor, channel, transporter or cell surface | Y1650 | ITLYDyDLLSKDEK | cancer, lung, non-small cell | N06c78 | SEQ ID NO: 294 |
| 285 | EDG4 | NP_004711.2 | Receptor, channel, transporter or cell surface | Y325 | ESVHyTSSAQGGASTR | cancer, gastric; cancer, lung; cancer, lung, non-small cell | H3255; KATO III; MKN-45; N06CS106 | SEQ ID NO: 295 |
| 286 | Ermelin | NP_036451.2 | Receptor, channel, transporter or cell surface | Y487 | YESQLSTNEEKVDTDDRTEGyLR | | CAKI-2 | SEQ ID NO: 296 |
| 287 | FZD5 | NP_003459.2 | Receptor, channel, transporter or cell surface | Y556 | SGGAMAAGDyPEASAALTGR | cancer, gastric | SNU-16 | SEQ ID NO: 297 |
| 288 | FZD5 | NP_003459.2 | Receptor, channel, transporter or cell surface | Y576 | TGPPGPAATyHK | cancer, gastric | SNU-16 | SEQ ID NO: 298 |
| 289 | GPA33 | NP_005805.1 | Receptor, channel, transporter or cell surface | Y301 | EREEEDDyRQEEQR | cancer, gastric | SNU-16 | SEQ ID NO: 299 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 290 | GPIP137 | NP_005889.3 | Receptor, channel, transporter or cell surface | Y78 | GKLDDyQER | cancer, leukemia, acute myelogenous (AML) | MV4-11 | SEQ ID NO: 300 |
| 291 | HMMR | NP_036617.1 | Receptor, channel, transporter or cell surface | Y698 | GNTNCyRAPMECQE | cancer, leukemia | Jurkat | SEQ ID NO: 301 |
| 292 | IL2RG | NP_000197.1 | Receptor, channel, transporter or cell surface | Y363 | GGALGEGPGASPCNQHSPYWAPPCyTLKPET | cancer, leukemia, acute myelogenous (AML) | CHRF | SEQ ID NO: 303 |
| 293 | LRP4 | NP_002325.1 | Receptor, channel, transporter or cell surface | Y1764 | FTDPGMGNLTySNPSYR | | EFM-19 | SEQ ID NO: 304 |
| 294 | NKCC1 | NP_001037.1 | Receptor, channel, transporter or cell surface | Y1211 | GNHQSVLTFyS | cancer, gastric | MKN-45 | SEQ ID NO: 305 |
| 295 | OR4C46 | NP_001004703.1 | Receptor, channel, transporter or cell surface | Y273 | AVAIFyTMITPMLNPLIYTLKNAQMK | cancer, leukemia, acute myelogenous (AML); cancer, multiple myeloma | KMS-11; Me-F2 | SEQ ID NO: 306 |
| 296 | OR4C46 | NP_001004703.1 | Receptor, channel, transporter or cell surface | Y285 | AVAIFYTMITPMLNPLIyTLKNAQMK | cancer, leukemia, acute myelogenous (AML); cancer, multiple myeloma | KMS-11; Me-F2 | SEQ ID NO: 307 |
| 297 | ORAI1 | NP_116179.2 | Receptor, channel, transporter or cell surface protein | Y300 | GDHPLTPGSHyA | cancer, bone, osteosarcoma/malignant fibrous histiocytoma; cancer, gastric; cancer, lung, non-small cell | 143.98.2; HCC827; KATO III; MKN-45; SNU-5 | SEQ ID NO: 308 |
| 298 | PTDSS2 | NP_110410.1 | Receptor, channel, transporter or cell surface | Y366 | ElyDFMDDPK | cancer, kidney/renal cell carcinoma/renal adenocarcinoma | SW1710 | SEQ ID NO: 309 |
| 299 | SLC11A2 | NP_000608.1 | Receptor, channel, transporter or cell surface | Y31 | GNINPAySNPSLSQSPGDSEEY | cancer, gastric | Hs746T | SEQ ID NO: 310 |
| 300 | SLC4A2 | NP_003031.2 | Receptor, channel, transporter or cell surface | Y1234 | EGVDEyNEMPMPV | cancer, gastric | KATO III | SEQ ID NO: 311 |
| 301 | SLC4A2 | NP_003031.2 | Receptor, channel, transporter or cell surface | Y66 | GGEEPGRSyGEEDFEYHR | cancer, gastric; cancer, leukemia | Jurkat; KATO III | SEQ ID NO: 312 |
| 302 | SLC4A4 | NP_003750.1 | Receptor, channel, transporter or cell surface | Y994 | GSLDSDNDDSDCPySEK | cancer, gastric | KATO III | SEQ ID NO: 313 |
| 303 | SLC5A3 | NP_008864.3 | Receptor, channel, transporter or cell surface | Y631 | EEGNPVASLGHSEAETPVDAySNGQAALMGEK | cancer, lymphoma, Hodgkin's disease | HD-MyZ | SEQ ID NO: 314 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 304 | SLITRK3 | NP_055741.2 | Receptor, channel, transporter or cell surface | Y904 | ERPQPAPCTVGFVDCLyGTVPK | | brain | SEQ ID NO: 315 |
| 305 | CIRBP | NP_001271.1 | RNA processing | Y135 | SGGyGGSRDYYSSR | cancer, leukemia | Jurkat | SEQ ID NO: 316 |
| 306 | CPSF1 | NP_037423.2 | RNA processing | Y748 | SGPEAEGLGSETSPTVDDEEEMLyGDSGSLFSPSKEEAR | cancer, leukemia | Jurkat | SEQ ID NO: 317 |
| 307 | DBR1 | NP_057300.2 | RNA processing | Y533 | NQAIyAAVDDDDDDAA | cancer, leukemia | Jurkat | SEQ ID NO: 318 |
| 308 | DCP2 | NP_689837.2 | RNA processing | Y370 | TDAVyDLPSSSE | cancer, leukemia | Jurkat | SEQ ID NO: 319 |
| 309 | DDX1 | NP_004930.1 | RNA processing | Y628 | VWyHVCSSR | cancer, gastric; cancer, leukemia, chronic myelogenous (CML); cancer, lung | K562; MKN-45; N06CS97; SNU-5 | SEQ ID NO: 320 |
| 310 | DDX1 | NP_004930.1 | RNA processing | Y731 | EAQTSFLHLGyLPNQLFR | cancer, nerve tissue, neuroblastoma | GI-LI-N | SEQ ID NO: 321 |
| 311 | DDX3 | NP_001347.3 | RNA processing | Y163 | LFSGGNTGINFEKyDDIPVEATGNNCPPHIE | cancer, leukemia | Jurkat | SEQ ID NO: 322 |
| 312 | DDX3 | NP_001347.3 | RNA processing | Y283 | ELAVQIyEEAR | cancer, leukemia, chronic myelogenous | K562 | SEQ ID NO: 323 |
| 313 | DDX3 | NP_001347.3 | RNA processing | Y466 | KGADSLEDFLYHEGyACTSIHGDR | cancer, gastric | SNU-16 | SEQ ID NO: 324 |
| 314 | DDX39 | NP_005795.2 | RNA processing | Y13 | NDLLDyDEEEEPQAPQE | cancer, leukemia | Jurkat | SEQ ID NO: 325 |
| 315 | DDX3Y | NP_004651.2 | RNA processing | Y241 | TAAFLLPILSQIyTDGPGEALK | | brain | SEQ ID NO: 326 |
| 316 | DDX3Y | NP_004651.2 | RNA processing | Y281 | ELAVQIyEEAR | cancer, leukemia, chronic myelogenous | K562 | SEQ ID NO: 327 |
| 317 | DDX3Y | NP_004651.2 | RNA processing | Y464 | KGADSLEDFLYHEGyACTSIHGDR | cancer, gastric | SNU-16 | SEQ ID NO: 328 |
| 318 | DDX5 | NP_004387.1 | RNA processing | Y442 | TGTAyTFFTPNNIK | cancer, lymphoma, Hodgkin's disease | L540 | SEQ ID NO: 329 |
| 319 | HNRPUL2 | NP_001073027.1 | RNA processing | Y660 | SRGQGyVGGQR | cancer, lung, non-small cell | cs105 | SEQ ID NO: 330 |
| 320 | HNRPUL2 | NP_001073027.1 | RNA processing | Y743 | NYYGyQGYR | cancer, colorectal carcinoma; cancer, leukemia, acute myelogenous (AML); cancer, lung, non-small cell; cancer, lung, non-small-cell, Squmous cell carcinoma; cancer, lung, | DMS 53; H520; MKPL-1; SNU-C2B; SW620; h2073 | SEQ ID NO: 331 |
| 321 | HNRPUL2 | NP_001073027.1 | RNA processing | Y746 | NYYGYQGyR | cancer, lymphoma, Hodgkin's disease | L540 | SEQ ID NO: 332 |
| 322 | DRBP1 | NP_694453.2 | RNA processing | Y204 | SSEQDyYSNMRQE | cancer, leukemia | Jurkat | SEQ ID NO: 333 |
| 323 | E1B-AP5 | NP_008971.2 | RNA processing | Y111 | QNQFyDTQVIKQENESGYER | cancer, leukemia | Jurkat | SEQ ID NO: 334 |
| 324 | ELAVL1 | NP_001410.2 | RNA processing | Y26 | TNLIVNyLPQNMTQDELR | cancer, leukemia, acute myelogenous (AML) | MKPL-1 | SEQ ID NO: 335 |
| 325 | EXOSC1 | NP_057130.1 | RNA processing | Y32 | HGyIFSSLAGCLMK | cancer, lymphoma, Hodgkin's disease | L540 | SEQ ID NO: 336 |
| 326 | FXR1 | NP_005078.2 | RNA processing | Y353 | ESIGNVQVLLEyHIAYLK | cancer, lung, non-small | h2073 | SEQ ID NO: 337 |
| 327 | FXR1 | NP_005078.2 | RNA processing | Y357 | ESIGNVQVLLEYHIAyLK | cancer, lung, non-small | h2073 | SEQ ID NO: 338 |
| 328 | hnRNP 2H9 | NP_036339.1 | RNA processing | Y100 | GFyDPPRR | cancer, colorectal; cancer, leukemia; cancer, lung, non-small cell; cancer, nerve | HL53A; Jurkat; KELLY; NCI-H716 | SEQ ID NO: 339 |
| 329 | hnRNP 2H9 | NP_036339.1 | RNA processing | Y156 | GGDGYDGGYGGFDDYGGyNNYGYGNDGFDDR | cancer, esophageal carcinoma; cancer, | Jurkat; SNU-1 | SEQ ID NO: 340 |
| 330 | hnRNP 2H9 | NP_036339.1 | RNA processing | Y181 | GMGGHGyGGAGDASSGFHGGHFVHMR | cancer, lymphoma, Hodgkin's disease | L540 | SEQ ID NO: 341 |
| 331 | hnRNP H | NP_005511.1 | RNA processing | Y236 | GAyGGGYGGYDDYNGYNDGYGFGSDR | cancer, leukemia; cancer, lung, non-small | Jurkat; cs012 | SEQ ID NO: 342 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 332 | hnRNP H | NP_005511.1 | RNA processing | Y240 | GAYGGGyGGYDDYNGYNDGYGFGSDR | cancer, gastric; cancer, leukemia | Jurkat; MKN-45 | SEQ ID NO: 343 |
| 333 | hnRNP H | NP_005511.1 | RNA processing | Y253 | GAYGGGYGGYDDYNGYNDGyGFGSDR | cancer, leukemia, acute myelogenous (AML); cancer, lung, non-small | MKPL-1; cs012 | SEQ ID NO: 344 |
| 334 | hnRNP H' | NP_062543.1 | RNA processing | Y298 | GLPyRATENDIYNFFSPLNPMR | cancer, lymphoma, Hodgkin's disease | L540 | SEQ ID NO: 345 |
| 335 | hnRNP R | NP_005817.1 | RNA processing | Y624 | FyQDTYGQQWK | cancer, leukemia | Jurkat | SEQ ID NO: 346 |
| 336 | hnRNP R | NP_005817.1 | RNA processing | Y628 | FYQDTyGQQWK | cancer, leukemia | Jurkat | SEQ ID NO: 347 |
| 337 | hnRNP U | NP_004492.2 | RNA processing | Y635 | GNFTLPEVAECFDEITyVELQKEEAQK | cancer, lung | DV-90 | SEQ ID NO: 348 |
| 338 | hnRNP-A1 | NP_112420.1 | RNA processing | Y244 | GGGGYGGSGDGyNGFGNDGGYGGGGPGYSGGSR | cancer, leukemia, acute myelogenous (AML) | MKPL-1 | SEQ ID NO: 349 |
| 339 | hnRNP-A1 | NP_112420.1 | RNA processing | Y253 | GGGGYGGSGDGYNGFGNDGGyGGGGPGYSGGSR | | L540 | SEQ ID NO: 350 |
| 340 | hnRNP-I | NP_002810.1 | RNA processing | Y456 | EGQEDQGLTKDyGNSPLHR | cancer, breast | Cal-148 | SEQ ID NO: 351 |
| 341 | HUMAGCGB | NP_037418.3 | RNA processing | Y379 | GQGGAyAFLK | cancer, lymphoma, Hodgkin's disease | L540 | SEQ ID NO: 352 |
| 342 | IGF2BP3 | NP_006538.2 | RNA processing | Y39 | TGyAFVDCPDESWALK | cancer, colorectal | NCI-H716 | SEQ ID NO: 353 |
| 343 | MPHOSPH10 | NP_005782.1 | RNA processing | Y452 | PKEDAyEYK | cancer, lung, non-small-cell | H520 | SEQ ID NO: 354 |
| 344 | MPHOSPH10 | NP_005782.1 | RNA processing | Y454 | PKEDAYEyK | cancer, lung, non-small-cell | H520 | SEQ ID NO: 355 |
| 345 | NOL5A | NP_006383.2 | RNA processing | Y210 | IINDNATyCR | cancer, breast | Cal-148 | SEQ ID NO: 356 |
| 346 | PABPN1 | NP_004634.1 | RNA processing | Y46 | GAPGGAGDyGNGLE | cancer, leukemia | Jurkat | SEQ ID NO: 357 |
| 347 | PSF | NP_005057.1 | RNA processing | Y691 | GMGPGTPAGyGR | cancer, lymphoma, Hodgkin's disease | L540 | SEQ ID NO: 358 |
| 348 | RBM10 | NP_005667.2 | RNA processing | Y435 | GTWATSEEPPVDySYYQQDE | cancer, leukemia | Jurkat | SEQ ID NO: 359 |
| 349 | RBM14 | NP_006319.1 | RNA processing | Y558 | GQPGNAYDGAGQPSAAyLSMSQGAVANANSTPPPYER | cancer, leukemia, acute myelogenous (AML) | MKPL-1 | SEQ ID NO: 360 |
| 350 | RBM15 | NP_073605.4 | RNA processing | Y336 | ERDYPFyER | cancer, leukemia | Jurkat | SEQ ID NO: 361 |
| 351 | RBM15 | NP_073605.4 | RNA processing | Y416 | GQTSTyGFLK | cancer, lymphoma, Hodgkin's disease | L540 | SEQ ID NO: 362 |
| 352 | SFRS5 | NP_008856.2 | RNA processing | Y55 | FEDPRDADDAVyE | cancer, leukemia | Jurkat | SEQ ID NO: 363 |
| 353 | SFRS9 | NP_003760.1 | RNA processing | Y17 | GGEGDGRIyVGNLPTDVR | cancer, leukemia, acute myelogenous (AML) | MKPL-1 | SEQ ID NO: 364 |
| 354 | SFRS9 | NP_003760.1 | RNA processing | Y35 | EKDLEDLFyKYGR | cancer, leukemia, acute myelogenous (AML) | MKPL-1 | SEQ ID NO: 365 |
| 355 | SLU7 | NP_006416.3 | RNA processing | Y297 | ENPyANAGKNPDEVSYAGDNFVR | cancer, leukemia, acute myelogenous (AML) | MKPL-1 | SEQ ID NO: 366 |
| 356 | snRNP70 | NP_003080.2 | RNA processing | Y414 | GLGNDSRDMyME | cancer, leukemia | Jurkat | SEQ ID NO: 367 |
| 357 | CGB | NP_001810.1 | Secreted | Y526 | LGELFNPYyDPLQWK | cancer, lung, non-small | N06bj639(27 | SEQ ID NO: 368 |
| 358 | DEFA1 | NP_004075.1 | Secreted protein | Y80 | yGTCIYQGR | cancer, lung; cancer, lung, non-small cell | N06CS22-1; N06CS22-2; N06CS98; N06CS98-2; N06bj567(7); N06bj638(26); csC52; csC56; | SEQ ID NO: 369 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 359 | DEFA3 | NP_005208.1 | Secreted protein | Y80 | yGTCIYQGR | cancer, lung; cancer, lung, non-small cell | N06CS22-1; N06CS22-2; N06CS98; N06CS98-2; N06bj567(7); N06bj638(26); csC52; csC56; | SEQ ID NO: 370 |
| 360 | DEFA3 | NP_005208.1 | Secreted protein | Y85 | YGTCIyQGR | cancer, laryngeal; cancer, lung; cancer, lung, non-small cell | BJ665; ENT03; ENT10; ENT14; HL145A; HL146A; HL83A; N06BJ591(11); N06BJ593(13); N06CS02; N06CS103; N06CS16; N06CS22(2)-R; N06CS22-2; N06CS39; N06CS75; N06CS77; N06CS87; N06CS91; N06CS93-2; N06CS94; N06CS97; N06CS98; N06CS98-2; N06CS98-R; N06N101; N06N102; N06N121; N06N127; N06N128; N06N131; N06N90; N06N93; N06c144; N06cs110; N06cs110-R; N06cs112; N06cs113; N06cs121; | SEQ ID NO: 371 |
| 361 | FBS1 | NP_071897.1 | Secreted protein | Y308 | LyGLEPAHPLLYSR | cancer, lymphoma, Hodgkin's disease | L540 | SEQ ID NO: 372 |
| 362 | FBS1 | NP_071897.1 | Secreted protein | Y318 | LYGLEPAHPLLySR | cancer, lymphoma, Hodgkin's disease | L540 | SEQ ID NO: 373 |
| 363 | FGA | NP_000499.1 | Secreted | Y277 | GGSTSyGTGSETESPR | cancer, lung | N06CS97 | SEQ ID NO: 374 |
| 364 | CEBPZ | NP_005751.2 | Transcriptional regulator | Y192 | WYDLEYSNEySLKPQPQDVVSK | cancer, leukemia, acute myelogenous (AML) | HEL; MV4-11 | SEQ ID NO: 376 |
| 365 | CNOT7 | NP_037486.2 | Transcriptional regulator | Y260 | YCGHLyGLGSGSSYVQNGTGNAYEEEANKQS | cancer, lymphoma, Hodgkin's disease | L540 | SEQ ID NO: 377 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 366 | DTX2 | NP_065943.1 | Transcriptional regulator | Y75 | FGLGSLAHSIPLGQADPSLAPyIIDLPSWTQFR | cancer, gastric | SNU-5 | SEQ ID NO: 378 |
| 367 | E2A | NP_003191.1 | Transcriptional regulator | Y150 | GTSQYyPSYSGSSR | cancer, leukemia | Jurkat | SEQ ID NO: 379 |
| 368 | E2A | NP_003191.1 | Transcriptional regulator | Y153 | GTSQYYPSySGSSR | cancer, leukemia | Jurkat | SEQ ID NO: 380 |
| 369 | Ets-1 | NP_005229.1 | Transcriptional regulator | Y140 | EDVKPyQVNGVNPAYPESR | cancer, leukemia | Jurkat | SEQ ID NO: 381 |
| 370 | FBP1 | NP_003893.2 | Transcriptional regulator | Y242 | ITGDPyKVQQAK | cancer, leukemia, chronic myelogenous | K562 | SEQ ID NO: 382 |
| 371 | FBP1 | NP_003893.2 | Transcriptional regulator | Y625 | QQAAyYAQTSPQGMPQHPPAPQGQ | cancer, leukemia | Jurkat; MKPL-1 | SEQ ID NO: 383 |
| 372 | FHL2 | NP_001441.4 | Transcriptional regulator | Y97 | EDQLLCTDCYSNEySSK | cancer, kidney | Caki-2 | SEQ ID NO: 384 |
| 373 | FLI1 | NP_002008.2 | Transcriptional regulator | Y451 | HPNTHVPSHLGSyY | cancer, leukemia | Jurkat | SEQ ID NO: 385 |
| 374 | JunB | NP_002220.1 | Transcriptional regulator | Y68 | GPGPEGGGGGSyFSGQGSDTGASLK | cancer, lymphoma, Hodgkin's disease | L540 | SEQ ID NO: 386 |
| 375 | MTA2 | NP_004730.2 | Transcriptional regulator | Y437 | GHLSRPEAQSLSPyTTSANR | cancer, leukemia, acute myelogenous (AML) | MKPL-1 | SEQ ID NO: 387 |
| 376 | NFkB-p100 | NP_002493.3 | Transcriptional regulator | Y55 | FRyGCEGPSHGGLPGASSEK | cancer, lymphoma, Hodgkin's disease | L540 | SEQ ID NO: 388 |
| 377 | SPT5 | NP_003160.2 | Transcriptional regulator | Y765 | RPGGMTSTyGR | cancer, leukemia | Jurkat | SEQ ID NO: 389 |
| 378 | SPT5 | NP_003160.2 | Transcriptional regulator | Y771 | TPMyGSQTPMYGSGSR | cancer, leukemia | Jurkat | SEQ ID NO: 390 |
| 379 | SSRP1 | NP_003137.1 | Transcriptional regulator | Y438 | EGMNPSyDEYADSDEDQHDAYLER | cancer, leukemia | Jurkat | SEQ ID NO: 391 |
| 380 | eEF1A-1 | AAH71619.1 | Translational regulator | Y233 | LPLQDVyK | cancer, leukemia | Jurkat | SEQ ID NO: 392 |
| 381 | eEF1A-2 | NP_001949.1 | Translational regulator | Y254 | LPLQDVyK | normal lung | N06BJ505(2) | SEQ ID NO: 393 |
| 382 | eIF2B-epsilon | NP_003898.2 | Translational regulator | Y319 | WVyPLTPEANFTDSTTQSCTHSR | cancer, lymphoma, Hodgkin's disease | L540 | SEQ ID NO: 395 |
| 383 | eIF3-beta | NP_003748.1 | Translational regulator | Y300 | SySSGGEDGYVR | cancer, leukemia, acute lymphocytic (ALL) | SEM | SEQ ID NO: 396 |
| 384 | eIF3S6IP | NP_057175.1 | Translational regulator | Y247 | QLEVyTSGGDPESVAGEYGR | cancer, leukemia, acute lymphocytic (ALL) | SUP-T13 | SEQ ID NO: 397 |
| 385 | eIF3S6IP | NP_057175.1 | Translational regulator | Y287 | LHSLLGDyYQAIK | cancer, lymphoma, Hodgkin's disease | L540 | SEQ ID NO: 398 |
| 386 | eIF3S6IP | NP_057175.1 | Translational regulator | Y288 | LHSLLGDYyQAIK | cancer, lymphoma, Hodgkin's disease | L540 | SEQ ID NO: 399 |
| 387 | eIF3S6IP | NP_057175.1 | Translational regulator | Y357 | TTYKyEMINK | cancer, lymphoma, Hodgkin's disease | L540 | SEQ ID NO: 400 |
| 388 | eIF3-zeta | NP_003744.1 | Translational regulator | Y506 | yLILKDPNK | | RSK2-3 | SEQ ID NO: 401 |
| 389 | eIF4B | NP_001408.2 | Translational regulator | Y258 | yDDRGSRDYDRGYDSR | cancer, leukemia | Jurkat | SEQ ID NO: 402 |
| 390 | PES1 | NP_055118.1 | Translational regulator | Y265 | AKAGEGTyALDSE | cancer, leukemia | Jurkat | SEQ ID NO: 403 |
| 391 | RPL18a | NP_000971.1 | Translational regulator | Y46 | FWyFVSQLK | cancer, lymphoma, Hodgkin's disease | L540 | SEQ ID NO: 405 |
| 392 | FAT | NP_005236.2 | Tumor suppressor | Y4489 | FNLNQyLPNFYPLDMSEPQTK | cancer, gastric; cancer, lung, non-small cell | A498; SNU-5; h2073 | SEQ ID NO: 406 |
| 393 | FAT | NP_005236.2 | Tumor suppressor | Y4519 | GTGENSTCREPHAPyPPGYQR | cancer, gastric | KATO III | SEQ ID NO: 407 |
| 394 | FAT | NP_005236.2 | Tumor suppressor | Y4523 | GTGENSTCREPHAPYPPGyQR | cancer, gastric | KATO III | SEQ ID NO: 408 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 395 | COPS3 | NP_003644.2 | Ubiquitin conjugating system | Y422 | SMGSQEDDSGNKPSSyS | cancer, esophageal carcinoma; cancer, gastric; cancer, kidney/renal cell carcinoma/renal adenocarcinoma; cancer, leukemia; cancer, lung, | 5637; H1781; HCC827; Jurkat; KATO III; Kyse140; LCLC-103H | SEQ ID NO: 409 |
| 396 | CYLD | NP_056062.1 | Ubiquitin conjugating system | Y181 | GQGFTDGVyQGK | | brain | SEQ ID NO: 410 |
| 397 | CYLD | NP_056062.1 | Ubiquitin conjugating system | Y356 | SELFyTLNGSSVDSQPQSK | cancer, lymphoma, Hodgkin's disease | L540 | SEQ ID NO: 411 |
| 398 | ETEA | NP_055428.1 | Ubiquitin conjugating system | Y297 | QQQDEAyLASLR | cancer, leukemia | Jurkat | SEQ ID NO: 412 |
| 399 | HECW2 | NP_065811.1 | Ubiquitin conjugating system | Y208 | GMFFNPDPyLK | cancer, lymphoma, Hodgkin's disease | HDLM-2 | SEQ ID NO: 413 |
| 400 | RC3H1 | NP_742068.1 | Ubiquitin conjugating system | Y593 | GSQLYPAQQTDVYyQDPR | cancer, leukemia | Jurkat | SEQ ID NO: 414 |
| 401 | SMURF1 | NP_065162.1 | Ubiquitin conjugating system | Y413 | EEIFEESyRQIMK | cancer, gastric | KATO III | SEQ ID NO: 415 |
| 402 | ACAD11 | NP_115545.3 | Unknown function | Y324 | MAGIAQGVySR | cancer, pancreatic carcinoma; cancer, thyroid, follicular | ML-1; MiaPaca | SEQ ID NO: 416 |
| 403 | ANKRD52 | EAW96919.1 | Unknown function | Y207 | GyGLLHTAAASGQIEVVKYLLR | | brain | SEQ ID NO: 417 |
| 404 | C17orf71 | NP_060619.4 | Unknown function | Y309 | LQHALEDQIyR | cancer, leukemia, acute lymphocytic (ALL) | CTV-1 | SEQ ID NO: 418 |
| 405 | C18orf8 | NP_037458.3 | Unknown function | Y610 | QTEDNMLFyTIFR | cancer, lymphoma, Hodgkin's disease | L540 | SEQ ID NO: 419 |
| 406 | C19orf2 | NP_775752.1 | Unknown | Y7 | VTRyPILGIPQAHR | cancer, gastric | SNU-16 | SEQ ID NO: 420 |
| 407 | C1orf10 | NP_776168.1 | Unknown | Y23 | ySTNSPNYR | cancer, lung, non-small | gzB1 | SEQ ID NO: 421 |
| 408 | C1orf10 | NP_776168.1 | Unknown | Y30 | YSTNSPNyR | cancer, lung, non-small | gzB1 | SEQ ID NO: 422 |
| 409 | C1orf162 | NP_777556.1 | Unknown function | Y120 | LSSIPGESLTyASTTFK | cancer, lymphoma, Hodgkin's disease | HDLM-2 | SEQ ID NO: 423 |
| 410 | C1orf162 | NP_777556.1 | Unknown function | Y148 | SNHLAENHSADFDPIVyAQIK | cancer, lymphoma, Hodgkin's disease | HDLM-2 | SEQ ID NO: 424 |
| 411 | C1orf21 | NP_110433.1 | Unknown function | Y34 | NYQNGDVFGDEyR | cancer, nerve tissue, neuroblastoma | LAN-5 | SEQ ID NO: 425 |
| 412 | C1orf32 | NP_955383.1 | Unknown function | Y566 | SASYyAWSPPGTYK | cancer, leukemia, chronic myelogenous | K562 | SEQ ID NO: 426 |
| 413 | C1orf82 | NP_079089.1 | Unknown | Y127 | TNKVyDITER | cancer, leukemia | Jurkat | SEQ ID NO: 427 |
| 414 | C1orf82 | NP_079089.1 | Unknown | Y319 | LKASENSESEySR | cancer, leukemia | Jurkat | SEQ ID NO: 428 |
| 415 | C22orf5 | NP_036396.2 | Unknown | Y243 | ELLSPySPVLKFFMVK | | brain | SEQ ID NO: 429 |
| 416 | C22orf9 | NP_056079.1 | Unknown | Y66 | LAySGSESGADGR | cancer, leukemia | Jurkat | SEQ ID NO: 430 |
| 417 | C2orf33 | NP_064579.3 | Unknown | Y35 | IQyEMEYTEGISQR | cancer, leukemia | Jurkat | SEQ ID NO: 431 |
| 418 | C2orf33 | NP_064579.3 | Unknown | Y39 | IQYEMEyTEGISQR | cancer, leukemia | Jurkat | SEQ ID NO: 432 |
| 419 | C3orf24 | NP_775743.1 | Unknown function | Y163 | SILLLyATYK | cancer, colorectal carcinoma | HT29 | SEQ ID NO: 433 |
| 420 | C3orf24 | NP_775743.1 | Unknown function | Y166 | QMLRSILLLYATyKK | cancer, colorectal carcinoma | HT29 | SEQ ID NO: 434 |
| 421 | C3orf58 | NP_775823.1 | Unknown | Y92 | NVyFAQYGEPREGGRRR | cancer, kidney | Caki-2 | SEQ ID NO: 435 |

Figure 2

| | Protein Name | Accession No. | Protein Type | Phospho-Residu | Phosphorylation Site Sequence | Disease | Cell Types | SEQ ID NO |
|---|---|---|---|---|---|---|---|---|
| 422 | C5orf32 | NP_115788.1 | Unknown function | Y64 | TTVyVVEDQR | cancer, gastric; cancer, lung, non-small cell; cancer, pancreatic | DV-90; H2452; H3255; H596; HP28; J82; KATO III; MKN-45; SNU-5; csC56 | SEQ ID NO: 437 |
| 423 | C6orf143 | NP_001010872.1 | Unknown function | Y523 | FEGyDNPENLK | cancer, gastric | MKN-45 | SEQ ID NO: 438 |
| 424 | C6orf143 | NP_001010872.1 | Unknown function | Y685 | HYVySTLTR | cancer, gastric; cancer, lung, non-small cell | HCC827; MKN-45 | SEQ ID NO: 439 |
| 425 | C6orf143 | NP_001010872.1 | Unknown function | Y896 | FNTEQIQyR | cancer, gastric | MKN-45 | SEQ ID NO: 440 |
| 426 | C6orf143 | NP_001010872.1 | Unknown function | Y986 | SSPLLNYNTGVyR | cancer, gastric; cancer, lung, non-small cell | MKN-45; N06cs59 | SEQ ID NO: 441 |
| 427 | C6orf149 | NP_065141.3 | Unknown function | Y26 | ESKRFSAyNYRTYAVR | cancer, leukemia, chronic myelogenous | K562 | SEQ ID NO: 442 |
| 428 | C6orf149 | NP_065141.3 | Unknown function | Y28 | ESKRFSAYNyRTYAVR | cancer, leukemia, chronic myelogenous | K562 | SEQ ID NO: 443 |
| 429 | C6orf149 | NP_065141.3 | Unknown function | Y31 | ESKRFSAYNYRTyAVR | cancer, leukemia, chronic myelogenous | K562 | SEQ ID NO: 444 |
| 430 | CCDC120 | NP_296375.1 | Unknown function | Y398 | SSEVLyERPQPTPAFSSR | cancer, leukemia, chronic myelogenous | K562 | SEQ ID NO: 445 |
| 431 | CCDC18 | NP_996769.2 | Unknown function | Y884 | SEEVyCLQK | cancer, leukemia, acute myelogenous (AML); cancer, leukemia, chronic myelogenous | HEL; K562; MV4-11 | SEQ ID NO: 446 |
| 432 | CHORDC1 | NP_036256.1 | Unknown function | Y292 | SyVTMTATKIEITMR | cancer, breast; cancer, lung, non-small cell | BC005; cs114 | SEQ ID NO: 447 |
| 433 | COBLL1 | NP_055715.3 | Unknown function | Y533 | STDGQEPHSVVyDTSNGKK | cancer, esophageal | Kyse270 | SEQ ID NO: 449 |
| 434 | COBLL1 | NP_055715.3 | Unknown function | Y742 | IDKNSTASYLKNyPLYR | cancer, gastric | SNU-16 | SEQ ID NO: 450 |
| 435 | DAZAP2 | NP_055579.1 | Unknown function | Y165 | KGNFFMGGSDGGyTIW | cancer, gastric | KATO III | SEQ ID NO: 451 |
| 436 | DENND2A | NP_056504.2 | Unknown function | Y370 | TLSEENVyEDILDPPMK | | S 2 | SEQ ID NO: 452 |
| 437 | DENND2C | NP_940861.3 | Unknown function | Y195 | SLENIySEPEGGQECGPSINPLPKPR | cancer, lung | gz21 | SEQ ID NO: 453 |
| 438 | DEPDC7 | NP_631899.2 | Unknown function | Y300 | ELLFDAIGRyYSSR | | 3T3(EGFR[deletion]|[EGF]) | SEQ ID NO: 454 |
| 439 | DKFZP451C023 | CAD89901.1 | Unknown function | Y48 | TLMLNEDKPSDDySAVLQR | cancer, laryngeal; cancer, lung, non-small cell | ENT02; ENT15; ENT19; ENT7; N06c78 | SEQ ID NO: 455 |
| 440 | MIER3 | NP_689835.3 | Unknown function | Y331 | YDyFAQQTR | cancer, leukemia | Jurkat | SEQ ID NO: 456 |
| 441 | DYX1C1 | NP_570722.2 | Unknown | Y128 | EDQKyALSVMMK | cancer, esophageal | Kyse270 | SEQ ID NO: 457 |
| 442 | FAM102A | NP_0010303 31.1 | Unknown function | Y376 | VSSGVyEPVVIESH | cancer, esophageal; cancer, gastric; cancer, leukemia; cancer, lung, small-cell | DMS 53; Jurkat:; KATO III; Kyse510 | SEQ ID NO: 458 |
| 443 | FAM81A | NP_689663.1 | Unknown function | Y21 | HSQSLTMAPySSVSLVEQLEDR | | brain | SEQ ID NO: 459 |
| 444 | FAM83E | NP_060178.1 | Unknown function | Y100 | QEPSGMAEGATTADVDAGSLSyWPGQSEQPAPVLR | cancer, breast | MT-3 | SEQ ID NO: 460 |
| 445 | FLJ00258 | NP_689619.1 | Unknown function | Y126 | NAADLPPPLPNKPPPEDyYEEALPLGPGK | cancer, kidney/renal cell carcinoma/renal adenocarcinoma | BC-3C | SEQ ID NO: 461 |

Figure 2

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 446 | AFAP1L2 | NP_115939.1 | Unknown function | Y459 | TDPEEFTYDyVDADR | cancer, gastric; cancer, kidney; cancer, kidney/renal cell carcinoma/renal adenocarcinoma; cancer, lung, non-small cell; cancer, ovarian | 5637; CAKI-2; CAL-29; EFO-21; H1838; HCC827; LCLC-103H; LXF-289; MKN-45; Scaber; UM- | SEQ ID NO: 463 |
| 447 | FLJ14732 | NP_115734.1 | Unknown function | Y283 | NLHHTQELLyESTKDFLQLR | cancer, leukemia, acute myelogenous (AML) | HEL | SEQ ID NO: 464 |
| 448 | FLJ20625 | NP_060377.1 | Unknown function | Y138 | IAAyAYSALSQIR | cancer, leukemia, chronic myelogenous | Baf3(FLT3|D835Y) | SEQ ID NO: 465 |
| 449 | FLJ22052 | NP_060395.4 | Unknown function | Y288 | KLyPQLSSVHQK | cancer, lung, non-small cell | H1703; N06BJ573(9); N06cs108; N06cs109; N06cs63; N06cs72 | SEQ ID NO: 466 |
| 450 | FLJ22052 | NP_060395.4 | Unknown function | Y920 | TTATVDTyESLLSDSNSNQSR | cancer, leukemia | Jurkat | SEQ ID NO: 467 |
| 451 | FLJ30976 | NP_659462.1 | Unknown function | Y415 | TTLCNMLAENyKGK | cancer, leukemia, acute lymphocytic (ALL); cancer, nerve tissue, | CHP126; SEM | SEQ ID NO: 468 |
| 452 | FLJ34633 | NP_689578.1 | Unknown function | Y216 | GSEEyYSFHESDLDLPEMGSGSMSSR | cancer, gastric | KATO III | SEQ ID NO: 469 |
| 453 | FLJ34633 | NP_689578.1 | Unknown function | Y217 | GSEEYySFHESDLDLPEMGSGSMSSR | cancer, gastric | KATO III | SEQ ID NO: 470 |
| 454 | FRMPD4 | NP_055543.1 | Unknown function | Y596 | HLyIDNAYSSDGLNQQLSQPGEAPCEADYR | cancer, lung, non-small cell | HL184A | SEQ ID NO: 471 |
| 455 | FRMPD4 | NP_055543.1 | Unknown function | Y601 | HLYIDNAySSDGLNQQLSQPGEAPCEADYR | cancer, lung, non-small cell | HL184A | SEQ ID NO: 472 |
| 456 | FRYL | NP_055845.1 | Unknown | Y93 | QNGTEDESyEYRPR | cancer, leukemia | Jurkat | SEQ ID NO: 473 |
| 457 | FRYL | NP_055845.1 | Unknown | Y95 | RQNGTEDESYEyRPR | cancer, leukemia | Jurkat | SEQ ID NO: 474 |
| 458 | HSPA12A | NP_079291.2 | Unknown function | Y21 | ETAPTSAySSPAR | cancer, lung, non-small cell | h2073 | SEQ ID NO: 475 |
| 459 | KIAA0376 | NP_056145.1 | Unknown function | Y808 | GRVyNYMNAVER | cancer, leukemia | Jurkat | SEQ ID NO: 476 |
| 460 | KIAA0376 | NP_056145.1 | Unknown function | Y810 | GRVYNyMNAVER | cancer, leukemia | Jurkat | SEQ ID NO: 477 |
| 461 | KIAA1109 | XP_371706.5 | Unknown function | Y3846 | FQTNyASTTHLMTGK | cancer, leukemia | Jurkat | SEQ ID NO: 478 |
| 462 | KIAA1239 | XP_049078.7 | Unknown function | Y1332 | GEIIySLDGSDCVHK | cancer, ovarian, epithelial carcinoma | OV90 | SEQ ID NO: 479 |
| 463 | LIMD2 | NP_085053.1 | Unknown function | Y102 | GNyDEGFGR | cancer, leukemia | Jurkat | SEQ ID NO: 480 |
| 464 | LSR7 | NP_061029.2 | Unknown | Y158 | GPVNyNVTTEFEK | cancer, leukemia | Jurkat | SEQ ID NO: 481 |
| 465 | NSUN2 | NP_060225.4 | Unknown function | Y646 | KLSSETySQAK | cancer, leukemia, acute myelogenous (AML) | Molm 14 | SEQ ID NO: 482 |
| 466 | PHF8 | NP_055922.1 | Unknown | Y267 | GEKIFyLIR | cancer, lung, non-small | N06bj594(14 | SEQ ID NO: 483 |
| 467 | POF1B | NP_079197.2 | Unknown function | Y166 | GSHFFPGNNVIyEK | cancer, gastric; cancer, leukemia, acute myelogenous (AML); cancer, lung, non-small | A549; CTV-1; DV-90; MKN-45 | SEQ ID NO: 484 |
| 468 | QSER1 | NP_001070254.1 | Unknown function | Y1411 | EFAATNSyLGYFGDAK | cancer, pancreatic | HP28 | SEQ ID NO: 485 |
| 469 | SNX22 | NP_079074.2 | Unknown | Y92 | GLEQRRQGLEAYIQGILyLNQEVPK | cancer, lung, non-small | HL183B | SEQ ID NO: 486 |
| 470 | JIP4 | NP_003962.3 | Unknown | Y900 | GNAGSAEDTVDISQTGVyTE | cancer, leukemia | Jurkat | SEQ ID NO: 487 |
| 471 | ST5 | NP_005409.3 | Unknown function | Y308 | GLPQLPSSCySVDR | cancer, lymphoma, Hodgkin's disease | HDLM-2 | SEQ ID NO: 488 |

| | A | B | C | D | E | F | G | H |
|---|---|---|---|---|---|---|---|---|
| 1 | Protein Name | Accession No. | Protein Type | Phospho-Residu | Phosphorylation Site Sequence | Disease | Cell Types | SEQ ID NO |
| 472 | SYF2 | NP_056299.1 | Unknown | Y226 | FyGKYTAEIK | | HL53B | SEQ ID NO: 489 |
| 473 | SYF2 | NP_056299.1 | Unknown | Y229 | FYGKyTAEIK | | HL53B | SEQ ID NO: 490 |
| 474 | CLTC | NP_004850.1 | Vesicle protein | Y883 | lyIDSNNNPER | cancer, breast, adenocarcinoma | CAL-85-1 | SEQ ID NO: 491 |
| 475 | CLTA | NP_001824.1 | Vesicle protein | Y94 | SNGPTDSyAAISQVDRLQSEPE | cancer, leukemia | Jurkat | SEQ ID NO: 492 |
| 476 | CSP | NP_079495.1 | Vesicle protein | Y17 | SLSTSGESLyHVLGLDK | cancer, gastric | 23132/87 | SEQ ID NO: 493 |
| 477 | CSP | NP_079495.1 | Vesicle protein | Y192 | TTQLTADSHPSyHTDGFN | cancer, leukemia | Jurkat | SEQ ID NO: 494 |
| 478 | EHBP1 | NP_056067.1 | Vesicle protein | Y319 | VQTPQyLNPFDEPE | cancer, leukemia | Jurkat | SEQ ID NO: 495 |
| 479 | EHD2 | NP_055416.2 | Vesicle protein | Y458 | YDEIFyNLAPADGK | cancer, gastric | KATO III | SEQ ID NO: 496 |
| 480 | epsin 3 | NP_060427.1 | Vesicle protein | Y176 | RYGEDySR | ancer, esophageal carcinoma; cancer, gastric; cancer, lung, non small cell | 23132/87; A498; H1781; H2342; H3255; HCC827; KATO III; Kyse70; | SEQ ID NO: 497 |
| 481 | EXOC1 | NP_060731.2 | Vesicle protein | Y769 | VlySLGQPLEKLNHF | cancer, gastric | Hs746T | SEQ ID NO: 498 |
| 482 | NSF | NP_006169.1 | Vesicle protein | Y259 | GILLyGPPGCGK | | brain | SEQ ID NO: 499 |
| 483 | NSF | NP_006169.1 | Vesicle protein | Y499 | GDFLASLENDIKPAFGTNQEDyASYIMNGIIK | | brain | SEQ ID NO: 500 |

SEQUENCE LISTING

```
<160> NUMBER OF SEQ ID NOS: 500

<210> SEQ ID NO 1
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 1

Met Xaa Glu Glu Asn Ser Gln Pro Arg
1               5

<210> SEQ ID NO 2
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 2

Ser Xaa Asn Pro Asp Leu Thr Gly Leu Cys Glu Pro Thr Pro His Asp
1               5                   10                  15

His Ile Lys

<210> SEQ ID NO 3
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 3

Ile Asn Met Leu Thr Ala Gly Xaa Ala Glu Arg
1               5                   10
```

```
<210> SEQ ID NO 4
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 4

Val Phe Xaa Leu Thr Tyr Thr Pro Glu Asp Val Glu
1               5                   10

<210> SEQ ID NO 5
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 5

Val Phe Tyr Leu Thr Xaa Thr Pro Glu Asp Val Glu
1               5                   10

<210> SEQ ID NO 6
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 6

Asn Phe His Xaa Pro Pro Asp Gly Tyr Ser Arg
1               5                   10

<210> SEQ ID NO 7
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 7

Gln Ile Ile Glu Asp Gln Ser Gly His Xaa Ile Trp Val Pro Ser Pro
1               5                   10                  15

Glu Lys Leu

<210> SEQ ID NO 8
<211> LENGTH: 26
<212> TYPE: PRT
<213> ORGANISM: Artificial sequence
```

```
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 8

Ser Gln Tyr Xaa Ser Thr Val Gly Gly Ser His Pro His Ser Glu Gln
1               5                   10                  15

Tyr Pro Asp Leu Leu Pro Leu Glu Ala Arg
            20                  25

<210> SEQ ID NO 9
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 9

Leu Gln Ile Thr His Glu Asn Ile Xaa Leu Trp Asp Ile His Asn Pro
1               5                   10                  15

Arg

<210> SEQ ID NO 10
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (20)..(20)
<223> OTHER INFORMATION: Phosphorylated Tyr

<400> SEQUENCE: 10

Met Cys Asp Ala Gly Glu Gly Leu Tyr Thr Phe Gln Thr Gln Glu Gly
1               5                   10                  15

Glu Gln Ile Xaa Gln Arg
            20

<210> SEQ ID NO 11
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (1)..(1)
<223> OTHER INFORMATION: Phosphorylated Tyr

<400> SEQUENCE: 11

Xaa Ser Glu Arg Tyr Asp Pro Glu Pro Lys
1               5                   10

<210> SEQ ID NO 12
<211> LENGTH: 10
<212> TYPE: PRT
<213> ORGANISM: Artificial sequence
```

```
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 12

Tyr Ser Glu Arg Xaa Asp Pro Glu Pro Lys
1               5                   10

<210> SEQ ID NO 13
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 13

Met Glu Glu Lys Asp Xaa Ser Glu Ala Asp Gly Leu Ser Glu Arg
1               5                   10                  15

<210> SEQ ID NO 14
<211> LENGTH: 27
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 14

Arg Asn Asp Ser Ile Tyr Glu Ala Ser Ser Leu Xaa Gly Ile Ser Ala
1               5                   10                  15

Met Asp Gly Val Pro Phe Thr Leu His Pro Arg
            20                  25

<210> SEQ ID NO 15
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 15

Ser Leu Ala Asp Ile Glu Glu Glu Xaa Asn Tyr Gly Phe Val Val Glu
1               5                   10                  15

Lys

<210> SEQ ID NO 16
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
```

```
<220> FEATURE:
<221> NAME/KEY: mod_res
<222> LOCATION: (11)..(11)
<223> OTHER INFORMATION: Phosphorylated Tyr

<400> SEQUENCE: 16

Ser Leu Ala Asp Ile Glu Glu Glu Tyr Asn Xaa Gly Phe Val Val Glu
1               5                   10                  15

Lys

<210> SEQ ID NO 17
<211> LENGTH: 25
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr

<400> SEQUENCE: 17

Pro His Ala Ser Leu Pro Pro Leu Pro Leu Xaa Asp Gln Pro Pro Ser
1               5                   10                  15

Ser Pro Tyr Pro Ser Pro Asp Lys Arg
            20                  25

<210> SEQ ID NO 18
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (19)..(19)
<223> OTHER INFORMATION: Phosphorylated Tyr

<400> SEQUENCE: 18

Ser Gly Phe Glu Pro Pro Gly Asp Phe Pro Phe Glu Asp Tyr Ser Gln
1               5                   10                  15

His Ile Xaa Arg
            20

<210> SEQ ID NO 19
<211> LENGTH: 18
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (16)..(16)
<223> OTHER INFORMATION: Phosphorylated Tyr

<400> SEQUENCE: 19

Thr Pro Thr Thr Pro Gly Phe Ala Ala Gln Asn Leu Pro Asn Gly Xaa
1               5                   10                  15

Pro Arg

<210> SEQ ID NO 20
<211> LENGTH: 11
<212> TYPE: PRT
<213> ORGANISM: Artificial sequence
<220> FEATURE:
```

<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 20

Thr Glu Leu Xaa Ala Val Ile Asp Ile Glu Arg
1               5                   10

<210> SEQ ID NO 21
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 21

Arg Asp Ser Val Lys Trp His Xaa Leu Cys Leu Arg
1               5                   10

<210> SEQ ID NO 22
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 22

Ser Gly Arg Leu Thr Gly Asp Pro Asp Val Leu Glu Xaa Tyr Lys
1               5                   10                  15

<210> SEQ ID NO 23
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 23

Ser Xaa Phe Gly Lys Leu Thr Gln Ser Lys
1               5                   10

<210> SEQ ID NO 24
<211> LENGTH: 28
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 24

```
Gln Ser Ala Phe Ser Asn Xaa Val Asn Val Glu Phe Gly Val Pro Phe
1               5                   10                  15

Pro Asn Pro Ala Asn Asp Leu Ser Asp Leu Leu Arg
            20                  25
```

<210> SEQ ID NO 25
<211> LENGTH: 19
<212> TYPE: PRT
<213> ORGANISM: Artificial sequence
<220> FEATURE:
<223> OTHER INFORMATION: Description of Artificial Sequence: Synthetic peptide
<220> FEATURE:
<221> NAME/KEY: mod_res
<222> LOCATION: (7)..(7)
<223> OTHER INFORMATION: Phosphorylated Tyr

<400> SEQUENCE: 25

```
Ala Thr Gln Gly Gly Thr Xaa Asn Phe Asp Pro Thr Ala Asn Leu Gln
1               5                   10                  15

Thr Lys Glu
```

<210> SEQ ID NO 26
<211> LENGTH: 16
<212> TYPE: PRT
<213> ORGANISM: Artificial sequence
<220> FEATURE:
<223> OTHER INFORMATION: Description of Artificial Sequence: Synthetic peptide
<220> FEATURE:
<221> NAME/KEY: mod_res
<222> LOCATION: (8)..(8)
<223> OTHER INFORMATION: Phosphorylated Tyr

<400> SEQUENCE: 26

```
Asp Ser Asp Ile Asp Gly Asp Xaa Arg Val Gln Asn Thr Ser Leu Glu
1               5                   10                  15
```

<210> SEQ ID NO 27
<211> LENGTH: 21
<212> TYPE: PRT
<213> ORGANISM: Artificial sequence
<220> FEATURE:
<223> OTHER INFORMATION: Description of Artificial Sequence: Synthetic peptide
<220> FEATURE:
<221> NAME/KEY: mod_res
<222> LOCATION: (9)..(9)
<223> OTHER INFORMATION: Phosphorylated Tyr

<400> SEQUENCE: 27

```
Gly Ala Leu Asp Thr Thr Asp Gly Xaa Met Gly Val Asn Gln Ala Pro
1               5                   10                  15

Glu Lys Leu Asp Lys
            20
```

<210> SEQ ID NO 28
<211> LENGTH: 13
<212> TYPE: PRT
<213> ORGANISM: Artificial sequence
<220> FEATURE:
<223> OTHER INFORMATION: Description of Artificial Sequence: Synthetic peptide
<220> FEATURE:
<221> NAME/KEY: mod_res
<222> LOCATION: (7)..(7)
<223> OTHER INFORMATION: Phosphorylated Tyr

<400> SEQUENCE: 28

```
Phe Ile Thr Val Cys Asp Xaa Thr Asn Pro Cys Thr Lys
1               5                   10

<210> SEQ ID NO 29
<211> LENGTH: 30
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr

<400> SEQUENCE: 29

Phe Thr Ser Gln Asp Ser Pro Asp Gly Gln Xaa Glu Asn Ser Glu Gly
1               5                   10                  15

Gly Trp Met Glu Asp Tyr Asp Tyr Val His Leu Gln Gly Lys
            20                  25                  30

<210> SEQ ID NO 30
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 30

Gly Gly Pro Ala Asp Pro Val Asp Xaa Leu Pro Ala Ala Pro Arg
1               5                   10                  15

<210> SEQ ID NO 31
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 31

Gly Ser Thr Val Thr Xaa His Leu Leu Gly Pro Gln Glu Glu
1               5                   10

<210> SEQ ID NO 32
<211> LENGTH: 25
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (22)..(22)
<223> OTHER INFORMATION: Phosphorylated Tyr

<400> SEQUENCE: 32

Gly Leu Gly Phe Ser Ile Ala Gly Gly Val Gly Asn Gln His Ile Pro
1               5                   10                  15

Gly Asp Asn Ser Ile Xaa Val Thr Lys
```

```
<210> SEQ ID NO 33
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 33

Phe Ile Glu Ala Gly Gln Xaa Asn Asp Asn Leu Tyr Gly Thr Ser Val
1               5                   10                  15

Gln Ser Val Arg
            20

<210> SEQ ID NO 34
<211> LENGTH: 25
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (22)..(22)
<223> OTHER INFORMATION: Phosphorylated Tyr

<400> SEQUENCE: 34

Gly Leu Gly Phe Ser Ile Ala Gly Gly Val Gly Asn Gln His Ile Pro
1               5                   10                  15

Gly Asp Asn Ser Ile Xaa Val Thr Lys
            20                  25

<210> SEQ ID NO 35
<211> LENGTH: 28
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (17)..(17)
<223> OTHER INFORMATION: Phosphorylated Tyr

<400> SEQUENCE: 35

Glu Asp Ser Val Leu Ser Tyr Glu Thr Val Thr Gln Met Glu Val His
1               5                   10                  15

Xaa Ala Arg Pro Ile Ile Ile Leu Gly Pro Thr Lys
            20                  25

<210> SEQ ID NO 36
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 36
```

```
Glu Ala Glu Asp Xaa Glu Leu Pro Glu Glu Ile Leu Glu Lys
1               5                   10
```

```
<210> SEQ ID NO 37
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 37

Phe Leu Glu Xaa Val Gln Leu Gly Thr Ser Asp Lys
1               5                   10
```

```
<210> SEQ ID NO 38
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 38

Phe Met Asp Xaa Val Gln Leu His Ser Thr Asp Lys
1               5                   10
```

```
<210> SEQ ID NO 39
<211> LENGTH: 26
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 39

Gly Pro Pro Asp His Glu Glu His Leu Xaa Val Asn Thr Gln Gly Leu
1               5                   10                  15

Asp Ala Pro Glu Pro Glu Asp Ser Pro Lys
            20                  25
```

```
<210> SEQ ID NO 40
<211> LENGTH: 27
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 40

Gly Val Gln Leu Xaa Asp Thr Pro Tyr Glu Glu Gln Asp Pro Glu Thr
1               5                   10                  15

Ala Asp Gly Pro Pro Ser Gly Gln Lys Pro Arg
            20                  25
```

```
<210> SEQ ID NO 41
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 41

Glu Gly Val Met Xaa Val Gly Ala Lys
1               5

<210> SEQ ID NO 42
<211> LENGTH: 34
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (28)..(28)
<223> OTHER INFORMATION: Phosphorylated Tyr

<400> SEQUENCE: 42

Ser Ala Asn Pro Ala Asn Pro Ala Ile Leu Ser Glu Ala Ser Ala Pro
1               5                   10                  15

Ile Pro His Asp Gly Asn Leu Tyr Pro Arg Leu Xaa Pro Glu Leu Ser
            20                  25                  30

Gln Tyr

<210> SEQ ID NO 43
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 43

Lys Leu Ala Asp Met Xaa Gly Gly Gly Glu Asp Asp
1               5                   10

<210> SEQ ID NO 44
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 44

Lys Asp Ile Lys Pro Glu Tyr Gln Xaa Met Pro Arg
1               5                   10

<210> SEQ ID NO 45
```

```
<211> LENGTH: 18
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (18)..(18)
<223> OTHER INFORMATION: Phosphorylated Tyr

<400> SEQUENCE: 45

Ile Thr Ile Gln Ala Leu Asp Leu Asp Glu Gly Pro Asn Gly Thr Val
1               5                   10                  15

Thr Xaa

<210> SEQ ID NO 46
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 46

Glu Asn Ser Glu Glu Leu Gln Leu Pro Glu Asn Pro Xaa Ala Gln Pro
1               5                   10                  15

Ser Pro Ile Arg
            20

<210> SEQ ID NO 47
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 47

Thr Glu Asp Glu Val Gln Ser Xaa Pro Ser Lys His Asp Tyr Val
1               5                   10                  15

<210> SEQ ID NO 48
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 48

Thr Asp Gly Val Met Gly Glu Xaa Glu Pro Lys
1               5                   10

<210> SEQ ID NO 49
<211> LENGTH: 16
<212> TYPE: PRT
<213> ORGANISM: Artificial sequence
```

```
<220> FEATURE:
<223> OTHER INFORMATION: Description of Artificial Sequence: Synthetic
      peptide
<220> FEATURE:
<221> NAME/KEY: mod_res
<222> LOCATION: (14)..(14)
<223> OTHER INFORMATION: Phosphorylated Tyr

<400> SEQUENCE: 49

Leu Thr Ser Leu Pro Pro Lys Gly Gly Thr Ser Asn Gly Xaa Ala Lys
1               5                   10                  15

<210> SEQ ID NO 50
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 50

Thr Glu Gly Thr Tyr Asp Leu Pro Xaa Trp Asp Arg
1               5                   10

<210> SEQ ID NO 51
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 51

Lys Pro Glu Glu Gly Lys Glu Ala Gly Xaa Ala Asp Leu Asp Pro Tyr
1               5                   10                  15

<210> SEQ ID NO 52
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 52

Leu Gly Glu Lys Val Xaa Leu Cys Asn Gln Asp Glu Asn His Lys
1               5                   10                  15

<210> SEQ ID NO 53
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr
```

```
<400> SEQUENCE: 53

Val Leu Thr Asn Xaa Met Phe Pro Gln Gln Pro Arg
1               5                  10

<210> SEQ ID NO 54
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (16)..(16)
<223> OTHER INFORMATION: Phosphorylated Tyr

<400> SEQUENCE: 54

Arg Pro Gly Gly Glu Pro Ser Pro Glu Gly Thr Thr Gly Gln Ser Xaa
1               5                  10                  15

Asn Gln Tyr Ser Gln Arg
            20

<210> SEQ ID NO 55
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (19)..(19)
<223> OTHER INFORMATION: Phosphorylated Tyr

<400> SEQUENCE: 55

Arg Pro Gly Gly Glu Pro Ser Pro Glu Gly Thr Thr Gly Gln Ser Tyr
1               5                  10                  15

Asn Gln Xaa Ser Gln Arg
            20

<210> SEQ ID NO 56
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 56

Asn Val Asn Ile Leu Ser Glu Pro Glu Ala Ala Xaa Thr Phe Lys
1               5                  10                  15

<210> SEQ ID NO 57
<211> LENGTH: 24
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (22)..(22)
<223> OTHER INFORMATION: Phosphorylated Tyr

<400> SEQUENCE: 57
```

```
Phe Leu Ala Ala Gly Thr His Leu Gly Gly Thr Asn Leu Asp Phe Gln
1               5                   10                  15

Met Glu Gln Tyr Ile Xaa Lys Arg
            20
```

<210> SEQ ID NO 58
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 58

```
Val Leu Thr Asn Xaa Met Phe Pro Gln Gln Pro Arg
1               5                   10
```

<210> SEQ ID NO 59
<211> LENGTH: 8
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 59

```
Phe Xaa Pro Glu Ser Ser Tyr Lys
1               5
```

<210> SEQ ID NO 60
<211> LENGTH: 8
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 60

```
Phe Tyr Pro Glu Ser Ser Xaa Lys
1               5
```

<210> SEQ ID NO 61
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 61

```
Phe Glu Arg Pro Met Asp Xaa Tyr Glu Asp Leu Lys
1               5                   10
```

<210> SEQ ID NO 62

```
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 62

Glu Xaa Asp Val Leu Tyr Leu Gly Thr Glu Asp Gly His Leu His Arg
1               5                   10                  15

<210> SEQ ID NO 63
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 63

Glu Tyr Asp Val Leu Xaa Leu Gly Thr Glu Asp Gly His Leu His Arg
1               5                   10                  15

<210> SEQ ID NO 64
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 64

Leu Ser Thr Pro Ser Ala Ser Thr Xaa
1               5

<210> SEQ ID NO 65
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (14)..(14)
<223> OTHER INFORMATION: Phosphorylated Tyr

<400> SEQUENCE: 65

Leu Gly Pro Asn Tyr Leu His Ile Pro Val Asn Cys Pro Xaa Arg
1               5                   10                  15

<210> SEQ ID NO 66
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
```

```
<222> LOCATION: (9)..(9)
<223> OTHER INFORMATION: Phosphorylated Tyr

<400> SEQUENCE: 66

Thr Gly Gln Ala Pro Gly Tyr Ser Xaa Thr Ala Ala Asn Lys
1               5                   10

<210> SEQ ID NO 67
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 67

Ser Gln Asn Asn Ile Xaa Ser Ala Cys Pro Arg
1               5                   10

<210> SEQ ID NO 68
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 68

Ser Gly Xaa Ile Glu Ala Asn Glu Leu Lys
1               5                   10

<210> SEQ ID NO 69
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 69

His Phe Asp Ala Asp Gly Asn Gly Xaa Ile Glu Gly Lys
1               5                   10

<210> SEQ ID NO 70
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr

<400> SEQUENCE: 70

Gly Gly Ala Arg Gln Asn Pro Gly Leu Ala Xaa Gly Asn Pro Tyr Ser
1               5                   10                  15
```

Gly Ile Gln Glu
            20

<210> SEQ ID NO 71
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (15)..(15)
<223> OTHER INFORMATION: Phosphorylated Tyr

<400> SEQUENCE: 71

Gly Gly Ala Arg Gln Asn Pro Gly Leu Ala Tyr Gly Asn Pro Xaa Ser
1               5                   10                  15

Gly Ile Gln Glu
            20

<210> SEQ ID NO 72
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 72

Ser Glu Asp Ser Glu Xaa Tyr Lys Ala Phe Glu Glu Ala Ala Glu His
1               5                   10                  15

Phe Gln Pro Tyr Ile Lys
            20

<210> SEQ ID NO 73
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 73

Leu Tyr Asp Leu Asp Asn Asp Gly Xaa Ile Thr Arg
1               5                   10

<210> SEQ ID NO 74
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 74

Glu Ser Leu Val Xaa Phe Leu Ile Gly Lys
1               5                   10

<210> SEQ ID NO 75
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 75

Glu Lys Asp Val Ser Glu Tyr Phe Xaa Glu Lys
1               5                   10

<210> SEQ ID NO 76
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr

<400> SEQUENCE: 76

Lys Val Ala Thr Ala Pro Pro Ala Pro Ala Xaa Lys
1               5                   10

<210> SEQ ID NO 77
<211> LENGTH: 38
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (27)..(27)
<223> OTHER INFORMATION: Phosphorylated Tyr

<400> SEQUENCE: 77

Leu Glu Gln Gln Gln Ser Ala Gly Gly Asp Ala Glu Gly Gly Asp
1               5                   10                  15

Asp Gly Asp Glu Val Pro Gln Ile Asp Ala Xaa Glu Leu Leu Glu Ala
            20                  25                  30

Val Glu Ile Leu Ser Lys
        35

<210> SEQ ID NO 78
<211> LENGTH: 38
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (33)..(33)
<223> OTHER INFORMATION: Phosphorylated Tyr

<400> SEQUENCE: 78

Gly Asn Lys Glu Phe Gly Asp Gln Ala Glu Ala Ala Gln Asp Ala Thr
1               5                   10                  15

Leu Thr Thr Thr Thr Phe Gln Asn Glu Asp Glu Lys Asn Lys Glu Val

```
                20                  25                  30

Xaa Met Thr Pro Leu Arg
        35

<210> SEQ ID NO 79
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 79

Glu Phe Cys Ser Tyr Leu Gln Xaa Leu Glu Tyr Leu Ser Gln Asn Arg
1               5                   10                  15

<210> SEQ ID NO 80
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 80

Ser Leu Glu Xaa Glu Lys Thr Glu Val Asn Ser Gly
1               5                   10

<210> SEQ ID NO 81
<211> LENGTH: 24
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 81

Val His Thr Val Glu Asp Xaa Gln Ala Ile Val Asp Ala Glu Trp Asn
1               5                   10                  15

Ile Leu Tyr Asp Lys Leu Glu Lys
            20

<210> SEQ ID NO 82
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 82

Thr Asp Met Asp Asn Gln Ile Val Val Ser Asp Xaa Ala Gln Met Asp
1               5                   10                  15
```

Arg

<210> SEQ ID NO 83
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 83

Glu Ile Ala Glu Ala Xaa Asp Val Leu Ser Asp Pro Lys
1               5                   10

<210> SEQ ID NO 84
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 84

Gln Val Ala Glu Ala Xaa Glu Val Leu Ser Asp Ala Lys
1               5                   10

<210> SEQ ID NO 85
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 85

Asn Pro Gln Met Pro Gln Xaa Ser Ser Pro Gln Pro Gly Ser Ala Leu
1               5                   10                  15

Ser Pro Arg

<210> SEQ ID NO 86
<211> LENGTH: 21
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 86

Gly Ser Pro His Pro Gly Val Gly Val Pro Thr Xaa Tyr Asn His Pro
1               5                   10                  15

Glu Ala Leu Lys Arg
                20

```
<210> SEQ ID NO 87
<211> LENGTH: 26
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 87

Leu Asp Xaa Gln Asp Pro Asp Ala Thr Ser Leu Lys Tyr Val Ser Gly
1               5                   10                  15

Asp Val Thr His Pro Gln Ala Gly Ala Glu
            20                  25

<210> SEQ ID NO 88
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 88

Leu Xaa Glu Ser Leu Thr Tyr Ser Gln Met Ser Arg
1               5                   10

<210> SEQ ID NO 89
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 89

Leu Tyr Glu Ser Leu Thr Xaa Ser Gln Met Ser Arg
1               5                   10

<210> SEQ ID NO 90
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 90

Glu Ser Tyr Ser Val Xaa Val Tyr Lys
1               5

<210> SEQ ID NO 91
<211> LENGTH: 9
<212> TYPE: PRT
<213> ORGANISM: Artificial sequence
<220> FEATURE:
```

```
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 91

Glu Ser Tyr Ser Val Xaa Val Tyr Lys
1               5

<210> SEQ ID NO 92
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 92

Glu Ser Tyr Ser Val Xaa Val Tyr Lys
1               5

<210> SEQ ID NO 93
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 93

Glu Met Lys Thr Xaa Ile Pro Pro Lys Gly Glu Thr Lys Lys
1               5                   10

<210> SEQ ID NO 94
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 94

Gly Asp Glu Glu Asn Asp Pro Asp Xaa Asp Pro Lys Lys Asp Gln Asn
1               5                   10                  15

Pro Ala Glu

<210> SEQ ID NO 95
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr
```

<400> SEQUENCE: 95

Asp Ser Pro Ser Xaa Gly Ser Leu Ser Arg
1               5                   10

<210> SEQ ID NO 96
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 96

His Gly Glu Tyr Gln Asp Asp Xaa Pro Arg Asp Tyr
1               5                   10

<210> SEQ ID NO 97
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 97

Ile Gln Val His Xaa Tyr Glu Asp Gly Asn Val Gln Leu Val Ser His
1               5                   10                  15

Lys

<210> SEQ ID NO 98
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 98

Met Asp Asp Glu Arg Xaa Phe Asn Glu
1               5

<210> SEQ ID NO 99
<211> LENGTH: 24
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (20)..(20)
<223> OTHER INFORMATION: Phosphorylated Tyr

<400> SEQUENCE: 99

Val Ser Val Met Gly Thr Asp Gln Ser Glu Ser Ile Asn Thr Ser Asn
1               5                   10                  15

```
Glu Thr Glu Xaa Leu Lys Gln Lys
            20
```

```
<210> SEQ ID NO 100
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 100

Asn Met Asn Ser Glu Asp Ile Xaa Ser Ser Leu Arg Gly Val Thr Glu
1               5                   10                  15
```

```
<210> SEQ ID NO 101
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 101

Arg Pro Thr Ala Thr Gly Asp Xaa Asp Lys Lys Asn Tyr Val
1               5                   10
```

```
<210> SEQ ID NO 102
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 102

Arg Pro Thr Ala Thr Gly Asp Tyr Asp Lys Lys Asn Xaa Val
1               5                   10
```

```
<210> SEQ ID NO 103
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 103

Met Leu Pro Asp Lys Asp Cys Arg Xaa Ala Leu Tyr Asp Ala Thr Tyr
1               5                   10                  15

Glu Thr Lys Glu Ser Lys
            20
```

```
<210> SEQ ID NO 104
```

```
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 104

Leu Leu Pro Leu Asn Asp Cys Arg Xaa Ala Leu Tyr Asp Ala Thr Tyr
1               5                   10                  15

Glu Thr Lys

<210> SEQ ID NO 105
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 105

Leu Ser Xaa Thr Glu Ala Glu Gly Glu Arg
1               5                   10

<210> SEQ ID NO 106
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 106

Val Lys Asp Lys Val Xaa Gly Cys Ala Asp Gly Glu Arg
1               5                   10

<210> SEQ ID NO 107
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (1)..(1)
<223> OTHER INFORMATION: Phosphorylated Tyr

<400> SEQUENCE: 107

Xaa Gly Leu Phe Pro Ala Asn Tyr Val Glu Leu Arg Gln
1               5                   10

<210> SEQ ID NO 108
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
```

```
<220> FEATURE:
<221> NAME/KEY: mod_res
<222> LOCATION: (9)..(9)
<223> OTHER INFORMATION: Phosphorylated Tyr

<400> SEQUENCE: 108

Leu Lys Lys Ala Gly Gly Ala Asn Xaa Asp Ala Gln Thr Glu
1               5                   10

<210> SEQ ID NO 109
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 109

Lys Thr Asp Xaa Glu Cys Thr Gly Ser Asn Ala Thr Tyr His Gly Ala
1               5                   10                  15

Lys

<210> SEQ ID NO 110
<211> LENGTH: 24
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 110

Ser Ala Ala Asp Trp Ala Leu Xaa Thr Tyr Glu Asp Gly Ser Asp Asp
1               5                   10                  15

Leu Lys Leu Ala Ala Ser Gly Glu
            20

<210> SEQ ID NO 111
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 111

Met His Xaa Pro Met Val Glu Tyr Cys Thr Pro Thr Thr Ser Gly Glu
1               5                   10                  15

Asp Val Arg

<210> SEQ ID NO 112
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
```

```
<221> NAME/KEY: mod_res
<222> LOCATION: (17)..(17)
<223> OTHER INFORMATION: Phosphorylated Tyr

<400> SEQUENCE: 112

Gly Phe Val Ile Pro Asp Glu Gly Gly Pro Gln Glu Glu Gln Glu Glu
1               5                   10                  15

Xaa

<210> SEQ ID NO 113
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 113

Thr Asn Pro Glu Val His Asn Xaa Gln Pro Gln Tyr His Pro Asn Ile
1               5                   10                  15

His Pro Ser Gln Pro Arg
            20

<210> SEQ ID NO 114
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 114

Thr Asn Pro Glu Val His Asn Tyr Gln Pro Gln Xaa His Pro Asn Ile
1               5                   10                  15

His Pro Ser Gln Pro Arg
            20

<210> SEQ ID NO 115
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 115

Leu Lys Leu Glu Trp Ala Xaa Gly Tyr Arg
1               5                   10

<210> SEQ ID NO 116
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
```

```
<221> NAME/KEY: mod_res
<222> LOCATION: (10)..(10)
<223> OTHER INFORMATION: Phosphorylated Tyr

<400> SEQUENCE: 116

Gly Ser Gly Asp Leu Gly Glu Pro Leu Xaa Glu Glu Pro Cys Asn Glu
1               5                   10                  15

<210> SEQ ID NO 117
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 117

Leu Ser Leu Gly Thr Xaa Ala Ser Leu His Gly Arg
1               5                   10

<210> SEQ ID NO 118
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr

<400> SEQUENCE: 118

Thr Leu Ser Cys Leu Asp His Val Ile Ser Xaa Tyr His Val Ala Ser
1               5                   10                  15

Asp Thr Glu Lys
            20

<210> SEQ ID NO 119
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 119

Ser Leu Gln Asp Glu Gly Ala Glu Pro Thr Gly Xaa Ser Ala Glu
1               5                   10                  15

<210> SEQ ID NO 120
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 120
```

```
Ile Glu Xaa Asn Asp Gln Asn Asp Gly Ser Cys Asp Val Lys
1               5                   10
```

<210> SEQ ID NO 121
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 121

```
Val Leu Asn Pro Ser Gly Ala Lys Thr Asp Thr Xaa Val Thr Asp Asn
1               5                   10                  15

Gly Asp Gly Thr Tyr Arg
            20
```

<210> SEQ ID NO 122
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (21)..(21)
<223> OTHER INFORMATION: Phosphorylated Tyr

<400> SEQUENCE: 122

```
Val Leu Asn Pro Ser Gly Ala Lys Thr Asp Thr Tyr Val Thr Asp Asn
1               5                   10                  15

Gly Asp Gly Thr Xaa Arg
            20
```

<210> SEQ ID NO 123
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 123

```
Met Gly Glu Ser Met Lys Thr Xaa Ala Glu Val Asp Arg
1               5                   10
```

<210> SEQ ID NO 124
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (14)..(14)
<223> OTHER INFORMATION: Phosphorylated Tyr

<400> SEQUENCE: 124

```
Ser Gly Phe Glu Pro Pro Gly Asp Ile Glu Phe Glu Asp Xaa Thr Gln
```

Pro Met Lys Arg
            20

<210> SEQ ID NO 125
<211> LENGTH: 24
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (19)..(19)
<223> OTHER INFORMATION: Phosphorylated Tyr

<400> SEQUENCE: 125

Phe Ser Thr Ser Gly Leu Ser Ile Ser Gly Leu Asn Pro Leu Pro Asn
1               5                   10                  15

Pro Ser Xaa Leu Leu Pro Pro Arg
            20

<210> SEQ ID NO 126
<211> LENGTH: 39
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (17)..(17)
<223> OTHER INFORMATION: Phosphorylated Tyr

<400> SEQUENCE: 126

Gly Ser Tyr Gly Ser Gly Gly Ser Ser Tyr Gly Ser Gly Gly Gly Ser
1               5                   10                  15

Xaa Gly Ser Gly Gly Gly Gly Gly Gly His Gly Ser Tyr Gly Ser Gly
            20                  25                  30

Ser Ser Ser Gly Gly Tyr Arg
        35

<210> SEQ ID NO 127
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 127

Phe Tyr Asp Ala Asn Xaa Asp Gly Lys Glu Tyr Asp Pro Val Glu Ala
1               5                   10                  15

Arg

<210> SEQ ID NO 128
<211> LENGTH: 18
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res

```
<222> LOCATION: (4)..(4)
<223> OTHER INFORMATION: Phosphorylated Tyr

<400> SEQUENCE: 128

Ser Cys Gln Xaa Leu Gln Val Pro Gln Asp Glu Trp Thr Gly Tyr Thr
1               5                   10                  15

Pro Arg

<210> SEQ ID NO 129
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 129

Glu Ser Gly Xaa Ile Ala Pro Gln Gly Ala Cys Asn Lys
1               5                   10

<210> SEQ ID NO 130
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 130

Gly Thr Phe Val Asp Xaa Gln Thr Thr Val Val Lys
1               5                   10

<210> SEQ ID NO 131
<211> LENGTH: 24
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (14)..(14)
<223> OTHER INFORMATION: Phosphorylated Tyr

<400> SEQUENCE: 131

Glu Arg Val Pro Glu Ala Gln Thr Gly Gln Ala Ser Asp Xaa Gly Leu
1               5                   10                  15

Phe Leu Ser Asp Glu Asp Pro Arg
            20

<210> SEQ ID NO 132
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr
```

```
<400> SEQUENCE: 132

Gly Glu Met Asn Xaa Thr Gln Glu Pro Pro Val Gln Lys
1               5                   10

<210> SEQ ID NO 133
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 133

Gly Gly Val Ser Xaa Arg Pro Ala Glu Val Ala Glu Thr Gly Ala
1               5                   10                  15

<210> SEQ ID NO 134
<211> LENGTH: 23
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (15)..(15)
<223> OTHER INFORMATION: Phosphorylated Tyr

<400> SEQUENCE: 134

Met Ala Lys Gln Leu Gln Ala Arg Arg Leu Asp Gly Ile Asp Xaa Asn
1               5                   10                  15

Pro Trp Val Glu Phe Val Lys
            20

<210> SEQ ID NO 135
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 135

Leu Lys Phe Asn Ala Leu Ile Thr Thr Xaa Glu Ile Leu Leu Lys Asp
1               5                   10                  15

Lys

<210> SEQ ID NO 136
<211> LENGTH: 8
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 136

Leu Xaa Ser Leu Gly Asn Gly Arg
```

<210> SEQ ID NO 137
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 137

His Ile Val Val Xaa His Arg Gly Arg
1               5

<210> SEQ ID NO 138
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 138

Gly Asp Ile Asn Pro Asn Ile Pro Xaa Pro Thr Arg
1               5                   10

<210> SEQ ID NO 139
<211> LENGTH: 8
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 139

Ile Tyr Gln Xaa Val Ile Asn Lys
1               5

<210> SEQ ID NO 140
<211> LENGTH: 41
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (29)..(29)
<223> OTHER INFORMATION: Phosphorylated Tyr

<400> SEQUENCE: 140

Gly Glu Pro Gly Leu His Leu Ala Pro Gly Thr Asp Asp His Asn His
1               5                   10                  15

His Leu Ala Leu Asp Pro Cys Leu Ser Asp Glu Asn Xaa Asp Phe Ser
            20                  25                  30

Ser Ala Glu Ser Gly Ser Ser Leu Arg
        35                  40

```
<210> SEQ ID NO 141
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 141

Leu Ser Leu Lys Asn Pro Glu Xaa Val Trp Val His Glu Lys
1               5                   10

<210> SEQ ID NO 142
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (15)..(15)
<223> OTHER INFORMATION: Phosphorylated Tyr

<400> SEQUENCE: 142

Gly Ile Arg Asp Asp Ile Glu Glu Glu Asp Asp Gln Glu Ala Xaa Phe
1               5                   10                  15

Arg

<210> SEQ ID NO 143
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 143

Lys Met Thr Pro Ser Xaa Glu Ile Arg
1               5

<210> SEQ ID NO 144
<211> LENGTH: 18
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 144

Val Ser Arg Glu Asp Phe Glu Trp Val Xaa Thr Asp Gln Pro His Ala
1               5                   10                  15

Asp Arg

<210> SEQ ID NO 145
<211> LENGTH: 20
<212> TYPE: PRT
```

```
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 145

His Xaa Ser Asp Tyr Phe Pro Leu Lys Leu Leu Lys Thr His Asp Ile
1               5                   10                  15

Cys Pro Ser Arg
            20

<210> SEQ ID NO 146
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 146

His Tyr Ser Asp Xaa Phe Pro Leu Lys Leu Leu Lys Thr His Asp Ile
1               5                   10                  15

Cys Pro Ser Arg
            20

<210> SEQ ID NO 147
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 147

Val Ile Glu Cys Ser Xaa Thr Ser Ala Asp Gly Gln Arg
1               5                   10

<210> SEQ ID NO 148
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 148

Lys Xaa Asn Pro Asp Ser Gly Leu Glu Val Leu Ala Val Gln Arg
1               5                   10                  15

<210> SEQ ID NO 149
<211> LENGTH: 12
<212> TYPE: PRT
<213> ORGANISM: Artificial sequence
<220> FEATURE:
```

```
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 149

Asn Phe Pro Pro Arg Phe Gln Asp Gly Xaa Tyr Ser
1               5                   10

<210> SEQ ID NO 150
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 150

Leu Asn Ser Ile Gly Asn Xaa Tyr Lys
1               5

<210> SEQ ID NO 151
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 151

Leu Asn Ser Ile Gly Asn Tyr Xaa Lys
1               5

<210> SEQ ID NO 152
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 152

Leu Xaa Leu Ala Pro Leu Thr Thr Cys Gly Asn Leu Pro Phe Arg
1               5                   10                  15

<210> SEQ ID NO 153
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 153
```

```
Arg Gly Phe Phe Ile Cys Asp Gln Pro Xaa Glu Pro Val Ser Pro Tyr
1               5                   10                  15

Ser Cys Lys

<210> SEQ ID NO 154
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 154

Thr Leu Val Xaa Gly Gly Ile Phe Leu Tyr Pro Ala Asn Lys
1               5                   10

<210> SEQ ID NO 155
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 155

Met Phe Asn Gly Glu Lys Ile Asn Xaa Thr Glu Gly Arg
1               5                   10

<210> SEQ ID NO 156
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 156

Phe Val Pro Xaa Leu Ile Ala Gly Ile Gln His Ser Cys Gln Asp Ile
1               5                   10                  15

Gly Ala Lys

<210> SEQ ID NO 157
<211> LENGTH: 8
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 157

Phe Arg Xaa Leu Met Ala Glu Lys
1               5
```

```
<210> SEQ ID NO 158
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (14)..(14)
<223> OTHER INFORMATION: Phosphorylated Tyr

<400> SEQUENCE: 158

Glu Met Asp Glu Ser Leu Ala Asn Leu Ser Glu Asp Glu Xaa Tyr Ser
1               5                   10                  15

Glu Glu Glu Arg
            20

<210> SEQ ID NO 159
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (15)..(15)
<223> OTHER INFORMATION: Phosphorylated Tyr

<400> SEQUENCE: 159

Glu Met Asp Glu Ser Leu Ala Asn Leu Ser Glu Asp Glu Tyr Xaa Ser
1               5                   10                  15

Glu Glu Glu Arg
            20

<210> SEQ ID NO 160
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 160

Phe Asp Pro Leu Val Ile Leu Lys Thr Leu Ser Ser Xaa Pro Ile Lys
1               5                   10                  15

<210> SEQ ID NO 161
<211> LENGTH: 29
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 161

Glu Gln Pro Ala Gly Ala Cys Glu Xaa Ser Tyr Cys Glu Asp Glu Ser
1               5                   10                  15

Ala Thr Gly Gly Cys Pro Phe Gly Pro Tyr Gln Gly Arg
            20                  25
```

<210> SEQ ID NO 162
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr

<400> SEQUENCE: 162

Glu Leu His Phe Glu Gly Glu Glu Val Asp Xaa Asp Val Ser Pro Ser
1               5                   10                  15

Asp Pro Lys

<210> SEQ ID NO 163
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 163

Gly Leu Gly Glu Phe Thr Pro Leu Xaa Pro Met Leu Phe Gly Gly Gly
1               5                   10                  15

Gln Glu Arg

<210> SEQ ID NO 164
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 164

Thr Thr Asn Lys Phe Pro Ser Glu Xaa Val Pro Thr Val Phe
1               5                   10

<210> SEQ ID NO 165
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 165

Asn Ala Ile Ser Leu Pro Gln Leu Asn Gln Ala Ala Xaa Asp Ser Leu
1               5                   10                  15

Val Val Gly Lys
            20

-continued

```
<210> SEQ ID NO 166
<211> LENGTH: 18
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 166

His Trp Gly Ala Gly Trp Asp Gly Gly His His Xaa Pro Glu Met Asp
1               5                   10                  15

Ala Arg

<210> SEQ ID NO 167
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 167

Lys Ala Gly Gln Ser Leu Gln Met Glu Phe Leu Xaa His Asn Lys
1               5                   10                  15

<210> SEQ ID NO 168
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (1)..(1)
<223> OTHER INFORMATION: Phosphorylated Tyr

<400> SEQUENCE: 168

Xaa Phe Asp Ser Asn Lys Asp Ala Tyr Ser Lys
1               5                   10

<210> SEQ ID NO 169
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 169

Tyr Phe Asp Ser Asn Lys Asp Ala Xaa Ser Lys
1               5                   10

<210> SEQ ID NO 170
<211> LENGTH: 12
<212> TYPE: PRT
<213> ORGANISM: Artificial sequence
<220> FEATURE:
```

```
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr

<400> SEQUENCE: 170

Tyr Ile Ser Lys Met Thr Thr Asn Pro Ile Xaa Glu
1               5                   10

<210> SEQ ID NO 171
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 171

Met Thr Thr Asn Pro Ile Tyr Glu His Ile Gly Xaa Ala Thr Leu Leu
1               5                   10                  15

Arg

<210> SEQ ID NO 172
<211> LENGTH: 24
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 172

Glu Asp Arg Pro Ile Ser Phe Xaa Gln Leu Gly Ser Asn Gln Leu Gln
1               5                   10                  15

Ser Asn Ala Val Ser Leu Ala Arg
            20

<210> SEQ ID NO 173
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 173

Glu Asp Gln Leu Glu Xaa Gln Glu Glu Leu Arg
1               5                   10

<210> SEQ ID NO 174
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
```

```
<221> NAME/KEY: mod_res
<222> LOCATION: (3)..(3)
<223> OTHER INFORMATION: Phosphorylated Tyr

<400> SEQUENCE: 174

Leu Phe Xaa Leu Asp Pro Asp Ala Gln Lys
1               5                   10

<210> SEQ ID NO 175
<211> LENGTH: 23
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 175

Leu Val Thr Ser Glu Ala Ser Xaa Tyr Lys Ser Leu Asn Leu Leu Val
1               5                   10                  15

Ser His Phe Met Glu Asn Glu
            20

<210> SEQ ID NO 176
<211> LENGTH: 23
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 176

Leu Val Thr Ser Glu Ala Ser Tyr Xaa Lys Ser Leu Asn Leu Leu Val
1               5                   10                  15

Ser His Phe Met Glu Asn Glu
            20

<210> SEQ ID NO 177
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 177

Gln Ile Pro Gly Asp Lys Xaa Gln Val Phe Asp Ser Ala Pro Arg
1               5                   10                  15

<210> SEQ ID NO 178
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
```

<223> OTHER INFORMATION: Phosphorylated Tyr

<400> SEQUENCE: 178

Val Xaa Ser Gln Leu Thr Met Gln Lys
1               5

<210> SEQ ID NO 179
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 179

Leu Ala Ala Pro Xaa Ser Gln Gly Leu Asp Asn
1               5                   10

<210> SEQ ID NO 180
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 180

Gln Gln Ser Ala Asp Gln Asp Ala Glu Ser Ala Xaa Thr Glu Pro Tyr
1               5                   10                  15

Lys

<210> SEQ ID NO 181
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 181

Glu Tyr Lys Pro Leu Ile Ile Xaa Asn Ala Ile Asp Ser Leu Thr Arg
1               5                   10                  15

<210> SEQ ID NO 182
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 182

Glu Tyr Gln Leu Asn Asp Ser Ala Ala Xaa Tyr Leu Asn Asp Leu Glu
1               5                   10                  15

Arg

<210> SEQ ID NO 183
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 183

Glu Gln Leu Xaa Ser Thr Ile Leu Ser His Gln Cys Gln Arg
1               5                   10

<210> SEQ ID NO 184
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 184

Phe Asn Val Asp Glu Xaa Ser Asp Leu Val Thr Leu Thr Lys
1               5                   10

<210> SEQ ID NO 185
<211> LENGTH: 31
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 185

Gly Gly Xaa Tyr Tyr Tyr His Asn Leu Glu Thr Gln Glu Gly Gly Trp
1               5                   10                  15

Asp Glu Pro Pro Asn Phe Val Gln Asn Ser Met Gln Leu Ser Arg
            20                  25                  30

<210> SEQ ID NO 186
<211> LENGTH: 31
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 186

Gly Gly Tyr Xaa Tyr Tyr His Asn Leu Glu Thr Gln Glu Gly Gly Trp
1               5                   10                  15

Asp Glu Pro Pro Asn Phe Val Gln Asn Ser Met Gln Leu Ser Arg
            20                  25                  30

```
<210> SEQ ID NO 187
<211> LENGTH: 31
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 187

Gly Gly Tyr Tyr Tyr Xaa His Asn Leu Glu Thr Gln Glu Gly Gly Trp
1               5                   10                  15

Asp Glu Pro Pro Asn Phe Val Gln Asn Ser Met Gln Leu Ser Arg
            20                  25                  30

<210> SEQ ID NO 188
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 188

Glu Ser Ser Trp Val Thr Pro Glu Ser Cys Phe Xaa Lys Glu Ser Trp
1               5                   10                  15

Leu Thr Gly Lys
            20

<210> SEQ ID NO 189
<211> LENGTH: 29
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 189

Phe Ala Val Asp Glu Xaa Ser Asp Met Val Ala Val Ala Lys Pro Met
1               5                   10                  15

Val Tyr Ile Thr Val Gly Glu Leu Val Asn Thr His Arg
            20                  25

<210> SEQ ID NO 190
<211> LENGTH: 27
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 190

Gly Pro Val Met Ser Gln Xaa Asp Asn Met Thr Pro Ala Val Gln Asp
```

Asp Leu Gly Gly Ile Tyr Val Ile His Leu Arg
            20                  25

<210> SEQ ID NO 191
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 191

Gly Ser Phe Glu Glu Ile Xaa Lys Phe Gln Arg
1               5                   10

<210> SEQ ID NO 192
<211> LENGTH: 26
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 192

Gly Glu Pro Gln Xaa Ser Ser His Ser Ser Ser Asn Thr Leu Ser Ser
1               5                   10                  15

Asn Ala Ser Ser Ser His Ser Asp Asp Arg
            20                  25

<210> SEQ ID NO 193
<211> LENGTH: 24
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 193

Gly Gly Ser Ser Asp Ser Gly Ile Asp Thr Thr Leu Xaa Thr Ser Ser
1               5                   10                  15

Pro Ser Cys Met Ser Leu Ala Lys
            20

<210> SEQ ID NO 194
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 194

```
Gly Pro Val Tyr Ser Arg Gly Ser Met Glu Asp Xaa Cys Asp Ser
1               5                   10                  15

Pro His Gly Glu
            20
```

<210> SEQ ID NO 195
<211> LENGTH: 27
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 195

```
Phe Pro Leu Xaa Asn Leu Gly Phe Gly His Asn Val Asp Phe Asn Phe
1               5                   10                  15

Leu Glu Val Met Ser Met Glu Asn Asn Gly Arg
            20                  25
```

<210> SEQ ID NO 196
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 196

```
Phe Val Tyr Pro Val Pro Xaa Thr Thr Arg Pro Pro Arg Lys Ser Glu
1               5                   10                  15

Glu Asp Gly Lys
            20
```

<210> SEQ ID NO 197
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 197

```
Glu Ser Leu Xaa Ser Gln Leu Pro Met Asp Cys Phe Thr Met Pro Ser
1               5                   10                  15

Tyr Ser Arg
```

<210> SEQ ID NO 198
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 198

Gly Asp Phe Pro Gly Thr Tyr Val Glu Xaa Ile Gly Arg
1               5                   10

<210> SEQ ID NO 199
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 199

Ser Arg Glu Xaa Asp Gln Leu Tyr Glu Glu Tyr Thr Arg
1               5                   10

<210> SEQ ID NO 200
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr

<400> SEQUENCE: 200

Gly Lys Ser Gln Asp Ser Asp Leu Lys Gln Xaa Trp Met Pro Asp Ser
1               5                   10                  15

Gln Cys Lys Glu
            20

<210> SEQ ID NO 201
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 201

Ala Leu Xaa Ser Thr Ala Met Glu Ser Ile Gln Gly Gly Ala Ala Arg
1               5                   10                  15

<210> SEQ ID NO 202
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 202

Pro Tyr Glu Tyr Tyr Lys Leu Xaa Leu Val Arg
1               5                   10

```
<210> SEQ ID NO 203
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 203

Gln Leu Leu Xaa Asp Phe Pro Trp Thr Asn Val Gly Lys
1               5                   10

<210> SEQ ID NO 204
<211> LENGTH: 8
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 204

Gly Phe Xaa Glu Ser Leu Ala Lys
1               5

<210> SEQ ID NO 205
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 205

Asp Arg Val Leu Tyr Val Leu Lys Leu Xaa Asp Lys
1               5                   10

<210> SEQ ID NO 206
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 206

Lys Ile Glu Asp Leu Ile Lys Xaa Leu Asp Pro Glu Tyr Ile Asp Arg
1               5                   10                  15

<210> SEQ ID NO 207
<211> LENGTH: 16
<212> TYPE: PRT
<213> ORGANISM: Artificial sequence
<220> FEATURE:
<223> OTHER INFORMATION: Description of Artificial Sequence: Synthetic
```

```
                peptide
<220> FEATURE:
<221> NAME/KEY: mod_res
<222> LOCATION: (7)..(7)
<223> OTHER INFORMATION: Phosphorylated Tyr

<400> SEQUENCE: 207

Ile Thr Asn Gln Val Ile Xaa Leu Asn Pro Pro Ile Glu Glu Cys Arg
1               5                   10                  15

<210> SEQ ID NO 208
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 208

Lys Arg Ala Gln Asp Val Asp Ala Thr Asn Pro Asn Xaa Glu
1               5                   10

<210> SEQ ID NO 209
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 209

Gly Gln Gly Ala Thr Ala Ala Gln Gln Gly Gly Xaa Glu Ile Pro Ala
1               5                   10                  15

Arg

<210> SEQ ID NO 210
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 210

Gly Val Leu Lys Ala Asp Xaa Val Arg
1               5

<210> SEQ ID NO 211
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr
```

-continued

```
<400> SEQUENCE: 211

Lys Val Lys Glu Leu Thr Xaa Gln Thr Glu Glu Asp Arg Lys
1               5                   10

<210> SEQ ID NO 212
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 212

Gly Gln Thr Val Gln Gln Val Xaa Asn Ala Val Gly Ala Leu Ala Lys
1               5                   10                  15

<210> SEQ ID NO 213
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 213

Glu Leu Thr Xaa Gln Thr Glu Glu Asp Arg Lys Asn Ile Leu Arg
1               5                   10                  15

<210> SEQ ID NO 214
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 214

Glu Ala Ile Phe Cys Ile Gln Xaa Asn Ile Arg
1               5                   10

<210> SEQ ID NO 215
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 215

Glu Leu Thr Xaa Gln Thr Glu Glu Asp Arg Lys
1               5                   10

<210> SEQ ID NO 216
<211> LENGTH: 16
```

```
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 216

Gly Gln Thr Val Gln Gln Val Xaa Asn Ala Val Gly Ala Leu Ala Lys
1               5                   10                  15

<210> SEQ ID NO 217
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 217

Gly Gln Asn Val Gln Gln Val Ile Xaa Ala Thr Gly Ala Leu Ala Lys
1               5                   10                  15

<210> SEQ ID NO 218
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 218

Gly Gln Thr Val Gln Gln Val Xaa Asn Ala Val Gly Ala Leu Ala Lys
1               5                   10                  15

<210> SEQ ID NO 219
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 219

Phe Asp Phe Ile Xaa Asp Leu Phe Glu His Val Ser Ser Arg
1               5                   10

<210> SEQ ID NO 220
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (18)..(18)
```

```
<223> OTHER INFORMATION: Phosphorylated Tyr

<400> SEQUENCE: 220

Ser Glu Gln Glu Glu Tyr Glu Ala Glu Gly Ile Ala Trp Glu Pro Val
1               5                   10                  15

Gln Xaa Phe Asn Asn Lys
            20

<210> SEQ ID NO 221
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 221

Trp Thr Pro Ile Gln Xaa Phe Asn Asn Lys
1               5                   10

<210> SEQ ID NO 222
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 222

Asn Arg Xaa Val Asp Ile Leu Pro Tyr Asp Tyr Asn Arg
1               5                   10

<210> SEQ ID NO 223
<211> LENGTH: 31
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 223

Glu Leu Gly Xaa Pro Arg Glu Glu Asp Glu Glu Glu Glu Asp Asp
1               5                   10                  15

Glu Glu Glu Glu Glu Glu Glu Asp Ser Gln Ala Glu Val Leu Lys
                20                  25                  30

<210> SEQ ID NO 224
<211> LENGTH: 26
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (17)..(17)
<223> OTHER INFORMATION: Phosphorylated Tyr
```

-continued

```
<400> SEQUENCE: 224

Leu Ser Val Gln Asp Leu Asn Asp Leu Ser Asp Gly Ser Gly Cys
1               5                   10                  15

Xaa Ser Leu Pro Ser Gln Pro Cys Asn Glu
            20                  25

<210> SEQ ID NO 225
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 225

Ile Tyr Ser Leu Asn Glu Gly Xaa Ala Lys
1               5                   10

<210> SEQ ID NO 226
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 226

Thr Leu Val Xaa Gly Gly Ile Phe Leu Tyr Pro Ala Asn Gln Lys
1               5                   10                  15

<210> SEQ ID NO 227
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 227

Phe Glu Asn Val Gln Thr Leu Thr Asp Ala Ile Xaa Asp Ile Ile Leu
1               5                   10                  15

Asp Met Lys

<210> SEQ ID NO 228
<211> LENGTH: 18
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 228

Glu Arg His Pro Xaa Thr Val Pro Tyr Gly Pro Gln Gly Val Tyr Ser
```

```
1               5                   10                  15
Asn Lys

<210> SEQ ID NO 229
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 229

Pro Xaa Met Ala Tyr Leu Glu Ile Val Thr Ser Asn Gly Pro Ser Lys
1               5                   10                  15

<210> SEQ ID NO 230
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 230

Pro Tyr Met Ala Xaa Leu Glu Ile Val Thr Ser Asn Gly Pro Ser Lys
1               5                   10                  15

<210> SEQ ID NO 231
<211> LENGTH: 21
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 231

Trp Arg Xaa Pro Ser Leu Ser Leu His Gly Ile Glu Gly Ala Phe Ser
1               5                   10                  15

Gly Ser Gly Ala Lys
            20

<210> SEQ ID NO 232
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (15)..(15)
<223> OTHER INFORMATION: Phosphorylated Tyr

<400> SEQUENCE: 232

Phe Glu Gly Gly Val Val Ile Ala Ala Asp Met Leu Gly Ser Xaa Gly
1               5                   10                  15

Ser Leu Ala Arg
```

```
<210> SEQ ID NO 233
<211> LENGTH: 8
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 233

Ile Xaa Gln Tyr Ile Gln Ser Arg
1               5

<210> SEQ ID NO 234
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (1)..(1)
<223> OTHER INFORMATION: Phosphorylated Tyr

<400> SEQUENCE: 234

Xaa Pro Asp Ser Lys Asp Leu Thr Met Val Leu Lys
1               5                   10

<210> SEQ ID NO 235
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 235

Gln Ile Tyr Tyr Ser Asp Lys Xaa Asp Asp Glu Glu Phe Glu Tyr Arg
1               5                   10                  15

<210> SEQ ID NO 236
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 236

Phe Thr Asp Glu Xaa Gln Leu Phe Glu Glu Leu Gly Lys
1               5                   10

<210> SEQ ID NO 237
<211> LENGTH: 14
<212> TYPE: PRT
<213> ORGANISM: Artificial sequence
<220> FEATURE:
```

```
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 237

Leu Ala Tyr Asn Glu Asn Asp Asn Thr Xaa Tyr Ala Met Lys
1               5                  10

<210> SEQ ID NO 238
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 238

Met Glu Asp Xaa Thr Lys Ile Glu Lys Ile Gly Glu Gly Thr Tyr Gly
1               5                  10                  15

Val Val Tyr Lys
            20

<210> SEQ ID NO 239
<211> LENGTH: 25
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 239

Leu Lys Ala Tyr Val Arg Asp Pro Xaa Ala Leu Asp Leu Ile Asp Lys
1               5                  10                  15

Leu Leu Val Leu Asp Pro Ala Gln Arg
            20                  25

<210> SEQ ID NO 240
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 240

Gly Lys Xaa Ser Glu Val Phe Glu Ala Ile Asn Ile Thr Asn Asn Glu
1               5                  10                  15

Lys

<210> SEQ ID NO 241
<211> LENGTH: 10
<212> TYPE: PRT
<213> ORGANISM: Artificial sequence
<220> FEATURE:
```

<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 241

Gln Xaa Thr Leu Glu Glu Phe Leu Asp Lys
1               5                   10

<210> SEQ ID NO 242
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 242

Gly Gln Xaa Glu His Tyr His Ala Ile Phe Asp Gln Met Gln Gln Gln
1               5                   10                  15

Arg

<210> SEQ ID NO 243
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 243

Gly Gln Tyr Glu His Xaa His Ala Ile Phe Asp Gln Met Gln Gln Gln
1               5                   10                  15

Arg

<210> SEQ ID NO 244
<211> LENGTH: 24
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 244

Glu Ala Arg Xaa Thr Met Pro Ser Ser Leu Leu Ala Pro Ala Lys His
1               5                   10                  15

Leu Ile Ala Ser Met Leu Ser Lys
            20

<210> SEQ ID NO 245
<211> LENGTH: 15
<212> TYPE: PRT
<213> ORGANISM: Artificial sequence
<220> FEATURE:
<223> OTHER INFORMATION: Description of Artificial Sequence: Synthetic

```
            peptide
<220> FEATURE:
<221> NAME/KEY: mod_res
<222> LOCATION: (7)..(7)
<223> OTHER INFORMATION: Phosphorylated Tyr

<400> SEQUENCE: 245

Gly Leu Leu Glu Glu Gln Xaa Phe Glu Leu Thr Gln Glu Ser Lys
1               5                   10                  15

<210> SEQ ID NO 246
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 246

Glu Asp Ile Gly Val Gly Ser Xaa Ser Val Cys Lys
1               5                   10

<210> SEQ ID NO 247
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 247

Phe Ser Leu Ser Gly Gly Xaa Trp Asn Ser Val Ser Asp Thr Ala Lys
1               5                   10                  15

<210> SEQ ID NO 248
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 248

Glu Asp Ile Gly Val Gly Ser Xaa Ser Val Cys Lys
1               5                   10

<210> SEQ ID NO 249
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 249
```

```
Gly Ala Met Ala Ala Thr Xaa Phe Ala Leu Asn Arg
1               5                   10
```

<210> SEQ ID NO 250
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 250

```
Glu Asp Ile Gly Val Gly Ser Xaa Ser Val Cys Lys
1               5                   10
```

<210> SEQ ID NO 251
<211> LENGTH: 33
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (31)..(31)
<223> OTHER INFORMATION: Phosphorylated Tyr

<400> SEQUENCE: 251

```
Gly Ser Ala Pro His Ser Glu Ser Asp Leu Pro Glu Gln Glu Glu Glu
1               5                   10                  15

Ile Leu Gly Ser Asp Asp Asp Glu Gln Glu Asp Pro Asn Asp Xaa Cys
            20                  25                  30

Lys
```

<210> SEQ ID NO 252
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr

<400> SEQUENCE: 252

```
Ile Gln Val Pro Ala Pro Phe Asp Leu Ser Xaa Lys
1               5                   10
```

<210> SEQ ID NO 253
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 253

```
His Gly Ser Leu Gln Glu Xaa Leu Gln Asn Asp Thr Gly Ser Lys
1               5                   10                  15
```

```
<210> SEQ ID NO 254
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 254

Asn Val Leu Val Gly Glu His Asn Ile Xaa Lys Val Ala Asp Phe Gly
1               5                   10                  15

Leu Ala Arg

<210> SEQ ID NO 255
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 255

Glu Glu Pro Ile Tyr Ile Ile Thr Glu Xaa Met Ala Lys
1               5                   10

<210> SEQ ID NO 256
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 256

Tyr Leu Ala Asn Met Asn Xaa Val His Arg
1               5                   10

<210> SEQ ID NO 257
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 257

Glu Ile Phe Thr Gly Val Glu Xaa Ser Ser Cys Asp Thr Ile Ala Lys
1               5                   10                  15

<210> SEQ ID NO 258
<211> LENGTH: 13
<212> TYPE: PRT
<213> ORGANISM: Artificial sequence
<220> FEATURE:
```

```
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 258

Val Leu Glu Asp Asp Pro Glu Ala Ala Xaa Thr Thr Arg
1               5                   10

<210> SEQ ID NO 259
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 259

Trp Thr Ala Pro Glu Ala Ile Ala Xaa Arg
1               5                   10

<210> SEQ ID NO 260
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 260

Val Leu Glu Asp Asp Pro Glu Ala Ala Xaa Thr Thr Thr Gly Gly Lys
1               5                   10                  15

<210> SEQ ID NO 261
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 261

Trp Thr Ala Pro Glu Ala Ile Ala Xaa Arg
1               5                   10

<210> SEQ ID NO 262
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 262
```

```
Glu Ala Val Xaa Ser Asp Lys Leu Gln His Tyr Ser Thr Gly Arg
1               5                   10                  15

<210> SEQ ID NO 263
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr

<400> SEQUENCE: 263

Glu Ala Val Tyr Ser Asp Lys Leu Gln His Xaa Ser Thr Gly Arg
1               5                   10                  15

<210> SEQ ID NO 264
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 264

Trp Thr Ala Pro Glu Ala Ile Ala Xaa Arg
1               5                   10

<210> SEQ ID NO 265
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 265

Trp Thr Ala Pro Glu Ala Ile Ala Xaa Arg
1               5                   10

<210> SEQ ID NO 266
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 266

Gly Met Glu Xaa Leu Ala Ser Lys Lys
1               5

<210> SEQ ID NO 267
<211> LENGTH: 28
<212> TYPE: PRT
```

```
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (16)..(16)
<223> OTHER INFORMATION: Phosphorylated Tyr

<400> SEQUENCE: 267

Leu Ser Ser Thr Ala Asp Thr Pro Met Leu Ala Gly Val Ser Glu Xaa
1               5                   10                  15

Glu Leu Pro Glu Asp Pro Lys Trp Glu Phe Pro Arg
            20                  25

<210> SEQ ID NO 268
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 268

Arg Pro Pro Gly Met Glu Xaa Ser Tyr Asp Ile Asn Arg
1               5                   10

<210> SEQ ID NO 269
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 269

Arg Pro Pro Gly Met Glu Tyr Ser Xaa Asp Ile Asn Arg
1               5                   10

<210> SEQ ID NO 270
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 270

Gly Met Glu Xaa Leu Ala Ser Gln Lys
1               5

<210> SEQ ID NO 271
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
```

```
<221> NAME/KEY: mod_res
<222> LOCATION: (12)..(12)
<223> OTHER INFORMATION: Phosphorylated Tyr

<400> SEQUENCE: 271

Met Asp Lys Pro Ala Asn Cys Thr Asn Glu Leu Xaa Met Met Met Arg
1               5                   10                  15

<210> SEQ ID NO 272
<211> LENGTH: 33
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (18)..(18)
<223> OTHER INFORMATION: Phosphorylated Tyr

<400> SEQUENCE: 272

Ser Ser Cys Ser Ser Gly Asp Asp Ser Val Phe Ser Pro Asp Pro Met
1               5                   10                  15

Pro Xaa Glu Pro Cys Leu Pro Gln Tyr Pro His Ile Asn Gly Ser Val
            20                  25                  30

Lys

<210> SEQ ID NO 273
<211> LENGTH: 33
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (25)..(25)
<223> OTHER INFORMATION: Phosphorylated Tyr

<400> SEQUENCE: 273

Ser Ser Cys Ser Ser Gly Asp Asp Ser Val Phe Ser Pro Asp Pro Met
1               5                   10                  15

Pro Tyr Glu Pro Cys Leu Pro Gln Xaa Pro His Ile Asn Gly Ser Val
            20                  25                  30

Lys

<210> SEQ ID NO 274
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 274

Gly Met Glu Xaa Leu Ala Ser Gln Lys
1               5

<210> SEQ ID NO 275
<211> LENGTH: 15
<212> TYPE: PRT
<213> ORGANISM: Artificial sequence
<220> FEATURE:
<223> OTHER INFORMATION: Description of Artificial Sequence: Synthetic
```

```
                        peptide
<220> FEATURE:
<221> NAME/KEY: mod_res
<222> LOCATION: (12)..(12)
<223> OTHER INFORMATION: Phosphorylated Tyr

<400> SEQUENCE: 275

Trp Met Ala Pro Glu Ser Leu Phe Glu Gly Ile Xaa Thr Ile Lys
1               5                   10                  15

<210> SEQ ID NO 276
<211> LENGTH: 30
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 276

Gly His Leu Asp Glu Gly Leu Ser Xaa Thr Ser Ile Phe Tyr Pro Val
1               5                   10                  15

Glu Val Phe Glu Ser Ser Leu Ser Asp Pro Gly Pro Gly Lys
            20                  25                  30

<210> SEQ ID NO 277
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 277

Gly Met Lys Xaa Leu Ala Ser Lys Lys
1               5

<210> SEQ ID NO 278
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 278

Gly Gly Pro Ile Tyr Ile Ile Thr Glu Xaa Cys Arg
1               5                   10

<210> SEQ ID NO 279
<211> LENGTH: 23
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (14)..(14)
<223> OTHER INFORMATION: Phosphorylated Tyr
```

<400> SEQUENCE: 279

Gly Ala Gly His Asp Pro Ala Pro Glu Gly Gln Ala Asp Xaa Asp Pro
1               5                   10                  15

Val Thr Pro Tyr Val Thr Glu
            20

<210> SEQ ID NO 280
<211> LENGTH: 23
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (20)..(20)
<223> OTHER INFORMATION: Phosphorylated Tyr

<400> SEQUENCE: 280

Gly Ala Gly His Asp Pro Ala Pro Glu Gly Gln Ala Asp Tyr Asp Pro
1               5                   10                  15

Val Thr Pro Xaa Val Thr Glu
            20

<210> SEQ ID NO 281
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 281

His Val His Ser Glu Asp Xaa Ser Lys Val Pro Lys Tyr
1               5                   10

<210> SEQ ID NO 282
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 282

His Val His Ser Glu Asp Tyr Ser Lys Val Pro Lys Xaa
1               5                   10

<210> SEQ ID NO 283
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr

<400> SEQUENCE: 283

-continued

```
Gly Gln Met Gly Pro Thr Glu Gln Gly Pro Xaa Ala Lys
1               5                   10

<210> SEQ ID NO 284
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 284

Ser Glu Ala Ala Gly Ser Pro Asp Gln Gly Ser Thr Xaa Ser Pro Ala
1               5                   10                  15

Arg

<210> SEQ ID NO 285
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 285

Glu Val Xaa Ser Val Asp Pro Tyr Asn Pro Ala Ser
1               5                   10

<210> SEQ ID NO 286
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 286

Asn Xaa Asn Lys Gln Ala Ser Glu Gln Asn Trp Ala Asn Tyr Ser Ala
1               5                   10                  15

Glu Gln Asn Arg
            20

<210> SEQ ID NO 287
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 287

Thr Thr Xaa Ile Gln Ser Tyr Asp His Gly Thr Ser Ile Glu Glu
1               5                   10                  15
```

```
<210> SEQ ID NO 288
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 288

Thr Thr Tyr Ile Gln Ser Xaa Asp His Gly Thr Ser Ile Glu Glu
1               5                   10                  15

<210> SEQ ID NO 289
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 289

Pro Ala Xaa Glu Glu Phe Tyr Asn Cys Arg
1               5                   10

<210> SEQ ID NO 290
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 290

Pro Ala Tyr Glu Glu Phe Xaa Asn Cys Arg
1               5                   10

<210> SEQ ID NO 291
<211> LENGTH: 28
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 291

Ser Arg Pro Ala Met Xaa Asp Val Ser Pro Ile Ala Tyr Glu Asp Tyr
1               5                   10                  15

Ser Pro Asp Asp Lys Pro Leu Val Thr Leu Ile Lys
            20                  25

<210> SEQ ID NO 292
<211> LENGTH: 28
<212> TYPE: PRT
```

```
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 292

Ser Arg Pro Ala Met Tyr Asp Val Ser Pro Ile Ala Xaa Glu Asp Tyr
1               5                   10                  15
Ser Pro Asp Asp Lys Pro Leu Val Thr Leu Ile Lys
            20                  25

<210> SEQ ID NO 293
<211> LENGTH: 28
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (16)..(16)
<223> OTHER INFORMATION: Phosphorylated Tyr

<400> SEQUENCE: 293

Ser Arg Pro Ala Met Tyr Asp Val Ser Pro Ile Ala Tyr Glu Asp Xaa
1               5                   10                  15
Ser Pro Asp Asp Lys Pro Leu Val Thr Leu Ile Lys
            20                  25

<210> SEQ ID NO 294
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 294

Ile Thr Leu Tyr Asp Xaa Asp Leu Leu Ser Lys Asp Glu Lys
1               5                   10

<210> SEQ ID NO 295
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 295

Glu Ser Val His Xaa Thr Ser Ser Ala Gln Gly Gly Ala Ser Thr Arg
1               5                   10                  15

<210> SEQ ID NO 296
<211> LENGTH: 23
<212> TYPE: PRT
<213> ORGANISM: Artificial sequence
<220> FEATURE:
```

```
<223> OTHER INFORMATION: Description of Artificial Sequence: Synthetic
      peptide
<220> FEATURE:
<221> NAME/KEY: mod_res
<222> LOCATION: (21)..(21)
<223> OTHER INFORMATION: Phosphorylated Tyr

<400> SEQUENCE: 296

Tyr Glu Ser Gln Leu Ser Thr Asn Glu Glu Lys Val Asp Thr Asp Asp
1               5                   10                  15

Arg Thr Glu Gly Xaa Leu Arg
            20

<210> SEQ ID NO 297
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 297

Ser Gly Gly Ala Met Ala Ala Gly Asp Xaa Pro Glu Ala Ser Ala Ala
1               5                   10                  15

Leu Thr Gly Arg
            20

<210> SEQ ID NO 298
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 298

Thr Gly Pro Pro Gly Pro Ala Ala Thr Xaa His Lys
1               5                   10

<210> SEQ ID NO 299
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 299

Glu Arg Glu Glu Glu Asp Asp Xaa Arg Gln Glu Glu Gln Arg
1               5                   10

<210> SEQ ID NO 300
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
```

```
<220> FEATURE:
<221> NAME/KEY: mod_res
<222> LOCATION: (6)..(6)
<223> OTHER INFORMATION: Phosphorylated Tyr

<400> SEQUENCE: 300

Gly Lys Leu Asp Asp Xaa Gln Glu Arg
1               5

<210> SEQ ID NO 301
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 301

Gly Asn Thr Asn Cys Xaa Arg Ala Pro Met Glu Cys Gln Glu
1               5                   10

<210> SEQ ID NO 302
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 302

Gly Leu Asn Leu Asp Asp Cys Ser Met Xaa Glu
1               5                   10

<210> SEQ ID NO 303
<211> LENGTH: 31
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (25)..(25)
<223> OTHER INFORMATION: Phosphorylated Tyr

<400> SEQUENCE: 303

Gly Gly Ala Leu Gly Glu Gly Pro Gly Ala Ser Pro Cys Asn Gln His
1               5                   10                  15

Ser Pro Tyr Trp Ala Pro Pro Cys Xaa Thr Leu Lys Pro Glu Thr
            20                  25                  30

<210> SEQ ID NO 304
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr
```

<400> SEQUENCE: 304

Phe Thr Asp Pro Gly Met Gly Asn Leu Thr Xaa Ser Asn Pro Ser Tyr
1               5                   10                  15

Arg

<210> SEQ ID NO 305
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 305

Gly Asn His Gln Ser Val Leu Thr Phe Xaa Ser
1               5                   10

<210> SEQ ID NO 306
<211> LENGTH: 26
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 306

Ala Val Ala Ile Phe Xaa Thr Met Ile Thr Pro Met Leu Asn Pro Leu
1               5                   10                  15

Ile Tyr Thr Leu Lys Asn Ala Gln Met Lys
            20                  25

<210> SEQ ID NO 307
<211> LENGTH: 26
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (18)..(18)
<223> OTHER INFORMATION: Phosphorylated Tyr

<400> SEQUENCE: 307

Ala Val Ala Ile Phe Tyr Thr Met Ile Thr Pro Met Leu Asn Pro Leu
1               5                   10                  15

Ile Xaa Thr Leu Lys Asn Ala Gln Met Lys
            20                  25

<210> SEQ ID NO 308
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr -continued

```
<400> SEQUENCE: 308

Gly Asp His Pro Leu Thr Pro Gly Ser His Xaa Ala
1               5                  10

<210> SEQ ID NO 309
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 309

Glu Ile Xaa Asp Phe Met Asp Asp Pro Lys
1               5                  10

<210> SEQ ID NO 310
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 310

Gly Asn Ile Asn Pro Ala Xaa Ser Asn Pro Ser Leu Ser Gln Ser Pro
1               5                  10                  15

Gly Asp Ser Glu Glu Tyr
            20

<210> SEQ ID NO 311
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 311

Glu Gly Val Asp Glu Xaa Asn Glu Met Pro Met Pro Val
1               5                  10

<210> SEQ ID NO 312
<211> LENGTH: 18
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 312

Gly Gly Glu Glu Pro Gly Arg Ser Xaa Gly Glu Glu Asp Phe Glu Tyr
1               5                  10                  15
```

His Arg

<210> SEQ ID NO 313
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (14)..(14)
<223> OTHER INFORMATION: Phosphorylated Tyr

<400> SEQUENCE: 313

Gly Ser Leu Asp Ser Asp Asn Asp Asp Ser Asp Cys Pro Xaa Ser Glu
1               5                   10                  15

Lys

<210> SEQ ID NO 314
<211> LENGTH: 32
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (21)..(21)
<223> OTHER INFORMATION: Phosphorylated Tyr

<400> SEQUENCE: 314

Glu Glu Gly Asn Pro Val Ala Ser Leu Gly His Ser Glu Ala Glu Thr
1               5                   10                  15

Pro Val Asp Ala Xaa Ser Asn Gly Gln Ala Ala Leu Met Gly Glu Lys
            20                  25                  30

<210> SEQ ID NO 315
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (17)..(17)
<223> OTHER INFORMATION: Phosphorylated Tyr

<400> SEQUENCE: 315

Glu Arg Pro Gln Pro Ala Pro Cys Thr Val Gly Phe Val Asp Cys Leu
1               5                   10                  15

Xaa Gly Thr Val Pro Lys
            20

<210> SEQ ID NO 316
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 316

Ser Gly Gly Xaa Gly Gly Ser Arg Asp Tyr Tyr Ser Ser Arg

```
<210> SEQ ID NO 317
<211> LENGTH: 39
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (24)..(24)
<223> OTHER INFORMATION: Phosphorylated Tyr

<400> SEQUENCE: 317

Ser Gly Pro Glu Ala Glu Gly Leu Gly Ser Glu Thr Ser Pro Thr Val
1               5                   10                  15

Asp Asp Glu Glu Glu Met Leu Xaa Gly Asp Ser Gly Ser Leu Phe Ser
            20                  25                  30

Pro Ser Lys Glu Glu Ala Arg
        35

<210> SEQ ID NO 318
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 318

Asn Gln Ala Ile Xaa Ala Ala Val Asp Asp Asp Asp Asp Asp Ala Ala
1               5                   10                  15

<210> SEQ ID NO 319
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 319

Thr Asp Ala Val Xaa Asp Leu Pro Ser Ser Ser Glu
1               5                   10

<210> SEQ ID NO 320
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 320

Val Trp Xaa His Val Cys Ser Ser Arg
1               5
```

```
<210> SEQ ID NO 321
<211> LENGTH: 18
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr

<400> SEQUENCE: 321

Glu Ala Gln Thr Ser Phe Leu His Leu Gly Xaa Leu Pro Asn Gln Leu
1               5                   10                  15

Phe Arg

<210> SEQ ID NO 322
<211> LENGTH: 31
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (14)..(14)
<223> OTHER INFORMATION: Phosphorylated Tyr

<400> SEQUENCE: 322

Leu Phe Ser Gly Gly Asn Thr Gly Ile Asn Phe Glu Lys Xaa Asp Asp
1               5                   10                  15

Ile Pro Val Glu Ala Thr Gly Asn Asn Cys Pro Pro His Ile Glu
            20                  25                  30

<210> SEQ ID NO 323
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 323

Glu Leu Ala Val Gln Ile Xaa Glu Glu Ala Arg
1               5                   10

<210> SEQ ID NO 324
<211> LENGTH: 24
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (15)..(15)
<223> OTHER INFORMATION: Phosphorylated Tyr

<400> SEQUENCE: 324

Lys Gly Ala Asp Ser Leu Glu Asp Phe Leu Tyr His Glu Gly Xaa Ala
1               5                   10                  15

Cys Thr Ser Ile His Gly Asp Arg
            20
```

```
<210> SEQ ID NO 325
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 325

Asn Asp Leu Leu Asp Xaa Asp Glu Glu Glu Pro Gln Ala Pro Gln
1               5                   10                  15

Glu

<210> SEQ ID NO 326
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 326

Thr Ala Ala Phe Leu Leu Pro Ile Leu Ser Gln Ile Xaa Thr Asp Gly
1               5                   10                  15

Pro Gly Glu Ala Leu Lys
            20

<210> SEQ ID NO 327
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 327

Glu Leu Ala Val Gln Ile Xaa Glu Glu Ala Arg
1               5                   10

<210> SEQ ID NO 328
<211> LENGTH: 24
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (15)..(15)
<223> OTHER INFORMATION: Phosphorylated Tyr

<400> SEQUENCE: 328

Lys Gly Ala Asp Ser Leu Glu Asp Phe Leu Tyr His Glu Gly Xaa Ala
1               5                   10                  15

Cys Thr Ser Ile His Gly Asp Arg
            20
```

```
<210> SEQ ID NO 329
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 329

Thr Gly Thr Ala Xaa Thr Phe Phe Thr Pro Asn Asn Ile Lys
1               5                   10

<210> SEQ ID NO 330
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 330

Ser Arg Gly Gln Gly Xaa Val Gly Gly Gln Arg
1               5                   10

<210> SEQ ID NO 331
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 331

Asn Tyr Tyr Gly Xaa Gln Gly Tyr Arg
1               5

<210> SEQ ID NO 332
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 332

Asn Tyr Tyr Gly Tyr Gln Gly Xaa Arg
1               5

<210> SEQ ID NO 333
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
```

```
<220> FEATURE:
<221> NAME/KEY: mod_res
<222> LOCATION: (6)..(6)
<223> OTHER INFORMATION: Phosphorylated Tyr

<400> SEQUENCE: 333

Ser Ser Glu Gln Asp Xaa Tyr Ser Asn Met Arg Gln Glu
1               5                   10

<210> SEQ ID NO 334
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 334

Gln Asn Gln Phe Xaa Asp Thr Gln Val Ile Lys Gln Glu Asn Glu Ser
1               5                   10                  15

Gly Tyr Glu Arg
            20

<210> SEQ ID NO 335
<211> LENGTH: 18
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 335

Thr Asn Leu Ile Val Asn Xaa Leu Pro Gln Asn Met Thr Gln Asp Glu
1               5                   10                  15

Leu Arg

<210> SEQ ID NO 336
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 336

His Gly Xaa Ile Phe Ser Ser Leu Ala Gly Cys Leu Met Lys
1               5                   10

<210> SEQ ID NO 337
<211> LENGTH: 18
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
```

-continued

<223> OTHER INFORMATION: Phosphorylated Tyr

<400> SEQUENCE: 337

Glu Ser Ile Gly Asn Val Gln Val Leu Leu Glu Xaa His Ile Ala Tyr
1               5                   10                  15

Leu Lys

<210> SEQ ID NO 338
<211> LENGTH: 18
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (16)..(16)
<223> OTHER INFORMATION: Phosphorylated Tyr

<400> SEQUENCE: 338

Glu Ser Ile Gly Asn Val Gln Val Leu Leu Glu Tyr His Ile Ala Xaa
1               5                   10                  15

Leu Lys

<210> SEQ ID NO 339
<211> LENGTH: 8
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 339

Gly Phe Xaa Asp Pro Pro Arg Arg
1               5

<210> SEQ ID NO 340
<211> LENGTH: 31
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (18)..(18)
<223> OTHER INFORMATION: Phosphorylated Tyr

<400> SEQUENCE: 340

Gly Gly Asp Gly Tyr Asp Gly Tyr Gly Phe Asp Asp Tyr Gly
1               5                   10                  15

Gly Xaa Asn Asn Tyr Gly Tyr Gly Asn Asp Gly Phe Asp Asp Arg
            20                  25                  30

<210> SEQ ID NO 341
<211> LENGTH: 26
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 341

Gly Met Gly Gly His Gly Xaa Gly Gly Ala Gly Asp Ala Ser Ser Gly
1               5                   10                  15

Phe His Gly Gly His Phe Val His Met Arg
            20                  25

<210> SEQ ID NO 342
<211> LENGTH: 26
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 342

Gly Ala Xaa Gly Gly Gly Tyr Gly Gly Tyr Asp Asp Tyr Asn Gly Tyr
1               5                   10                  15

Asn Asp Gly Tyr Gly Phe Gly Ser Asp Arg
            20                  25

<210> SEQ ID NO 343
<211> LENGTH: 26
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 343

Gly Ala Tyr Gly Gly Gly Xaa Gly Gly Tyr Asp Asp Tyr Asn Gly Tyr
1               5                   10                  15

Asn Asp Gly Tyr Gly Phe Gly Ser Asp Arg
            20                  25

<210> SEQ ID NO 344
<211> LENGTH: 26
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (20)..(20)
<223> OTHER INFORMATION: Phosphorylated Tyr

<400> SEQUENCE: 344

Gly Ala Tyr Gly Gly Gly Tyr Gly Gly Tyr Asp Asp Tyr Asn Gly Tyr
1               5                   10                  15

Asn Asp Gly Xaa Gly Phe Gly Ser Asp Arg
            20                  25

<210> SEQ ID NO 345
<211> LENGTH: 22
<212> TYPE: PRT
<213> ORGANISM: Artificial sequence
<220> FEATURE:
<223> OTHER INFORMATION: Description of Artificial Sequence: Synthetic
      peptide

```
<220> FEATURE:
<221> NAME/KEY: mod_res
<222> LOCATION: (4)..(4)
<223> OTHER INFORMATION: Phosphorylated Tyr

<400> SEQUENCE: 345

Gly Leu Pro Xaa Arg Ala Thr Glu Asn Asp Ile Tyr Asn Phe Phe Ser
1               5                   10                  15

Pro Leu Asn Pro Met Arg
            20

<210> SEQ ID NO 346
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 346

Phe Xaa Gln Asp Thr Tyr Gly Gln Gln Trp Lys
1               5                   10

<210> SEQ ID NO 347
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 347

Phe Tyr Gln Asp Thr Xaa Gly Gln Gln Trp Lys
1               5                   10

<210> SEQ ID NO 348
<211> LENGTH: 27
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (17)..(17)
<223> OTHER INFORMATION: Phosphorylated Tyr

<400> SEQUENCE: 348

Gly Asn Phe Thr Leu Pro Glu Val Ala Glu Cys Phe Asp Glu Ile Thr
1               5                   10                  15

Xaa Val Glu Leu Gln Lys Glu Glu Ala Gln Lys
            20                  25

<210> SEQ ID NO 349
<211> LENGTH: 33
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
```

<222> LOCATION: (12)..(12)
<223> OTHER INFORMATION: Phosphorylated Tyr

<400> SEQUENCE: 349

Gly Gly Gly Gly Tyr Gly Gly Ser Gly Asp Gly Xaa Asn Gly Phe Gly
1               5                   10                  15

Asn Asp Gly Gly Tyr Gly Gly Gly Pro Gly Tyr Ser Gly Gly Ser
            20                  25                  30

Arg

<210> SEQ ID NO 350
<211> LENGTH: 33
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (21)..(21)
<223> OTHER INFORMATION: Phosphorylated Tyr

<400> SEQUENCE: 350

Gly Gly Gly Gly Tyr Gly Gly Ser Gly Asp Gly Tyr Asn Gly Phe Gly
1               5                   10                  15

Asn Asp Gly Gly Xaa Gly Gly Gly Pro Gly Tyr Ser Gly Gly Ser
            20                  25                  30

Arg

<210> SEQ ID NO 351
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 351

Glu Gly Gln Glu Asp Gln Gly Leu Thr Lys Asp Xaa Gly Asn Ser Pro
1               5                   10                  15

Leu His Arg

<210> SEQ ID NO 352
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 352

Gly Gln Gly Gly Ala Xaa Ala Phe Leu Lys
1               5                   10

<210> SEQ ID NO 353
<211> LENGTH: 16
<212> TYPE: PRT
<213> ORGANISM: Artificial sequence
<220> FEATURE:

```
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 353

Thr Gly Xaa Ala Phe Val Asp Cys Pro Asp Glu Ser Trp Ala Leu Lys
1               5                   10                  15

<210> SEQ ID NO 354
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 354

Pro Lys Glu Asp Ala Xaa Glu Tyr Lys
1               5

<210> SEQ ID NO 355
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 355

Pro Lys Glu Asp Ala Tyr Glu Xaa Lys
1               5

<210> SEQ ID NO 356
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 356

Ile Ile Asn Asp Asn Ala Thr Xaa Cys Arg
1               5                   10

<210> SEQ ID NO 357
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 357
```

```
Gly Ala Pro Gly Gly Ala Gly Asp Xaa Gly Asn Gly Leu Glu
1               5                   10

<210> SEQ ID NO 358
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 358

Gly Met Gly Pro Gly Thr Pro Ala Gly Xaa Gly Arg
1               5                   10

<210> SEQ ID NO 359
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 359

Gly Thr Trp Ala Thr Ser Glu Glu Pro Pro Val Asp Xaa Ser Tyr Tyr
1               5                   10                  15

Gln Gln Asp Glu
            20

<210> SEQ ID NO 360
<211> LENGTH: 37
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (17)..(17)
<223> OTHER INFORMATION: Phosphorylated Tyr

<400> SEQUENCE: 360

Gly Gln Pro Gly Asn Ala Tyr Asp Gly Ala Gly Gln Pro Ser Ala Ala
1               5                   10                  15

Xaa Leu Ser Met Ser Gln Gly Ala Val Ala Asn Ala Asn Ser Thr Pro
            20                  25                  30

Pro Pro Tyr Glu Arg
        35

<210> SEQ ID NO 361
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr
```

-continued

```
<400> SEQUENCE: 361

Glu Arg Asp Tyr Pro Phe Xaa Glu Arg
1               5

<210> SEQ ID NO 362
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 362

Gly Gln Thr Ser Thr Xaa Gly Phe Leu Lys
1               5                   10

<210> SEQ ID NO 363
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 363

Phe Glu Asp Pro Arg Asp Ala Asp Asp Ala Val Xaa Glu
1               5                   10

<210> SEQ ID NO 364
<211> LENGTH: 18
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 364

Gly Gly Glu Gly Asp Gly Arg Ile Xaa Val Gly Asn Leu Pro Thr Asp
1               5                   10                  15

Val Arg

<210> SEQ ID NO 365
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 365

Glu Lys Asp Leu Glu Asp Leu Phe Xaa Lys Tyr Gly Arg
1               5                   10
```

```
<210> SEQ ID NO 366
<211> LENGTH: 23
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 366

Glu Asn Pro Xaa Ala Asn Ala Gly Lys Asn Pro Asp Glu Val Ser Tyr
1               5                   10                  15

Ala Gly Asp Asn Phe Val Arg
            20

<210> SEQ ID NO 367
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 367

Gly Leu Gly Asn Asp Ser Arg Asp Met Xaa Met Glu
1               5                   10

<210> SEQ ID NO 368
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 368

Leu Gly Glu Leu Phe Asn Pro Tyr Xaa Asp Pro Leu Gln Trp Lys
1               5                   10                  15

<210> SEQ ID NO 369
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (1)..(1)
<223> OTHER INFORMATION: Phosphorylated Tyr

<400> SEQUENCE: 369

Xaa Gly Thr Cys Ile Tyr Gln Gly Arg
1               5

<210> SEQ ID NO 370
<211> LENGTH: 9
<212> TYPE: PRT
<213> ORGANISM: Artificial sequence
<220> FEATURE:
```

```
<223> OTHER INFORMATION: Description of Artificial Sequence: Synthetic
      peptide
<220> FEATURE:
<221> NAME/KEY: mod_res
<222> LOCATION: (1)..(1)
<223> OTHER INFORMATION: Phosphorylated Tyr

<400> SEQUENCE: 370

Xaa Gly Thr Cys Ile Tyr Gln Gly Arg
1               5

<210> SEQ ID NO 371
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 371

Tyr Gly Thr Cys Ile Xaa Gln Gly Arg
1               5

<210> SEQ ID NO 372
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 372

Leu Xaa Gly Leu Glu Pro Ala His Pro Leu Leu Tyr Ser Arg
1               5                   10

<210> SEQ ID NO 373
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 373

Leu Tyr Gly Leu Glu Pro Ala His Pro Leu Leu Xaa Ser Arg
1               5                   10

<210> SEQ ID NO 374
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 374
```

Gly Gly Ser Thr Ser Xaa Gly Thr Gly Ser Glu Thr Glu Ser Pro Arg
1               5                   10                  15

<210> SEQ ID NO 375
<211> LENGTH: 21
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 375

Leu Arg Arg Asp Ala Gly Gly Arg Gly Gly Val Xaa Glu His Leu Gly
1               5                   10                  15

Gly Ala Pro Arg Arg
            20

<210> SEQ ID NO 376
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 376

Trp Tyr Asp Leu Glu Tyr Ser Asn Glu Xaa Ser Leu Lys Pro Gln Pro
1               5                   10                  15

Gln Asp Val Val Ser Lys
            20

<210> SEQ ID NO 377
<211> LENGTH: 31
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 377

Tyr Cys Gly His Leu Xaa Gly Leu Gly Ser Gly Ser Ser Tyr Val Gln
1               5                   10                  15

Asn Gly Thr Gly Asn Ala Tyr Glu Glu Glu Ala Asn Lys Gln Ser
            20                  25                  30

<210> SEQ ID NO 378
<211> LENGTH: 33
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (22)..(22)
<223> OTHER INFORMATION: Phosphorylated Tyr -continued

```
<400> SEQUENCE: 378

Phe Gly Leu Gly Ser Leu Ala His Ser Ile Pro Leu Gly Gln Ala Asp
1               5                   10                  15

Pro Ser Leu Ala Pro Xaa Ile Ile Asp Leu Pro Ser Trp Thr Gln Phe
            20                  25                  30

Arg

<210> SEQ ID NO 379
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 379

Gly Thr Ser Gln Tyr Xaa Pro Ser Tyr Ser Gly Ser Ser Arg
1               5                   10

<210> SEQ ID NO 380
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 380

Gly Thr Ser Gln Tyr Tyr Pro Ser Xaa Ser Gly Ser Ser Arg
1               5                   10

<210> SEQ ID NO 381
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 381

Glu Asp Val Lys Pro Xaa Gln Val Asn Gly Val Asn Pro Ala Tyr Pro
1               5                   10                  15

Glu Ser Arg

<210> SEQ ID NO 382
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 382
```

```
Ile Thr Gly Asp Pro Xaa Lys Val Gln Gln Ala Lys
1               5                   10

<210> SEQ ID NO 383
<211> LENGTH: 24
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 383

Gln Gln Ala Ala Xaa Tyr Ala Gln Thr Ser Pro Gln Gly Met Pro Gln
1               5                   10                  15

His Pro Pro Ala Pro Gln Gly Gln
            20

<210> SEQ ID NO 384
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (14)..(14)
<223> OTHER INFORMATION: Phosphorylated Tyr

<400> SEQUENCE: 384

Glu Asp Gln Leu Leu Cys Thr Asp Cys Tyr Ser Asn Glu Xaa Ser Ser
1               5                   10                  15

Lys

<210> SEQ ID NO 385
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 385

His Pro Asn Thr His Val Pro Ser His Leu Gly Ser Xaa Tyr
1               5                   10

<210> SEQ ID NO 386
<211> LENGTH: 25
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 386

Gly Pro Gly Pro Glu Gly Gly Gly Gly Ser Xaa Phe Ser Gly Gln
1               5                   10                  15
```

```
Gly Ser Asp Thr Gly Ala Ser Leu Lys
            20                  25

<210> SEQ ID NO 387
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (14)..(14)
<223> OTHER INFORMATION: Phosphorylated Tyr

<400> SEQUENCE: 387

Gly His Leu Ser Arg Pro Glu Ala Gln Ser Leu Ser Pro Xaa Thr Thr
1               5                   10                  15

Ser Ala Asn Arg
            20

<210> SEQ ID NO 388
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 388

Phe Arg Xaa Gly Cys Glu Gly Pro Ser His Gly Gly Leu Pro Gly Ala
1               5                   10                  15

Ser Ser Glu Lys
            20

<210> SEQ ID NO 389
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 389

Arg Pro Gly Gly Met Thr Ser Thr Xaa Gly Arg
1               5                   10

<210> SEQ ID NO 390
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 390

Thr Pro Met Xaa Gly Ser Gln Thr Pro Met Tyr Gly Ser Gly Ser Arg
```

```
<210> SEQ ID NO 391
<211> LENGTH: 24
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 391

Glu Gly Met Asn Pro Ser Xaa Asp Glu Tyr Ala Asp Ser Asp Glu Asp
1               5                   10                  15

Gln His Asp Ala Tyr Leu Glu Arg
            20

<210> SEQ ID NO 392
<211> LENGTH: 8
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 392

Leu Pro Leu Gln Asp Val Xaa Lys
1               5

<210> SEQ ID NO 393
<211> LENGTH: 8
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 393

Leu Pro Leu Gln Asp Val Xaa Lys
1               5

<210> SEQ ID NO 394
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 394

Lys Xaa Ile Val Asp Phe Leu Met Glu Asn Gly Ser Ile Thr Ser Ile
1               5                   10                  15

Arg
```

```
<210> SEQ ID NO 395
<211> LENGTH: 23
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 395

Trp Val Xaa Pro Leu Thr Pro Glu Ala Asn Phe Thr Asp Ser Thr Thr
1               5                   10                  15

Gln Ser Cys Thr His Ser Arg
            20

<210> SEQ ID NO 396
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 396

Ser Xaa Ser Ser Gly Gly Glu Asp Gly Tyr Val Arg
1               5                   10

<210> SEQ ID NO 397
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 397

Gln Leu Glu Val Xaa Thr Ser Gly Gly Asp Pro Glu Ser Val Ala Gly
1               5                   10                  15

Glu Tyr Gly Arg
            20

<210> SEQ ID NO 398
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 398

Leu His Ser Leu Leu Gly Asp Xaa Tyr Gln Ala Ile Lys
1               5                   10

<210> SEQ ID NO 399
<211> LENGTH: 13
```

-continued

```
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 399

Leu His Ser Leu Leu Gly Asp Tyr Xaa Gln Ala Ile Lys
1               5                   10

<210> SEQ ID NO 400
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 400

Thr Thr Tyr Lys Xaa Glu Met Ile Asn Lys
1               5                   10

<210> SEQ ID NO 401
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (1)..(1)
<223> OTHER INFORMATION: Phosphorylated Tyr

<400> SEQUENCE: 401

Xaa Leu Ile Leu Lys Asp Pro Asn Lys
1               5

<210> SEQ ID NO 402
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (1)..(1)
<223> OTHER INFORMATION: Phosphorylated Tyr

<400> SEQUENCE: 402

Xaa Asp Asp Arg Gly Ser Arg Asp Tyr Asp Arg Gly Tyr Asp Ser Arg
1               5                   10                  15

<210> SEQ ID NO 403
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
```

<223> OTHER INFORMATION: Phosphorylated Tyr

<400> SEQUENCE: 403

Ala Lys Ala Gly Glu Gly Thr Xaa Ala Leu Asp Ser Glu
1               5                   10

<210> SEQ ID NO 404
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 404

Gly Ala Thr Xaa Gly Lys Pro Val His His Gly Val Asn Gln Leu Lys
1               5                   10                  15

<210> SEQ ID NO 405
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 405

Phe Trp Xaa Phe Val Ser Gln Leu Lys
1               5

<210> SEQ ID NO 406
<211> LENGTH: 21
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 406

Phe Asn Leu Asn Gln Xaa Leu Pro Asn Phe Tyr Pro Leu Asp Met Ser
1               5                   10                  15

Glu Pro Gln Thr Lys
            20

<210> SEQ ID NO 407
<211> LENGTH: 21
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (15)..(15)
<223> OTHER INFORMATION: Phosphorylated Tyr

<400> SEQUENCE: 407

Gly Thr Gly Glu Asn Ser Thr Cys Arg Glu Pro His Ala Pro Xaa Pro

```
1               5                   10                  15
Pro Gly Tyr Gln Arg
                20

<210> SEQ ID NO 408
<211> LENGTH: 21
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (19)..(19)
<223> OTHER INFORMATION: Phosphorylated Tyr

<400> SEQUENCE: 408

Gly Thr Gly Glu Asn Ser Thr Cys Arg Glu Pro His Ala Pro Tyr Pro
1               5                   10                  15

Pro Gly Xaa Gln Arg
                20

<210> SEQ ID NO 409
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (16)..(16)
<223> OTHER INFORMATION: Phosphorylated Tyr

<400> SEQUENCE: 409

Ser Met Gly Ser Gln Glu Asp Asp Ser Gly Asn Lys Pro Ser Ser Xaa
1               5                   10                  15

Ser

<210> SEQ ID NO 410
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 410

Gly Gln Gly Phe Thr Asp Gly Val Xaa Gln Gly Lys
1               5                   10

<210> SEQ ID NO 411
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 411

Ser Glu Leu Phe Xaa Thr Leu Asn Gly Ser Ser Val Asp Ser Gln Pro
```

```
1               5                  10                  15

Gln Ser Lys

<210> SEQ ID NO 412
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 412

Gln Gln Gln Asp Glu Ala Xaa Leu Ala Ser Leu Arg
1               5                  10

<210> SEQ ID NO 413
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 413

Gly Met Phe Phe Asn Pro Asp Pro Xaa Leu Lys
1               5                  10

<210> SEQ ID NO 414
<211> LENGTH: 18
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (14)..(14)
<223> OTHER INFORMATION: Phosphorylated Tyr

<400> SEQUENCE: 414

Gly Ser Gln Leu Tyr Pro Ala Gln Gln Thr Asp Val Tyr Xaa Gln Asp
1               5                  10                  15

Pro Arg

<210> SEQ ID NO 415
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 415

Glu Glu Ile Phe Glu Glu Ser Xaa Arg Gln Ile Met Lys
1               5                  10

<210> SEQ ID NO 416
```

```
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 416

Met Ala Gly Ile Ala Gln Gly Val Xaa Ser Arg
1               5                   10

<210> SEQ ID NO 417
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 417

Gly Xaa Gly Leu Leu His Thr Ala Ala Ala Ser Gly Gln Ile Glu Val
1               5                   10                  15

Val Lys Tyr Leu Leu Arg
            20

<210> SEQ ID NO 418
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 418

Leu Gln His Ala Leu Glu Asp Gln Ile Xaa Arg
1               5                   10

<210> SEQ ID NO 419
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 419

Gln Thr Glu Asp Asn Met Leu Phe Xaa Thr Ile Phe Arg
1               5                   10

<210> SEQ ID NO 420
<211> LENGTH: 14
<212> TYPE: PRT
<213> ORGANISM: Artificial sequence
<220> FEATURE:
<223> OTHER INFORMATION: Description of Artificial Sequence: Synthetic
```

```
                            peptide
<220> FEATURE:
<221> NAME/KEY: mod_res
<222> LOCATION: (4)..(4)
<223> OTHER INFORMATION: Phosphorylated Tyr

<400> SEQUENCE: 420

Val Thr Arg Xaa Pro Ile Leu Gly Ile Pro Gln Ala His Arg
1               5                   10

<210> SEQ ID NO 421
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (1)..(1)
<223> OTHER INFORMATION: Phosphorylated Tyr

<400> SEQUENCE: 421

Xaa Ser Thr Asn Ser Pro Asn Tyr Arg
1               5

<210> SEQ ID NO 422
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 422

Tyr Ser Thr Asn Ser Pro Asn Xaa Arg
1               5

<210> SEQ ID NO 423
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr

<400> SEQUENCE: 423

Leu Ser Ser Ile Pro Gly Glu Ser Leu Thr Xaa Ala Ser Thr Thr Phe
1               5                   10                  15

Lys

<210> SEQ ID NO 424
<211> LENGTH: 21
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (17)..(17)
<223> OTHER INFORMATION: Phosphorylated Tyr
```

```
<400> SEQUENCE: 424

Ser Asn His Leu Ala Glu Asn His Ser Ala Asp Phe Asp Pro Ile Val
1               5                   10                  15

Xaa Ala Gln Ile Lys
            20

<210> SEQ ID NO 425
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 425

Asn Tyr Gln Asn Gly Asp Val Phe Gly Asp Glu Xaa Arg
1               5                   10

<210> SEQ ID NO 426
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 426

Ser Ala Ser Tyr Xaa Ala Trp Ser Pro Pro Gly Thr Tyr Lys
1               5                   10

<210> SEQ ID NO 427
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 427

Thr Asn Lys Val Xaa Asp Ile Thr Glu Arg
1               5                   10

<210> SEQ ID NO 428
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr

<400> SEQUENCE: 428

Leu Lys Ala Ser Glu Asn Ser Glu Ser Glu Xaa Ser Arg
1               5                   10
```

```
<210> SEQ ID NO 429
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 429

Glu Leu Leu Ser Pro Xaa Ser Pro Val Leu Lys Phe Phe Met Val Lys
1               5                   10                  15

<210> SEQ ID NO 430
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 430

Leu Ala Xaa Ser Gly Ser Glu Ser Gly Ala Asp Gly Arg
1               5                   10

<210> SEQ ID NO 431
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 431

Ile Gln Xaa Glu Met Glu Tyr Thr Glu Gly Ile Ser Gln Arg
1               5                   10

<210> SEQ ID NO 432
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 432

Ile Gln Tyr Glu Met Glu Xaa Thr Glu Gly Ile Ser Gln Arg
1               5                   10

<210> SEQ ID NO 433
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
```

```
<220> FEATURE:
<221> NAME/KEY: mod_res
<222> LOCATION: (6)..(6)
<223> OTHER INFORMATION: Phosphorylated Tyr

<400> SEQUENCE: 433

Ser Ile Leu Leu Leu Xaa Ala Thr Tyr Lys
1               5                   10

<210> SEQ ID NO 434
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 434

Gln Met Leu Arg Ser Ile Leu Leu Leu Tyr Ala Thr Xaa Lys Lys
1               5                   10                  15

<210> SEQ ID NO 435
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 435

Asn Val Xaa Phe Ala Gln Tyr Gly Glu Pro Arg Glu Gly Gly Arg Arg
1               5                   10                  15

Arg

<210> SEQ ID NO 436
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 436

Asn Val Tyr Phe Ala Gln Xaa Gly Glu Pro Arg Glu Gly Gly Arg Arg
1               5                   10                  15

Arg

<210> SEQ ID NO 437
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr
```

```
<400> SEQUENCE: 437

Thr Thr Val Xaa Val Val Glu Asp Gln Arg
1               5                   10

<210> SEQ ID NO 438
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 438

Phe Glu Gly Xaa Asp Asn Pro Glu Asn Leu Lys
1               5                   10

<210> SEQ ID NO 439
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 439

His Tyr Val Xaa Ser Thr Leu Thr Arg
1               5

<210> SEQ ID NO 440
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 440

Phe Asn Thr Glu Gln Ile Gln Xaa Arg
1               5

<210> SEQ ID NO 441
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 441

Ser Ser Pro Leu Leu Asn Tyr Asn Thr Gly Val Xaa Arg
1               5                   10

<210> SEQ ID NO 442
```

-continued

```
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 442

Glu Ser Lys Arg Phe Ser Ala Xaa Asn Tyr Arg Thr Tyr Ala Val Arg
1               5                   10                  15

<210> SEQ ID NO 443
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 443

Glu Ser Lys Arg Phe Ser Ala Tyr Asn Xaa Arg Thr Tyr Ala Val Arg
1               5                   10                  15

<210> SEQ ID NO 444
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 444

Glu Ser Lys Arg Phe Ser Ala Tyr Asn Tyr Arg Thr Xaa Ala Val Arg
1               5                   10                  15

<210> SEQ ID NO 445
<211> LENGTH: 18
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 445

Ser Ser Glu Val Leu Xaa Glu Arg Pro Gln Pro Thr Pro Ala Phe Ser
1               5                   10                  15

Ser Arg

<210> SEQ ID NO 446
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
```

```
<220> FEATURE:
<221> NAME/KEY: mod_res
<222> LOCATION: (5)..(5)
<223> OTHER INFORMATION: Phosphorylated Tyr

<400> SEQUENCE: 446

Ser Glu Glu Val Xaa Cys Leu Gln Lys
1               5

<210> SEQ ID NO 447
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 447

Ser Xaa Val Thr Met Thr Ala Thr Lys Ile Glu Ile Thr Met Arg
1               5                   10                  15

<210> SEQ ID NO 448
<211> LENGTH: 21
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 448

Val Thr Leu Pro Asn Xaa Asp Asn Val Pro Gly Asn Leu Met Leu Ser
1               5                   10                  15

Ala Leu Gly Leu Arg
            20

<210> SEQ ID NO 449
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 449

Ser Thr Asp Gly Gln Glu Pro His Ser Val Val Xaa Asp Thr Ser Asn
1               5                   10                  15

Gly Lys Lys

<210> SEQ ID NO 450
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
```

```
<223> OTHER INFORMATION: Phosphorylated Tyr

<400> SEQUENCE: 450

Ile Asp Lys Asn Ser Thr Ala Ser Tyr Leu Lys Asn Xaa Pro Leu Tyr
1               5                   10                  15
Arg

<210> SEQ ID NO 451
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 451

Lys Gly Asn Phe Phe Met Gly Gly Ser Asp Gly Gly Xaa Thr Ile Trp
1               5                   10                  15

<210> SEQ ID NO 452
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 452

Thr Leu Ser Glu Glu Asn Val Xaa Glu Asp Ile Leu Asp Pro Pro Met
1               5                   10                  15
Lys

<210> SEQ ID NO 453
<211> LENGTH: 25
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 453

Ser Leu Glu Asn Ile Xaa Ser Glu Pro Glu Gly Gln Glu Cys Gly Pro
1               5                   10                  15
Ser Ile Asn Pro Leu Pro Lys Pro Arg
            20                  25

<210> SEQ ID NO 454
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr
```

-continued

<400> SEQUENCE: 454

Glu Leu Leu Phe Asp Ala Ile Gly Arg Xaa Tyr Ser Ser Arg
1               5                   10

<210> SEQ ID NO 455
<211> LENGTH: 19
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (13)..(13)
<223> OTHER INFORMATION: Phosphorylated Tyr

<400> SEQUENCE: 455

Thr Leu Met Leu Asn Glu Asp Lys Pro Ser Asp Asp Xaa Ser Ala Val
1               5                   10                  15

Leu Gln Arg

<210> SEQ ID NO 456
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 456

Tyr Asp Xaa Phe Ala Gln Gln Thr Arg
1               5

<210> SEQ ID NO 457
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 457

Glu Asp Gln Lys Xaa Ala Leu Ser Val Met Met Lys
1               5                   10

<210> SEQ ID NO 458
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 458

Val Ser Ser Gly Val Xaa Glu Pro Val Val Ile Glu Ser His
1               5                   10

<210> SEQ ID NO 459
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 459

His Ser Gln Ser Leu Thr Met Ala Pro Xaa Ser Ser Val Ser Leu Val
1               5                   10                  15

Glu Gln Leu Glu Asp Arg
            20

<210> SEQ ID NO 460
<211> LENGTH: 35
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (22)..(22)
<223> OTHER INFORMATION: Phosphorylated Tyr

<400> SEQUENCE: 460

Gln Glu Pro Ser Gly Met Ala Glu Gly Ala Thr Thr Ala Asp Val Asp
1               5                   10                  15

Ala Gly Ser Leu Ser Xaa Trp Pro Gly Gln Ser Glu Gln Pro Ala Pro
            20                  25                  30

Val Leu Arg
        35

<210> SEQ ID NO 461
<211> LENGTH: 29
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (18)..(18)
<223> OTHER INFORMATION: Phosphorylated Tyr

<400> SEQUENCE: 461

Asn Ala Ala Asp Leu Pro Pro Pro Leu Pro Asn Lys Pro Pro Pro Glu
1               5                   10                  15

Asp Xaa Tyr Glu Glu Ala Leu Pro Leu Gly Pro Gly Lys
            20                  25

<210> SEQ ID NO 462
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 462

```
Gly Gln Glu Asn Gln Leu Val Ala Leu Ile Pro Xaa Ser Asp Gln Arg
1               5                   10                  15

<210> SEQ ID NO 463
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 463

Thr Asp Pro Glu Glu Phe Thr Tyr Asp Xaa Val Asp Ala Asp Arg
1               5                   10                  15

<210> SEQ ID NO 464
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 464

Asn Leu His His Thr Gln Glu Leu Leu Xaa Glu Ser Thr Lys Asp Phe
1               5                   10                  15

Leu Gln Leu Arg
            20

<210> SEQ ID NO 465
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 465

Ile Ala Ala Xaa Ala Tyr Ser Ala Leu Ser Gln Ile Arg
1               5                   10

<210> SEQ ID NO 466
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 466

Lys Leu Xaa Pro Gln Leu Ser Ser Val His Gln Lys
1               5                   10
```

```
<210> SEQ ID NO 467
<211> LENGTH: 21
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 467

Thr Thr Ala Thr Val Asp Thr Xaa Glu Ser Leu Leu Ser Asp Ser Asn
1               5                   10                  15

Ser Asn Gln Ser Arg
            20

<210> SEQ ID NO 468
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (11)..(11)
<223> OTHER INFORMATION: Phosphorylated Tyr

<400> SEQUENCE: 468

Thr Thr Leu Cys Asn Met Leu Ala Glu Asn Xaa Lys Gly Lys
1               5                   10

<210> SEQ ID NO 469
<211> LENGTH: 26
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 469

Gly Ser Glu Glu Xaa Tyr Ser Phe His Glu Ser Asp Leu Asp Leu Pro
1               5                   10                  15

Glu Met Gly Ser Gly Ser Met Ser Ser Arg
            20                  25

<210> SEQ ID NO 470
<211> LENGTH: 26
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 470

Gly Ser Glu Glu Tyr Xaa Ser Phe His Glu Ser Asp Leu Asp Leu Pro
1               5                   10                  15

Glu Met Gly Ser Gly Ser Met Ser Ser Arg
            20                  25
```

-continued

```
<210> SEQ ID NO 471
<211> LENGTH: 30
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 471

His Leu Xaa Ile Asp Asn Ala Tyr Ser Ser Asp Gly Leu Asn Gln Gln
1               5                   10                  15

Leu Ser Gln Pro Gly Glu Ala Pro Cys Glu Ala Asp Tyr Arg
            20                  25                  30

<210> SEQ ID NO 472
<211> LENGTH: 30
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 472

His Leu Tyr Ile Asp Asn Ala Xaa Ser Ser Asp Gly Leu Asn Gln Gln
1               5                   10                  15

Leu Ser Gln Pro Gly Glu Ala Pro Cys Glu Ala Asp Tyr Arg
            20                  25                  30

<210> SEQ ID NO 473
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (9)..(9)
<223> OTHER INFORMATION: Phosphorylated Tyr

<400> SEQUENCE: 473

Gln Asn Gly Thr Glu Asp Glu Ser Xaa Glu Tyr Arg Pro Arg
1               5                   10

<210> SEQ ID NO 474
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 474

Arg Gln Asn Gly Thr Glu Asp Glu Ser Tyr Glu Xaa Arg Pro Arg
1               5                   10                  15

<210> SEQ ID NO 475
```

```
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 475

Glu Thr Ala Pro Thr Ser Ala Xaa Ser Ser Pro Ala Arg
1               5                   10

<210> SEQ ID NO 476
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (4)..(4)
<223> OTHER INFORMATION: Phosphorylated Tyr

<400> SEQUENCE: 476

Gly Arg Val Xaa Asn Tyr Met Asn Ala Val Glu Arg
1               5                   10

<210> SEQ ID NO 477
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 477

Gly Arg Val Tyr Asn Xaa Met Asn Ala Val Glu Arg
1               5                   10

<210> SEQ ID NO 478
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 478

Phe Gln Thr Asn Xaa Ala Ser Thr Thr His Leu Met Thr Gly Lys
1               5                   10                  15

<210> SEQ ID NO 479
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
```

```
<222> LOCATION: (5)..(5)
<223> OTHER INFORMATION: Phosphorylated Tyr

<400> SEQUENCE: 479

Gly Glu Ile Ile Xaa Ser Leu Asp Gly Ser Asp Cys Val His Lys
1               5                   10                  15

<210> SEQ ID NO 480
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 480

Gly Asn Xaa Asp Glu Gly Phe Gly Arg
1               5

<210> SEQ ID NO 481
<211> LENGTH: 13
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 481

Gly Pro Val Asn Xaa Asn Val Thr Thr Glu Phe Glu Lys
1               5                   10

<210> SEQ ID NO 482
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (7)..(7)
<223> OTHER INFORMATION: Phosphorylated Tyr

<400> SEQUENCE: 482

Lys Leu Ser Ser Glu Thr Xaa Ser Gln Ala Lys
1               5                   10

<210> SEQ ID NO 483
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 483

Gly Glu Lys Ile Phe Xaa Leu Ile Arg
1               5
```

```
<210> SEQ ID NO 484
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 484

Gly Ser His Phe Phe Pro Gly Asn Asn Val Ile Xaa Glu Lys
1               5                   10

<210> SEQ ID NO 485
<211> LENGTH: 16
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (8)..(8)
<223> OTHER INFORMATION: Phosphorylated Tyr

<400> SEQUENCE: 485

Glu Phe Ala Ala Thr Asn Ser Xaa Leu Gly Tyr Phe Gly Asp Ala Lys
1               5                   10                  15

<210> SEQ ID NO 486
<211> LENGTH: 25
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (18)..(18)
<223> OTHER INFORMATION: Phosphorylated Tyr

<400> SEQUENCE: 486

Gly Leu Glu Gln Arg Arg Gln Gly Leu Glu Ala Tyr Ile Gln Gly Ile
1               5                   10                  15

Leu Xaa Leu Asn Gln Glu Val Pro Lys
            20                  25

<210> SEQ ID NO 487
<211> LENGTH: 20
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (18)..(18)
<223> OTHER INFORMATION: Phosphorylated Tyr

<400> SEQUENCE: 487

Gly Asn Ala Gly Ser Ala Glu Asp Thr Val Asp Ile Ser Gln Thr Gly
1               5                   10                  15

Val Xaa Thr Glu
            20

<210> SEQ ID NO 488
```

```
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 488

Gly Leu Pro Gln Leu Pro Ser Ser Cys Xaa Ser Val Asp Arg
1               5                   10

<210> SEQ ID NO 489
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 489

Phe Xaa Gly Lys Tyr Thr Ala Glu Ile Lys
1               5                   10

<210> SEQ ID NO 490
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 490

Phe Tyr Gly Lys Xaa Thr Ala Glu Ile Lys
1               5                   10

<210> SEQ ID NO 491
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (2)..(2)
<223> OTHER INFORMATION: Phosphorylated Tyr

<400> SEQUENCE: 491

Ile Xaa Ile Asp Ser Asn Asn Asn Pro Glu Arg
1               5                   10

<210> SEQ ID NO 492
<211> LENGTH: 22
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
```

```
<222> LOCATION: (8)..(8)
<223> OTHER INFORMATION: Phosphorylated Tyr

<400> SEQUENCE: 492

Ser Asn Gly Pro Thr Asp Ser Xaa Ala Ala Ile Ser Gln Val Asp Arg
1               5                   10                  15

Leu Gln Ser Glu Pro Glu
            20

<210> SEQ ID NO 493
<211> LENGTH: 17
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (10)..(10)
<223> OTHER INFORMATION: Phosphorylated Tyr

<400> SEQUENCE: 493

Ser Leu Ser Thr Ser Gly Glu Ser Leu Xaa His Val Leu Gly Leu Asp
1               5                   10                  15

Lys

<210> SEQ ID NO 494
<211> LENGTH: 18
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (12)..(12)
<223> OTHER INFORMATION: Phosphorylated Tyr

<400> SEQUENCE: 494

Thr Thr Gln Leu Thr Ala Asp Ser His Pro Ser Xaa His Thr Asp Gly
1               5                   10                  15

Phe Asn

<210> SEQ ID NO 495
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 495

Val Gln Thr Pro Gln Xaa Leu Asn Pro Phe Asp Glu Pro Glu
1               5                   10

<210> SEQ ID NO 496
<211> LENGTH: 14
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
```

```
<223> OTHER INFORMATION: Phosphorylated Tyr

<400> SEQUENCE: 496

Tyr Asp Glu Ile Phe Xaa Asn Leu Ala Pro Ala Asp Gly Lys
1               5                   10

<210> SEQ ID NO 497
<211> LENGTH: 8
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (6)..(6)
<223> OTHER INFORMATION: Phosphorylated Tyr

<400> SEQUENCE: 497

Arg Tyr Gly Glu Asp Xaa Ser Arg
1               5

<210> SEQ ID NO 498
<211> LENGTH: 15
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (3)..(3)
<223> OTHER INFORMATION: Phosphorylated Tyr

<400> SEQUENCE: 498

Val Ile Xaa Ser Leu Gly Gln Pro Leu Glu Lys Leu Asn His Phe
1               5                   10                  15

<210> SEQ ID NO 499
<211> LENGTH: 12
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (5)..(5)
<223> OTHER INFORMATION: Phosphorylated Tyr

<400> SEQUENCE: 499

Gly Ile Leu Leu Xaa Gly Pro Pro Gly Cys Gly Lys
1               5                   10

<210> SEQ ID NO 500
<211> LENGTH: 32
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: mod_res
<222> LOCATION: (22)..(22)
<223> OTHER INFORMATION: Phosphorylated Tyr

<400> SEQUENCE: 500

Gly Asp Phe Leu Ala Ser Leu Glu Asn Asp Ile Lys Pro Ala Phe Gly
1               5                   10                  15
```

```
Thr Asn Gln Glu Asp Xaa Ala Ser Tyr Ile Met Asn Gly Ile Ile Lys
            20                  25                  30
```

TYROSINE PHOSPHORYLATION SITES

RELATED APPLICATIONS

Pursuant to 35 U.S.C. §119(e) this application claims the benefit of, and priority to, provisional application U.S. Ser. No. 60/925,253, filed Apr. 19, 2007, the disclosure of which is incorporated herein, in its entirety, by reference.

FIELD OF THE INVENTION

The invention relates generally to novel tyrosine phosphorylation sites, methods and compositions for detecting, quantitating and modulating same.

BACKGROUND OF THE INVENTION

The activation of proteins by post-translational modification is an important cellular mechanism for regulating most aspects of biological organization and control, including growth, development, homeostasis, and cellular communication. Protein phosphorylation, for example, plays a critical role in the etiology of many pathological conditions and diseases, including to mention but a few: cancer, developmental disorders, autoimmune diseases, and diabetes. Yet, in spite of the importance of protein modification, it is not yet well understood at the molecular level, due to the extraordinary complexity of signaling pathways, and the slow development of technology necessary to unravel it.

Protein phosphorylation on a proteome-wide scale is extremely complex as a result of three factors: the large number of modifying proteins, e.g., kinases, encoded in the genome, the much larger number of sites on substrate proteins that are modified by these enzymes, and the dynamic nature of protein expression during growth, development, disease states, and aging. The human genome, for example, encodes over 520 different protein kinases, making them the most abundant class of enzymes known. (Hunter, Nature 411: 355-65 (2001)). Most kinases phosphorylate many different substrate proteins, at distinct tyrosine, serine, and/or threonine residues. Indeed, it is estimated that one-third of all proteins encoded by the human genome are phosphorylated, and many are phosphorylated at multiple sites by different kinases.

Many of these phosphorylation sites regulate critical biological processes and may prove to be important diagnostic or therapeutic targets for molecular medicine. For example, of the more than 100 dominant oncogenes identified to date, 46 are protein kinases. See Hunter, supra. Understanding which proteins are modified by these kinases will greatly expand our understanding of the molecular mechanisms underlying oncogenic transformation. Therefore, the identification of, and ability to detect, phosphorylation sites on a wide variety of cellular proteins is crucially important to understanding the key signaling proteins and pathways implicated in the progression of disease states like cancer.

Carcinoma and/or leukemia is one of the two main categories of cancer, and is generally characterized by the formation of malignant tumors or cells of epithelial tissue original, such as skin, digestive tract, glands, etc. Carcinoma and/or leukemias are malignant by definition, and tend to metastasize to other areas of the body. The most common forms of carcinoma and/or leukemia are skin cancer, lung cancer, breast cancer, and colon cancer, as well as other numerous but less prevalent carcinoma and/or leukemias. Current estimates show that, collectively, various carcinoma and/or leukemias will account for approximately 1.65 million cancer diagnoses in the United States alone, and more than 300,000 people will die from some type of carcinoma and/or leukemia during 2005. (Source: American Cancer Society (2005)). The worldwide incidence of carcinoma and/or leukemia is much higher.

As with many cancers, deregulation of receptor tyrosine kinases (RTKs) appears to be a central theme in the etiology of carcinoma and/or leukemias. Constitutively active RTKs can contribute not only to unrestricted cell proliferation, but also to other important features of malignant tumors, such as evading apoptosis, the ability to promote blood vessel growth, the ability to invade other tissues and build metastases at distant sites (see Blume-Jensen et al., Nature 411: 355-365 (2001)). These effects are mediated not only through aberrant activity of RTKs themselves, but, in turn, by aberrant activity of their downstream signaling molecules and substrates.

The importance of RTKs in carcinoma and/or leukemia progression has led to a very active search for pharmacological compounds that can inhibit RTK activity in tumor cells, and more recently to significant efforts aimed at identifying genetic mutations in RTKs that may occur in, and affect progression of, different types of carcinoma and/or leukemias (see, e.g., Bardell et al., Science 300: 949 (2003); Lynch et al., N. Eng. J. Med. 350: 2129-2139 (2004)). For example, non-small cell lung carcinoma and/or leukemia patients carrying activating mutations in the epidermal growth factor receptor (EGFR), an RTK, appear to respond better to specific EGFR inhibitors than do patients without such mutations (Lynch et al., supra.; Paez et al., Science 304: 1497-1500 (2004)).

Clearly, identifying activated RTKs and downstream signaling molecules driving the oncogenic phenotype of carcinoma and/or leukemias would be highly beneficial for understanding the underlying mechanisms of this prevalent form of cancer, identifying novel drug targets for the treatment of such disease, and for assessing appropriate patient treatment with selective kinase inhibitors of relevant targets when and if they become available. The identification of key signaling mechanisms is highly desirable in many contexts in addition to cancer.

Leukemia, another form of cancer, is a disease in which a number of underlying signal transduction events have been elucidated and which has become a disease model for phosphoproteomic research and development efforts. As such, it represent a paradigm leading the way for many other programs seeking to address many classes of diseases (See, *Harrison's Principles of Internal Medicine*, McGraw-Hill, New York, N.Y.).

Most varieties of leukemia are generally characterized by genetic alterations e.g., chromosomal translocations, deletions or point mutations resulting in the constitutive activation of protein kinase genes, and their products, particularly tyrosine kinases. The most well known alteration is the oncogenic role of the chimeric BCR-Abl gene. See Nowell, *Science* 132: 1497 (1960)). The resulting BCR-Abl kinase protein is constitutively active and elicits characteristic signaling pathways that have been shown to drive the proliferation and survival of CML cells (see Daley, *Science* 247: 824-830 (1990); Raitano et al., *Biochim. Biophys. Acta*. December 9; 1333(3): F201-16 (1997)).

The recent success of Imanitib (also known as ST1571 or Gleevec®), the first molecularly targeted compound designed to specifically inhibit the tyrosine kinase activity of BCR-Abl, provided critical confirmation of the central role of BCR-Abl signaling in the progression of CML (see Schindler et al., *Science* 289: 1938-1942 (2000); Nardi et al., *Curr. Opin. Hematol.* 11:35-43 (2003)).

The success of Gleevec® now serves as a paradigm for the development of targeted drugs designed to block the activity of other tyrosine kinases known to be involved in many diseased including leukemias and other malignancies (see, e.g., Sawyers, *Curr. Opin. Genet. Dev.* February; 12(1): 111-5 (2002); Druker, *Adv. Cancer Res.* 91:1-30 (2004)). For example, recent studies have demonstrated that mutations in the FLT3 gene occur in one third of adult patients with AML. FLT3 (Fms-like tyrosine kinase 3) is a member of the class III receptor tyrosine kinase (RTK) family including FMS, platelet-derived growth factor receptor (PDGFR) and c-KIT (see Rosnet et al., *Crit. Rev. Oncog.* 4: 595-613 (1993). In 20-27% of patients with AML, internal tandem duplication in the juxta-membrane region of FLT3 can be detected (see Yokota et al., *Leukemia* 11: 1605-1609 (1997)). Another 7% of patients have mutations within the active loop of the second kinase domain, predominantly substitutions of aspartate residue 835 (D835), while additional mutations have been described (see Yamamoto et al., *Blood* 97: 2434-2439 (2001); Abu-Duhier et al., *Br. J. Haematol.* 113: 983-988 (2001)). Expression of mutated FLT3 receptors results in constitutive tyrosine phosphorylation of FLT3, and subsequent phosphorylation and activation of downstream molecules such as STAT5, Akt and MAPK, resulting in factor-independent growth of hematopoietic cell lines.

Altogether, FLT3 is the single most common activated gene in AML known to date. This evidence has triggered an intensive search for FLT3 inhibitors for clinical use leading to at least four compounds in advanced stages of clinical development, including: PKC412 (by Novartis), CEP-701 (by Cephalon), MLN518 (by Millenium Pharmaceuticals), and SU5614 (by Sugen/Pfizer) (see Stone et al., *Blood* (in press) (2004); Smith et al., *Blood* 103: 3669-3676 (2004); Clark et al., *Blood* 104: 2867-2872 (2004); and Spiekerman et al., *Blood* 101: 1494-1504 (2003)).

There is also evidence indicating that kinases such as FLT3, c-KIT and Abl are implicated in some cases of ALL (see Cools et al., *Cancer Res.* 64: 6385-6389 (2004); Hu, *Nat. Genet.* 36: 453-461 (2004); and Graux et al., *Nat. Genet.* 36: 1084-1089 (2004)). In contrast, very little is know regarding any causative role of protein kinases in CLL, except for a high correlation between high expression of the tyrosine kinase ZAP70 and the more aggressive form of the disease (see Rassenti et al., *N. Eng. J. Med.* 351: 893-901 (2004)).

Although a few key RTKs and various other signaling proteins involved in carcinoma and/or leukemia and leukemia progression are, known, there is relatively scarce information about kinase-driven signaling pathways and phosphorylation sites that underlie the different types of cancer. Therefore there is presently an incomplete and inaccurate understanding of how protein activation within signaling pathways is driving these complex cancers. Accordingly, there is a continuing and pressing need to unravel the molecular mechanisms of kinase-driven ontogenesis in cancer by identifying the downstream signaling proteins mediating cellular transformation in these cancers.

Presently, diagnosis of many types of cancer is often made by tissue biopsy and detection of different cell surface markers. However, misdiagnosis can occur since certain types of cancer can be negative for certain markers and because these markers may not indicate which genes or protein kinases may be deregulated. Although the genetic translocations and/or mutations characteristic of a particular form of cancer can be sometimes detected, it is clear that other downstream effectors of constitutively active kinases having potential diagnostic, predictive, or therapeutic value, remain to be elucidated.

Accordingly, identification of downstream signaling molecules and phosphorylation sites involved in different types of diseases including for example, carcinoma and/or leukemia and development of new reagents to detect and quantify these sites and proteins may lead to improved diagnostic/prognostic markers, as well as novel drug targets, for the detection and treatment of many diseases.

SUMMARY OF THE INVENTION

The present invention provides in one aspect novel tyrosine phosphorylation sites (Table 1) identified in carcinoma and/or leukemia. The novel sites occur in proteins such as: Adaptor/Scaffold proteins, adhesion/extra cellular matrix proteins, cell cycle regulation, chaperone proteins, chromatin or DNA binding/repair/proteins, cytoskeleton proteins, endoplasmic reticulum or golgi proteins, enzyme proteins, g proteins or regulator proteins, kinases, protein kinases receptor/channel/transporter/cell surface proteins, transcriptional regulators, ubiquitan conjugating proteins, RNA processing proteins, secreted proteins, motor or contractile proteins, apoptosis proteins of unknown function and vesicle proteins.

In another aspect, the invention provides peptides comprising the novel phosphorylation sites of the invention, and proteins and peptides that are mutated to eliminate the novel phosphorylation sites.

In another aspect, the invention provides modulators that modulate tyrosine phosphorylation at a novel phosphorylation site of the invention, including small molecules, peptides comprising a novel phosphorylation site, and binding molecules that specifically bind at a novel phosphorylation site, including but not limited to antibodies or antigen-binding fragments thereof.

In another aspect, the invention provides compositions for detecting, quantitating or modulating a novel phosphorylation site of the invention, including peptides comprising a novel phosphorylation site and antibodies or antigen-binding fragments thereof that specifically bind at a novel phosphorylation site. In certain embodiments, the compositions for detecting, quantitating or modulating a novel phosphorylation site of the invention are Heavy-Isotype Labeled Peptides (AQUA peptides) comprising a novel phosphorylation site.

In another aspect, the invention discloses phosphorylation site specific antibodies or antigen-binding fragments thereof. In one embodiment, the antibodies specifically bind to an amino acid sequence comprising a phosphorylation site identified in Table 1 when the tyrosine identified in Column D is phosphorylated, and do not significantly bind when the tyrosine is not phosphorylated. In another embodiment, the antibodies specifically bind to an amino acid sequence comprising a phosphorylation site when the tyrosine is not phosphorylated, and do not significantly bind when the tyrosine is phosphorylated.

In another aspect, the invention provides a method for making phosphorylation site-specific antibodies.

In another aspect, the invention provides compositions comprising a peptide, protein, or antibody of the invention, including pharmaceutical compositions.

In a further aspect, the invention provides methods of treating or preventing carcinoma and/or leukemia in a subject, wherein the carcinoma and/or leukemia is associated with the phosphorylation state of a novel phosphorylation site in Table 1, whether phosphorylated or dephosphorylated. In certain embodiments, the methods comprise administering to a subject a therapeutically effective amount of a peptide comprising a novel phosphorylation site of the invention. In certain embodiments, the methods comprise administering to a subject a therapeutically effective amount of an antibody or antigen-binding fragment thereof that specifically binds at a novel phosphorylation site of the invention.

In a further aspect, the invention provides methods for detecting and quantitating phosphorylation at a novel tyrosine phosphorylation site of the invention.

In another aspect, the invention provides a method for identifying an agent that modulates tyrosine phosphorylation at a novel phosphorylation site of the invention, comprising: contacting a peptide or protein comprising a novel phosphorylation site of the invention with a candidate agent, and determining the phosphorylation state or level at the novel phosphorylation site. A change in the phosphorylation state or level at the specified tyrosine in the presence of the test agent, as compared to a control, indicates that the candidate agent potentially modulates tyrosine phosphorylation at a novel phosphorylation site of the invention.

In another aspect, the invention discloses immunoassays for binding, purifying, quantifying and otherwise generally detecting the phosphorylation of a protein or peptide at a novel phosphorylation site of the invention.

Also provided are pharmaceutical compositions and kits comprising one or more antibodies or peptides of the invention and methods of using them.

BRIEF DESCRIPTION OF THE DRAWINGS

FIG. 2 is a table (corresponding to Table 1) summarizing the 482 novel phosphorylation sites of the invention: Column A=the parent proteins from which the phosphorylation sites are derived; Column B=the SwissProt accession number for the human homologue of the identified parent proteins; Column C=the protein type/classification; Column D=the tyrosine residues at which phosphorylation occurs (each number refers to the amino acid residue position of the tyrosine in the parent human protein, according to the published sequence retrieved by the SwissProt accession number); Column E=flanking sequences of the phosphorylatable tyrosine residues; sequences (SEQ ID NOs: 1-19, 21-22, 25-27, 29-136, 138-144, 147-204, 206-232, 234-257, 259-277, 279-301, 303-374, 376-393, 395-403, 405-435, 437-447, 449-461, 463-500) were identified using Trypsin digestion of the parent proteins; in each sequence, the tyrosine (see corresponding rows in Column D) appears in lowercase; Column F=the type of carcinoma and/or leukemia in which each of the phosphorylation site was discovered; Column G=the cell type(s)/Tissue/Patient Sample in which each of the phosphorylation site was discovered; and Column H=the SEQ ID NOs of the trypsin-digested peptides identified in Column E.

DETAILED DESCRIPTION OF THE INVENTION

The inventors have discovered and disclosed herein novel tyrosine phosphorylation sites in signaling proteins extracted from carcinoma and/or leukemia cells. The newly discovered phosphorylation sites significantly extend our knowledge of kinase substrates and of the proteins in which the novel sites occur. The disclosure herein of the novel phosphorylation sites and reagents including peptides and antibodies specific for the sites add important new tools for the elucidation of signaling pathways that are associate with a host of biological processes including cell division, growth, differentiation, developmental changes and disease. Their discovery in carcinoma and/or leukemia cells provides and focuses further elucidation of the disease process. And, the novel sites provide additional diagnostic and therapeutic targets.

1. Novel Phosphorylation Sites in Carcinoma and/or Leukemia

In one aspect, the invention provides 482 novel tyrosine phosphorylation sites in signaling proteins from cellular extracts from a variety of human carcinoma and/or leukemia-derived cell lines and tissue samples (such as H1993, lung HCC827, etc., as further described below in Examples), identified using the techniques described in "Immunoaffinity Isolation of Modified Peptides From Complex Mixtures," U.S. Patent Publication No. 20030044848, Rush et al, using Table 1 summarizes the identified novel phosphorylation sites.

These phosphorylation sites thus occur in proteins found in carcinoma and/or leukemia. The sequences of the human homologues are publicly available in SwissProt database and their Accession numbers listed in Column B of Table 1. The novel sites occur in proteins such as: adaptor/scaffold proteins; adhesion or extracellular matrix proteins; cytoskeletal proteins; enzyme proteins; G proteins or regulator proteins; non-protein kinase proteins; motor or contractile proteins; phosphatase proteins; protein kinases; receptor, channel, transporter or cell surface proteins; RNA processing proteins; and transcriptional regulator proteins. (see Column C of Table 1).

Figure 1:
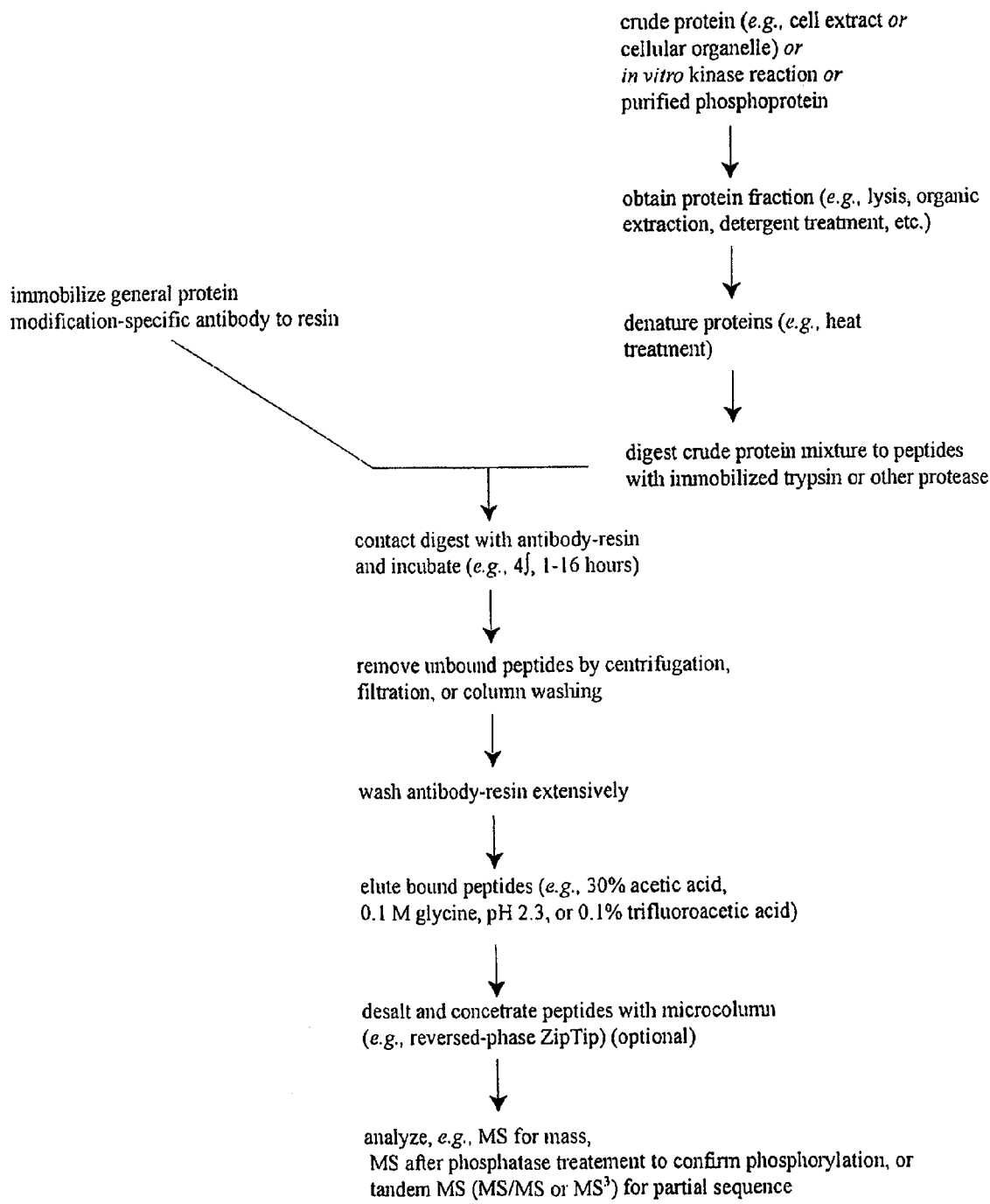
FIG. 1 is a diagram depicting the immuno-affinity isolation and mass-spectrometric characterization methodology (IAP) used in the Examples to identify the novel phosphorylation sites disclosed herein.
Figure 3:
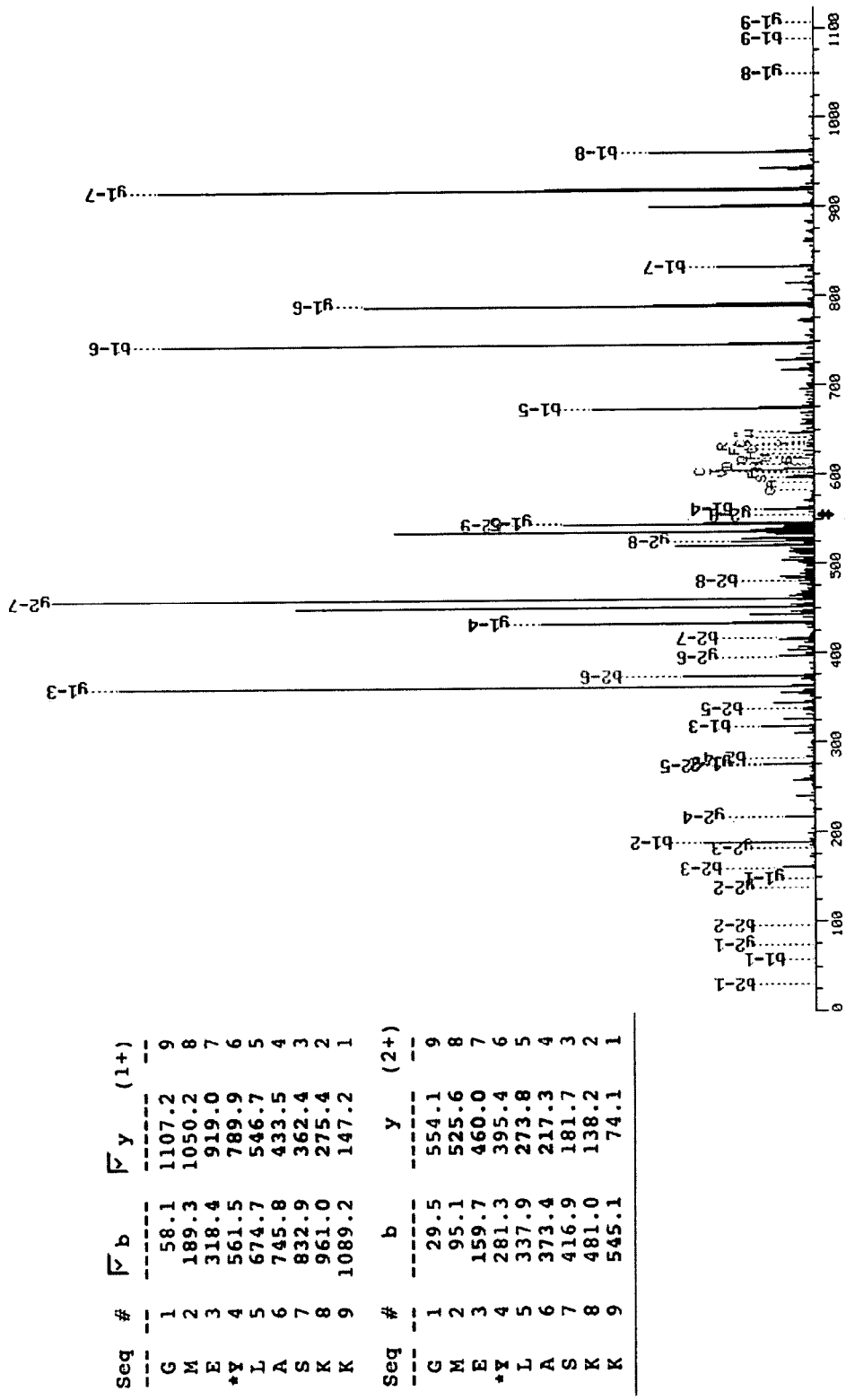
FIG. 3 is an exemplary mass spectrograph depicting the detection of the phosphorylation of tyrosine 522 in FGFR1, as further described in Example 1 (red and blue indicate ions detected in MS/MS spectrum); Y* (and pY) indicates the phosphorylated tyrosine (corresponds to lowercase "y" in Column E of Table 1; SEQ ID NO: 261).
Figure 4:
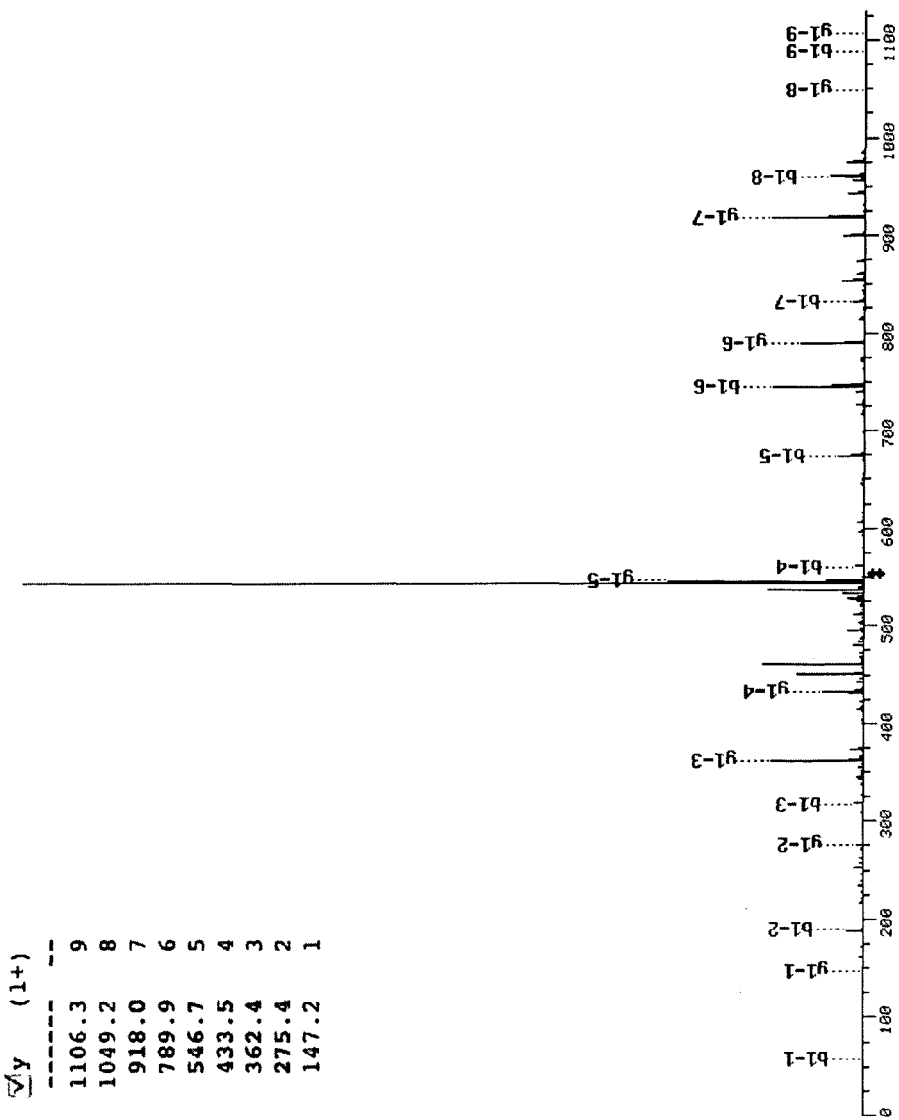
FIG. 4 is an exemplary mass spectrograph depicting the detection of the phosphorylation of tyrosine 1194 in Met, as further described in Example 1 (red and blue indicate ions detected in MS/MS spectrum); Y* (and pY) indicates the phosphorylated tyrosine (corresponds to lowercase "y" in Column E of Table 1; SEQ ID NO: 277).
Figure 5:
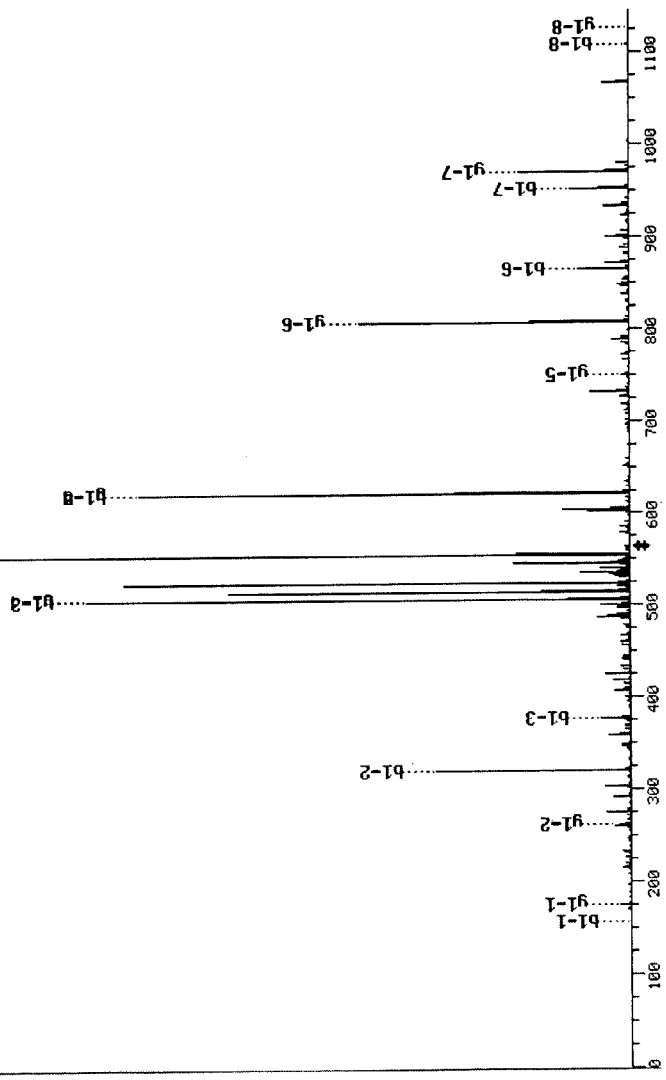
FIG. 5 is an exemplary mass spectrograph depicting the detection of the phosphorylation of tyrosine 176 in epsin 3, as further described in Example 1 (red and blue indicate ions detected in MS/MS spectrum); Y* (and pY) indicates the phosphorylated tyrosine (corresponds to lowercase "y" in Column E of Table 1; SEQ ID NO: 497).
Figure 6:
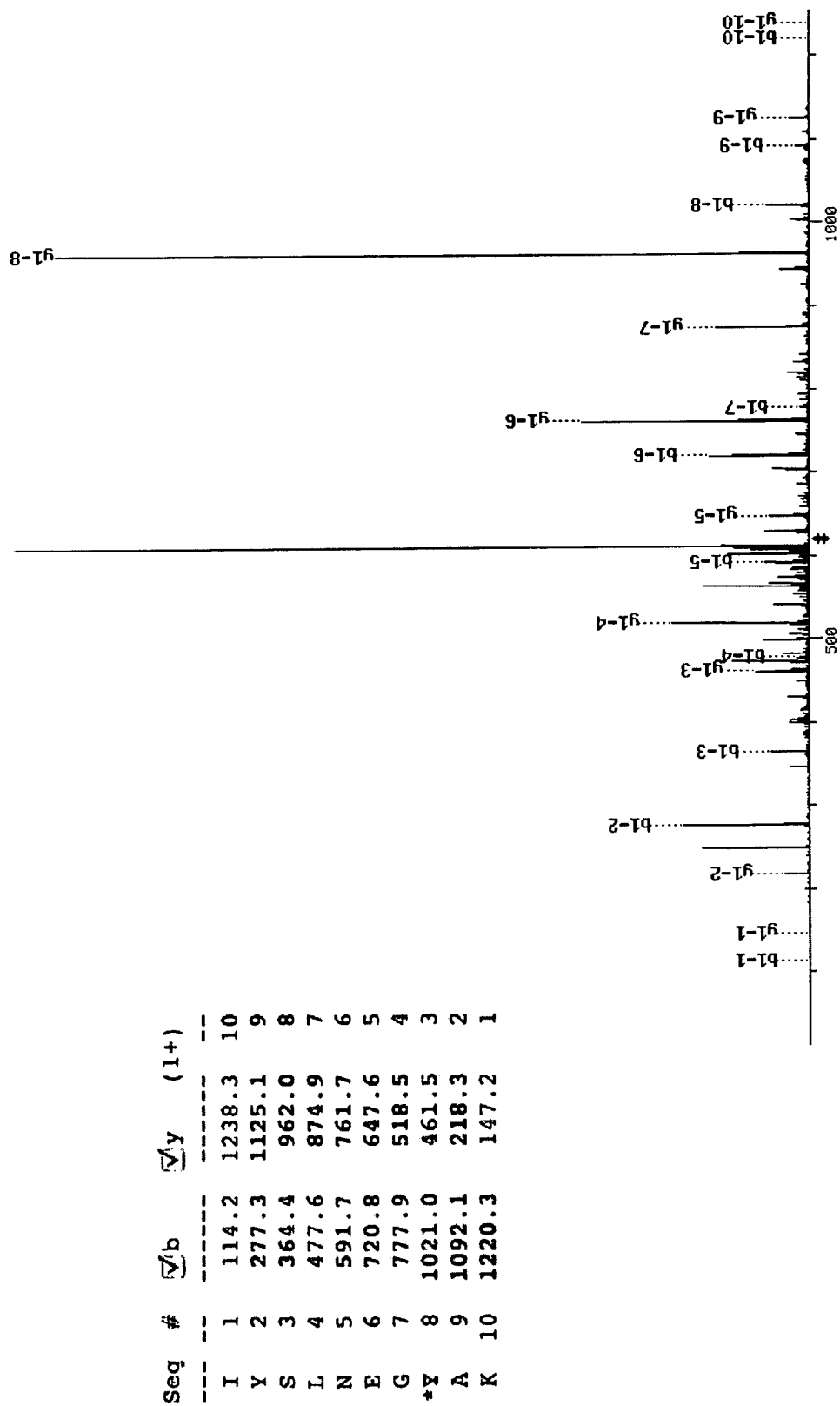
FIG. 6 is an exemplary mass spectrograph depicting the detection of the phosphorylation of tyrosine 216 in FBP2, as further described in Example 1 (red and blue indicate ions detected in MS/MS spectrum); Y* (and pY) indicates the phosphorylated tyrosine (corresponds to lowercase "y" in Column E of Table 1; SEQ ID NO: 225).

The novel phosphorylation sites of the invention were identified according to the methods described by Rush et al., U.S. Patent Publication No. 20030044848, which are herein incorporated by reference in its entirety. Briefly, phosphorylation sites were isolated and characterized by immunoaffinity isolation and mass-spectrometric characterization (IAP) (FIG. 1), using the following human carcinoma and/or leukemia-derived cell lines and tissue samples: 101206; 143.98.2; 23132/87; 23132/87: 10% serum; 3T3 (EGFR|deletion||EGF); 42-MG-BA; 5637; 639L; 8-MG-BA; A172; A498; A549; A704; AML-30410; B13_AML; B18_AML; BC-3C; BC004; BC005; BC007; BJ629; BJ630; BJ631; BJ635; BJ665; BT1; BT2; Baf3(FGFR1|truncation: 10ZF); Baf3(FLT3|D835Y); Baf3(FLT3|K663Q); Baf3 (Jak2|Jak2|V617F); Baf3(TEL-FGFR3); CAKI-2; CAL-29; CAL-51; CAL-85-1; CCF-STTG1; CHP-212; CHP126; CHRF; CMK; CML-06/164; COLO-699; CTV-1; Caki-2; Cal-148; Calu-3; CaoV4; Colo680N; DK-MG; DMS 53; DMS 79; DU.528; DV-90; Detroit562; EFM-19; EFO-21;

ENT01; ENT02; ENT03; ENT05; ENT10; ENT12; ENT14; ENT15; ENT19; ENT7; EOL-1; ES2; EVSA-T; FUOV1; GAMG; GI-CA-N; GI-LI-N; GMS-10; H1435; H1437; H1568; H1650; H1651; H1703; H1734; H1781; H1838; H1915; H1975; H2023; H2052; H2066; H2085; H2135; H2172; H2342; H2452; H28; H3255; H358; H4; H446; H4; H520; H524; H596; H810; HCC1143; HCC1395; HCC1428; HCC15; HCC1806; HCC1937; HCC827; HCT 116; HCT15; HCT8; HD-MyZ; HDLM-2; HEL; HL130A; HL131B; HL145A; HL146A; HL152A; HL183A; HL183B; HL184A; HL184B; HL1881; HL213A; HL226A; HL226B; HL233B; HL234A; HL25A; HL53A; HL53B; HL55A; HL59A; HL66A; HL68A; HL83A; HL84A; HL98A; HP28; HT29; Hs746T; IMR32; J82; Jurkat; K562; KATO III; KELLY; KG-1; KMS-11; KPL-1; Kyse140; Kyse270; Kyse410; Kyse450; Kyse510; Kyse70; L428; L540; LAN-1; LAN-5; LCLC-103H; LN-405; LN18; LXF-289; M059J; M059K; MDAH2774; MHH-NB-11; MKN-45; MKPL-1; ML-1; MT-3; MV4-11; Me-F2; MiaPaca; Molm 14; N06BJ505(2); N06BJ573(9); N06BJ591(11); N06BJ593(13); N06BJ606 (19); N06CS02; N06CS06; N06CS103; N06CS106; N06CS107; N06CS16; N06CS17; N06CS22(2)-R; N06CS22-1; N06CS22-2; N06CS23; N06CS39; N06CS40; N06CS75; N06CS77; N06CS87; N06CS90; N06CS91; N06CS93-2; N06CS94; N06CS97; N06CS98; N06CS98-2; N06CS98-R; N06N101; N06N102; N06N103; N06N106; N06N121; N06N127; N06N128; N06N131; N06N80; N06N90; N06N93; N06bj523(3); N06bj567(7); N06bj594 (14); N06bj595(15); N06bj638(26); N06bj639(27); N06bj667(29); N06c144; N06c78; N06cs108; N06cs109; N06cs110; N06cs110-R; N06cs112; N06cs113; N06cs117; N06cs121; N06cs122; N06cs123; N06cs123(2); N06cs126; N06cs128; N06cs132; N06cs132-1; N06cs59; N06cs63; N06cs72; N06cs76; N06cs88; N06cs92; NALM-19; NCI-H716; OPM-1; OV90; PA-1; RSK2-3; RSK2-4; S 2; SCLC T1; SCLC T4; SEM; SK-ES-1; SK-N-AS; SK-N-BE(2); SK-N-DZ; SK-N-FI; SK-OV-3; SNB-19; SNU-1; SNU-16; SNU-5; SNU-C2B; SUP-T13; SW1088; SW1710; SW480; SW620; Scaber; T17; T98G; TOV112D; TOV21G; U118 MG; UM-UC-1; UT-7; ZR-75-30; brain; cs012; cs015; cs018; cs019; cs024; cs025; cs026; cs037; cs041; cs042; cs057; cs068; cs069; cs070; cs103; cs104; cs105; cs106; cs107; cs110; cs114; cs133; cs136; csC44; csC45; csC50; csC52; csC56; csC60; csC66; csC71; gz21; gz30; gz33; gz41; gz42; gz7; gz73; gz74; gz75; gzB1; h2073; sw48. In addition to the newly discovered phosphorylation sites (all having a phosphorylatable tyrosine), many known phosphorylation sites were also identified.

The immunoaffinity/mass spectrometric technique described in Rush et al, i.e., the "IAP" method, is described in detail in the Examples and briefly summarized below.

The IAP method generally comprises the following steps: (a) a proteinaceous preparation (e.g., a digested cell extract) comprising phosphopeptides from two or more different proteins is obtained from an organism; (b) the preparation is contacted with at least one immobilized general phosphotyrosine-specific antibody; (c) at least one phosphopeptide specifically bound by the immobilized antibody in step (b) is isolated; and (d) the modified peptide isolated in step (c) is characterized by mass spectrometry (MS) and/or tandem mass spectrometry (MS-MS). Subsequently, (e) a search program (e.g., Sequest) may be utilized to substantially match the spectra obtained for the isolated, modified peptide during the characterization of step (d) with the spectra for a known peptide sequence. A quantification step, e.g., using SILAC or AQUA, may also be used to quantify isolated peptides in order to compare peptide levels in a sample to a baseline.

In the IAP method as disclosed herein, a general phosphotyrosine-specific monoclonal antibody (commercially available from Cell Signaling Technology, Inc., Beverly, Mass., Cat #9411 (p-Tyr-100)) may be used in the immunoaffinity step to isolate the widest possible number of phospho-tyrosine containing peptides from the cell extracts.

As described in more detail in the Examples, lysates may be prepared from various carcinoma and/or leukemia cell lines or tissue samples and digested with trypsin after treatment with DTT and iodoacetamide to alkylate cysteine residues. Before the immunoaffinity step, peptides may be pre-fractionated (e.g., by reversed-phase solid phase extraction using Sep-Pak $C_{18}$ columns) to separate peptides from other cellular components. The solid phase extraction cartridges may then be eluted (e.g., with acetonitrile). Each lyophilized peptide fraction can be redissolved and treated with phosphotyrosine-specific antibody (e.g., P-Tyr-100, CST #9411) immobilized on protein Agarose. Immunoaffinity-purified peptides can be eluted and a portion of this fraction may be concentrated (e.g., with Stage or Zip tips) and analyzed by LC-MS/MS (e.g., using a ThermoFinnigan LCQ Deca XP Plus ion trap mass spectrometer or LTQ). MS/MS spectra can be evaluated using, e.g., the program Sequest with the NCBI human protein database.

The novel phosphorylation sites identified are summarized in Table 1/FIG. 2. Column A lists the parent (signaling) protein in which the phosphorylation site occurs. Column D identifies the tyrosine residue at which phosphorylation occurs (each number refers to the amino acid residue position of the tyrosine in the parent human protein, according to the published sequence retrieved by the SwissProt accession number). Column E shows flanking sequences of the identified tyrosine residues (which are the sequences of trypsin-digested peptides). FIG. 2 also shows the particular type of carcinoma and/or leukemia (see Column G) and cell line(s) (see Column F) in which a particular phosphorylation site was discovered.

TABLE 1

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| 2 | Cbl | NP_005179.2 | Adaptor/scaffold | Y141 | MyEENSQPR | SEQ ID NO: 1 |
| 3 | Cbl-b | NP_733762.2 | Adaptor/scaffold | Y337 | SyNPDLTGLCEPTPHDHIK | SEQ ID NO: 2 |
| 4 | CNKSR2 | NP_055742.2 | Adaptor/scaffold | Y671 | INMLTAGyAER | SEQ ID NO: 3 |
| 5 | CSDE1 | NP_001007554.1 | Adaptor/scaffold | Y138 | VFyLTYTPEDVE | SEQ ID NO: 4 |

TABLE 1-continued

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| 6 | CSDE1 | NP_001007554.1 | Adaptor/scaffold | Y141 | VFYLTyTPEDVE | SEQ ID NO: 5 |
| 7 | CTNND1 | NP_001322.1 | Adaptor/scaffold | Y208 | NFHyPPDGYSR | SEQ ID NO: 6 |
| 8 | DLG3 | NP_066943.2 | Adaptor/scaffold | Y808 | QIIEDQSGHyIWVPSPEKL | SEQ ID NO: 7 |
| 9 | DNMBP | NP_056036.1 | Adaptor/scaffold | Y430 | SQYySTVGGSHPHSEQYPDLLPLEAR | SEQ ID NO: 8 |
| 10 | Dok4 | NP_060580.2 | Adaptor/scaffold | Y165 | LQITHENIyLWDIHNPR | SEQ ID NO: 9 |
| 11 | Dok4 | NP_060580.2 | Adaptor/scaffold | Y220 | MCDAGEGLYTFQTQEGEQIyQR | SEQ ID NO: 10 |
| 12 | ENTH | NP_055481.1 | Adaptor/scaffold | Y172 | ySERYDPEPK | SEQ ID NO: 11 |
| 13 | ENTH | NP_055481.1 | Adaptor/scaffold | Y176 | YSERyDPEPK | SEQ ID NO: 12 |
| 14 | EPB41L1 | NP_036288.2 | Adaptor/scaffold | Y68 | MEEKDySEADGLSER | SEQ ID NO: 13 |
| 15 | FAM125A | NP_612410.1 | Adaptor/scaffold | Y210 | RNDSIYEASSLyGISAMDGVPFTLHPR | SEQ ID NO: 14 |
| 16 | FAM125A | NP_612410.1 | Adaptor/scaffold | Y254 | SLADIEEEyNYGFVVEK | SEQ ID NO: 15 |
| 17 | FAM125A | NP_612410.1 | Adaptor/scaffold | Y256 | SLADIEEEYNyGFVVEK | SEQ ID NO: 16 |
| 18 | FCHSD2 | NP_055639.1 | Adaptor/scaffold | Y603 | PHASLPPLPLyDQPPSSPYPSPDKR | SEQ ID NO: 17 |
| 19 | FNBP1L | NP_060207.2 | Adaptor/scaffold | Y291 | SGFEPPGDFPFEDYSQHIyR | SEQ ID NO: 18 |
| 20 | FRS2 | NP_006645.3 | Adaptor/scaffold | Y150 | TPTTPGFAAQNLPNGyPR | SEQ ID NO: 19 |
| 21 | FRS2 | NP_006645.3 | Adaptor/scaffold | Y59 | RDSVKWHyLCLR | SEQ ID NO: 21 |
| 22 | Gab1 | NP_002030.2 | Adaptor/scaffold | Y47 | SGRLTGDPDVLEyK | SEQ ID NO: 22 |
| 23 | KPNA3 | NP_002258.2 | Adaptor/scaffold | Y506 | ATQGGTyNFDPTANLQTKE | SEQ ID NO: 25 |
| 24 | KPNA4 | NP_002259.1 | Adaptor/scaffold | Y66 | DSDIDGDyRVQNTSLE | SEQ ID NO: 26 |
| 25 | MACF1 | NP_149033.2 | Adaptor/scaffold | Y2230 | GALDTTDGyMGVNQAPEKLDK | SEQ ID NO: 27 |
| 26 | P1300as | NP_055382.2 | Adaptor/scaffold | Y653 | FTSQDSPDGQyENSEGGWMEDYDVHLQGK | SEQ ID NO: 29 |
| 27 | PAR3-beta | NP_689739.4 | Adaptor/scaffold | Y1034 | GGPADPVDyLPAAPR | SEQ ID NO: 30 |
| 28 | PEX14 | NP_004556.1 | Adaptor/scaffold | Y290 | GSTVTyHLLGPQEE | SEQ ID NO: 31 |
| 29 | PSD-93 | NP_001355.2 | Adaptor/scaffold | Y223 | GLGFSIAGGVGNQHIPGDNSIyVTK | SEQ ID NO: 32 |
| 30 | PSD-93 | NP_001355.2 | Adaptor/scaffold | Y750 | FIEAGQyNDNLYGTSVQSVR | SEQ ID NO: 33 |
| 31 | PSD-95 | NP_001356.1 | Adaptor/scaffold | Y233 | GLGFSIAGGVGNQHIPGDNSIyVTK | SEQ ID NO: 34 |
| 32 | PSD-95 | NP_001356.1 | Adaptor/scaffold | Y576 | EDSVLSYETVTQMEVHyARPIIILGPTK | SEQ ID NO: 35 |
| 33 | SAPAP3 | NP_001073887.1 | Adaptor/scaffold | Y823 | EAEDyELPEEILEK | SEQ ID NO: 36 |
| 34 | SHANK1 | NP_057232.2 | Adaptor/scaffold | Y186 | FLEyVQLGTSDK | SEQ ID NO: 37 |
| 35 | SHANK3 | XP_037493.7 | Adaptor/scaffold | Y122 | FMDyVQLHSTDK | SEQ ID NO: 38 |
| 36 | Shc2 | XP_944665.2 | Adaptor/scaffold | Y412 | GPPDHEEHLyVNTQGLDAPEPEDSPK | SEQ ID NO: 39 |
| 37 | SHD | NP_064594.2 | Adaptor/scaffold | Y144 | GVQLyDTPYEEQDPETADGPPSGQKPR | SEQ ID NO: 40 |

TABLE 1-continued

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| 38 | SNCG | NP_003078.1 | Adaptor/scaffold | Y39 | EGVMyVGAK | SEQ ID NO: 41 |
| 39 | syntenin | NP_001007068.1 | Adaptor/scaffold | Y50 | SANPANPAILSEASAPIPHDGNLYPRLyPELSQY | SEQ ID NO: 42 |
| 40 | CDH1 | NP_004351.1 | Adhesion or extracellular matrix protein | Y876 | KLADMyGGGEDD | SEQ ID NO: 43 |
| 41 | CDH1 | NP_001788.2 | Adhesion or extracellular matrix protein | Y702 | KDIKPEYQyMPR | SEQ ID NO: 44 |
| 42 | CDH23 | NP_071407.2 | Adhesion or extracellular matrix protein | Y1672 | ITIQALDLDEGPNGTVTy | SEQ ID NO: 45 |
| 43 | CGNL1 | NP_116255.2 | Adhesion or extracellular matrix protein | Y108 | ENSEELQLPENPyAQPSPIR | SEQ ID NO: 46 |
| 44 | claudin 18 | NP_057453.1 | Adhesion or extracellular matrix protein | Y254 | TEDEVQSyPSKHDYV | SEQ ID NO: 47 |
| 45 | CNTN6 | NP_055276.1 | Adhesion or extracellular matrix protein | Y225 | TDGVMGEyEPK | SEQ ID NO: 48 |
| 46 | COL17A1 | NP_000485.3 | Adhesion or extracellular matrix protein | Y40 | LTSLPPKGGTSNGyAK | SEQ ID NO: 49 |
| 47 | DCBLD2 | NP_563615.3 | Adhesion or extracellular matrix protein | Y569 | TEGTYDLPyWDR | SEQ ID NO: 50 |
| 48 | DCBLD2 | NP_563615.3 | Adhesion or extracellular matrix protein | Y649 | KPEEGKEAGyADLDPY | SEQ ID NO: 51 |
| 49 | DSC2 | NP_077740.1 | Adhesion or extracellular matrix protein | Y839 | LGEKVyLCNQDENHK | SEQ ID NO: 52 |
| 50 | Erbin | NP_061165.1 | Adhesion or extracellular matrix protein | Y425 | VLTNyMFPQQPR | SEQ ID NO: 53 |
| 51 | FN1 | NP_002017.1 | Adhesion or extracellular matrix protein | Y2319 | RPGGEPSPEGTTGQSyNQYSQR | SEQ ID NO: 54 |
| 52 | FN1 | NP_002017.1 | Adhesion or extracellular matrix protein | Y2322 | RPGGEPSPEGTTGQSYNQySQR | SEQ ID NO: 55 |
| 53 | FRAS1 | NP_079350.4 | Adhesion or extracellular matrix protein | Y3985 | NVNILSEPEAAyTFK | SEQ ID NO: 56 |
| 54 | laminin receptor 1 | NP_001005472.1 | Adhesion or extracellular matrix protein | Y39 | FLAAGTHLGGTNLDFQMEQYIyKR | SEQ ID NO: 57 |
| 55 | LRRC7 | NP_065845.1 | Adhesion or extracellular matrix protein | Y425 | VLTNyMFPQQPR | SEQ ID NO: 58 |
| 56 | occludin | NP_002529.1 | Adhesion or extracellular matrix protein | Y337 | FyPESSYK | SEQ ID NO: 59 |

TABLE 1-continued

Novel Phosphorylation Sites in Carcinoma and/or leukemia.

| 1 | Protein Name | Accession No. | Protein Type | Phospho-Residue | Phosphorylation Site Sequence | SEQ ID NO |
|---|---|---|---|---|---|---|
| 57 | occludin | NP_002529.1 | Adhesion or extracellular matrix protein | Y342 | FYPESSyK | SEQ ID NO: 60 |
| 58 | PVRL3 | NP_056295.1 | Adhesion or extracellular matrix protein | Y510 | FERPMDyYEDLK | SEQ ID NO: 61 |
| 59 | SEMA4F | NP_004254.2 | Adhesion or extracellular matrix protein | Y450 | EyDVLYLGTEDGHLHR | SEQ ID NO: 62 |
| 60 | SEMA4F | NP_004254.2 | Adhesion or extracellular matrix protein | Y454 | EYDVLyLGTEDGHLHR | SEQ ID NO: 63 |
| 61 | BNIP3L | NP_004322.1 | Apoptosis | Y219 | LSTPSASTy | SEQ ID NO: 64 |
| 62 | catalase | NP_001743.1 | Apoptosis | Y379 | LGPNYLHIPVNCPyR | SEQ ID NO: 65 |
| 63 | CYCS | NP_061820.1 | Apoptosis | Y49 | TGQAPGYSyTAANK | SEQ ID NO: 66 |
| 64 | FAIM3 | NP_005440.1 | Apoptosis | Y315 | SQNNIySACPR | SEQ ID NO: 67 |
| 65 | CALB2 | NP_001731.1 | Calcium-binding protein | Y126 | SGyIEANELK | SEQ ID NO: 68 |
| 66 | CALB2 | NP_001731.1 | Calcium-binding protein | Y35 | HFDADGNGyIEGK | SEQ ID NO: 69 |
| 67 | CALCOCO2 | NP_005822.1 | Calcium-binding protein | Y376 | GGARQNPGLAyGNPYSGIQE | SEQ ID NO: 70 |
| 68 | CALCOCO2 | NP_005822.1 | Calcium-binding protein | Y380 | GGARQNPGLAYGNPYSGIQE | SEQ ID NO: 71 |
| 69 | calsequestrin 2 | NP_001223.2 | Calcium-binding protein | Y178 | SEDSEyYKAFEEAAEHFQPYIK | SEQ ID NO: 72 |
| 70 | FREQ | NP_055101.2 | Calcium-binding protein | Y115 | LYDLDNDGyITR | SEQ ID NO: 73 |
| 71 | Cdc27 | NP_001247.2 | Cell cycle regulation | Y740 | ESLVyFLIGK | SEQ ID NO: 74 |
| 72 | CEP350 | NP_055625.3 | Cell cycle regulation | Y2612 | EKDVSEYFyEK | SEQ ID NO: 75 |
| 73 | CEP350 | NP_055625.3 | Cell cycle regulation | Y337 | KVATAPPAPAyK | SEQ ID NO: 76 |
| 74 | ch-TOG | NP_055571.2 | Cell cycle regulation | Y268 | LEQQQSAGGDAEGGGDDGDEVPQIDAy ELLEAVEILSK | SEQ ID NO: 77 |
| 75 | HCAP-G | NP_071741.2 | Cell cycle regulation | Y929 | GNKEFGDQAEAAQDATLTTTTFQNEDE KNKEVyMTPLR | SEQ ID NO: 78 |
| 76 | SKB1 | NP_006100.2 | Cell cycle regulation | Y283 | EFCSYLQyLEYLSQNR | SEQ ID NO: 79 |
| 77 | CCT6B | NP_006575.2 | Chaperone | Y239 | SLEyEKTEVNSG | SEQ ID NO: 80 |
| 78 | CCT7 | NP_001009570.1 | Chaperone | Y59 | VHTVEDyQAIVDAEWNILYDKLEK | SEQ ID NO: 81 |
| 79 | CCT-delta | NP_006421.2 | Chaperone | Y269 | TDMDNQIVVSDyAQMDR | SEQ ID NO: 82 |
| 80 | DNAJB5 | NP_036398.3 | Chaperone | Y52 | EIAEAyDVLSDPK | SEQ ID NO: 83 |
| 81 | DNAJB6 | NP_490647.1 | Chaperone | Y53 | QVAEAyEVLSDAK | SEQ ID NO: 84 |
| 82 | ARID1A | NP_006006.3 | Chromatin, DNA-binding, | Y762 | NPQMPQySSPQPGSALSPR | SEQ ID NO: 85 |

TABLE 1-continued

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| | | | DNA repair or DNA replication protein | | | |
| 83 | C14orf43 | NP_919254.2 | Chromatin, DNA-binding, DNA repair or DNA replication protein | Y158 | GSPHPGVGVPTyYNHPEALKR | SEQ ID NO: 86 |
| 84 | CHD1L | NP_004275.2 | Chromatin, DNA-binding, DNA repair or DNA replication protein | Y709 | LDyQDPDATSLKYVSGDVTHPQAGAE | SEQ ID NO: 87 |
| 85 | CHD-6 | NP_115597.3 | Chromatin, DNA-binding, DNA repair or DNA replication protein | Y1640 | LyESLTYSQMSR | SEQ ID NO: 88 |
| 86 | CHD-6 | NP_115597.3 | Chromatin, DNA-binding, DNA repair or DNA replication protein | Y1645 | LYESLTySQMSR | SEQ ID NO: 89 |
| 87 | H2BK | NP_542160.1 | Chromatin, DNA-binding, DNA repair or DNA replication protein | Y41 | ESYSVyVYK | SEQ ID NO: 90 |
| 88 | H2BL | NP_003510.1 | Chromatin, DNA-binding, DNA repair or DNA replication protein | Y41 | ESYSVyVYK | SEQ ID NO: 91 |
| 89 | HIST2H2BF | NP_001019770.1 | Chromatin, DNA-binding, DNA repair or DNA replication protein | Y41 | ESYSVyVYK | SEQ ID NO: 92 |
| 90 | HMGB1 | NP_002119.1 | Chromatin, DNA-binding, DNA repair or DNA replication protein | Y78 | EMKTyIPPKGETKK | SEQ ID NO: 93 |
| 91 | NAP1L1 | NP_004528.1 | Chromatin, DNA-binding, DNA repair or DNA replication protein | Y377 | GDEENDPDyDPKKDQNPAE | SEQ ID NO: 94 |
| 92 | ARVCF | NP_001661.1 | Cytoskeletal protein | Y201 | DSPSyGSLSR | SEQ ID NO: 95 |
| 93 | calponin 3 | NP_001830.1 | Cytoskeletal protein | Y316 | HGEYQDDyPRDY | SEQ ID NO: 96 |
| 94 | CAPZA2 | NP_006127.1 | Cytoskeletal protein | Y198 | IQVHyYEDGNVQLVSHK | SEQ ID NO: 97 |
| 95 | CCDC6 | NP_005427.2 | Cytoskeletal protein | Y336 | MDDERyFNE | SEQ ID NO: 98 |
| 96 | CDK5RAP2 | NP_060719.4 | Cytoskeletal protein | Y1111 | VSVMGTDQSESINTSNETEyLKQK | SEQ ID NO: 99 |
| 97 | CLASP2 | NP_055912.1 | Cytoskeletal protein | Y1150 | NMNSEDIySSLRGVTE | SEQ ID NO: 100 |

TABLE 1-continued

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| 98 | claudin 5 | NP_003268.1 | Cytoskeletal protein | Y212 | RPTATGDyDKKNYV | SEQ ID NO: 101 |
| 99 | claudin 5 | NP_003268.1 | Cytoskeletal protein | Y217 | RPTATGDYDKKNyV | SEQ ID NO: 102 |
| 100 | cofilin 1 | NP005498.1 | Cytoskeletal protein | Y82 | MLPDKDCRyALYDATYETKESK | SEQ ID NO: 103 |
| 101 | cofilin 2 | NP_068733.1 | Cytoskeletal protein | Y82 | LLPLNDCRyALYDATYETK | SEQ ID NO: 104 |
| 102 | cordon-bleu | NP_056013.2 | Cytoskeletal protein | Y1143 | LSyTEAEGER | SEQ ID NO: 105 |
| 103 | cordon-bleu | NP_056013.2 | Cytoskeletal protein | Y652 | VKDKVyGCADGER | SEQ ID NO: 106 |
| 104 | cortactin | NP_005222.2 | Cytoskeletal protein | Y538 | yGLFPANYVELRQ | SEQ ID NO: 107 |
| 105 | COTL1 | NP_066972.1 | Cytoskeletal protein | Y137 | LKKAGGANyDAQTE | SEQ ID NO: 108 |
| 106 | CTNND2 | NP_001323.1 | Cytoskeletal protein | Y1090 | KTDyECTGSNATYHGAK | SEQ ID NO: 109 |
| 107 | DBN1 | NP_004386.2 | Cytoskeletal protein | Y32 | SAADWALyTYEDGSDDLKLAASGE | SEQ ID NO: 110 |
| 108 | dystrophin | NP_004014.1 | Cytoskeletal protein | Y894 | MHyPMVEYCTPTTSGEDVR | SEQ ID NO: 111 |
| 109 | EB1 | NP_036457.1 | Cytoskeletal protein | Y268 | GFVIPDEGGPQEEQEEy | SEQ ID NO: 112 |
| 110 | EHM2 | NP_061987.3 | Cytoskeletal protein | Y447 | TNPEVHNyQPQYHPNIHPSQPR | SEQ ID NO: 113 |
| 111 | EHM2 | NP_061987.3 | Cytoskeletal protein | Y451 | TNPEVHNYQPQyHPNIHPSQPR | SEQ ID NO: 114 |
| 112 | EML4 | NP_061936.2 | Cytoskeletal protein | Y265 | LKLEWAyGYR | SEQ ID NO: 115 |
| 113 | EML4 | NP_061936.2 | Cytoskeletal protein | Y954 | GSGDLGEPLyEEPCNE | SEQ ID NO: 116 |
| 114 | eplin | NP_057441.1 | Cytoskeletal protein | Y429 | LSLGTyASLHGR | SEQ ID NO: 117 |
| 115 | EXOC7 | NP_001013861.1 | Cytoskeletal protein | Y90 | TLSCLDHVISyYHVASDTEK | SEQ ID NO: 118 |
| 116 | ezrin | NP_003370.2 | Cytoskeletal protein | Y499 | SLQDEGAEPTGySAE | SEQ ID NO: 119 |
| 117 | FLNB | NP_001448.2 | Cytoskeletal protein | Y596 | IEyNDQNDGSCDVK | SEQ ID NO: 120 |
| 118 | FLNC | NP_001449.3 | Cytoskeletal protein | Y1303 | VLNPSGAKTDTyVTDNGDGTYR | SEQ ID NO: 121 |
| 119 | FLNC | NP_001449.3 | Cytoskeletal protein | Y1312 | VLNPSGAKTDTYVTDNGDGTyR | SEQ ID NO: 122 |
| 120 | FNBP1 | NP_055848.1 | Cytoskeletal protein | Y234 | MGESMKTyAEVDR | SEQ ID NO: 123 |
| 121 | FNBP1 | NP_055848.1 | Cytoskeletal protein | Y287 | SGFEPPGDIEFEDyTQPMKR | SEQ ID NO: 124 |
| 122 | INA | NP_116116.1 | Cytoskeletal protein | Y425 | FSTSGLSISGLNPLPNPSyLLPPR | SEQ ID NO: 125 |

TABLE 1-continued

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| 123 | K1 | NP_006112.3 | Cytoskeletal protein | Y566 | GSYGSGGSSYGSGGGSyGSGGGGGGH GSYGSGSSSGGYR | SEQ ID NO: 126 |
| 124 | RP1 | NP_055083.1 | Cytoskeletal protein | Y162 | FYDANyDGKEYDPVEAR | SEQ ID NO: 127 |
| 125 | SAPAP1 | NP_004737.2 | Cytoskeletal protein | Y317 | SCQyLQVPQDEWTGYTPR | SEQ ID NO: 128 |
| 126 | SHRM | NP_065910.2 | Cytoskeletal protein | Y500 | ESGyIAPQGACNK | SEQ ID NO: 129 |
| 127 | talin 2 | NP_055874.1 | Cytoskeletal protein | Y1854 | GTFVDyQTTVVK | SEQ ID NO: 130 |
| 128 | talin 2 | NP_055874.1 | Cytoskeletal protein | Y49 | ERVPEAQTGQASDyGLFLSDEDPR | SEQ ID NO: 131 |
| 129 | OSBPL3 | NP_056365.1 | Endoplasmic reticulum or golgi | Y47 | GEMNyTQEPPVQK | SEQ ID NO: 132 |
| 130 | CA9 | NP_001207.1 | Enzyme, misc. | Y449 | GGVSyRPAEVAETGA | SEQ ID NO: 133 |
| 131 | CCBL1 | NP_004050.3 | Enzyme, misc. | Y15 | MAKQLQARRLDGIDyNPWVEFVK | SEQ ID NO: 134 |
| 132 | CHD2 | NP_001262.3 | Enzyme, misc. | Y596 | LKFNALITTyEILLKDK | SEQ ID NO: 135 |
| 133 | CNP | NP_149124.3 | Enzyme, misc. | Y373 | LySLGNGR | SEQ ID NO: 136 |
| 134 | CPT1A | NP_001867.2 | Enzyme, misc. | Y514 | GDINPNIPyPTR | SEQ ID NO: 138 |
| 135 | CTPS | NP_001896.1 | Enzyme, misc. | Y96 | IYQyVINK | SEQ ID NO: 139 |
| 136 | DDHD1 | NP_085140.1 | Enzyme, misc. | Y89 | GEPGLHLAPGTDDHNHHLALDPCLSDE NyDFSSAESGSSLR | SEQ ID NO: 140 |
| 137 | DDX10 | NP_004389.2 | Enzyme, misc. | Y273 | LSLKNPEyVWVHEK | SEQ ID NO: 141 |
| 138 | DDX42 | NP_031398.2 | Enzyme, misc. | Y160 | GIRDDIEEEDDQEAyFR | SEQ ID NO: 142 |
| 139 | DDX9 | NP_001348.2 | Enzyme, misc. | Y21 | KMTPSyEIR | SEQ ID NO: 143 |
| 140 | DEGS1 | NP_003667.1 | Enzyme, misc. | Y14 | VSREDFEWVyTDQPHADR | SEQ ID NO: 144 |
| 141 | DHCR7 | NP_001351.2 | Enzyme, misc. | Y382 | VIECSyTSADGQR | SEQ ID NO: 147 |
| 142 | DHX33 | NP_064547.2 | Enzyme, misc. | Y380 | KyNPDSGLEVLAVQR | SEQ ID NO: 148 |
| 143 | DHX36 | NP_065916.1 | Enzyme, misc. | Y1006 | NFPPRFQDGyYS | SEQ ID NO: 149 |
| 144 | Diminuto | NP_055577.1 | Enzyme, misc. | Y299 | LNSIGNyYK | SEQ ID NO: 150 |
| 145 | Diminuto | NP_055577.1 | Enzyme, misc. | Y300 | LNSIGNYyK | SEQ ID NO: 151 |
| 146 | DUS3L | NP_064560.1 | Enzyme, misc. | Y308 | LyLAPLTTCGNLPFR | SEQ ID NO: 152 |
| 147 | EPRS | NP_004437.2 | Enzyme, misc. | Y684 | RGFFICDQPyEPVSPYSCK | SEQ ID NO: 153 |
| 148 | FBPase | NP_000498.2 | Enzyme, misc. | Y259 | TLVyGGIFLYPANK | SEQ ID NO: 154 |
| 149 | G6PI | NP_000166.2 | Enzyme, misc. | Y92 | MFNGEKINyTEGR | SEQ ID NO: 155 |
| 150 | IMPDH2 | NP_000875.2 | Enzyme, misc. | Y459 | FVPyLIAGIQHSCQDIGAK | SEQ ID NO: 156 |
| 151 | LDH-B | NP_002291.1 | Enzyme, misc. | Y173 | FRyLMAEK | SEQ ID NO: 157 |
| 152 | LSD1 | NP_055828.2 | Enzyme, misc. | Y135 | EMDESLANLSEDEyYSEEER | SEQ ID NO: 158 |
| 153 | LSD1 | NP_055828.2 | Enzyme, misc. | Y136 | EMDESLANLSEDEYySEEER | SEQ ID NO: 159 |
| 154 | ACSM2A | NP_001010845.1 | Enzyme, misc. | Y303 | FDPLVILKTLSSyPIK | SEQ ID NO: 160 |

TABLE 1-continued

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| 155 | NTE | NP_006693.3 | Enzyme, misc. | Y431 | EQPAGACEySYCEDESATGGCPFGPYQGR | SEQ ID NO: 161 |
| 156 | PLD1 | NP_002653.1 | Enzyme, misc. | Y42 | ELHFEGEEVDyDVSPSDPK | SEQ ID NO: 162 |
| 157 | SCLY | NP_057594.2 | Enzyme, misc. | Y280 | GLGEFTPLyPMLFGGGQER | SEQ ID NO: 163 |
| 158 | Cdc42 | NP_001782.1 | G protein or regulator | Y32 | TTNKFPSEyVPTVF | SEQ ID NO: 164 |
| 159 | Cdc42EP1 | NP_689449.1 | G protein or regulator | Y130 | NAISLPQLNQAAyDSLVVGK | SEQ ID NO: 165 |
| 160 | Cdc42EP1 | NP_689449.1 | G protein or regulator | Y331 | HWGAGWDGGHHyPEMDAR | SEQ ID NO: 166 |
| 161 | CENTD1 | NP_056045.2 | G protein or regulator | Y867 | KAGQSLQMEFLyHNK | SEQ ID NO: 167 |
| 162 | CENTD2 | NP_056057.1 | G protein or regulator | Y119 | yFDSNKDAYSK | SEQ ID NO: 168 |
| 163 | CENTD2 | NP_056057.1 | G protein or regulator | Y127 | YFDSNKDAySK | SEQ ID NO: 169 |
| 164 | ARHGAP3 | NP_004058.1 | G protein or regulator | Y153 | YISKMTTNPIyE | SEQ ID NO: 170 |
| 165 | ARHGAP3 | NP_004058.1 | G protein or regulator | Y158 | MTTNPIYEHIGyATLLR | SEQ ID NO: 171 |
| 166 | DDEF2 | NP_003878.1 | G protein or regulator | Y724 | EDRPISFyQLGSNQLQSNAVSLAR | SEQ ID NO: 172 |
| 167 | DOCK10 | NP_055504.1 | G protein or regulator | Y1126 | EDQLEyQEELR | SEQ ID NO: 173 |
| 168 | DOCK9 | NP_056111.1 | G protein or regulator | Y340 | LFyLDPDAQK | SEQ ID NO: 174 |
| 169 | ephexin1 | NP_062824.1 | G protein or regulator | Y288 | LVTSEASyYKSLNLLVSHFMENE | SEQ ID NO: 175 |
| 170 | ephexin1 | NP_062824.1 | G protein or regulator | Y289 | LVTSEASYyKSLNLLVSHFMENE | SEQ ID NO: 176 |
| 171 | ephexin1 | NP_062824.1 | G protein or regulator | Y537 | QIPGDKyQVFDSAPR | SEQ ID NO: 177 |
| 172 | EPS8L2 | NP_073609.2 | G protein or regulator | Y678 | VySQLTMQK | SEQ ID NO: 178 |
| 173 | EVI5L | NP_660288.1 | G protein or regulator | Y788 | LAAPySQGLDN | SEQ ID NO: 179 |
| 174 | FGD5 | NP_689749.2 | G protein or regulator | Y603 | QQSADQDAESAyTEPYK | SEQ ID NO: 180 |
| 175 | G-alpha(z) | NP_002064.1 | G protein or regulator | Y75 | EYKPLIIyNAIDSLTR | SEQ ID NO: 181 |
| 176 | G-alpha2(i) | NP_002061.1 | G protein or regulator | Y155 | EYQLNDSMyYLNDLER | SEQ ID NO: 182 |
| 177 | GPSM3 | NP_071390.1 | G protein or regulator | Y108 | EQLySTILSHQCQR | SEQ ID NO: 183 |
| 178 | IQGAP1 | NP_003861.1 | G protein or regulator | Y1284 | FNVDEySDLVTLTK | SEQ ID NO: 184 |
| 179 | IQGAP1 | NP_003861.1 | G protein or regulator | Y694 | GGyYYYHNLETQEGGWDEPPNFVQNSMQLSR | SEQ ID NO: 185 |
| 180 | IQGAP1 | NP_003861.1 | G protein or regulator | Y695 | GGYyYYHNLETQEGGWDEPPNFVQNSMQLSR | SEQ ID NO: 186 |

TABLE 1-continued

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| 181 | IQGAP1 | NP_003861.1 | G protein or regulator | Y697 | GGYYYyHNLETQEGGWDEPPNFVQNSMQLSR | SEQ ID NO: 187 |
| 182 | IQGAP2 | AAB37765.1 | G protein or regulator | Y630 | ESSWVTPESCFyKESWLTGK | SEQ ID NO: 188 |
| 183 | IQGAP3 | NP_839943.2 | G protein or regulator | Y1268 | FAVDEySDMVAVAKPMVYITVGELVNTHR | SEQ ID NO: 189 |
| 184 | RICS | NP_055530.2 | G protein or regulator | Y1424 | GPVMSQyDNMTPAVQDDLGGIYVIHLR | SEQ ID NO: 190 |
| 185 | RRAS2 | NP_036382.2 | G protein or regulator | Y105 | GSFEEIyKFQR | SEQ ID NO: 191 |
| 186 | SIPA1L3 | NP_055888.1 | G protein or regulator | Y1265 | GEPQySSHSSSNTLSSNASSSHSDDR | SEQ ID NO: 192 |
| 187 | SIPA1L3 | NP_055888.1 | G protein or regulator | Y1316 | GGSSDSGIDTTLyTSSPSCMSLAK | SEQ ID NO: 193 |
| 188 | SRGAP2 | NP_056141.2 | G protein or regulator | Y699 | GPVYSRGGSMEDyCDSPHGE | SEQ ID NO: 194 |
| 189 | ITIH1 | NP_002206.1 | Inhibitor protein | Y431 | FPLyNLGFGHNVDFNFLEVMSMENNGR | SEQ ID NO: 195 |
| 190 | EM55 | NP_002427.1 | Kinase (non-protein) | Y316 | FVYPVPyTTRPPRKSEEDGK | SEQ ID NO: 196 |
| 191 | PIK3CA | NP_006209.2 | Kinase (non-protein) | Y294 | ESLySQLPMDCFTMPSYSR | SEQ ID NO: 197 |
| 192 | PIK3R1 | NP_852664.1 | Kinase (non-protein) | Y76 | GDFPGTYVEyIGR | SEQ ID NO: 198 |
| 193 | PIK3R2 | NP_005018.1 | Kinase (non-protein) | Y460 | SREyDQLYEEYTR | SEQ ID NO: 199 |
| 194 | PIP5K | NP_055855.2 | Kinase (non-protein) | Y154 | GKSQDSDLKQyWMPDSQCKE | SEQ ID NO: 200 |
| 195 | PIP5KG | NP_036530.1 | Kinase (non-protein) | Y354 | ALySTAMESIQGGAAR | SEQ ID NO: 201 |
| 196 | ephrin-B1 | NP_004420.1 | Ligand, receptor tyrosine kinase | Y79 | PYEYYKLyLVR | SEQ ID NO: 202 |
| 197 | FRMD6 | NP_689543.1 | Lipid binding protein | Y262 | QLLyDFPWTNVGK | SEQ ID NO: 203 |
| 198 | PLEKHA1 | NP_001001974.1 | Lipid binding protein | Y345 | GFyESLAK | SEQ ID NO: 204 |
| 199 | DCTN3 | NP_009165.1 | Motor or contractile protein | Y67 | KIEDLIKyLDPEYIDR | SEQ ID NO: 206 |
| 200 | DNCH1 | NP_001367.2 | Motor or contractile protein | Y970 | ITNQVIyLNPPIEECR | SEQ ID NO: 207 |
| 201 | KIF2A | NP_004511.1 | Motor or contractile protein | Y168 | KRAQDVDATNPNyE | SEQ ID NO: 208 |
| 202 | KNSL8 | NP_958929.1 | Motor or contractile protein | Y205 | GQGATAAQQGGyEIPAR | SEQ ID NO: 209 |
| 203 | MRLC2V | NP_000423.2 | Motor or contractile protein | Y118 | GVLKADyVR | SEQ ID NO: 210 |

TABLE 1-continued

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| 204 | MYH1 | NP_005954.3 | Motor or contractile protein | Y1856 | KVKELTyQTEEDRK | SEQ ID NO: 211 |
| 205 | MYH1 | NP_005954.3 | Motor or contractile protein | Y424 | GQTVQQVyNAVGALAK | SEQ ID NO: 212 |
| 206 | MYH2 | NP_060004.2 | Motor or contractile protein | Y1858 | ELTyQTEEDRKNILR | SEQ ID NO: 213 |
| 207 | MYH2 | NP_060004.2 | Motor or contractile protein | Y822 | EAIFCIQyNIR | SEQ ID NO: 214 |
| 208 | MYH4 | NP_060003.2 | Motor or contractile protein | Y1856 | ELTyQTEEDRK | SEQ ID NO: 215 |
| 209 | MYH4 | NP_060003.2 | Motor or contractile protein | Y424 | GQTVQQVyNAVGALAK | SEQ ID NO: 216 |
| 210 | MYH7 | NP_000248.2 | Motor or contractile protein | Y422 | GQNVQQVIyATGALAK | SEQ ID NO: 217 |
| 211 | MYH8 | NP_002463.1 | Motor or contractile protein | Y424 | GQTVQQVyNAVGALAK | SEQ ID NO: 218 |
| 212 | MYO10 | NP_036466.1 | Motor or contractile protein | Y585 | FDFIyDLFEHVSSR | SEQ ID NO: 219 |
| 213 | MYO1C | NP_203693.3 | Motor or contractile protein | Y438 | SEQEEYEAEGIAWEPVQyFNNK | SEQ ID NO: 220 |
| 214 | MYO1F | NP_036467.2 | Motor or contractile protein | Y438 | WTPIQyFNNK | SEQ ID NO: 221 |
| 215 | CD45 | NP_002829.2 | Phosphatase | Y681 | NRyVDILPYDYNR | SEQ ID NO: 222 |
| 216 | DARPP-32 | NP_115568.2 | Phosphatase | Y116 | ELGyPREEDEEEEEDDEEEEEEEDSQAEVLK | SEQ ID NO: 223 |
| 217 | DUSP3 | NP_004081.1 | Phosphatase | Y23 | LSVQDLNDLLSDGSGCySLPSQPCNE | SEQ ID NO: 224 |
| 218 | FBP2 | NP_003828.2 | Phosphatase | Y216 | IYSLNEGyAK | SEQ ID NO: 225 |
| 219 | FBP2 | NP_003828.2 | Phosphatase | Y259 | TLVyGGIFLYPANQK | SEQ ID NO: 226 |
| 220 | INPP5F | NP_055752.1 | Phosphatase | Y430 | FENVQTLTDAIyDIILDMK | SEQ ID NO: 227 |
| 221 | PTPN14 | NP_005392.2 | Phosphatase | Y496 | ERHPyTVPYGPQGVYSNK | SEQ ID NO: 228 |
| 222 | CMA1 | NP_001827.1 | Protease | Y35 | PyMAYLEIVTSNGPSK | SEQ ID NO: 229 |
| 223 | CMA1 | NP_001827.1 | Protease | Y38 | PYMAyLEIVTSNGPSK | SEQ ID NO: 230 |
| 224 | CNDP2 | NP_060705.1 | Protease | Y311 | WRyPSLSLHGIEGAFSGSGAK | SEQ ID NO: 231 |
| 225 | PSMB4 | NP_002787.2 | Protease | Y75 | FEGGVVIAADMLGSyGSLAR | SEQ ID NO: 232 |
| 226 | DYRK4 | NP_003836.1 | Protein kinase, dual-specificity | Y356 | yPDSKDLTMVLK | SEQ ID NO: 234 |
| 227 | CKS1 | NP_001817.1 | Protein kinase, regulatory subunit | Y12 | QIYYSDKyDDEEFEYR | SEQ ID NO: 235 |

TABLE 1-continued

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| 228 | CaMK2-delta | NP_001212.2 | Protein kinase, Ser/Thr (non-receptor) | Y14 | FTDEyQLFEELGK | SEQ ID NO: 236 |
| 229 | CAMKK2 | NP_006540.3 | Protein kinase, Ser/Thr (non-receptor) | Y190 | LAYNENDNTyYAMK | SEQ ID NO: 237 |
| 230 | Cdc2 | NP_001777.1 | Protein kinase, Ser/Thr (non-receptor) | Y4 | MEDyTKIEKIGEGTYGVVYK | SEQ ID NO: 238 |
| 231 | CDK9 | NP_001252.1 | Protein kinase, Ser/Thr (non-receptor) | Y287 | LKAYVRDPyALDLIDKLLVLDPAQR | SEQ ID NO: 239 |
| 232 | CK2-alpha1 | NP_001886.1 | Protein kinase, Ser/Thr (non-receptor) | Y50 | GKySEVFEAINITNNEK | SEQ ID NO: 240 |
| 233 | CRIK | NP_009105.1 | Protein kinase, Ser/Thr (non-receptor) | Y1759 | QyTLEEFLDK | SEQ ID NO: 241 |
| 234 | Nek1 | NP_036356.1 | Protein kinase, Ser/Thr (non-receptor) | Y443 | GQyEHYHAIFDQMQQQR | SEQ ID NO: 242 |
| 235 | Nek1 | NP_036356.1 | Protein kinase, Ser/Thr (non-receptor) | Y446 | GQYEHyHAIFDQMQQQR | SEQ ID NO: 243 |
| 236 | PLK2 | NP_006613.2 | Protein kinase, Ser/Thr (non-receptor) | Y297 | EARyTMPSSLLAPAKHLIASMLSK | SEQ ID NO: 244 |
| 237 | ROCK1 | NP_005397.1 | Protein kinase, Ser/Thr (non-receptor) | Y913 | GLLEEQYFELTQESK | SEQ ID NO: 245 |
| 238 | RSK2 | NP_004577.1 | Protein kinase, Ser/Thr (non-receptor) | Y433 | EDIGVGSySVCK | SEQ ID NO: 246 |
| 239 | RSK2 | NP_004577.1 | Protein kinase, Ser/Thr (non-receptor) | Y644 | FSLSGGyWNSVSDTAK | SEQ ID NO: 247 |
| 240 | RSK3 | NP_001006933.1 | Protein kinase, Ser/Thr (non-receptor) | Y434 | EDIGVGSySVCK | SEQ ID NO: 248 |
| 241 | RSK3 | NP_001006933.1 | Protein kinase, Ser/Thr (non-receptor) | Y707 | GAMAATYFALNR | SEQ ID NO: 249 |
| 242 | RSK4 | NP_055311.1 | Protein kinase, Ser/Thr (non-receptor) | Y437 | EDIGVGSySVCK | SEQ ID NO: 250 |
| 243 | SRPK1 | NP_003128.3 | Protein kinase, Ser/Thr (non-receptor) | Y62 | GSAPHSESDLPEQEEEILGSDDDEQEDPNDyCK | SEQ ID NO: 251 |
| 244 | FRK | NP_002022.1 | Protein kinase, Tyr (non-receptor) | Y221 | IQVPAPFDLSyK | SEQ ID NO: 252 |
| 245 | FRK | NP_002022.1 | Protein kinase, Tyr (non-receptor) | Y317 | HGSLQEyLQNDTGSK | SEQ ID NO: 253 |

TABLE 1-continued

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| 246 | FRK | NP_002022.1 | Protein kinase, Tyr (non-receptor) | Y368 | NVLVGEHNIyKVADFGLAR | SEQ ID NO: 254 |
| 247 | Lyn | NP_002341.1 | Protein kinase, Tyr (non-receptor) | Y321 | EEPIYIITEyMAK | SEQ ID NO: 255 |
| 248 | EphA2 | NP_004422.2 | Protein kinase, Tyr (receptor) | Y735 | YLANMNyVHR | SEQ ID NO: 256 |
| 249 | EphA3 | NP_005224.2 | Protein kinase, Tyr (receptor) | Y937 | EIFTGVEySSCDTIAK | SEQ ID NO: 257 |
| 250 | EphA4 | NP_004429.1 | Protein kinase, Tyr (receptor) | Y798 | WTAPEAIAyR | SEQ ID NO: 259 |
| 251 | EphA6 | XP_914973.6 | Protein kinase, Tyr (receptor) | Y831 | VLEDDPEAAyTTTGGK | SEQ ID NO: 260 |
| 252 | EphA6 | NP_001073917.2 | Protein kinase, Tyr (receptor) | Y934 | WTAPEAIAyR | SEQ ID NO: 261 |
| 253 | EphB1 | NP_004432.1 | Protein kinase, Tyr (receptor) | Y575 | EAVySDKLQHYSTGR | SEQ ID NO: 262 |
| 254 | EphB1 | NP_004432.1 | Protein kinase, Tyr (receptor) | Y582 | EAVYSDKLQHySTGR | SEQ ID NO: 263 |
| 255 | EphB1 | NP_004432 1 | Protein kinase, Tyr (receptor) | Y798 | WTAPEAIAyR | SEQ ID NO: 264 |
| 256 | EphB3 | NP_004434.2 | Protein kinase, Tyr (receptor) | Y812 | WTAPEAIAyR | SEQ ID NO: 265 |
| 257 | FGFR1 | NP_075594.1 | Protein kinase, Tyr (receptor) | Y522 | GMEyLASKK | SEQ ID NO: 266 |
| 258 | FGFR2 | NP_000132.1 | Protein kinase, Tyr (receptor) | Y466 | LSSTADTPMLAGVSEyELPEDPKWEFPR | SEQ ID NO: 267 |
| 259 | FGFR2 | NP_000132.1 | Protein kinase, Tyr (receptor) | Y586 | RPPGMEySYDINR | SEQ ID NO: 268 |
| 260 | FGFR2 | NP_000132.1 | Protein kinase, Tyr (receptor) | Y588 | RPPGMEYSyDINR | SEQ ID NO: 269 |
| 261 | FGFR2 | NP_000132.1 | Protein kinase, Tyr (receptor) | Y616 | GMEyLASQK | SEQ ID NO: 270 |
| 262 | FGFR2 | NP_000132.1 | Protein kinase, Tyr (receptor) | Y733 | MDKPANCTNELyMMMR | SEQ ID NO: 271 |
| 263 | FGFR2 | NP_000132.1 | Protein kinase, Tyr (receptor) | Y805 | SSCSSGDDSVFSPDPMPyEPCLPQYPHINGSVK | SEQ ID NO: 272 |
| 264 | FGFR2 | NP_000132.1 | Protein kinase, Tyr (receptor) | Y812 | SSCSSGDDSVFSPDPMPYEPCLPQyPHINGSVK | SEQ ID NO: 273 |
| 265 | FGFR3 | NP_000133.1 | Protein kinase, Tyr (receptor) | Y607 | GMEyLASQK | SEQ ID NO: 274 |
| 266 | FLT3 | NP_004110.2 | Protein kinase, Tyr (receptor) | Y865 | WMAPESLFEGIyTIK | SEQ ID NO: 275 |
| 267 | Lmr2 | NP_055731.2 | Protein kinase, Tyr (receptor) | Y500 | GHLDEGLSyTSIFYPVEVFESSLSDPGPGK | SEQ ID NO: 276 |
| 268 | Met | NP_000236.2 | Protein kinase, Tyr (receptor) | Y1194 | GMKyLASKK | SEQ ID NO: 277 |
| 269 | CD229 | NP_002339.2 | Receptor, channel, transporter or | Y583 | GAGHDPAPEGQADyDPVTPYVTE | SEQ ID NO: 279 |

TABLE 1-continued

Novel Phosphorylation Sites in Carcinoma and/or leukemia.

| 1 | Protein Name | Accession No. | Protein Type | Phospho-Residue | Phosphorylation Site Sequence | SEQ ID NO |
|---|---|---|---|---|---|---|
| | | | cell surface protein | | | |
| 270 | CD229 | NP_002339.2 | Receptor, channel, transporter or cell surface protein | Y589 | GAGHDPAPEGQADYDPVTPyVTE | SEQ ID NO: 280 |
| 271 | CD82 | NP_002222.1 | Receptor, channel, transporter or cell surface protein | Y261 | HVHSEDySKVPKY | SEQ ID NO: 281 |
| 272 | CD82 | NP_002222.1 | Receptor, channel, transporter or cell surface protein | Y267 | HVHSEDYSKVPKy | SEQ ID NO: 282 |
| 273 | CLCC1 | NP_001041675.1 | Receptor, channel, transporter or cell surface protein | Y412 | GQMGPTEQGPyAK | SEQ ID NO: 283 |
| 274 | CLCC1 | NP_001041675.1 | Receptor, channel, transporter or cell surface protein | Y531 | SEAAGSPDQGSTySPAR | SEQ ID NO: 284 |
| 275 | CR2 | NP_001006659.1 | Receptor, channel, transporter or cell surface protein | Y1083 | EVySVDPYNPAS | SEQ ID NO: 285 |
| 276 | Cx43 | NP_000156.1 | Receptor, channel, transporter or cell surface protein | Y301 | NyNKQASEQNWANYSAEQNR | SEQ ID NO: 286 |
| 277 | DNAJC1 | NP_071760.2 | Receptor, channel, transporter or cell surface protein | Y295 | TTyIQSYDHGTSIEE | SEQ ID NO: 287 |
| 278 | DNAJC1 | NP_071760.2 | Receptor, channel, transporter or cell surface protein | Y299 | TTYIQSyDHGTSIEE | SEQ ID NO: 288 |
| 279 | DNER | NP_620711.3 | Receptor, channel, transporter or cell surface protein | Y677 | PAyEEFYNCR | SEQ ID NO: 289 |
| 280 | DNER | NP_620711.3 | Receptor, channel, transporter or cell surface protein | Y681 | PAYEEFyNCR | SEQ ID NO: 290 |
| 281 | DNER | NP_620711.3 | Receptor, channel, transporter or cell surface protein | Y711 | SRPAMyDVSPIAYEDYSPDDKPLVTLIK | SEQ ID NO: 291 |

TABLE 1-continued

Novel Phosphorylation Sites in Carcinoma and/or leukemia.

| 1 | Protein Name | Accession No. | Protein Type | Phospho-Residue | Phosphorylation Site Sequence | SEQ ID NO |
|---|---|---|---|---|---|---|
| 282 | DNER | NP_620711.3 | Receptor, channel, transporter or cell surface protein | Y718 | SRPAMYDVSPIAyEDYSPDDKPLVTLIK | SEQ ID NO: 292 |
| 283 | DNER | NP_620711.3 | Receptor, channel, transporter or cell surface protein | Y721 | SRPAMYDVSPIAYEDySPDDKPLVTLIK | SEQ ID NO: 293 |
| 284 | DYSF | NP_003485.1 | Receptor, channel, transporter or cell surface protein | Y1650 | ITLYDyDLLSKDEK | SEQ ID NO: 294 |
| 285 | EDG4 | NP_004711.2 | Receptor, channel, transporter or cell surface protein | Y325 | ESVHyTSSAQGGASTR | SEQ ID NO: 295 |
| 286 | Emelin | NP_036451.2 | Receptor, channel, transporter or cell surface protein | Y487 | YESQLSTNEEKVDTDDRTEGyLR | SEQ ID NO: 296 |
| 287 | FZD5 | NP_003459.2 | Receptor, channel, transporter or cell surface protein | Y556 | SGGAMAAGDyPEASAALTGR | SEQ ID NO: 297 |
| 288 | FZD5 | NP_003459.2 | Receptor, channel, transporter or cell surface protein | Y576 | TGPPGPAATyHK | SEQ ID NO: 298 |
| 289 | GPA33 | NP_005805.1 | Receptor, channel, transporter or cell surface protein | Y301 | EREEEDDyRQEEQR | SEQ ID NO: 299 |
| 290 | GPIP137 | NP_005889.3 | Receptor, channel, transporter or cell surface protein | Y78 | GKLDDyQER | SEQ ID NO: 300 |
| 291 | HMMR | NP_036617.1 | Receptor, channel, transporter or cell surface protein | Y698 | GNTNCyRAPMECQE | SEQ ID NO: 301 |
| 292 | IL2RG | NP_000197.1 | Receptor, channel, transporter or cell surface protein | Y363 | GGALGEGPGASPCNQHSPYWAPPCyTLKPET | SEQ ID NO: 303 |
| 293 | LRP4 | NP_002325.1 | Receptor, channel, transporter or cell surface protein | Y1764 | FTDPGMGNLTySNPSYR | SEQ ID NO: 304 |
| 294 | NKCC1 | NP_001037.1 | Receptor, channel, transporter or | Y1211 | GNHQSVLTFyS | SEQ ID NO: 305 |

TABLE 1-continued

Novel Phosphorylation Sites in Carcinoma and/or leukemia.

| 1 | Protein Name | Accession No. | Protein Type | Phospho-Residue | Phosphorylation Site Sequence | SEQ ID NO |
|---|---|---|---|---|---|---|
| | | | cell surface protein | | | |
| 295 | OR4C46 | NP_001004703.1 | Receptor, channel, transporter or cell surface protein | Y273 | AVAIFyTMITPMLNPLIYTLKNAQMK | SEQ ID NO: 306 |
| 296 | OR4C46 | NP_001004703.1 | Receptor, channel, transporter or cell surface protein | Y285 | AVAIFYTMITPMLNPLIyTLKNAQMK | SEQ ID NO: 307 |
| 297 | ORAI1 | NP_16179.2 | Receptor, channel, transporter or cell surface protein | Y300 | GDHPLTPGSHyA | SEQ ID NO: 308 |
| 298 | PTDSS2 | NP_110410.1 | Receptor, channel, transporter or cell surface protein | Y366 | EIyDFMDDPK | SEQ ID NO: 309 |
| 299 | SLC11A2 | NP_000608.1 | Receptor, channel, transporter or cell surface protein | Y31 | GNINPAySNPSLSQSPGDSEEY | SEQ ID NO: 310 |
| 300 | SLC4A2 | NP_003031.2 | Receptor, channel, transporter or cell surface protein | Y1234 | EGVDEyNEMPMPV | SEQ ID NO: 311 |
| 301 | SLC4A2 | NP_003031.2 | Receptor, channel, transporter or cell surface protein | Y66 | GGEEPGRSyGEEDFEYHR | SEQ ID NO: 312 |
| 302 | SLC4A4 | NP_003750.1 | Receptor, channel, transporter or cell surface protein | Y994 | GSLDSDNDDSDCPySEK | SEQ ID NO: 313 |
| 303 | SLC5A3 | NP_008864.3 | Receptor, channel, transporter or cell surface protein | Y631 | EEGNPVASLGHSEAETPVDAySNGQAALMGEK | SEQ ID NO: 314 |
| 304 | SLITRK3 | NP_055741.2 | Receptor, channel, transporter or cell surface protein | Y904 | ERPQPAPCTVGFVDCLyGTVPK | SEQ ID NO: 315 |
| 305 | CIRBP | NP_001271.1 | RNA processing | Y135 | SGGyGGSRDYYSSR | SEQ ID NO: 316 |
| 306 | CPSF1 | NP_037423.2 | RNA processing | Y748 | SGPEAEGLGSETSPTVDDEEEMLyGDSGSLFSPSKEEAR | SEQ ID NO: 317 |
| 307 | DBR1 | NP_057300.2 | RNA processing | Y533 | NQAIyAAVDDDDDDAA | SEQ ID NO: 318 |
| 308 | DCP2 | NP_689837.2 | RNA processing | Y370 | TDAVyDLPSSSE | SEQ ID NO: 319 |
| 309 | DDX1 | NP_004930.1 | RNA processing | Y628 | VWyHVCSSR | SEQ ID NO: 320 |
| 310 | DDX1 | NP_004930.1 | RNA processing | Y731 | EAQTSFLHLGyLPNQLFR | SEQ ID NO: 321 |

TABLE 1-continued

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| 311 | DDX3 | NP_001347.3 | RNA processing | Y163 | LFSGGNTGINFEKyDDIPVEATGNNCPPHIE | SEQ ID NO: 322 |
| 312 | DDX3 | NP_001347.3 | RNA processing | Y283 | ELAVQIyEEAR | SEQ ID NO: 323 |
| 313 | DDX3 | NP_001347.3 | RNA processing | Y466 | KGADSLEDFLYHEGyACTSIHGDR | SEQ ID NO: 324 |
| 314 | DDX39 | NP_005795.2 | RNA processing | Y13 | NDLLDyDEEEEPQAPQE | SEQ ID NO: 325 |
| 315 | DDX3Y | NP_004651.2 | RNA processing | Y241 | TAAFLLPILSQIyTDGPGEALK | SEQ ID NO: 326 |
| 316 | DDX3Y | NP_004651.2 | RNA processing | Y281 | ELAVQIYEEAR | SEQ ID NO: 327 |
| 317 | DDX3Y | NP_004651.2 | RNA processing | Y464 | KGADSLEDFLYHEGyACTSIHGDR | SEQ ID NO: 328 |
| 318 | DDX5 | NP_004387.1 | RNA processing | Y442 | TGTAyTFFTPNNIK | SEQ ID NO: 329 |
| 319 | HNRPUL2 | NP_001073027.1 | RNA processing | Y660 | SRGQGyVGGQR | SEQ ID NO: 330 |
| 320 | HNRPUL2 | NP_001073027.1 | RNA processing | Y743 | NYYGyQGYR | SEQ ID NO: 331 |
| 321 | HNRPUL2 | NP_001073027.1 | RNA processing | Y746 | NYYGYQGyR | SEQ ID NO: 332 |
| 322 | DRBP1 | NP_694453.2 | RNA processing | Y204 | SSEQDyYSNMRQE | SEQ ID NO: 333 |
| 323 | E1B-AP5 | NP_008971.2 | RNA processing | Y111 | QNQFyDTQVIKQENESGYER | SEQ ID NO: 334 |
| 324 | ELAVL1 | NP_001410.2 | RNA processing | Y26 | TNLIVNyLPQNMTQDELR | SEQ ID NO: 335 |
| 325 | EXOSC1 | NP_057130.1 | RNA processing | Y32 | HGyIFSSLAGCLMK | SEQ ID NO: 336 |
| 326 | FXR1 | NP_005078.2 | RNA processing | Y353 | ESIGNVQVLLEyHIAYLK | SEQ ID NO: 337 |
| 327 | FXR1 | NP_005078.2 | RNA processing | Y357 | ESIGNVQVLLEYHIAyLK | SEQ ID NO: 338 |
| 328 | hnRNP 2H9 | NP_036339.1 | RNA processing | Y100 | GFyDPPRR | SEQ ID NO: 339 |
| 329 | hnRNP 2H9 | NP_036339.1 | RNA processing | Y156 | GGDGYDGGYGGFDDYGGyNNYGYGNDGFDDR | SEQ ID NO: 340 |
| 330 | hnRNP 2H9 | NP_036339.1 | RNA processing | Y181 | GMGGHGyGGAGDASSGFHGGHFVHMR | SEQ ID NO: 341 |
| 331 | hnRNP H | NP_005511.1 | RNA processing | Y236 | GAyGGGYGGYDDYNGYNDGYGFGSDR | SEQ ID NO: 342 |
| 332 | hnRNP H | NP_005511.1 | RNA processing | Y240 | GAYGGGyGGYDDYNGYNDGYGFGSDR | SEQ ID NO: 343 |
| 333 | hnRNP H | NP_005511.1 | RNA processing | Y253 | GAYGGGYGGYDDYNGYNDGyGFGSDR | SEQ ID NO: 344 |
| 334 | hnRNP H | NP_062543.1 | RNA processing | Y298 | GLPyRATENDIYNFFSPLNPMR | SEQ ID NO: 345 |
| 335 | hnRNP R | NP_005817.1 | RNA processing | Y624 | FyQDTYGQWK | SEQ ID NO: 346 |
| 336 | hnRNP R | NP_005817.1 | RNA processing | Y628 | FYQDTyGQWK | SEQ ID NO: 347 |
| 337 | hnRNP U | NP_004492.2 | RNA processing | Y635 | GNFTLPEVAECFDEITyVELQKEEAQK | SEQ ID NO: 348 |
| 338 | hnRNP-A1 | NP_112420.1 | RNA processing | Y244 | GGGGYGGSGDGyNGFGNDGGYGGGGPGYSGGSR | SEQ ID NO: 349 |
| 339 | hnRNP-A1 | NP_112420.1 | RNA processing | Y253 | GGGGYGGSGDGYNGFGNDGGyGGGGPGYSGGSR | SEQ ID NO: 350 |

TABLE 1-continued

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| 340 | hnRNP-I | NP_002810.1 | RNA processing | Y456 | EGQEDQGLTKDyGNSPLHR | SEQ ID NO: 351 |
| 341 | HUMAGCGB | NP_037418.3 | RNA processing | Y379 | GQGGAyAFLK | SEQ ID NO: 352 |
| 342 | IGF2BP3 | NP_006538.2 | RNA processing | Y39 | TGyAFVDCPDESWALK | SEQ ID NO: 353 |
| 343 | MPHOSPH10 | NP_005782.1 | RNA processing | Y452 | PKEDAyEYK | SEQ ID NO: 354 |
| 344 | MPHOSPH10 | NP_005782.1 | RNA processing | Y454 | PKEDAYEyK | SEQ ID NO: 355 |
| 345 | NOL5A | NP_006383.2 | RNA processing | Y210 | IINDNATyCR | SEQ ID NO: 356 |
| 346 | PABPN1 | NP_004634.1 | RNA processing | Y46 | GAPGGAGDyGNGLE | SEQ ID NO: 357 |
| 347 | PSF | NP_005057.1 | RNA processing | Y691 | GMGPGTPAGyGR | SEQ ID NO: 358 |
| 348 | RBM10 | NP_005667.2 | RNA processing | Y435 | GTWATSEEPPVDySYYQQDE | SEQ ID NO: 359 |
| 349 | RBM14 | NP_006319.1 | RNA processing | Y558 | GQPGNAYDGAGQPSAAyLSMSQGAVANANSTPPPYER | SEQ ID NO: 360 |
| 350 | RBM15 | NP_073605.4 | RNA processing | Y336 | ERDYPFyER | SEQ ID NO: 361 |
| 351 | RBM15 | NP_073605.4 | RNA processing | Y416 | GQTSTyGFLK | SEQ ID NO: 362 |
| 352 | SFRS5 | NP_008856.2 | RNA processing | Y55 | FEDPRDADDAVyE | SEQ ID NO: 363 |
| 353 | SFRS9 | NP_003760.1 | RNA processing | Y17 | GGEGDGRIyVGNLPTDVR | SEQ ID NO: 364 |
| 354 | SFRS9 | NP_003760.1 | RNA processing | Y35 | EKDLEDLFyKYGR | SEQ ID NO: 365 |
| 355 | SLU7 | NP_006416.3 | RNA processing | Y297 | ENPyANAGKNPDEVSYAGDNFVR | SEQ ID NO: 366 |
| 356 | snRNP 70 | NP_003080.2 | RNA processing | Y414 | GLGNDSRDMyME | SEQ ID NO: 367 |
| 357 | CGB | NP_001810.1 | Secreted protein | Y526 | LGELFNPYyDPLQWK | SEQ ID NO: 368 |
| 358 | DEFA1 | NP_004075.1 | Secreted protein | Y80 | yGTCIYQGR | SEQ ID NO: 369 |
| 359 | DEFA3 | NP_005208.1 | Secreted protein | Y80 | yGTCIYQGR | SEQ ID NO: 370 |
| 360 | DEFA3 | NP_005208.1 | Secreted protein | Y85 | YGTCIyQGR | SEQ ID NO: 371 |
| 361 | FBS1 | NP_071897.1 | Secreted protein | Y308 | LyGLEPAHPLLYSR | SEQ ID NO: 372 |
| 362 | FBS1 | NP_071897.1 | Secreted protein | Y318 | LYGLEPAHPLLySR | SEQ ID NO: 373 |
| 363 | FGA | NP_000499.1 | Secreted protein | Y277 | GGSTSyGTGSETESPR | SEQ ID NO: 374 |
| 364 | CEBPZ | NP_005751.2 | Transcriptional regulator | Y192 | WYDLEYSNEySLKPQPQDVVSK | SEQ ID NO: 376 |
| 365 | CNOT7 | NP_037486.2 | Transcriptional regulator | Y260 | YCGHLyGLGSGSSYVQNGTGNAYEEEANKQS | SEQ ID NO: 377 |
| 366 | DTX2 | NP_065943.1 | Transcriptional regulator | Y75 | FGLGSLAHSIPLGQADPSLAPyIIDLPSWTSEQFR | SEQ ID NO: 378 |
| 367 | E2A | NP_003191.1 | Transcriptional regulator | Y150 | GTSQYyPSYSGSSR | SEQ ID NO: 379 |
| 368 | E2A | NP_003191.1 | Transcriptional regulator | Y153 | GTSQYYPSySGSSR | SEQ ID NO: 380 |
| 369 | Ets-1 | NP_005229.1 | Transcriptional regulator | Y140 | EDVKPyQVNGVNPAYPESR | SEQ ID NO: 381 |

TABLE 1-continued

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| 370 | FBP1 | NP_003893.2 | Transcriptional regulator | Y242 | ITGDPyKVQQAK | SEQ ID NO: 382 |
| 371 | FBP1 | NP_003893.2 | Transcriptional regulator | Y625 | QQAAyYAQTSPQGMPQHPPAPQGQ | SEQ ID NO: 383 |
| 372 | FHL2 | NP_001441.4 | Transcriptional regulator | Y97 | EDQLLCTDCYSNEySSK | SEQ ID NO: 384 |
| 373 | FLI1 | NP_002008.2 | Transcriptional regulator | Y451 | HPNTHVPSHLGSyY | SEQ ID NO: 385 |
| 374 | JunB | NP_002220.1 | Transcriptional regulator | Y68 | GPGPEGGGGGSyFSGQGSDTGASLK | SEQ ID NO: 386 |
| 375 | MTA2 | NP_004730.2 | Transcriptional regulator | Y437 | GHLSRPEAQSLSPyTTSANR | SEQ ID NO: 387 |
| 376 | NFkB-p100 | NP_002493.3 | Transcriptional regulator | Y55 | FRyGCEGPSHGGLPGASSEK | SEQ ID NO: 388 |
| 377 | SPT5 | NP_003160.2 | Transcriptional regulator | Y765 | RPGGMTSTyGR | SEQ ID NO: 389 |
| 378 | SPT5 | NP_003160.2 | Transcriptional regulator | Y771 | TPMyGSQTPMYGSGSR | SEQ ID NO: 390 |
| 379 | SSRP1 | NP_003137.1 | Transcriptional regulator | Y438 | EGMNPSyDEYADSDEDQHDAYLER | SEQ ID NO: 391 |
| 380 | eEF1A-1 | AAH71619.1 | Translational regulator | Y233 | LPLQDVyK | SEQ ID NO: 392 |
| 381 | eEF1A-2 | NP_001949.1 | Translational regulator | Y254 | LPLQDVyK | SEQ ID NO: 393 |
| 382 | eIF2B-epsilon | NP_003898.2 | Translational regulator | Y319 | WVyPLTPEANFTDSTTQSCTHSR | SEQ ID NO: 395 |
| 383 | eIF3-beta | NP_003748.1 | Translational regulator | Y300 | SySSGGEDGYVR | SEQ ID NO: 396 |
| 384 | eIF3S6IP | NP_057175.1 | Translational regulator | Y247 | QLEVyTSGGDPESVAGEYGR | SEQ ID NO: 397 |
| 385 | eIF3S6IP | NP_057175.1 | Translational regulator | Y287 | LHSLLGDyYQAIK | SEQ ID NO: 398 |
| 386 | eIF3S6IP | NP_057175.1 | Translational regulator | Y288 | LHSLLGDYyQAIK | SEQ ID NO: 399 |
| 387 | eIF3S6IP | NP_057175.1 | Translational regulator | Y357 | TTYKyEMINK | SEQ ID NO: 400 |
| 388 | eIF3-zeta | NP_003744.1 | Translational regulator | Y506 | yLILKDPNK | SEQ ID NO: 401 |
| 389 | eIF4B | NP_001408.2 | Translational regulator | Y258 | yDDRGSRDYDRGYDSR | SEQ ID NO: 402 |
| 390 | PES1 | NP_055118.1 | Translational regulator | Y265 | AKAGEGTyALDSE | SEQ ID NO: 403 |
| 391 | RPL18a | NP_000971.1 | Translational regulator | Y46 | FWyFVSQLK | SEQ ID NO: 405 |
| 392 | FAT | NP_005236.2 | Tumor suppressor | Y4489 | FNLNQyLPNFYPLDMSEPQTK | SEQ ID NO: 406 |
| 393 | FAT | NP_005236.2 | Tumor suppressor | Y4519 | GTGENSTCREPHAPyPPGYQR | SEQ ID NO: 407 |
| 394 | FAT | NP_005236.2 | Tumor suppressor | Y4523 | GTGENSTCREPHAPYPPGyQR | SEQ ID NO: 408 |

TABLE 1-continued

Novel Phosphorylation Sites in Carcinoma and/or leukemia.

| 1 | Protein Name | Accession No. | Protein Type | Phospho-Residue | Phosphorylation Site Sequence | SEQ ID NO |
|---|---|---|---|---|---|---|
| 395 | COPS3 | NP_003644.2 | Ubiquitin conjugating system | Y422 | SMGSQEDDSGNKPSSyS | SEQ ID NO: 409 |
| 396 | CYLD | NP_056062.1 | Ubiquitin conjugating system | Y181 | GQGFTDGVyQGK | SEQ ID NO: 410 |
| 397 | CYLD | NP_056062.1 | Ubiquitin conjugating system | Y356 | SELFyTLNGSSVDSQPQSK | SEQ ID NO: 411 |
| 398 | ETEA | NP_055428.1 | Ubiquitin conjugating system | Y297 | QQQDEAyLASLR | SEQ ID NO: 412 |
| 399 | HECW2 | NP_065811.1 | Ubiquitin conjugating system | Y208 | GMFFNPDPyLK | SEQ ID NO: 413 |
| 400 | RC3H1 | NP_742068.1 | Ubiquitin conjugating system | Y593 | GSQLYPAQQTDVYyQDPR | SEQ ID NO: 414 |
| 401 | SMURF1 | NP_065162.1 | Ubiquitin conjugating system | Y413 | EEIFEESyRQIMK | SEQ ID NO: 415 |
| 402 | ACAD11 | NP_115545.3 | Unknown function | Y324 | MAGIAQGVySR | SEQ ID NO: 416 |
| 403 | ANKRD52 | EAW96919.1 | Unknown function | Y207 | GyGLLHTAAASGQIEWKYLLR | SEQ ID NO: 417 |
| 404 | C17orf71 | NP_060619.4 | Unknown function | Y309 | LQHALEDQIyR | SEQ ID NO: 418 |
| 405 | C18orf8 | NP_037458.3 | Unknown function | Y610 | QTEDNMLFyTIFR | SEQ ID NO: 419 |
| 406 | C19orf21 | NP_775752.1 | Unknown function | Y7 | VTRyPILGIPQAHR | SEQ ID NO: 420 |
| 407 | C1orf101 | NP_776168.1 | Unknown function | Y23 | ySTNSPNYR | SEQ ID NO: 421 |
| 408 | C1orf101 | NP_776168.1 | Unknown function | Y30 | YSTNSPNyR | SEQ ID NO: 422 |
| 409 | C1orf162 | NP_777556.1 | Unknown function | Y120 | LSSIPGESLTyASTTFK | SEQ ID NO: 423 |
| 410 | C1orf162 | NP_777556.1 | Unknown function | Y148 | SNHLAENHSADFDPIVyAQIK | SEQ ID NO: 424 |
| 411 | C1orf21 | NP_110433.1 | Unknown function | Y34 | NYQNGDVFGDEyR | SEQ ID NO: 425 |
| 412 | C1orf32 | NP_955383.1 | Unknown function | Y566 | SASYyAWSPPGTYK | SEQ ID NO: 426 |
| 413 | C1orf82 | NP_079089.1 | Unknown function | Y127 | TNKVyDITER | SEQ ID NO: 427 |
| 414 | C1orf82 | NP_079089.1 | Unknown function | Y319 | LKASENSESEySR | SEQ ID NO: 428 |
| 415 | C22orf5 | NP_036396.2 | Unknown function | Y243 | ELLSPySPVLKFFMVK | SEQ ID NO: 429 |
| 416 | C22orf9 | NP_056079.1 | Unknown function | Y66 | LAySGSESGADGR | SEQ ID NO: 430 |

TABLE 1-continued

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| 417 | C2orf33 | NP_064579.3 | Unknown function | Y35 | IQyEMEYTEGISQR | SEQ ID NO: 431 |
| 418 | C2orf33 | NP_064579.3 | Unknown function | Y39 | IQYEMEyTEGISQR | SEQ ID NO: 432 |
| 419 | C3orf24 | NP_775743.1 | Unknown function | Y163 | SILLLyATYK | SEQ ID NO: 433 |
| 420 | C3orf24 | NP_775743.1 | Unknown function | Y166 | QMLRSILLLYATyKK | SEQ ID NO: 434 |
| 421 | C3orf58 | NP_775823.1 | Unknown function | Y92 | NVyFAQYGEPREGGRRR | SEQ ID NO: 435 |
| 422 | C5orf32 | NP_115788.1 | Unknown function | Y64 | TTVyVVEDQR | SEQ ID NO: 437 |
| 423 | C6orf143 | NP_001010872.1 | Unknown function | Y523 | FEGyDNPENLK | SEQ ID NO: 438 |
| 424 | C6orf143 | NP_001010872.1 | Unknown function | Y685 | HYVySTLTR | SEQ ID NO: 439 |
| 425 | C6orf143 | NP_001010872.1 | Unknown function | Y896 | FNTEQIQyR | SEQ ID NO: 440 |
| 426 | C6orf143 | NP_001010872.1 | Unknown function | Y986 | SSPLLNYNTGVyR | SEQ ID NO: 441 |
| 427 | C6orf149 | NP_065141.3 | Unknown function | Y26 | ESKRFSAyNYRTYAVR | SEQ ID NO: 442 |
| 428 | C6orf149 | NP_065141.3 | Unknown function | Y28 | ESKRFSAYNyRTYAVR | SEQ ID NO: 443 |
| 429 | C6orf149 | NP_065141.3 | Unknown function | Y31 | ESKRFSAYNYRTyAVR | SEQ ID NO: 444 |
| 430 | CCDC120 | NP_296375.1 | Unknown function | Y398 | SSEVLyERPQPTPAFSSR | SEQ ID NO: 445 |
| 431 | CCDC18 | NP_996769.2 | Unknown function | Y884 | SEEVyCLQK | SEQ ID NO: 446 |
| 432 | CHORDC1 | NP_036256.1 | Unknown function | Y292 | SyVTMTATKIEITMR | SEQ ID NO: 447 |
| 433 | COBLL1 | NP_055715.3 | Unknown function | Y533 | STDGQEPHSVVyDTSNGKK | SEQ ID NO: 449 |
| 434 | COBLL1 | NP_055715.3 | Unknown function | Y742 | IDKNSTASYLKNyPLYR | SEQ ID NO: 450 |
| 435 | DAZAP2 | NP_055579.1 | Unknown function | Y165 | KGNFFMGGSDGGyTIW | SEQ ID NO: 451 |
| 436 | DENND2A | NP_056504.2 | Unknown function | Y370 | TLSEENVyEDILDPPMK | SEQ ID NO: 452 |
| 437 | DENND2C | NP_940861.3 | Unknown function | Y195 | SLENIySEPEGQECGPSINPLPKPR | SEQ ID NO: 453 |
| 438 | DEPDC7 | NP_631899.2 | Unknown function | Y300 | ELLFDAIGRyYSSR | SEQ ID NO: 454 |
| 439 | DKFZP451C023 | CAD89901.1 | Unknown function | Y48 | TLMLNEDKPSDDySAVLQR | SEQ ID NO: 455 |
| 440 | MIER3 | NP_689835.3 | Unknown function | Y331 | YDyFAQQTR | SEQ ID NO: 456 |
| 441 | DYX1C1 | NP_570722.2 | Unknown function | Y128 | EDQKyALSVMMK | SEQ ID NO: 457 |

TABLE 1-continued

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| 442 | FAM102A | NP_001030331.1 | Unknown function | Y376 | VSSGVyEPVVIESH | SEQ ID NO: 458 |
| 443 | FAM81A | NP_689663.1 | Unknown function | Y21 | HSQSLTMAPySSVSLVEQLEDR | SEQ ID NO: 459 |
| 444 | FAM83E | NP_060178.1 | Unknown function | Y100 | QEPSGMAEGATTADVDAGSLSyWPGQSEQPAPVLR | SEQ ID NO: 460 |
| 445 | FLJ00258 | NP_689619.1 | Unknown function | Y126 | NAADLPPPLPNKPPPEDyYEEALPLGPGK | SEQ ID NO: 461 |
| 446 | AFAP1L2 | NP_115939.1 | Unknown function | Y459 | TDPEEFTYDyVDADR | SEQ ID NO: 463 |
| 447 | FLJ14732 | NP_115734.1 | Unknown function | Y283 | NLHHTQELLyESTKDFLQLR | SEQ ID NO: 464 |
| 448 | FLJ20625 | NP_060377.1 | Unknown function | Y138 | IAAyAYSALSQIR | SEQ ID NO: 465 |
| 449 | FLJ22052 | NP_060395.4 | Unknown function | Y288 | KLyPQLSSVHQK | SEQ ID NO: 466 |
| 450 | FLJ22052 | NP_060395.4 | Unknown function | Y920 | TTATVDTyESLLSDSNSNQSR | SEQ ID NO: 467 |
| 451 | FLJ30976 | NP_659462.1 | Unknown function | Y415 | TTLCNMLAENyKGK | SEQ ID NO: 468 |
| 452 | FLJ34633 | NP_689578.1 | Unknown function | Y216 | GSEEyYSFHESDLDLPEMGSGSMSSR | SEQ ID NO: 469 |
| 453 | FLJ34633 | NP_689578.1 | Unknown function | Y217 | GSEEYySFHESDLDLPEMGSGSMSSR | SEQ ID NO: 470 |
| 454 | FRMPD4 | NP_055543.1 | Unknown function | Y596 | HLyIDNAYSSDGLNQQLSQPGEAPCEADYR | SEQ ID NO: 471 |
| 455 | FRMPD4 | NP_055543.1 | Unknown function | Y601 | HLYIDNAySSDGLNQQLSQPGEAPCEADYR | SEQ ID NO: 472 |
| 456 | FRYL | NP_055845.1 | Unknown function | Y93 | QNGTEDESyEYRPR | SEQ ID NO: 473 |
| 457 | FRYL | NP_055845.1 | Unknown function | Y95 | RQNGTEDESYEyRPR | SEQ ID NO: 474 |
| 458 | HSPA12A | NP_079291.2 | Unknown function | Y21 | ETAPTSAySSPAR | SEQ ID NO: 475 |
| 459 | KIAA0376 | NP_056145.1 | Unknown function | Y808 | GRVyNYMNAVER | SEQ ID NO: 476 |
| 460 | KIAA0376 | NP_056145.1 | Unknown function | Y810 | GRVYNyMNAVER | SEQ ID NO: 477 |
| 461 | KIAA1109 | XP_371706.5 | Unknown function | Y3846 | FQTNyASTTHLMTGK | SEQ ID NO: 478 |
| 462 | KIAA1239 | XP_049078.7 | Unknown function | Y1332 | GEIIySLDGSDCVHK | SEQ ID NO: 479 |
| 463 | LIMD2 | NP_085053.1 | Unknown function | Y102 | GNyDEGFGR | SEQ ID NO: 480 |
| 464 | LSR7 | NP_061029.2 | Unknown function | Y158 | GPVNyNVTTEFEK | SEQ ID NO: 481 |
| 465 | NSUN2 | NP_060225.4 | Unknown function | Y646 | KLSSETySQAK | SEQ ID NO: 482 |
| 466 | PHF8 | NP_055922.1 | Unknown function | Y267 | GEKIFyLIR | SEQ ID NO: 483 |

TABLE 1-continued

Novel Phosphorylation Sites in Carcinoma and/or leukemia.

| | Protein Name | Accession No. | Protein Type | Phospho-Residue | Phosphorylation Site Sequence | SEQ ID NO |
|---|---|---|---|---|---|---|
| 467 | POF1B | NP_079197.2 | Unknown function | Y166 | GSHFFPGNNVIyEK | SEQ ID NO: 484 |
| 468 | QSER1 | NP_001070254.1 | Unknown function | Y1411 | EFAATNSyLGYFGDAK | SEQ ID NO: 485 |
| 469 | SNX22 | NP_079074.2 | Unknown function | Y92 | GLEQRRQGLEAYIQGILyLNQEVPK | SEQ ID NO: 486 |
| 470 | JIP4 | NP_003962.3 | Unknown function | Y900 | GNAGSAEDTVDISQTGVyTE | SEQ ID NO: 487 |
| 471 | ST5 | NP_005409.3 | Unknown function | Y308 | GLPQLPSSCySVDR | SEQ ID NO: 488 |
| 472 | SYF2 | NP_056299.1 | Unknown function | Y226 | FyGKYTAEIK | SEQ ID NO: 489 |
| 473 | SYF2 | NP_056299.1 | Unknown function | Y229 | FYGKyTAEIK | SEQ ID NO: 490 |
| 474 | CLTC | NP_004850.1 | Vesicle protein | Y883 | IyIDSNNNPER | SEQ ID NO: 491 |
| 475 | CLTA | NP_001824.1 | Vesicle protein | Y94 | SNGPTDSyAAISQVDRLQSEPE | SEQ ID NO: 492 |
| 476 | CSP | NP_079495.1 | Vesicle protein | Y17 | SLSTSGESLyHVLGLDK | SEQ ID NO: 493 |
| 477 | CSP | NP_079495.1 | Vesicle protein | Y192 | TTQLTADSHPSyHTDGFN | SEQ ID NO: 494 |
| 478 | EHBP1 | NP_056067.1 | Vesicle protein | Y319 | VQTPQyLNPFDEPE | SEQ ID NO: 495 |
| 479 | EHD2 | NP_055416.2 | Vesicle protein | Y458 | YDEIFyNLAPADGK | SEQ ID NO: 496 |
| 480 | epsin 3 | NP_060427.1 | Vesicle protein | Y176 | RYGEDySR | SEQ ID NO: 497 |
| 481 | EXOC1 | NP_060731.2 | Vesicle protein | Y769 | VIySLGQPLEKLNHF | SEQ ID NO: 498 |
| 482 | NSF | NP_006169.1 | Vesicle protein | Y259 | GILLyGPPGCGK | SEQ ID NO: 499 |
| 483 | NSF | NP_006169.1 | Vesicle protein | Y499 | GDFLASLENDIKPAFGTNQEDyASYIMNGIIK | SEQ ID NO: 500 |

One of skill in the art will appreciate that, in many instances the utility of the instant invention is best understood in conjunction with an appreciation of the many biological roles and significance of the various target signaling proteins/polypeptides of the invention. The foregoing is illustrated in the following paragraphs summarizing the knowledge in the art relevant to a few non-limiting representative peptides containing selected phosphorylation sites according to the invention.

CDH1 (Cadherin 1, E-cadherin, uvomorulin), phosphorylated at Y876, is among the proteins listed in this patent. It is a calcium-dependent glycoprotein that mediates cell-cell adhesion and migration and is necessary for epithelial morphogenesis (Nature Cell Biology 2002; 4:E101-E108.). Formation of adherens junctions between cells depends on the CDH1 cytoplasmic domain in which Y876 is located. When situated in an adherens junction, the cytoplasmic domain forms complexes with proteins such as catenins, Cdc42, PAR, atypical PKC, serves as a scaffold for forming adjacent tight junctions, activates PI(3) kinase, promotes actin polymerization and stabilizes microtubules (Nature Cell Biology 2002; 4:E101-E108.). Increased tyrosine phosphorylation of cadherins has been shown to suppress adhesion, suggesting a role for pY876 in regulating the stability of the adherens junction (J Cell Biol. 1995 August; 130(4):977-86.). 33-55% of sporadic diffuse-type gastric cancers carry somatic mutations of CDH1, and germline mutations in the gene cause the disease (Cancer Cell 2004 February; 5(2):121-125.). In addition, altered expression of CDH1 may be therapeutic for breast and colon cancer (Human PSD™, Biobase Corporation, Beverly, Mass.). Molecular probes for pY876 may be useful for diagnostic and/or therapeutic purposes for lung neoplasms (Anticancer Res 2003 July-August; 23(4):3367-71.) and gastric cancer (Cancer Cell 2004 February; 5(2):121-125. PhosphoSite®, Cell Signaling Technology, Danvers, Mass. Human PSD™, Biobase Corporation, Beverly, Mass.).

FGFR2, phosphorylated at Y466, Y586, Y588, Y616, Y733, Y805, and Y812, is among the proteins listed in this patent. Fibroblast growth factor receptor 2 is a receptor tyrosine kinase of the highly-conserved FGFR family that binds fibroblast growth factor (FGF) and acts in induction of apoptosis, skeletal development, cell migration and differentiation (Human PSD™, Biobase Corporation, Beverly, Mass.). Consistent with its role in development, mutations in the FGFR2 gene are known to cause at least three craniosynostotic conditions—Crouzon syndrome (Nat. Genet. 1994 September; 8(1):98-103. Nat. Genet. 1994 November; 8(3):275-9), Apert syndrome (Science. 2003 Aug. 1; 301 (5633):643-6. Nat. Genet. 1996 May; 13(1):48-53. Nat. Genet. 1995 February; 9(2):165-72), Pfeiffer syndrome (Eur J Hum Genet. 2006 March; 14(3):289-98)—as well as autosomal dominant lacrimoauriculodentodigital (LADD) syndrome (Nat. Genet. 2006 April; 38(4):414-7). The gene is also associated with gastric cancer (Cancer Res. 2001 May 1; 61(9):3541-3) and breast cancer (Nature. 2007 Jun. 28; 447 (7148):1087-93. Nat. Genet. 2007 July; 39(7):870-4). Y586, Y588, Y616, and Y733 are all within the kinase catalytic domain, and their phosphorylation may affect catalytic activity or recognition of substrate. Molecular probes to these and other sites on the protein would provide valuable tools to study the function of this protein in normal and pathological states (PhosphoSite®, Cell Signaling Technology, Danvers, Mass.).

CaMK2-delta, phosphorylated at Y14, is among the proteins listed in this patent. Calcium calmodulin dependent protein kinase II delta is a member of the CaMKII enzyme complex which is composed of four different chains: alpha, beta, gamma, and delta. The different chains assemble into homo- or heteromultimeric holoenzymes composed of 8 to 12 subunits (J Biol. Chem. 2007 Mar. 9; 282(10):7219-31. PhosphoSite®, Cell Signaling Technology, Danvers, Mass.). CAMK2-delta differs from the other subunits in having a variable domain, generated by alternative splicing, that acts as a nuclear localization signal. When the CAMK2-delta subunit predominates in the holoenzyme, as it does in the adult heart, the complex is expressed in the nucleus (J Biol. Chem. 2007 Mar. 9; 282(10):7219-31). Each of the CaMK2 chains contains a site at the N-terminus of the kinase catalytic domain that is paralogous to but distinct from Y14, suggesting that regulation of this site may have been evolutionarily conserved. The sequence differences surrounding the phosphorylation site may distinguish substrates of different kinases or affect the phosphorylation efficiency of a single kinase. An antibody to Y14 would be useful in clarifying these possibilities. Disregulation of CAMK2-delta is associated with cardiac hypertrophy and dilated cardiomyopathy (Circ Res. 2003 May 2; 92(8):912-9. J Biol. Chem. 2002 Jan. 11; 277 (2):1261-7), and molecular probes specific for this protein and its modification would be valuable in assessing its role in this disease (Human PSD™, Biobase Corporation, Beverly, Mass.).

Cdc42, phosphorylated at Y32, is among the proteins listed in this patent. Cell division cycle 42 (GTP binding protein 25 kD) is a Rho GTPase which regulates signaling pathways that control diverse cellular functions including cell morphology, migration, endocytosis and cell cycle progression (PhosphoSite®, Cell Signaling Technology, Danvers, Mass. Human PSD™, Biobase Corporation, Beverly, Mass.). In particular, Cdc42 activity is prominent at the leading edge of motile cells (Science 2004 Sep. 10; 305(5690):1615-1619. Mol Cell Biol. 2002 September; 22(18):6582-91) where it is controlled by LKB1. Disregulation of Cdc42 in the absence of LKB1 is associated with non-small cell lung cancer (Cancer Res. 2008 Feb. 1; 68(3):740-8) and with breast neoplasms (Br J Cancer 2002 Sep. 9; 87(6):635-44.). Y32 is located within the docking site for guanine nucleotide exchange factor, and is a potential target for therapeutic intervention in cancer. Molecular probes to this site may provide insight into regulation of Cdc42 activity.

SKB1 (protein arginine methyltransferase 5; PRMT5), phosphorylated at Y283, is among the proteins listed in this patent. By methylating its target proteins on arginine residues, SKB1 modulates the accessibility of DNA for transcription and replication (Human PSD™, Biobase Corporation, Beverly, Mass.) and enables small nuclear ribonucleoproteins to function within the spliceosome (J Cell Biol 2007; 178(5): 733-740.). Abnormally high levels of SKB1 expression are found in lymphoid cancer, mantle cell lymphoma and gastric cancer samples (EMBO J 2007; 26:3558-3569. Human PSD™, Biobase Corporation, Beverly, Mass.). Y283 resides in the catalytic domain of the enzyme, and molecular probes of its phosphorylation state may provide insight into its activity in normal and pathological tissues. The SKB1 protein has potential diagnostic and/or therapeutic implications based on association with lymphoid cancer, mantle cell lymphoma, gastric cancer and breast neoplasms (EMBO J 2007; 26:3558-3569. Biochem Biophys Res Commun 2005 Apr. 8; 329(2):522-30. PhosphoSite®, Cell Signaling Technology, Danvers, Mass. Human PSD™, Biobase Corporation, Beverly, Mass.).

Three ribosomal protein S6 kinase family members are among the proteins listed in this patent. RSK2 Y433 (SEQ ID NO: 246), RSK3 Y434 (SEQ ID NO: 248), and RSK4 Y437 (SEQ ID NO: 250) are paralogous sites. RSK2 Y644 (SEQ ID NO: 247) is unique to this member. RSK3 Y707 (SEQ ID NO: 249) has paralogous sites in the other members that are not described here. The ribosomal S6 kinases participate in the transduction of signals from extracellular stimuli, such as hormones and neurotransmitters (Mol Cell Endocrinol 1999 May 25; 151(1-2):65-77.). The RSKs are distantly related to CK2-alpha1, also among the proteins listed in this patent. Based on the CK2-alpha1 crystal structure, RSK2 Y433, RSK3 Y434, RSK4 Y437 and CK2-alpha1 (SEQ ID NO: 240) are within the phosphate anchor element of the active site (EMBO J 1998; 17:2451-2462.). Phosphorylation of these sites may affect kinase activity. Mutations in the RSK2 gene cause Coffin-Lowry mental retardation syndrome, and the protein is prominently expressed in brain structures that are essential for cognitive function and learning (Am J Hum Genet 1998 December; 63(6):1631-40. PhosphoSite®, Cell Signaling Technology, Danvers, Mass. Human PSD™, Biobase Corporation, Beverly, Mass.). Molecular probes to these proteins would provide insight into the activation of cells and into their effects on development of the nervous system.

Claudin 5, phosphorylated at Y212 and Y217, is among the proteins listed in this patent. The claudin family of proteins contributes to tight junction function, and different members of the family may have distinct effects on the barrier properties of the junction (Am J Physiol Lung Cell Mol Physiol 2003 August; 285:L1166-L1178.). In claudin 4, phosphorylation of a site similar to but distinct from Y217 has been shown to increase the permeability of tight junctions, and a need for specific antibodies to the various claudin family members was stated in the same report (J Biol Chem 2005 December; 280(51):42375-42382.). pY212 and pY217 of claudin 5 were observed in numerous lung cancer samples (Cell 2007 Dec. 14; 131(6):1190-1203.), and expression of the protein differentiates lung squamous cell carcinomas from adenocarcinomas (Mod Pathol 2007 September; 20(9): 947-54.), suggesting that molecular probes to this protein would valuable in the diagnosis and/or treatment of lung cancers. In addition, polymorphism in the gene locus may be associated with schizophrenia (PhosphoSite®, Cell Signaling Technology, Danvers, Mass. Human PSD™, Biobase Corporation, Beverly, Mass.).

Three members of the discs large homologue family (DLG3, PSD-93, PDS-95), as well as two of the proteins that are known to interact with them (SAPAP1, SAPAP3), are among the proteins listed in this patent. Discs large proteins participate in multi-protein complexes at areas of intercellular contact, such as synapses, where they contribute to cell proliferation, neuron adhesion and synaptic transmission (Genes Dev. 2004 Aug. 15; 18(16):1909-25); SAPAP proteins bind to DLG proteins at excitatory synapses with SAPAP1 found in cell bodies and SAPAP3 in dendrites (J Comp Neurol. 2004 Apr. 19; 472(1):24-39). Searches for safer and more effective anesthetics have shown that the inhaled anesthetic halothane disrupts interactions between DLG proteins and nNOS and NMDA receptors and that more targeted anesthetics may be developed by designing drugs to disrupt the interactions of specific DLG proteins. PSD-93 Y223 (SEQ ID NO: 32) and PSD95 Y233 (SEQ ID NO: 34) are adjacent to the halothane binding site, and molecular probes against these sites would provide insight into the molecular mechanisms of anesthetics (Mol. Interv. 2004 August; 4(4):215-21. J Biol. Chem. 2003 Sep. 19; 278(38): 36669-75). Consistent with its role in neuronal function, mutation of DLG3 is associated with X-linked mental retardation, and its chromosomal position correlates with Parkinson disease (Human PSD™, Biobase Corporation, Beverly, Mass.); antibodies to Y808 (SEQ ID NO: 7) or other parts of the protein may serve as useful tools in dissecting the molecular mechanisms of these diseases. Similarly, SAPAP1 is upregulated in schizophrenia (Neuropsychopharmacology. 2003 October; 28(10): 1831-9) and its gene maps to a chromosomal region associated with psychiatric illness. (Psychiatry Genet. 2005 March; 15(1):37-44. PhosphoSite®, Cell Signaling Technology, Danvers, Mass. Human PSD™, Biobase Corporation, Beverly, Mass.).

Cbl (Cas-Br-M ecotropic retroviral transforming sequence), phosphorylated at Y141, is among the proteins listed in this patent. Cbl is an ubiquitin protein ligase that acts in cell migration, apoptosis, and microtubule polymerization. Its increased phosphorylation correlates with several neoplasms, and mouse Cbl is associated with AIDS. This protein has potential diagnostic and/or therapeutic implications based on association with myelocytic leukemia and lymphocytic leukemia (Am J Hum Genet 1996 November; 59(5): 990-8. PhosphoSite®, Cell Signaling Technology, Danvers, Mass., Human PSD™, Biobase Corporation, Beverly, Mass.).

LSD1, phosphorylated at Y135, is among the proteins listed in this patent. Lysine-specific histone demethylase 1 is a transcription corepressor that plays a role in hydrogen peroxide and formaldehyde biosynthetic processes. It may also play a role in chromatin modification and silencing. LSD1 expression is upregulated in prostate carcinoma. (PhosphoSite®, Cell Signaling Technology, Danvers, Mass. Human PSD™, Biobase Corporation, Beverly, Mass.).

PIK3R2, phosphorylated at Y460, is among the proteins listed in this patent. Phosphoinositide-3-kinase regulatory polypeptide 2 is a regulatory subunit of phosphatidylinositol 3-kinase that acts in signal transduction, cell motility and differentiation; tumorigenic fusion to USP8 gene may lead to chronic myeloproliferative disorder. (PhosphoSite®, Cell Signaling Technology, Danvers, Mass. Human PSD™, Biobase Corporation, Beverly, Mass.).

CD82, phosphorylated at Y261, is among the proteins listed in this patent. It plays a role in T cell development, induces apoptosis, and inhibits cell migration, motility and adhesion. Its increased expression is associated with non small cell lung carcinoma; aberrant expression is associated with multiple neoplasms. CD82 has potential diagnostic and/or therapeutic implications based on association with colorectal neoplasms (Anticancer Res 2001 September-October; 21(5):3581-7. PhosphoSite®, Cell Signaling Technology, Danvers, Mass., Human PSD™, Biobase Corporation, Beverly, Mass.).

KPNA3, phosphorylated at Y506, is among the proteins listed in this patent. Karyopherin alpha 3 binds to nuclear localization signals (NLS) and plays a role in nuclear import. Its gene expression is downregulated in B cell chronic lymphocytic leukemia. (PhosphoSite®, Cell Signaling Technology, Danvers, Mass. Human PSD™, Biobase Corporation, Beverly, Mass.).

FLT3, phosphorylated at Y865, is among the proteins listed in this patent. Fms-related receptor tyrosine kinase 3 is a receptor for the hematopoietic growth factor FLT3LG that stimulates proliferation of stem and progenitor cells. Internal tandem duplication or mutations in the gene are associated with acute myeloid leukemia (AML). This protein has potential diagnostic and/or therapeutic implications based on association with myelocytic leukemia (Blood 2000 Dec. 1; 96(12):3907-14. PhosphoSite®, Cell Signaling Technology, Danvers, Mass. Human PSD™, Biobase Corporation, Beverly, Mass.).

Ets-1, phosphorylated at Y140, is among the proteins listed in this patent. V-ets avian erythroblastosis virus E26 oncogene homolog 1 is a transcriptional activator of genes involved in angiogenesis, immune response, apoptosis, cell proliferation, adhesion, and migration; it is also associated with cancer and rheumatoid arthritis. This protein has potential diagnostic and/or therapeutic implications based on association adenocarcinoma and colonic neoplasms (Anticancer Res 2002 May-June; 22(3):1581-4. PhosphoSite®, Cell Signaling Technology Danvers, Mass. Human PSD™, Biobase Corporation, Beverly, Mass.).

CTNND1, phosphorylated at Y208, is among the proteins listed in this patent. Catenin (cadherin associated protein) delta 1, links cadherin E (CDH1) to cytoskeleton, regulates GTPase activation, apoptosis, cell proliferation and cell migration. Its altered expression is associated with several cancers. This protein has potential diagnostic and/or therapeutic implications based on association with colorectal neoplasms, stomach neoplasms, and pancreatic neoplasms (Anticancer Res 1999 September-October; 19(5C):4401-5. PhosphoSite®, Cell Signaling Technology, Danvers, Mass. Human PSD™ Biobase Corporation, (Beverly, Mass.).

COPS3, phosphorylated at Y422, is among the proteins listed in this patent. It is a component of the COP9 signalosome complex (CSN), a complex involved in various cellular and developmental processes. The CSN complex regulates the ubiquitin (Ubl) conjugation pathway by mediating the deneddylation of the cullin subunits of SCF-type E3 ligase complexes, leading to a decrease in the Ubl ligase activity of SCF-type complexes such as SCF, CSA or DDB2. The complex is also involved in phosphorylation of p53/TP53, c-jun/JUN, IkappaBalpha/NFKBIA, ITPK1 and IRF8/ICSBP, possibly via its association with CK2 and PKD kinases. CSN-dependent phosphorylation of TP53 and JUN promotes and protects degradation by the Ubl system, respectively (PhosphoSite®, Cell Signaling Technology, Danvers, Mass.). Amplification and overexpression of COPS3 is associated with osteosarcoma, and molecular probes, such as antibodies against pY422, have potential diagnostic value for this disease (Cancer. 2007 May 1; 109(9):1870-6; Oncogene 2003 Aug. 14; 22(34):5358-61. Human PSD™, Biobase Corporation, Beverly, Mass.).

The invention identifies peptide sequences comprising phosphorylation sites useful to profile phosphotyrosine signaling in the analysis of oncogenesis and specifically in lung cancer (e.g., in non-small lung cancer, NSLC). For most solid tumors the tyrosine kinases that drive disease remain unknown, limiting the ability to identify drug targets and predict response. Tyrosine kinase signaling across 41 NSCLC cells lines and 150 NSCLC tumors have implicated a number of known oncogenic kinases such as EGFR and c-Met as well as novel ALK and ROS fusion proteins, along with others such as PDGFRα and DDR1. The compendium of phosphorylated sites provided herein constitutes a fundamental tool to profile a given sample across many possible target phosphorylation determinants offering a unique tool to characterize a given tumor to identify drug targets and predict response. The invention also provides peptides comprising a novel phosphorylation site of the invention. In one particular embodiment, the peptides comprise any one of the an amino acid sequences as set forth in column E of Table 1 and FIG. 2, which are trypsin-digested peptide fragments of the parent proteins. Alternatively, a parent signaling protein listed in Table 1 may be digested with another protease, and the sequence of a peptide fragment comprising a phosphorylation site can be obtained in a similar way. Suitable proteases include, but are not limited to, serine proteases (e.g. hepsin), metallo proteases (e.g. PUMP1), chymotrypsin, cathepsin, pepsin, thermolysin, carboxypeptidases, etc.

The invention also provides proteins and peptides that are mutated to eliminate a novel phosphorylation site of the invention. Such proteins and peptides are particular useful as research tools to understand complex signaling transduction pathways of cancer cells, for example, to identify new upstream kinase(s) or phosphatase(s) or other proteins that regulates the activity of a signaling protein; to identify downstream effector molecules that interact with a signaling protein, etc.

Various methods that are well known in the art can be used to eliminate a phosphorylation site. For example, the phosphorylatable tyrosine may be mutated into a non-phosphorylatable residue, such as phenylalanine. A "phosphorylatable" amino acid refers to an amino acid that is capable of being modified by addition of a phosphate group (any includes both phosphorylated form and unphosphorylated form). Alternatively, the tyrosine may be deleted. Residues other than the tyrosine may also be modified (e.g., delete or mutated) if such modification inhibits the phosphorylation of the tyrosine residue. For example, residues flanking the tyrosine may be deleted or mutated, so that a kinase can not recognize/phosphorylate the mutated protein or the peptide. Standard mutagenesis and molecular cloning techniques can be used to create amino acid substitutions or deletions.

2. Modulators of the Phosphorylation Sites

In another aspect, the invention provides a modulator that modulates tyrosine phosphorylation at a novel phosphorylation site of the invention, including small molecules, peptides comprising a novel phosphorylation site, and binding molecules that specifically bind at a novel phosphorylation site, including but not limited to antibodies or antigen-binding fragments thereof.

Modulators of a phosphorylation site include any molecules that directly or indirectly counteract, reduce, antagonize or inhibit tyrosine phosphorylation of the site. The modulators may compete or block the binding of the phosphorylation site to its upstream kinase(s) or phosphatase(s), or to its downstream signaling transduction molecule(s).

The modulators may directly interact with a phosphorylation site. The modulator may also be a molecule that does not directly interact with a phosphorylation site. For example, the modulators can be dominant negative mutants, i.e., proteins and peptides that are mutated to eliminate the phosphorylation site. Such mutated proteins or peptides could retain the binding ability to a downstream signaling molecule but lose the ability to trigger downstream signaling transduction of the wild type parent signaling protein.

The modulators include small molecules that modulate the tyrosine phosphorylation at a novel phosphorylation site of the invention. Chemical agents, referred to in the art as "small molecule" compounds are typically organic, non-peptide molecules, having a molecular weight less than 10,000, less than 5,000, less than 1,000, or less than 500 daltons. This class of modulators includes chemically synthesized molecules, for instance, compounds from combinatorial chemical libraries. Synthetic compounds may be rationally designed or identified based on known or inferred properties of a phosphorylation site of the invention or may be identified by screening compound libraries. Alternative appropriate modulators of this class are natural products, particularly secondary metabolites from organisms such as plants or fungi, which can also be identified by screening compound libraries. Methods for generating and obtaining compounds are well known in the art (Schreiber S L, Science 151: 1964-1969 (2000); Radmann J. and Gunther J., Science 151: 1947-1948 (2000)).

The modulators also include peptidomimetics, small protein-like chains designed to mimic peptides. Peptidomimetics may be analogues of a peptide comprising a phosphorylation site of the invention. Peptidomimetics may also be analogues of a modified peptide that are mutated to eliminate a phosphorylation site of the invention. Peptidomimetics (both peptide and non-peptidyl analogues) may have improved properties (e.g., decreased proteolysis, increased retention or increased bioavailability). Peptidomimetics generally have improved oral availability, which makes them especially suited to treatment of disorders in a human or animal.

In certain embodiments, the modulators are peptides comprising a novel phosphorylation site of the invention. In certain embodiments, the modulators are antibodies or antigen-binding fragments thereof that specifically bind at a novel phosphorylation site of the invention.

3. Heavy-Isotope Labeled Peptides (AQUA Peptides)

In another aspect, the invention provides peptides comprising a novel phosphorylation site of the invention. In a particular embodiment, the invention provides Heavy-Isotope Labeled Peptides (AQUA peptides) comprising a novel phosphorylation site. Such peptides are useful to generate phosphorylation site-specific antibodies for a novel phosphorylation site. Such peptides are also useful as potential diagnostic tools for screening carcinoma and/or leukemia, or as potential therapeutic agents for treating carcinoma and/or leukemia.

The peptides may be of any length, typically six to fifteen amino acids. The novel tyrosine phosphorylation site can occur at any position in the peptide; if the peptide will be used as an immunogen, it preferably is from seven to twenty amino acids in length. In some embodiments, the peptide is labeled with a detectable marker.

"Heavy-isotope labeled peptide" (used interchangeably with AQUA peptide) refers to a peptide comprising at least one heavy-isotope label, as described in WO/03016861, "Absolute Quantification of Proteins and Modified Forms Thereof by Multistage Mass Spectrometry" (Gygi et al.) (the teachings of which are hereby incorporated herein by reference, in their entirety). The amino acid sequence of an AQUA peptide is identical to the sequence of a proteolytic fragment of the parent protein in which the novel phosphorylation site occurs. AQUA peptides of the invention are highly useful for detecting, quantitating or modulating a phosphorylation site of the invention (both in phosphorylated and unphosphorylated forms) in a biological sample.

A peptide of the invention, including an AQUA peptides comprises any novel phosphorylation site. Preferably, the peptide or AQUA peptide comprises a novel phosphorylation site of a protein in Table 1 that is a adaptor/scaffold proteins; adhesion or extracellular matrix proteins; cytoskeletal proteins; enzyme proteins; G proteins or regulator proteins; non-protein kinase proteins; motor or contractile proteins; phosphatase proteins; protein kinases; receptor, channel, transporter or cell surface proteins; RNA processing proteins; and transcriptional regulator proteins.

Particularly preferred peptides and AQUA peptides are these comprising a novel tyrosine phosphorylation site (shown as a lower case "y" in a sequence listed in Table 1) selected from the group consisting of SEQ ID NOs: 320 (DDX1), 322 (DDX3), 323 (DDX3), 327 (DDX3Y), 154 (FBPase), 155 (G6PI), 200 (PIP5K), 222 (CD45), 223 (DARPP-32), 225 (FBP2), 238 (Cdc2), 239 (CDK9), 240 (CK2-alpha1), 247 (RSK2), 250 (RSK4), 251 (SRPK1), 266 (FGFR1), 268 (FGFR2), 275 (FLT3), 277 (Met), 35 (PSD-95), 97 (CAPZA2), 103 (cofilin 1), 286 (Cx43), 164 (Cdc42), 63 (SEMA4F), 215 (MYH4), 217 (MYH7), 221 (MYO1F), 68 (CALB2), 73 (FREQ), 84 (DNAJB6), 93 (HMGB1), 97 (CAPZA2), 103 (cofilin 1), 164 (Cdc42), 215 (MYH4), 217 (MYH7), 221 (MYO1F), 278 (PDGFRb), 286 (Cx43), 491 (CLTC), and 499 (NSF).

In some embodiments, the peptide or AQUA peptide comprises the amino acid sequence shown in any one of the above listed SEQ ID NOs. In some embodiments, the peptide or AQUA peptide consists of the amino acid sequence in said SEQ ID NOs. In some embodiments, the peptide or AQUA peptide comprises a fragment of the amino acid sequence in said SEQ ID NOs., wherein the fragment is six to twenty amino acid long and includes the phosphorylatable tyrosine. In some embodiments, the peptide or AQUA peptide consists of a fragment of the amino acid sequence in said SEQ ID NOs., wherein the fragment is six to twenty amino acid long and includes the phosphorylatable tyrosine.

In certain embodiments, the peptide or AQUA peptide comprises any one of the SEQ ID NOs listed in column H, which are trypsin-digested peptide fragments of the parent proteins.

It is understood that parent protein listed in Table 1 may be digested with any suitable protease (e.g., serine proteases (e.g. trypsin, hepsin), metallo proteases (e.g. PUMP1), chymotrypsin, cathepsin, pepsin, thermolysin, carboxypeptidases, etc), and the resulting peptide sequence comprising a phosphorylated site of the invention may differ from that of trypsin-digested fragments (as set forth in Column E), depending the cleavage site of a particular enzyme. An AQUA peptide for a particular parent protein sequence should be chosen based on the amino acid sequence of the parent protein and the particular protease for digestion; that is, the AQUA peptide should match the amino acid sequence of a proteolytic fragment of the parent protein in which the novel phosphorylation site occurs.

An AQUA peptide is preferably at least about 6 amino acids long. The preferred ranged is about 7 to 15 amino acids.

The AQUA method detects and quantifies a target protein in a sample by introducing a known quantity of at least one heavy-isotope labeled peptide standard (which has a unique signature detectable by LC-SRM chromatography) into a digested biological sample. By comparing to the peptide standard, one may readily determines the quantity of a peptide having the same sequence and protein modification(s) in the biological sample. Briefly, the AQUA methodology has two stages: (1) peptide internal standard selection and validation; method development; and (2) implementation using validated peptide internal standards to detect and quantify a target protein in a sample. The method is a powerful technique for detecting and quantifying a given peptide/protein within a complex biological mixture, such as a cell lysate, and may be used, e.g., to quantify change in protein phosphorylation as a result of drug treatment, or to quantify a protein in different biological states.

Generally, to develop a suitable internal standard, a particular peptide (or modified peptide) within a target protein sequence is chosen based on its amino acid sequence and a particular protease for digestion. The peptide is then generated by solid-phase peptide synthesis such that one residue is replaced with that same residue containing stable isotopes ($^{13}C$, $^{15}N$). The result is a peptide that is chemically identical to its native counterpart formed by proteolysis, but is easily distinguishable by MS via a mass shift. A newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or the modified form of the protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al. supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by digestion (e.g., trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures. Because an absolute amount of the AQUA peptide is added (e.g. 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard may be developed for a known phosphorylation site previously identified by the IAP-LC-MS/MS method within a target protein. One AQUA peptide incorporating the phosphorylated form of the site, and a second AQUA peptide incorporating the unphosphorylated form of site may be developed. In this way, the two standards may be used to detect and quantify both the phosphorylated and unphosphorylated forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g. PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, peptides longer than about 20 amino acids are not preferred. The preferred ranged is about 7 to 15 amino acids. A peptide sequence is also selected that is not likely to be chemically reactive during mass spectrometry, thus sequences comprising cysteine, tryptophan, or methionine are avoided.

A peptide sequence that is outside a phosphorylation site may be selected as internal standard to determine the quantity of all forms of the target protein. Alternatively, a peptide encompassing a phosphorylated site may be selected as internal standard to detect and quantify only the phosphorylated form of the target protein. Peptide standards for both phosphorylated form and unphosphorylated form can be used together, to determine, the extent of phosphorylation in a particular sample.

The peptide is labeled using one or more labeled amino acids (i.e. the label is an actual part of the peptide) or less preferably, labels may be attached after synthesis according to standard methods. Preferably, the label is a mass-altering label selected based on the following considerations: The mass should be unique to shift fragment masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^{13}C$, $^{15}N$, $^{17}O$, $^{18}O$, or $^{34}S$, are among preferred labels. Pairs of peptide internal standards that incorporate a different isotope label may also be prepared. Preferred amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g. an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry ($MS^n$) to obtain a fragment ion spectrum, to obtain a peptide fragmentation signature. Preferably, peptide fragments have significant differences in m/z ratios to enable peaks corresponding to each fragment to be well separated, and a signature that is unique for the target peptide is obtained. If a suitable fragment signature is not obtained at the first stage, additional stages of MS are performed until a unique signature is obtained.

Fragment ions in the MS/MS and $MS^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably used. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g., by HPLC, reverse-phase HPLC, capillary electrophoresis, ion exchange chromatography, etc.) to isolate the labeled internal standard and its corresponding target peptide from other peptides in the sample. Microcapillary LC is a preferred method.

Each isolated peptide is then examined by monitoring of a selected reaction in the MS. This involves using the prior knowledge gained by the characterization of the peptide internal standard and then requiring the MS to continuously monitor a specific ion in the MS/MS or $MS^n$ spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra.

Accordingly, AQUA internal peptide standards (heavy-isotope labeled peptides) may be produced, as described above, for any of the 482 novel phosphorylation sites of the invention (see Table 1/FIG. 2). For example, peptide standards for a given phosphorylation site (e.g., an AQUA peptide having the sequence INMLTAGyAER (SEQ ID NO: 3), wherein "y" corresponds to phosphorylatable tyrosine 671 of CNKSR2) may be produced for both the phosphorylated and unphosphorylated forms of the sequence. Such standards may be used to detect and quantify both phosphorylated form and unphosphorylated form of the parent signaling protein (e.g., CNKSR2) in a biological sample.

Heavy-isotope labeled equivalents of a phosphorylation site of the invention, both in phosphorylated and unphosphorylated form, can be readily synthesized and their unique MS and LC-SRM signature determined, so that the peptides are validated as AQUA peptides and ready for use in quantification.

The novel phosphorylation sites of the invention are particularly well suited for development of corresponding AQUA peptides, since the IAP method by which they were identified (see Part A above and Example 1) inherently confirmed that such peptides are in fact produced by enzymatic digestion (e.g., trypsinization) and are in fact suitably fractionated/ionized in MS/MS. Thus, heavy-isotope labeled equivalents of these peptides (both in phosphorylated and unphosphorylated form) can be readily synthesized and their unique MS and LC-SRM signature determined, so that the peptides are validated as AQUA peptides and ready for use in quantification experiments.

Accordingly, the invention provides heavy-isotope labeled peptides (AQUA peptides) that may be used for detecting, quantitating, or modulating any of the phosphorylation sites of the invention (Table 1). For example, an AQUA peptide having the sequence FMDyVQLHSTDK (SEQ ID NO: 38), wherein y (Tyr 122) may be either phosphotyrosine or tyrosine, and wherein V=labeled valine (e.g., $^{14}$C)) is provided for the quantification of phosphorylated (or unphosphorylated) form of SHANK3 (an adaptor/scaffold protein) in a biological sample.

Example 4 is provided to further illustrate the construction and use, by standard methods described above, of exemplary AQUA peptides provided by the invention. For example, AQUA peptides corresponding to both the phosphorylated and unphosphorylated forms of SEQ ID NO:38 (a trypsin-digested fragment of SHANK3, with a tyrosine 122 phosphorylation site) may be used to quantify the amount of phosphorylated SHANK3 in a biological sample, e.g., a tumor cell sample or a sample before or after treatment with a therapeutic agent.

Peptides and AQUA peptides provided by the invention will be highly useful in the further study of signal transduction anomalies underlying cancer, including carcinoma and/or leukemias. Peptides and AQUA peptides of the invention may also be used for identifying diagnostic/bio-markers of carcinoma and/or leukemias, identifying new potential drug targets, and/or monitoring the effects of test therapeutic agents on signaling proteins and pathways.

4. Phosphorylation Site-Specific Antibodies

In another aspect, the invention discloses phosphorylation site-specific binding molecules that specifically bind at a novel tyrosine phosphorylation site of the invention, and that distinguish between the phosphorylated and unphosphorylated forms. In one embodiment, the binding molecule is an antibody or an antigen-binding fragment thereof. The antibody may specifically bind to an amino acid sequence comprising a phosphorylation site identified in Table 1.

In some embodiments, the antibody or antigen-binding fragment thereof specifically binds the phosphorylated site. In other embodiments, the antibody or antigen-binding fragment thereof specially binds the unphosphorylated site. An antibody or antigen-binding fragment thereof specially binds an amino acid sequence comprising a novel tyrosine phosphorylation site in Table 1 when it does not significantly bind any other site in the parent protein and does not significantly bind a protein other than the parent protein. An antibody of the invention is sometimes referred to herein as a "phospho-specific" antibody.

An antibody or antigen-binding fragment thereof specially binds an antigen when the dissociation constant is ≦1 mM, preferably ≦100 nM, and more preferably ≦10 nM.

In some embodiments, the antibody or antigen-binding fragment of the invention binds an amino acid sequence that comprises a novel phosphorylation site of a protein in Table 1 that is a adaptor/scaffold proteins; adhesion or extracellular matrix proteins; cytoskeletal proteins; enzyme proteins; G proteins or regulator proteins; non-protein kinase proteins; motor or contractile proteins; phosphatase proteins; protein kinases; receptor, channel, transporter or cell surface proteins; RNA processing proteins; and transcriptional regulator proteins.

In particularly preferred embodiments, an antibody or antigen-binding fragment thereof of the invention specially binds an amino acid sequence comprising a novel tyrosine phosphorylation site shown as a lower case "y" in a sequence listed in Table 1 selected from the group consisting of SEQ ID NOS: 320 (DDX1), 322 (DDX3), 323 (DDX3), 327 (DDX3Y), 154 (FBPase), 155 (G6PI), 200 (PIP5K), 222 (CD45), 223 (DARPP-32), 225 (FBP2), 238 (Cdc2), 239 (CDK9), 240 (CK2-alpha1), 247 (RSK2), 250 (RSK4), 251 (SRPK1), 266 (FGFR1), 268 (FGFR2), 275 (FLT3), 277 (Met), 35 (PSD-95), 97 (CAPZA2), 103 (cofilin 1), 286 (Cx43), 164 (Cdc42), 63 (SEMA4F), 215 (MYH4), 217 (MYH7), 221 (MYO1F), 68 (CALB2), 73 (FREQ), 84 (DNAJB6), 93 (HMGB1), 97 (CAPZA2), 103 (cofilin 1), 164 (Cdc42), 215 (MYH4), 217 (MYH7), 221 (MYO1F), 278 (PDGFRb), 286 (Cx43), 491 (CLTC), and 499 (NSF).

In some embodiments, an antibody or antigen-binding fragment thereof of the invention specifically binds an amino acid sequence comprising any one of the above listed SEQ ID NOs. In some embodiments, an antibody or antigen-binding fragment thereof of the invention especially binds an amino acid sequence comprises a fragment of one of said SEQ ID NOs., wherein the fragment is four to twenty amino acid long and includes the phosphorylatable tyrosine.

In certain embodiments, an antibody or antigen-binding fragment thereof of the invention specially binds an amino acid sequence that comprises a peptide produced by proteolysis of the parent protein with a protease wherein said peptide comprises a novel tyrosine phosphorylation site of the invention. In some embodiments, the peptides are produced from trypsin digestion of the parent protein. The parent protein comprising the novel tyrosine phosphorylation site can be from any species, preferably from a mammal including but not limited to non-human primates, rabbits, mice, rats, goats, cows, sheep, and guinea pigs. In some embodiments, the parent protein is a human protein and the antibody binds an epitope comprising the novel tyrosine phosphorylation site shown by a lower case "y" in Column E of Table 1. Such peptides include any one of the SEQ ID NOs.

An antibody of the invention can be an intact, four immunoglobulin chain antibody comprising two heavy chains and two light chains. The heavy chain of the antibody can be of any isotype including IgM, IgG, IgE, IgG, IgA or IgD or sub-isotype including IgG1, IgG2, IgG3, IgG4, IgE1, IgE2, etc. The light chain can be a kappa light chain or a lambda light chain.

Also within the invention are antibody molecules with fewer than 4 chains, including single chain antibodies, Camelid antibodies and the like and components of the antibody, including a heavy chain or a light chain. The term "antibody" (or "antibodies") refers to all types of immunoglobulins. The term "an antigen-binding fragment of an antibody" refers to any portion of an antibody that retains specific binding of the intact antibody. An exemplary antigen-binding fragment of an antibody is the heavy chain and/or light chain CDR, or the heavy and/or light chain variable region. The term "does not bind," when appeared in context of an antibody's binding to one phospho-form (e.g., phosphorylated form) of a sequence, means that the antibody does not substantially react with the other phospho-form (e.g., non-phosphorylated form) of the same sequence. One of skill in the art will appreciate that the expression may be applicable in those instances when (1) a phospho-specific antibody either does not apparently bind to the non-phospho form of the antigen as ascertained in commonly used experimental detection systems (Western blotting, IHC, Immunofluorescence, etc.); (2) where there is some reactivity with the surrounding amino acid sequence, but that the phosphorylated residue is an immunodominant feature of the reaction. In cases such as these, there is an apparent difference in affinities for the two sequences. Dilutional analyses of such antibodies indicates that the antibodies apparent affinity for the phosphorylated form is at least 10-100 fold higher than for the non-phosphorylated form; or where (3) the phospho-specific antibody reacts no more than an appropriate control antibody would react under identical experimental conditions. A control antibody preparation might be, for instance, purified immunoglobulin from a pre-immune animal of the same species, an isotype- and species-matched monoclonal antibody. Tests using control antibodies to demonstrate specificity are recognized by one of skill in the art as appropriate and definitive.

In some embodiments an immunoglobulin chain may comprise in order from 5' to 3', a variable region and a constant region. The variable region may comprise three complementarity determining regions (CDRs), with interspersed framework (FR) regions for a structure FR1, CDR1, FR2, CDR2, FR3, CDR3 and FR4. Also within the invention are heavy or light chain variable regions, framework regions and CDRs. An antibody of the invention may comprise a heavy chain constant region that comprises some or all of a CH1 region, hinge, CH2 and CH3 region.

An antibody of the invention may have an binding affinity ($K_D$) of $1 \times 10^{-7}$ M or less. In other embodiments, the antibody binds with a $K_D$ of $1 \times 10^{-8}$ M, $1 \times 10^{-9}$ M, $1 \times 10^{-10}$ M, $1 \times 10^{-11}$ M, $1 \times 10^{-12}$ M or less. In certain embodiments, the $K_D$ is 1 µM to 500 pM, between 500 pM to 1 µM, between 1 µM to 100 nM, or between 100 mM to 10 nM.

Antibodies of the invention can be derived from any species of animal, preferably a mammal. Non-limiting exemplary natural antibodies include antibodies derived from human, chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Natural antibodies are the antibodies produced by a host animal. "Genetically altered antibodies" refer to antibodies wherein the amino acid sequence has been varied from that of a native antibody. Because of the relevance of recombinant DNA techniques to this application, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

The antibodies of the invention include antibodies of any isotype including IgM, IgG, IgD, IgA and IgE, and any sub-isotype, including IgG1, IgG2a, IgG2b, IgG3 and IgG4, IgE1, IgE2 etc. The light chains of the antibodies can either be kappa light chains or lambda light chains.

Antibodies disclosed in the invention may be polyclonal or monoclonal. As used herein, the term "epitope" refers to the smallest portion of a protein capable of selectively binding to the antigen binding site of an antibody. It is well accepted by those skilled in the art that the minimal size of a protein epitope capable of selectively binding to the antigen binding site of an antibody is about five or six to seven amino acids.

Other antibodies specifically contemplated are oligoclonal antibodies. As used herein, the phrase "oligoclonal antibodies" refers to a predetermined mixture of distinct monoclonal antibodies. See, e.g., PCT publication WO 95/20401; U.S. Pat. Nos. 5,789,208 and 6,335,163. In one embodiment, oligoclonal antibodies consisting of a predetermined mixture of antibodies against one or more epitopes are generated in a single cell. In other embodiments, oligoclonal antibodies comprise a plurality of heavy chains capable of pairing with a common light chain to generate antibodies with multiple specificities (e.g., PCT publication WO 04/009618). Oligoclonal antibodies are particularly useful when it is desired to target multiple epitopes on a single target molecule. In view of the assays and epitopes disclosed herein, those skilled in the art can generate or select antibodies or mixtures of antibodies that are applicable for an intended purpose and desired need.

Recombinant antibodies against the phosphorylation sites identified in the invention are also included in the present application. These recombinant antibodies have the same amino acid sequence as the natural antibodies or have altered amino acid sequences of the natural antibodies in the present application. They can be made in any expression systems including both prokaryotic and eukaryotic expression systems or using phage display methods (see, e.g., Dower et al., WO91/17271 and McCafferty et al., WO92/01047; U.S. Pat. No. 5,969,108, which are herein incorporated by reference in their entirety).

Antibodies can be engineered in numerous ways. They can be made as single-chain antibodies (including small modular immunopharmaceuticals or SMIPs™), Fab and F(ab')$_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203.

The genetically altered antibodies should be functionally equivalent to the above-mentioned natural antibodies. In certain embodiments, modified antibodies provide improved stability or/and therapeutic efficacy. Examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as long as the therapeutic utility is maintained. Antibodies of this application can be modified post-translationally (e.g., acetylation, and/or phosphorylation) or can be modified synthetically (e.g., the attachment of a labeling group).

Antibodies with engineered or variant constant or Fc regions can be useful in modulating effector functions, such as, for example, antigen-dependent cytotoxicity (ADCC) and complement-dependent cytotoxicity (CDC). Such antibodies with engineered or variant constant or Fc regions may be useful in instances where a parent singling protein (Table 1) is expressed in normal tissue; variant antibodies without effector function in these instances may elicit the desired therapeutic response while not damaging normal tissue. Accordingly, certain aspects and methods of the present disclosure relate to antibodies with altered effector functions that comprise one or more amino acid substitutions, insertions, and/or deletions.

In certain embodiments, genetically altered antibodies are chimeric antibodies and humanized antibodies.

The chimeric antibody is an antibody having portions derived from different antibodies. For example, a chimeric antibody may have a variable region and a constant region derived from two different antibodies. The donor antibodies may be from different species. In certain embodiments, the variable region of a chimeric antibody is non-human, e.g., murine, and the constant region is human.

The genetically altered antibodies used in the invention include CDR grafted humanized antibodies. In one embodiment, the humanized antibody comprises heavy and/or light chain CDRs of a non-human donor immunoglobulin and heavy chain and light chain frameworks and constant regions of a human acceptor immunoglobulin. The method of making humanized antibody is disclosed in U.S. Pat. Nos. 5,530,101; 5,585,089; 5,693,761; 5,693,762; and 6,180,370 each of which is incorporated herein by reference in its entirety.

Antigen-binding fragments of the antibodies of the invention, which retain the binding specificity of the intact antibody, are also included in the invention. Examples of these antigen-binding fragments include, but are not limited to, partial or full heavy chains or light chains, variable regions, or CDR regions of any phosphorylation site-specific antibodies described herein.

In one embodiment of the application, the antibody fragments are truncated chains (truncated at the carboxyl end). In certain embodiments, these truncated chains possess one or more immunoglobulin activities (e.g., complement fixation activity). Examples of truncated chains include, but are not limited to, Fab fragments (consisting of the VL, VH, CL and CH1 domains); Fd fragments (consisting of the VH and CH1 domains); Fv fragments (consisting of VL and VH domains of a single chain of an antibody); dAb fragments (consisting of a VH domain); isolated CDR regions; $(Fab')_2$ fragments, bivalent fragments (comprising two Fab fragments linked by a disulphide bridge at the hinge region). The truncated chains can be produced by conventional biochemical techniques, such as enzyme cleavage, or recombinant DNA techniques, each of which is known in the art. These polypeptide fragments may be produced by proteolytic cleavage of intact antibodies by methods well known in the art, or by inserting stop codons at the desired locations in the vectors using site-directed mutagenesis, such as after CH1 to produce Fab fragments or after the hinge region to produce $(Fab')_2$ fragments. Single chain antibodies may be produced by joining VL- and VH-coding regions with a DNA that encodes a peptide linker connecting the VL and VH protein fragments Papain digestion of antibodies produces two identical antigen-binding fragments, called "Fab" fragments, each with a single antigen-binding site, and a residual "Fc" fragment, whose name reflects its ability to crystallize readily. Pepsin treatment of an antibody yields an $F(ab')_2$ fragment that has two antigen-combining sites and is still capable of cross-linking antigen.

"Fv" usually refers to the minimum antibody fragment that contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the CDRs confer antigen-binding specificity to the antibody. However, even a single variable domain (or half of an Fv comprising three CDRs specific for an antigen) has the ability to recognize and bind antigen, although likely at a lower affinity than the entire binding site.

Thus, in certain embodiments, the antibodies of the application may comprise 1, 2, 3, 4, 5, 6, or more CDRs that recognize the phosphorylation sites identified in Column E of Table 1.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments that have hinge cysteines between them. Other chemical couplings of antibody fragments are also known.

"Single-chain Fv" or "scFv" antibody fragments comprise the $V_H$ and $V_L$ domains of an antibody, wherein these domains are present in a single polypeptide chain. In certain embodiments, the Fv polypeptide further comprises a polypeptide linker between the $V_H$ and $V_L$ domains that enables the scFv to form the desired structure for antigen binding. For a review of scFv see Pluckthun in The Pharmacology of Monoclonal Antibodies, vol. 113, Rosenburg and Moore, eds. (Springer-Verlag: New York, 1994), pp. 269-315.

SMIPs are a class of single-chain peptides engineered to include a target binding region and effector domain (CH2 and CH3 domains). See, e.g., U.S. Patent Application Publication No. 20050238646. The target binding region may be derived from the variable region or CDRs of an antibody, e.g., a phosphorylation site-specific antibody of the application. Alternatively, the target binding region is derived from a protein that binds a phosphorylation site.

Bispecific antibodies may be monoclonal, human or humanized antibodies that have binding specificities for at least two different antigens. In the present case, one of the binding specificities is for the phosphorylation site, the other one is for any other antigen, such as for example, a cell-surface protein or receptor or receptor subunit. Alternatively, a therapeutic agent may be placed on one arm. The therapeutic agent can be a drug, toxin, enzyme, DNA, radionuclide, etc.

In some embodiments, the antigen-binding fragment can be a diabody. The term "diabody" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444-6448 (1993).

Camelid antibodies refer to a unique type of antibodies that are devoid of light chain, initially discovered from animals of the camelid family. The heavy chains of these so-called heavy-chain antibodies bind their antigen by one single domain, the variable domain of the heavy immunoglobulin chain, referred to as VHH. VHHs show homology with the variable domain of heavy chains of the human VHIII family. The VHHs obtained from an immunized camel, dromedary, or llama have a number of advantages, such as effective production in microorganisms such as *Saccharomyces cerevisiae*.

In certain embodiments, single chain antibodies, and chimeric, humanized or primatized (CDR-grafted) antibodies, as well as chimeric or CDR-grafted single chain antibodies, comprising portions derived from different species, are also encompassed by the present disclosure as antigen-binding fragments of an antibody. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., U.S. Pat. Nos. 4,816,567 and 6,331,415; U.S. Pat. No. 4,816,397; European Patent No. 0,120,694; WO 86/01533; European Patent No. 0,194,276 B1; U.S. Pat. No. 5,225,539; and European Patent No. 0,239,400 B1. See also, Newman et al., BioTechnology, 10: 1455-1460 (1992), regarding primatized antibody. See, e.g., Ladner et al., U.S. Pat. No. 4,946,778; and Bird et al., Science, 242: 423-426 (1988)), regarding single chain antibodies.

In addition, functional fragments of antibodies, including fragments of chimeric, humanized, primatized or single chain antibodies, can also be produced. Functional fragments of the subject antibodies retain at least one binding function and/or modulation function of the full-length antibody from which they are derived.

Since the immunoglobulin-related genes contain separate functional regions, each having one or more distinct biological activities, the genes of the antibody fragments may be fused to functional regions from other genes (e.g., enzymes, U.S. Pat. No. 5,004,692, which is incorporated by reference in its entirety) to produce fusion proteins or conjugates having novel properties.

Non-immunoglobulin binding polypeptides are also contemplated. For example, CDRs from an antibody disclosed herein may be inserted into a suitable non-immunoglobulin scaffold to create a non-immunoglobulin binding polypeptide. Suitable candidate scaffold structures may be derived from, for example, members of fibronectin type III and cadherin superfamilies.

Also contemplated are other equivalent non-antibody molecules, such as protein binding domains or aptamers, which bind, in a phospho-specific manner, to an amino acid sequence comprising a novel phosphorylation site of the invention. See, e.g., Neuberger et al., Nature 312: 604 (1984). Aptamers are oligonucleic acid or peptide molecules that bind a specific target molecule. DNA or RNA aptamers are typically short oligonucleotides, engineered through repeated rounds of selection to bind to a molecular target. Peptide aptamers typically consist of a variable peptide loop attached at both ends to a protein scaffold. This double structural constraint generally increases the binding affinity of the peptide aptamer to levels comparable to an antibody (nanomolar range).

The invention also discloses the use of the phosphorylation site-specific antibodies with immunotoxins. Conjugates that are immunotoxins including antibodies have been widely described in the art. The toxins may be coupled to the antibodies by conventional coupling techniques or immunotoxins containing protein toxin portions can be produced as fusion proteins. In certain embodiments, antibody conjugates may comprise stable linkers and may release cytotoxic agents inside cells (see U.S. Pat. Nos. 6,867,007 and 6,884,869). The conjugates of the present application can be used in a corresponding way to obtain such immunotoxins. Illustrative of such immunotoxins are those described by Byers et al., Seminars Cell Biol 2:59-70 (1991) and by Fanger et al., Immunol Today 12:51-54 (1991). Exemplary immunotoxins include radiotherapeutic agents, ribosome-inactivating proteins (RIPs), chemotherapeutic agents, toxic peptides, or toxic proteins.

The phosphorylation site-specific antibodies disclosed in the invention may be used singly or in combination. The antibodies may also be used in an array format for high throughput uses. An antibody microarray is a collection of immobolized antibodies, typically spotted and fixed on a solid surface (such as glass, plastic and silicon chip).

In another aspect, the antibodies of the invention modulate at least one, or all, biological activities of a parent protein identified in Column A of Table 1. The biological activities of a parent protein identified in Column A of Table 1 include: 1) ligand binding activities (for instance, these neutralizing antibodies may be capable of competing with or completely blocking the binding of a parent signaling protein to at least one, or all, of its ligands; 2) signaling transduction activities, such as receptor dimerization, or tyrosine phosphorylation; and 3) cellular responses induced by a parent signaling protein, such as oncogenic activities (e.g., cancer cell proliferation mediated by a parent signaling protein), and/or angiogenic activities.

In certain embodiments, the antibodies of the invention may have at least one activity selected from the group consisting of: 1) inhibiting cancer cell growth or proliferation; 2) inhibiting cancer cell survival; 3) inhibiting angiogenesis; 4) inhibiting cancer cell metastasis, adhesion, migration or invasion; 5) inducing apoptosis of cancer cells; 6) incorporating a toxic conjugate; and 7) acting as a diagnostic marker.

In certain embodiments, the phosphorylation site specific antibodies disclosed in the invention are especially indicated for diagnostic and therapeutic applications as described herein. Accordingly, the antibodies may be used in therapies, including combination therapies, in the diagnosis and prognosis of disease, as well as in the monitoring of disease progression. The invention, thus, further includes compositions comprising one or more embodiments of an antibody or an antigen binding portion of the invention as described herein. The composition may further comprise a pharmaceutically acceptable carrier. The composition may comprise two or more antibodies or antigen-binding portions, each with specificity for a different novel tyrosine phosphorylation site of the invention or two or more different antibodies or antigen-binding portions all of which are specific for the same novel tyrosine phosphorylation site of the invention. A composition of the invention may comprise one or more antibodies or antigen-binding portions of the invention and one or more additional reagents, diagnostic agents or therapeutic agents.

The present application provides for the polynucleotide molecules encoding the antibodies and antibody fragments and their analogs described herein. Because of the degeneracy of the genetic code, a variety of nucleic acid sequences encode each antibody amino acid sequence. The desired nucleic acid sequences can be produced by de novo solid-phase DNA synthesis or by PCR mutagenesis of an earlier prepared variant of the desired polynucleotide. In one embodiment, the codons that are used comprise those that are typical for human or mouse (see, e.g., Nakamura, Y., Nucleic Acids Res. 28: 292 (2000)).

The invention also provides immortalized cell lines that produce an antibody of the invention. For example, hybridoma clones, constructed as described above, that produce monoclonal antibodies to the targeted signaling protein phosphorylation sties disclosed herein are also provided. Similarly, the invention includes recombinant cells producing an antibody of the invention, which cells may be constructed by well known techniques; for example the antigen combining site of the monoclonal antibody can be cloned by PCR and single-chain antibodies produced as phage-displayed recombinant antibodies or soluble antibodies in E. coli (see, e.g., ANTIBODY ENGINEERING PROTOCOLS, 1995, Humana Press, Sudhir Paul editor.)

5. Methods of Making Phosphorylation Site-Specific Antibodies

In another aspect, the invention provides a method for making phosphorylation site-specific antibodies.

Polyclonal antibodies of the invention may be produced according to standard techniques by immunizing a suitable animal (e.g., rabbit, goat, etc.) with an antigen comprising a novel tyrosine phosphorylation site of the invention. (i.e. a phosphorylation site shown in Table 1) in either the phosphorylated or unphosphorylated state, depending upon the desired specificity of the antibody, collecting immune serum from the animal, and separating the polyclonal antibodies from the immune serum, in accordance with known procedures and screening and isolating a polyclonal antibody specific for the novel tyro sine phosphorylation site of interest as further described below. Methods for immunizing non-human animals such as mice, rats, sheep, goats, pigs, cattle and horses are well known in the art. See, e.g., Harlow and Lane, *Antibodies: A Laboratory Manual*, New York: Cold Spring Harbor Press, 1990.

The immunogen may be the full length protein or a peptide comprising the novel tyro sine phosphorylation site of interest. In some embodiments the immunogen is a peptide of from 7 to 20 amino acids in length, preferably about 8 to 17 amino acids in length. In some embodiments, the peptide antigen desirably will comprise about 3 to 8 amino acids on each side of the phosphorylatable tyrosine. In yet other embodiments, the peptide antigen desirably will comprise four or more amino acids flanking each side of the phosphorylatable amino acid and encompassing it. Peptide antigens suitable for producing antibodies of the invention may be designed, constructed and employed in accordance with well-known techniques. See, e.g., Antibodies: A Laboratory Manual, Chapter 5, p. 75-76, Harlow & Lane Eds., Cold Spring Harbor Laboratory (1988); Czernik, *Methods In Enzymology*, 201: 264-283 (1991); Merrifield, *J. Am. Chem. Soc.* 85: 21-49 (1962)).

Suitable peptide antigens may comprise all or partial sequence of a trypsin-digested fragment as set forth in Column E of Table 1/FIG. 2. Suitable peptide antigens may also comprise all or partial sequence of a peptide fragment produced by another protease digestion.

Preferred immunogens are those that comprise a novel phosphorylation site of a protein in Table 1 that is a adaptor/scaffold proteins; adhesion or extracellular matrix proteins; cytoskeletal proteins; enzyme proteins; G proteins or regulator proteins; non-protein kinase proteins; motor or contractile proteins; phosphatase proteins; protein kinases; receptor, channel, transporter or cell surface proteins; RNA processing proteins; and transcriptional regulator proteins. In some embodiments, the peptide immunogen is an AQUA peptide, for example, any one of SEQ ID NOS: 1-19, 21-22, 25-27, 29-136, 138-144, 147-204, 206-232, 234-257, 259-277, 279-301, 303-374, 376-393, 395-403, 405-435, 437-447, 449-461, 463-500.

Particularly preferred immunogens are peptides comprising any one of the novel tyrosine phosphorylation site shown as a lower case "y" in a sequence listed in Table 1 selected from the group consisting of SEQ ID NOS: 320 (DDX1), 322 (DDX3), 323 (DDX3), 327 (DDX3Y), 154 (FBPase), 155 (G6PI), 200 (PIP5K), 222 (CD45), 223 (DARPP-32), 225 (FBP2), 238 (Cdc2), 239 (CDK9), 240 (CK2-alpha1), 247 (RSK2), 250 (RSK4), 251 (SRPK1), 266 (FGFR1), 268 (FGFR2), 275 (FLT3), 277 (Met), 35 (PSD-95), 97 (CAPZA2), 103 (cofilin 1), 286 (Cx43), 164 (Cdc42), 63 (SEMA4F), 215 (MYH4), 217 (MYH7), 221 (MYO1F), 68 (CALB2), 73 (FREQ), 84 (DNAJB6), 93 (HMGB1), 97 (CAPZA2), 103 (cofilin 1), 164 (Cdc42), 215 (MYH4), 217 (MYH7), 221 (MYO1F), 278 (PDGFRb), 286 (Cx43), 491 (CLTC), and 499 (NSF).

In some embodiments the immunogen is administered with an adjuvant. Suitable adjuvants will be well known to those of skill in the art. Exemplary adjuvants include complete or incomplete Freund's adjuvant, RIBI (muramyl dipeptides) or ISCOM (immunostimulating complexes).

For example, a peptide antigen comprising the novel adaptor/scaffold protein phosphorylation site in SEQ ID NO: 4 shown by the lower case "y" in Table 1 may be used to produce antibodies that specifically bind the novel tyrosine phosphorylation site.

When the above-described methods are used for producing polyclonal antibodies, following immunization, the polyclonal antibodies which secreted into the bloodstream can be recovered using known techniques. Purified forms of these antibodies can, of course, be readily prepared by standard purification techniques, such as for example, affinity chromatography with Protein A, anti-immunoglobulin, or the antigen itself. In any case, in order to monitor the success of immunization, the antibody levels with respect to the antigen in serum will be monitored using standard techniques such as ELISA, RIA and the like.

Monoclonal antibodies of the invention may be produced by any of a number of means that are well-known in the art. In some embodiments, antibody-producing B cells are isolated from an animal immunized with a peptide antigen as described above. The B cells may be from the spleen, lymph nodes or peripheral blood. Individual B cells are isolated and screened as described below to identify cells producing an antibody specific for the novel tyrosine phosphorylation site of interest. Identified cells are then cultured to produce a monoclonal antibody of the invention.

Alternatively, a monoclonal phosphorylation site-specific antibody of the invention may be produced using standard hybridoma technology, in a hybridoma cell line according to the well-known technique of Kohler and Milstein. See *Nature* 265: 495-97 (1975); Kohler and Milstein, *Eur. J. Immunol.* 6: 511 (1976); see also, Current Protocols in Molecular Biology, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse or other species and, after a sufficient time (in keeping with conventional techniques), the animal is sacrificed and spleen cells obtained. The spleen cells are then immortalized by any of a number of standard means. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cells is used, the myeloma cells preferably do not secrete immunoglobulin polypeptides (a non-secretory cell line). Typically the antibody producing cell and the immortalized cell (such as but not limited to myeloma cells) with which it is fused are from the same species. Rabbit fusion hybridomas, for example, may be produced as described in U.S. Pat. No. 5,675,063, C. Knight, Issued Oct. 7, 1997. The immortalized antibody producing cells, such as hybridoma cells, are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

The invention also encompasses antibody-producing cells and cell lines, such as hybridomas, as described above.

Polyclonal or monoclonal antibodies may also be obtained through in vitro immunization. For example, phage display techniques can be used to provide libraries containing a repertoire of antibodies with varying affinities for a particular antigen. Techniques for the identification of high affinity human antibodies from such libraries are described by Griffiths et al., (1994) *EMBO J.*, 13:3245-3260; Nissim et al., ibid, pp. 692-698 and by Griffiths et al., ibid, 12:725-734, which are incorporated by reference.

The antibodies may be produced recombinantly using methods well known in the art for example, according to the methods disclosed in U.S. Pat. No. 4,349,893 (Reading) or U.S. Pat. No. 4,816,567 (Cabilly et al.) The antibodies may also be chemically constructed by specific antibodies made according to the method disclosed in U.S. Pat. No. 4,676,980 (Segel et al.)

Once a desired phosphorylation site-specific antibody is identified, polynucleotides encoding the antibody, such as heavy, light chains or both (or single chains in the case of a single chain antibody) or portions thereof such as those encoding the variable region, may be cloned and isolated from antibody-producing cells using means that are well known in the art. For example, the antigen combining site of the monoclonal antibody can be cloned by PCR and single-chain antibodies produced as phage-displayed recombinant antibodies or soluble antibodies in *E. coli* (see, e.g., Antibody Engineering Protocols, 1995, Humana Press, Sudhir Paul editor.)

Accordingly, in a further aspect, the invention provides such nucleic acids encoding the heavy chain, the light chain, a variable region, a framework region or a CDR of an antibody of the invention. In some embodiments, the nucleic acids are operably linked to expression control sequences. The invention, thus, also provides vectors and expression control sequences useful for the recombinant expression of an antibody or antigen-binding portion thereof of the invention. Those of skill in the art will be able to choose vectors and expression systems that are suitable for the host cell in which the antibody or antigen-binding portion is to be expressed.

Monoclonal antibodies of the invention may be produced recombinantly by expressing the encoding nucleic acids in a suitable host cell under suitable conditions. Accordingly, the invention further provides host cells comprising the nucleic acids and vectors described above.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990).

If monoclonal antibodies of a single desired isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.*, 82: 8653 (1985); Spira et al., *J. Immunol. Methods*, 74: 307 (1984)). Alternatively, the isotype of a monoclonal antibody with desirable propertied can be changed using antibody engineering techniques that are well-known in the art.

Phosphorylation site-specific antibodies of the invention, whether polyclonal or monoclonal, may be screened for epitope and phospho-specificity according to standard techniques. See, e.g., Czernik et al., *Methods in Enzymology,* 201: 264-283 (1991). For example, the antibodies may be screened against the phosphorylated and/or unphosphorylated peptide library by ELISA to ensure specificity for both the desired antigen (i.e. that epitope including a phosphorylation site of the invention and for reactivity only with the phosphorylated (or unphosphorylated) form of the antigen. Peptide competition assays may be carried out to confirm lack of reactivity with other phospho-epitopes on the parent protein. The antibodies may also be tested by Western blotting against cell preparations containing the parent signaling protein, e.g., cell lines over-expressing the parent protein, to confirm reactivity with the desired phosphorylated epitope/target.

Specificity against the desired phosphorylated epitope may also be examined by constructing mutants lacking phosphorylatable residues at positions outside the desired epitope that are known to be phosphorylated, or by mutating the desired phospho-epitope and confirming lack of reactivity. Phosphorylation site-specific antibodies of the invention may exhibit some limited cross-reactivity to related epitopes in non-target proteins. This is not unexpected as most antibodies exhibit some degree of cross-reactivity, and anti-peptide antibodies will often cross-react with epitopes having high homology to the immunizing peptide. See, e.g., Czernik, supra. Cross-reactivity with non-target proteins is readily characterized by Western blotting alongside markers of known molecular weight. Amino acid sequences of cross-reacting proteins may be examined to identify phosphorylation sites with flanking sequences that are highly homologous to that of a phosphorylation site of the invention.

In certain cases, polyclonal antisera may exhibit some undesirable general cross-reactivity to phosphotyrosine itself, which may be removed by further purification of antisera, e.g., over a phosphotyramine column. Antibodies of the invention specifically bind their target protein (i.e. a protein listed in Column A of Table 1) only when phosphorylated (or only when not phosphorylated, as the case may be) at the site disclosed in corresponding Columns D/E, and do not (substantially) bind to the other form (as compared to the form for which the antibody is specific).

Antibodies may be further characterized via immunohistochemical (IHC) staining using normal and diseased tissues to examine phosphorylation and activation state and level of a phosphorylation site in diseased tissue. IHC may be carried out according to well-known techniques. See, e.g., Antibodies: A Laboratory Manual, Chapter 10, Harlow & Lane Eds., Cold Spring Harbor Laboratory (1988). Briefly, paraffin-embedded tissue (e.g., tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies may be further characterized by flow cytometry carried out according to standard methods. See Chow et al., *Cytometry (Communications in Clinical Cytometry)* 46: 72-78 (2001). Briefly and by way of example, the following protocol for cytometric analysis may be employed: samples may be centrifuged on Ficoll gradients to remove lysed erythrocytes and cell debris. Adherring cells may be scrapped off plates and washed with PBS. Cells may then be fixed with 2% paraformaldehyde for 10 minutes at 37° C. followed by permeabilization in 90% methanol for 30 minutes on ice. Cells may then be stained with the primary phosphorylation site-specific antibody of the invention (which detects a parent signaling protein enumerated in Table 1), washed and labeled with a fluorescent-labeled secondary antibody. Additional fluorochrome-conjugated marker antibodies (e.g., CD45, CD34) may also be added at this time to aid in the subsequent identification of specific hematopoietic cell types. The cells would then be analyzed on a flow cytometer (e.g. a Beckman Coulter FC500) according to the specific protocols of the instrument used.

Antibodies of the invention may also be advantageously conjugated to fluorescent dyes (e.g. Alexa488, PE) for use in multi-parametric analyses along with other signal transduction (phospho-CrkL, phospho-Erk 1/2) and/or cell marker (CD34) antibodies.

Phosphorylation site-specific antibodies of the invention may specifically bind to a signaling protein or polypeptide listed in Table 1 only when phosphorylated at the specified tyrosine residue, but are not limited only to binding to the listed signaling proteins of human species, per se. The invention includes antibodies that also bind conserved and highly homologous or identical phosphorylation sites in respective signaling proteins from other species (e.g., mouse, rat, monkey, yeast), in addition to binding the phosphorylation site of the human homologue. The term "homologous" refers to two or more sequences or subsequences that have at least about 85%, at least 90%, at least 95%, or higher nucleotide or amino acid residue identity, when compared and aligned for maximum correspondence, as measured using sequence comparison method (e.g., BLAST) and/or by visual inspection. Highly homologous or identical sites conserved in other species can readily be identified by standard sequence comparisons (such as BLAST).

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Antibody variable domains with the desired binding specificities (antibody-antigen combining sites) can be fused to immunoglobulin constant domain sequences. In certain embodiments, the fusion is with an immunoglobulin heavy-chain constant domain, including at least part of the hinge, CH2, and CH3 regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, for example, Suresh et al., Methods in Enzymology, 121:210 (1986); WO 96/27011; Brennan et al., Science 229:81 (1985); Shalaby et al., J. Exp. Med. 175: 217-225 (1992); Kostelny et al., J. Immunol. 148(5):1547-1553 (1992); Hollinger et al., Proc. Natl. Acad. Sci. USA 90:6444-6448 (1993); Gruber et al., J. Immunol. 152:5368 (1994); and Tutt et al., J. Immunol. 147:60 (1991). Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. A strategy for making bispecific antibody fragments by the use of single-chain Fv (scFv) dimers has also been reported. See Gruber et al., J. Immunol., 152:5368 (1994). Alternatively, the antibodies can be "linear antibodies" as described in Zapata et al. Protein Eng. 8(10): 1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

To produce the chimeric antibodies, the portions derived from two different species (e.g., human constant region and murine variable or binding region) can be joined together chemically by conventional techniques or can be prepared as single contiguous proteins using genetic engineering techniques. The DNA molecules encoding the proteins of both the light chain and heavy chain portions of the chimeric antibody can be expressed as contiguous proteins. The method of making chimeric antibodies is disclosed in U.S. Pat. No. 5,677,427; U.S. Pat. No. 6,120,767; and U.S. Pat. No. 6,329,508, each of which is incorporated by reference in its entirety.

Fully human antibodies may be produced by a variety of techniques. One example is trioma methodology. The basic approach and an exemplary cell fusion partner, SPAZ-4, for use in this approach have been described by Oestberg et al., Hybridoma 2:361-367 (1983); Oestberg, U.S. Pat. No. 4,634,664; and Engleman et al., U.S. Pat. No. 4,634,666 (each of which is incorporated by reference in its entirety).

Human antibodies can also be produced from non-human transgenic animals having transgenes encoding at least a segment of the human immunoglobulin locus. The production and properties of animals having these properties are described in detail by, see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety.

Various recombinant antibody library technologies may also be utilized to produce fully human antibodies. For example, one approach is to screen a DNA library from human B cells according to the general protocol outlined by Huse et al., Science 246:1275-1281 (1989). The protocol described by Huse is rendered more efficient in combination with phage-display technology. See, e.g., Dower et al., WO 91/17271 and McCafferty et al., WO 92/01047; U.S. Pat. No. 5,969,108, (each of which is incorporated by reference in its entirety).

Eukaryotic ribosome can also be used as means to display a library of antibodies and isolate the binding human antibodies by screening against the target antigen, as described in Coia G, et al., J. Immunol. Methods 1: 254 (1-2):191-7 (2001); Hanes J. et al., Nat. Biotechnol. 18(12):1287-92 (2000); Proc. Natl. Acad. Sci. U.S.A. 95(24):14130-5 (1998); Proc. Natl. Acad. Sci. U.S.A. 94(10):4937-42 (1997), each which is incorporated by reference in its entirety.

The yeast system is also suitable for screening mammalian cell-surface or secreted proteins, such as antibodies. Antibody libraries may be displayed on the surface of yeast cells for the purpose of obtaining the human antibodies against a target antigen. This approach is described by Yeung, et al., Biotechnol. Prog. 18(2):212-20 (2002); Boeder, E. T., et al., Nat. Biotechnol. 15(6):553-7 (1997), each of which is herein incorporated by reference in its entirety. Alternatively, human antibody libraries may be expressed intracellularly and screened via the yeast two-hybrid system (WO0200729A2, which is incorporated by reference in its entirety).

Recombinant DNA techniques can be used to produce the recombinant phosphorylation site-specific antibodies described herein, as well as the chimeric or humanized phosphorylation site-specific antibodies, or any other genetically-altered antibodies and the fragments or conjugate thereof in any expression systems including both prokaryotic and eukaryotic expression systems, such as bacteria, yeast, insect cells, plant cells, mammalian cells (for example, NS0 cells).

Once produced, the whole antibodies, their dimers, individual light and heavy chains, or other immunoglobulin forms of the present application can be purified according to standard procedures of the art, including ammonium sulfate precipitation, affinity columns, column chromatography, gel electrophoresis and the like (see, generally, Scopes, R., Protein Purification (Springer-Verlag, N.Y., 1982)). Once purified, partially or to homogeneity as desired, the polypeptides may then be used therapeutically (including extracorporeally) or in developing and performing assay procedures, immunofluorescent staining, and the like. (See, generally, Immunological Methods, Vols. I and II (Lefkovits and Pernis, eds., Academic Press, NY, 1979 and 1981).

6. Therapeutic Uses

In a further aspect, the invention provides methods and compositions for therapeutic uses of the peptides or proteins comprising a phosphorylation site of the invention, and phosphorylation site-specific antibodies of the invention.

In one embodiment, the invention provides for a method of treating or preventing carcinoma and/or leukemia in a subject, wherein the carcinoma and/or leukemia is associated with the phosphorylation state of a novel phosphorylation site in Table 1, whether phosphorylated or dephosphorylated, comprising: administering to a subject in need thereof a therapeutically effective amount of a peptide comprising a novel phosphorylation site (Table 1) and/or an antibody or antigen-binding fragment thereof that specifically bind a novel phosphorylation site of the invention (Table 1). The antibodies may be full-length antibodies, genetically engineered antibodies, antibody fragments, and antibody conjugates of the invention.

The term "subject" refers to a vertebrate, such as for example, a mammal, or a human. Although present application are primarily concerned with the treatment of human subjects, the disclosed methods may also be used for the treatment of other mammalian subjects such as dogs and cats for veterinary purposes.

In one aspect, the disclosure provides a method of treating carcinoma and/or leukemia in which a peptide or an antibody that reduces at least one biological activity of a targeted signaling protein is administered to a subject. For example, the peptide or the antibody administered may disrupt or modulate the interaction of the target signaling protein with its ligand. Alternatively, the peptide or the antibody may interfere with, thereby reducing, the down-stream signal transduction of the parent signaling protein. An antibody that specifically binds the novel tyrosine phosphorylation site only when the tyrosine is phosphorylated, and that does not substantially bind to the same sequence when the tyrosine is not phosphorylated, thereby prevents downstream signal transduction triggered by a phospho-tyrosine. Alternatively, an antibody that specifically binds the unphosphorylated target phosphorylation site reduces the phosphorylation at that site and thus reduces activation of the protein mediated by phosphorylation of that site. Similarly, an unphosphorylated peptide may compete with an endogenous phosphorylation site for same kinases, thereby preventing or reducing the phosphorylation of the endogenous target protein. Alternatively, a peptide comprising a phosphorylation novel tyrosine site of the invention but lacking the ability to trigger signal transduction may competitively inhibit interaction of the endogenous protein with the same down-stream ligand(s).

The antibodies of the invention may also be used to target cancer cells for effector-mediated cell death. The antibody disclosed herein may be administered as a fusion molecule that includes a phosphorylation site-targeting portion joined to a cytotoxic moiety to directly kill cancer cells. Alternatively, the antibody may directly kill the cancer cells through complement-mediated or antibody-dependent cellular cytotoxicity.

Accordingly in one embodiment, the antibodies of the present disclosure may be used to deliver a variety of cytotoxic compounds. Any cytotoxic compound can be fused to the present antibodies. The fusion can be achieved chemically or genetically (e.g., via expression as a single, fused molecule). The cytotoxic compound can be a biological, such as a polypeptide, or a small molecule. As those skilled in the art will appreciate, for small molecules, chemical fusion is used, while for biological compounds, either chemical or genetic fusion can be used.

Non-limiting examples of cytotoxic compounds include therapeutic drugs, radiotherapeutic agents, ribosome-inactivating proteins (RIPs), chemotherapeutic agents, toxic peptides, toxic proteins, and mixtures thereof. The cytotoxic drugs can be intracellularly acting cytotoxic drugs, such as short-range radiation emitters, including, for example, short-range, high-energy α-emitters. Enzymatically active toxins and fragments thereof, including ribosome-inactivating proteins, are exemplified by saporin, luffin, momordins, ricin, trichosanthin, gelonin, abrin, etc. Procedures for preparing enzymatically active polypeptides of the immunotoxins are described in WO84/03508 and WO85/03508, which are hereby incorporated by reference. Certain cytotoxic moieties are derived from adriamycin, chlorambucil, daunomycin, methotrexate, neocarzinostatin, and platinum, for example.

Exemplary chemotherapeutic agents that may be attached to an antibody or antigen-binding fragment thereof include taxol, doxorubicin, verapamil, podophyllotoxin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, transplatinum, 5-fluorouracil, vincristin, vinblastin, or methotrexate.

Procedures for conjugating the antibodies with the cytotoxic agents have been previously described and are within the purview of one skilled in the art.

Alternatively, the antibody can be coupled to high energy radiation emitters, for example, a radioisotope, such as $^{131}$I, a γ-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", Monoclonal Antibodies for Cancer Detection and Therapy, Baldwin et al. (eds.), pp. 303-316 (Academic Press 1985), which is hereby incorporated by reference. Other suitable radioisotopes include α-emitters, such as $^{212}$Bi, $^{213}$Bi, and $^{211}$At, and β-emitters, such as $^{186}$Re and $^{90}$Y.

Because many of the signaling proteins in which novel tyrosine phosphorylation sites of the invention occur also are expressed in normal cells and tissues, it may also be advantageous to administer a phosphorylation site-specific antibody with a constant region modified to reduce or eliminate ADCC or CDC to limit damage to normal cells. For example, effector function of an antibodies may be reduced or eliminated by utilizing an IgG1 constant domain instead of an IgG2/4 fusion domain. Other ways of eliminating effector function can be envisioned such as, e.g., mutation of the sites known to interact with FcR or insertion of a peptide in the hinge region, thereby eliminating critical sites required for FcR interaction. Variant antibodies with reduced or no effector function also include variants as described previously herein.

The peptides and antibodies of the invention may be used in combination with other therapies or with other agents. Other agents include but are not limited to polypeptides, small molecules, chemicals, metals, organometallic compounds, inorganic compounds, nucleic acid molecules, oligonucleotides, aptamers, spiegelmers, antisense nucleic acids, locked nucleic acid (LNA) inhibitors, peptide nucleic acid (PNA) inhibitors, immunomodulatory agents, antigen-binding fragments, prodrugs, and peptidomimetic compounds. In certain embodiments, the antibodies and peptides of the invention may be used in combination with cancer therapies known to one of skill in the art.

In certain aspects, the present disclosure relates to combination treatments comprising a phosphorylation site-specific antibody described herein and immunomodulatory compounds, vaccines or chemotherapy. Illustrative examples of suitable immunomodulatory agents that may be used in such combination therapies include agents that block negative regulation of T cells or antigen presenting cells (e.g., anti-CTLA4 antibodies, anti-PD-L1 antibodies, anti-PDL-2 antibodies, anti-PD-1 antibodies and the like) or agents that enhance positive co-stimulation of T cells (e.g., anti-CD40 antibodies or anti 4-1BB antibodies) or agents that increase NK cell number or T-cell activity (e.g., inhibitors such as IMiDs, thalidomide, or thalidomide analogs). Furthermore, immunomodulatory therapy could include cancer vaccines such as dendritic cells loaded with tumor cells, proteins, peptides, RNA, or DNA derived from such cells, patient derived heat-shock proteins (hsp's) or general adjuvants stimulating the immune system at various levels such as CpG, Luivac®, Biostim®, Ribomunyl®, Imudon®, Bronchovaxom® or any other compound or other adjuvant activating receptors of the innate immune system (e.g., toll like receptor agonist, anti-CTLA-4 antibodies, etc.). Also, immunomodulatory therapy could include treatment with cytokines such as IL-2, GM-CSF and IFN-gamma.

Furthermore, combination of antibody therapy with chemotherapeutics could be particularly useful to reduce overall tumor burden, to limit angiogenesis, to enhance tumor accessibility, to enhance susceptibility to ADCC, to result in increased immune function by providing more tumor antigen, or to increase the expression of the T cell attractant LIGHT.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into groups, including, for example, the following classes of agents: anti-metabolites/anti-cancer agents, such as pyrimidine analogs (5-fluorouracil, floxuridine, capecitabine, gemcitabine and cytarabine) and purine analogs, folate inhibitors and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristine, vinblastine, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); immunomodulatory agents (thalidomide and analogs thereof such as lenalidomide (Revlimid, CC-5013) and CC-4047 (Actimid)), cyclophosphamide; anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisone, and prenisolone); growth factor signal transduction kinase inhibitors; mitochondrial dysfunction inducers and caspase activators; and chromatin disruptors.

In certain embodiments, pharmaceutical compounds that may be used for combinatory anti-angiogenesis therapy include: (1) inhibitors of release of "angiogenic molecules," such as bFGF (basic fibroblast growth factor); (2) neutralizers of angiogenic molecules, such as anti-βbFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like. For additional proposed inhibitors of angiogenesis, see Blood et al., Biochim. Biophys. Acta, 1032:89-118 (1990), Moses et al., Science, 248:1408-1410 (1990), Ingber et al., Lab. Invest., 59:44-51 (1988), and U.S. Pat. Nos. 5,092,885, 5,112,946, 5,192,744, 5,202,352, and 6,573,256. In addition, there are a wide variety of compounds that can be used to inhibit angiogenesis, for example, peptides or agents that block the VEGF-mediated angiogenesis pathway, endostatin protein or derivatives, lysine binding fragments of angiostatin, melanin or melanin-promoting compounds, plasminogen fragments (e.g., Kringles 1-3 of plasminogen), troponin subunits, inhibitors of vitronectin $\alpha_\nu\beta_3$, peptides derived from Saposin B, antibiotics or analogs (e.g., tetracycline or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718, 6,462,075, 6,465,431, 6,475,784, 6,482,802, 6,482,810, 6,500,431, 6,500,924, 6,518,298, 6,521,439, 6,525,019, 6,538,103, 6,544,758, 6,544,947, 6,548,477, 6,559,126, and 6,569,845.

7. Diagnostic Uses

In a further aspect, the invention provides methods for detecting and quantitating phosphorylation at a novel tyrosine phosphorylation site of the invention. For example, peptides, including AQUA peptides of the invention, and antibodies of the invention are useful in diagnostic and prognostic evaluation of carcinoma and/or leukemias, wherein the carcinoma and/or leukemia is associated with the phosphorylation state of a novel phosphorylation site in Table 1, whether phosphorylated or dephosphorylated.

Methods of diagnosis can be performed in vitro using a biological sample (e.g., blood sample, lymph node biopsy or tissue) from a subject, or in vivo. The phosphorylation state or level at the tyrosine residue identified in the corresponding row in Column D of Table 1 may be assessed. A change in the phosphorylation state or level at the phosphorylation site, as compared to a control, indicates that the subject is suffering from, or susceptible to, carcinoma and/or leukemia.

In one embodiment, the phosphorylation state or level at a novel phosphorylation site is determined by an AQUA peptide comprising the phosphorylation site. The AQUA peptide may be phosphorylated or unphosphorylated at the specified tyrosine position.

In another embodiment, the phosphorylation state or level at a phosphorylation site is determined by an antibody or antigen-binding fragment thereof, wherein the antibody specifically binds the phosphorylation site. The antibody may be one that only binds to the phosphorylation site when the tyrosine residue is phosphorylated, but does not bind to the same sequence when the tyrosine is not phosphorylated; or vice versa.

In particular embodiments, the antibodies of the present application are attached to labeling moieties, such as a detectable marker. One or more detectable labels can be attached to the antibodies. Exemplary labeling moieties include radiopaque dyes, radiocontrast agents, fluorescent molecules, spin-labeled molecules, enzymes, or other labeling moieties of diagnostic value, particularly in radiologic or magnetic resonance imaging techniques.

A radiolabeled antibody in accordance with this disclosure can be used for in vitro diagnostic tests. The specific activity of an antibody, binding portion thereof, probe, or ligand, depends upon the half-life, the isotopic purity of the radioactive label, and how the label is incorporated into the biological agent. In immunoassay tests, the higher the specific activity, in general, the better the sensitivity. Radioisotopes useful as labels, e.g., for use in diagnostics, include iodine ($^{131}$I or $^{125}$I), indium ($^{111}$In), technetium ($^{99}$Tc), phosphorus ($^{32}$P), carbon ($^{14}$C), and tritium ($^{3}$H), or one of the therapeutic isotopes listed above.

Fluorophore and chromophore labeled biological agents can be prepared from standard moieties known in the art. Since antibodies and other proteins absorb light having wavelengths up to about 310 nm, the fluorescent moieties may be selected to have substantial absorption at wavelengths above 310 nm, such as for example, above 400 nm. A variety of suitable fluorescers and chromophores are described by Stryer, Science, 162:526 (1968) and Brand et al., Annual Review of Biochemistry, 41:843-868 (1972), which are hereby incorporated by reference. The antibodies can be labeled with fluorescent chromophore groups by conventional procedures such as those disclosed in U.S. Pat. Nos. 3,940,475, 4,289,747, and 4,376,110, which are hereby incorporated by reference.

The control may be parallel samples providing a basis for comparison, for example, biological samples drawn from a healthy subject, or biological samples drawn from healthy tissues of the same subject. Alternatively, the control may be a pre-determined reference or threshold amount. If the subject is being treated with a therapeutic agent, and the progress of the treatment is monitored by detecting the tyrosine phosphorylation state level at a phosphorylation site of the invention, a control may be derived from biological samples drawn from the subject prior to, or during the course of the treatment.

In certain embodiments, antibody conjugates for diagnostic use in the present application are intended for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. In certain embodiments, secondary binding ligands are biotin and avidin or streptavidin compounds.

Antibodies of the invention may also be optimized for use in a flow cytometry (FC) assay to determine the activation/phosphorylation status of a target signaling protein in subjects before, during, and after treatment with a therapeutic agent targeted at inhibiting tyrosine phosphorylation at the phosphorylation site disclosed herein. For example, bone marrow cells or peripheral blood cells from patients may be analyzed by flow cytometry for target signaling protein phosphorylation, as well as for markers identifying various hematopoietic cell types. In this manner, activation status of the malignant cells may be specifically characterized. Flow cytometry may be carried out according to standard methods. See, e.g., Chow et al., *Cytometry (Communications in Clinical Cytometry)* 46: 72-78 (2001).

Alternatively, antibodies of the invention may be used in immunohistochemical (IHC) staining to detect differences in signal transduction or protein activity using normal and diseased tissues. IHC may be carried out according to well-known techniques. See, e.g., Antibodies: A Laboratory Manual, supra.

Peptides and antibodies of the invention may be also be optimized for use in other clinically-suitable applications, for example bead-based multiplex-type assays, such as IGEN, Luminex™ and/or Bioplex™ assay formats, or otherwise optimized for antibody arrays formats, such as reversed-phase array applications (see, e.g. Paweletz et al., *Oncogene* 20(16): 1981-89 (2001)). Accordingly, in another embodiment, the invention provides a method for the multiplex detection of the phosphorylation state or level at two or more phosphorylation sites of the invention (Table 1) in a biological sample, the method comprising utilizing two or more antibodies or AQUA peptides of the invention. In one preferred embodiment, two to five antibodies or AQUA peptides of the invention are used. In another preferred embodiment, six to ten antibodies or AQUA peptides of the invention are used, while in another preferred embodiment eleven to twenty antibodies or AQUA peptides of the invention are used.

In certain embodiments the diagnostic methods of the application may be used in combination with other cancer diagnostic tests.

The biological sample analyzed may be any sample that is suspected of having abnormal tyrosine phosphorylation at a novel phosphorylation site of the invention, such as a homogenized neoplastic tissue sample.

8. Screening Assays

In another aspect, the invention provides a method for identifying an agent that modulates tyrosine phosphorylation at a novel phosphorylation site of the invention, comprising: a) contacting a candidate agent with a peptide or protein comprising a novel phosphorylation site of the invention; and b) determining the phosphorylation state or level at the novel phosphorylation site. A change in the phosphorylation level of the specified tyrosine in the presence of the test agent, as compared to a control, indicates that the candidate agent potentially modulates tyrosine phosphorylation at a novel phosphorylation site of the invention.

In one embodiment, the phosphorylation state or level at a novel phosphorylation site is determined by an AQUA peptide comprising the phosphorylation site. The AQUA peptide may be phosphorylated or unphosphorylated at the specified tyrosine position.

In another embodiment, the phosphorylation state or level at a phosphorylation site is determined by an antibody or antigen-binding fragment thereof, wherein the antibody specifically binds the phosphorylation site. The antibody may be one that only binds to the phosphorylation site when the tyrosine residue is phosphorylated, but does not bind to the same sequence when the tyrosine is not phosphorylated; or vice versa.

In particular embodiments, the antibodies of the present application are attached to labeling moieties, such as a detectable marker.

The control may be parallel samples providing a basis for comparison, for example, the phosphorylation level of the target protein or peptide in absence of the testing agent. Alternatively, the control may be a pre-determined reference or threshold amount.

9. Immunoassays

In another aspect, the present application concerns immunoassays for binding, purifying, quantifying and otherwise generally detecting the phosphorylation state or level at a novel phosphorylation site of the invention.

Assays may be homogeneous assays or heterogeneous assays. In a homogeneous assay the immunological reaction usually involves a phosphorylation site-specific antibody of the invention, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels that may be used include free radicals, radioisotopes, fluorescent dyes, enzymes, bacteriophages, coenzymes, and so forth.

In a heterogeneous assay approach, the reagents are usually the specimen, a phosphorylation site-specific antibody of the invention, and suitable means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal using means for producing such signal. The signal is related to the presence of the analyte in the specimen. Means for producing a detectable signal include the use of radioactive labels, fluorescent labels, enzyme labels, and so forth.

Phosphorylation site-specific antibodies disclosed herein may be conjugated to a solid support suitable for a diagnostic assay (e.g., beads, plates, slides or wells formed from materials such as latex or polystyrene) in accordance with known techniques, such as precipitation.

In certain embodiments, immunoassays are the various types of enzyme linked immunoadsorbent assays (ELISAs) and radioimmunoassays (RIA) known in the art. Immunohistochemical detection using tissue sections is also particularly useful. However, it will be readily appreciated that detection is not limited to such techniques, and Western blotting, dot and slot blotting, FACS analyses, and the like may also be used. The steps of various useful immunoassays have been described in the scientific literature, such as, e.g., Nakamura et al., in Enzyme Immunoassays: Heterogeneous and Homogeneous Systems, Chapter 27 (1987), incorporated herein by reference.

In general, the detection of immunocomplex formation is well known in the art and may be achieved through the application of numerous approaches. These methods are based upon the detection of radioactive, fluorescent, biological or enzymatic tags. Of course, one may find additional advantages through the use of a secondary binding ligand such as a second antibody or a biotin/avidin ligand binding arrangement, as is known in the art.

The antibody used in the detection may itself be conjugated to a detectable label, wherein one would then simply detect this label. The amount of the primary immune complexes in the composition would, thereby, be determined.

Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are washed extensively to remove any non-specifically bound labeled secondary antibodies or ligands, and the remaining label in the secondary immune complex is detected.

An enzyme linked immunoadsorbent assay (ELISA) is a type of binding assay. In one type of ELISA, phosphorylation site-specific antibodies disclosed herein are immobilized onto a selected surface exhibiting protein affinity, such as a well in a polystyrene microtiter plate. Then, a suspected neoplastic tissue sample is added to the wells. After binding and washing to remove non-specifically bound immune complexes, the bound target signaling protein may be detected.

In another type of ELISA, the neoplastic tissue samples are immobilized onto the well surface and then contacted with the phosphorylation site-specific antibodies disclosed herein. After binding and washing to remove non-specifically bound immune complexes, the bound phosphorylation site-specific antibodies are detected.

Irrespective of the format used, ELISAs have certain features in common, such as coating, incubating or binding, washing to remove non-specifically bound species, and detecting the bound immune complexes.

The radioimmunoassay (RIA) is an analytical technique which depends on the competition (affinity) of an antigen for antigen-binding sites on antibody molecules. Standard curves are constructed from data gathered from a series of samples each containing the same known concentration of labeled antigen, and various, but known, concentrations of unlabeled antigen. Antigens are labeled with a radioactive isotope tracer. The mixture is incubated in contact with an antibody. Then the free antigen is separated from the antibody and the antigen bound thereto. Then, by use of a suitable detector, such as a gamma or beta radiation detector, the percent of either the bound or free labeled antigen or both is determined. This procedure is repeated for a number of samples containing various known concentrations of unlabeled antigens and the results are plotted as a standard graph. The percent of bound tracer antigens is plotted as a function of the antigen concentration. Typically, as the total antigen concentration increases the relative amount of the tracer antigen bound to the antibody decreases. After the standard graph is prepared, it is thereafter used to determine the concentration of antigen in samples undergoing analysis.

In an analysis, the sample in which the concentration of antigen is to be determined is mixed with a known amount of tracer antigen. Tracer antigen is the same antigen known to be in the sample but which has been labeled with a suitable radioactive isotope. The sample with tracer is then incubated in contact with the antibody. Then it can be counted in a suitable detector which counts the free antigen remaining in the sample. The antigen bound to the antibody or immunoadsorbent may also be similarly counted. Then, from the standard curve, the concentration of antigen in the original sample is determined.

10. Pharmaceutical Formulations and Methods of Administration

Methods of administration of therapeutic agents, particularly peptide and antibody therapeutics, are well-known to those of skill in the art.

Peptides of the invention can be administered in the same manner as conventional peptide type pharmaceuticals. Preferably, peptides are administered parenterally, for example, intravenously, intramuscularly, intraperitoneally, or subcutaneously. When administered orally, peptides may be proteolytically hydrolyzed. Therefore, oral application may not be usually effective. However, peptides can be administered orally as a formulation wherein peptides are not easily hydrolyzed in a digestive tract, such as liposome-microcapsules. Peptides may be also administered in suppositories, sublingual tablets, or intranasal spray.

If administered parenterally, a preferred pharmaceutical composition is an aqueous solution that, in addition to a peptide of the invention as an active ingredient, may contain for example, buffers such as phosphate, acetate, etc., osmotic pressure-adjusting agents such as sodium chloride, sucrose, and sorbitol, etc., antioxidative or antioxygenic agents, such as ascorbic acid or tocopherol and preservatives, such as antibiotics. The parenterally administered composition also may be a solution readily usable or in a lyophilized form which is dissolved in sterile water before administration.

The pharmaceutical formulations, dosage forms, and uses described below generally apply to antibody-based therapeutic agents, but are also useful and can be modified, where necessary, for making and using therapeutic agents of the disclosure that are not antibodies.

To achieve the desired therapeutic effect, the phosphorylation site-specific antibodies or antigen-binding fragments thereof can be administered in a variety of unit dosage forms. The dose will vary according to the particular antibody. For example, different antibodies may have different masses and/or affinities, and thus require different dosage levels. Antibodies prepared as Fab or other fragments will also require differing dosages than the equivalent intact immunoglobulins, as they are of considerably smaller mass than intact immunoglobulins, and thus require lower dosages to reach the same molar levels in the patient's blood. The dose will also vary depending on the manner of administration, the particular symptoms of the patient being treated, the overall health, condition, size, and age of the patient, and the judgment of the prescribing physician. Dosage levels of the antibodies for human subjects are generally between about 1 mg per kg and about 100 mg per kg per patient per treatment, such as for example, between about 5 mg per kg and about 50 mg per kg per patient per treatment. In terms of plasma concentrations, the antibody concentrations may be in the range from about 25 µg/mL to about 500 µg/mL. However, greater amounts may be required for extreme cases and smaller amounts may be sufficient for milder cases.

Administration of an antibody will generally be performed by a parenteral route, typically via injection such as intra-articular or intravascular injection (e.g., intravenous infusion) or intramuscular injection. Other routes of administration, e.g., oral (p.o.), may be used if desired and practicable for the particular antibody to be administered. An antibody can also be administered in a variety of unit dosage forms and their dosages will also vary with the size, potency, and in vivo half-life of the particular antibody being administered. Doses of a phosphorylation site-specific antibody will also vary depending on the manner of administration, the particular symptoms of the patient being treated, the overall health, condition, size, and age of the patient, and the judgment of the prescribing physician.

The frequency of administration may also be adjusted according to various parameters. These include the clinical response, the plasma half-life of the antibody, and the levels of the antibody in a body fluid, such as, blood, plasma, serum, or synovial fluid. To guide adjustment of the frequency of administration, levels of the antibody in the body fluid may be monitored during the course of treatment.

Formulations particularly useful for antibody-based therapeutic agents are also described in U.S. Patent App. Publication Nos. 20030202972, 20040091490 and 20050158316. In certain embodiments, the liquid formulations of the application are substantially free of surfactant and/or inorganic salts. In another specific embodiment, the liquid formulations have a pH ranging from about 5.0 to about 7.0. In yet another specific embodiment, the liquid formulations comprise histidine at a concentration ranging from about 1 mM to about 100 mM. In still another specific embodiment, the liquid formulations comprise histidine at a concentration ranging from 1 mM to 100 mM. It is also contemplated that the liquid formulations may further comprise one or more excipients such as a saccharide, an amino acid (e.g., arginine, lysine, and methionine) and a polyol. Additional descriptions and methods of preparing and analyzing liquid formulations can be found, for example, in PCT publications WO 03/106644, WO 04/066957, and WO 04/091658.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the pharmaceutical compositions of the application.

In certain embodiments, formulations of the subject antibodies are pyrogen-free formulations which are substantially free of endotoxins and/or related pyrogenic substances. Endotoxins include toxins that are confined inside microorganisms and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with monoclonal antibodies, it is advantageous to remove even trace amounts of endotoxin.

The amount of the formulation which will be therapeutically effective can be determined by standard clinical techniques. In addition, in vitro assays may optionally be used to help identify optimal dosage ranges. The precise dose to be used in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. The dosage of the compositions to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. For example, the actual patient body weight may be used to calculate the dose of the formulations in milliliters (mL) to be administered. There may be no downward adjustment to "ideal" weight. In such a situation, an appropriate dose may be calculated by the following formula:

Dose(mL)=[patient weight(kg)×dose level(mg/kg)/drug concentration(mg/mL)]

For the purpose of treatment of disease, the appropriate dosage of the compounds (for example, antibodies) will depend on the severity and course of disease, the patient's clinical history and response, the toxicity of the antibodies, and the discretion of the attending physician. The initial candidate dosage may be administered to a patient. The proper dosage and treatment regimen can be established by monitoring the progress of therapy using conventional techniques known to those of skill in the art.

The formulations of the application can be distributed as articles of manufacture comprising packaging material and a pharmaceutical agent which comprises, e.g., the antibody and a pharmaceutically acceptable carrier as appropriate to the mode of administration. The packaging material will include a label which indicates that the formulation is for use in the treatment of prostate cancer.

11. Kits

Antibodies and peptides (including AQUA peptides) of the invention may also be used within a kit for detecting the phosphorylation state or level at a novel phosphorylation site of the invention, comprising at least one of the following: an AQUA peptide comprising the phosphorylation site, or an antibody or an antigen-binding fragment thereof that binds to an amino acid sequence comprising the phosphorylation site. Such a kit may further comprise a packaged combination of reagents in predetermined amounts with instructions for performing the diagnostic assay. Where the antibody is labeled with an enzyme, the kit will include substrates and co-factors required by the enzyme. In addition, other additives may be included such as stabilizers, buffers and the like. The relative amounts of the various reagents may be varied widely to provide for concentrations in solution of the reagents that substantially optimize the sensitivity of the assay. Particularly, the reagents may be provided as dry powders, usually lyophilized, including excipients that, on dissolution, will provide a reagent solution having the appropriate concentration.

The following Examples are provided only to further illustrate the invention, and are not intended to limit its scope, except as provided in the claims appended hereto. The invention encompasses modifications and variations of the methods taught herein which would be obvious to one of ordinary skill in the art.

Example 1

Isolation of Phosphotyrosine-Containing Peptides from Extracts of Carcinoma and/or Leukemia Cell Lines and Identification of Novel Phosphorylation Sites In order to discover novel tyrosine phosphorylation sites in leukemia, IAP isolation techniques were used to identify phosphotyrosine-containing peptides in cell extracts from human leukemia cell lines and patient cell lines identified in Column G of Table 1 including: 101206; 143.98.2; 23132/87; 23132/87: 10% serum; 3T3(EGFR|deletion||EGF); 42-MG-BA; 5637; 639L; 8-MG-BA; A172; A498; A549; A704; AML-30410; B13_AML; B18_AML; BC-3C; BC004; BC005; BC007; BJ629; BJ630; BJ631; BJ635; BJ665; BT1; BT2; Baf3(FGFR1|truncation: 10ZF); Baf3(FLT3|D835Y); Baf3(FLT3|K663Q); Baf3(Jak2|Jak2|V617F); Baf3(TEL-FGFR3); CAKI-2; CAL-29; CAL-51; CAL-85-1; CCF-STTG1; CHP-212; CHP126; CHRF; CMK; CML-06/164; COLO-699; CTV-1; Caki-2; Cal-148; Calu-3; CaoV4; Colo680N; DK-MG; DMS 53; DMS 79; DU.528; DV-90; Detroit562; EFM-19; EFO-21; ENT01; ENT02; ENT03; ENT05; ENT10; ENT12; ENT14; ENT15; ENT19; ENT7; EOL-1; ES2; EVSA-T; FUOV1; GAMG; GI-CA-N; GI-L1-N; GMS-10; H1435; H1437; H1568; H1650; H1651; H1703; H1734; H1781; H1838; H1915; H1975; H2023; H2052; H2066; H2085; H2135; H2172; H2342; H2452; H28; H3255; H358; H4; H446; H4; H520; H524; H596; H810; HCC1143; HCC1395; HCC1428; HCC15; HCC1806; HCC1937; HCC827; HCT 116; HCT15; HCT8; HD-MyZ; HDLM-2; HEL; HL130A; HL131B; HL145A; HL146A; HL152A; HL183A; HL183B; HL184A; HL184B; HL1881; HL213A; HL226A; HL226B; HL233B; HL234A; HL25A; HL53A; HL53B; HL55A; HL59A; HL66A; HL68A; HL83A; HL84A; HL98A; HP28; HT29; Hs746T; IMR32;

J82; Jurkat; K562; KATO III; KELLY; KG-1; KMS-11; KPL-1; Kyse140; Kyse270; Kyse410; Kyse450; Kyse510; Kyse70; L428; L540; LAN-1; LAN-5; LCLC-103H; LN-405; LN18; LXF-289; M059J; M059K; MDAH2774; MHH-NB-11; MKN-45; MKPL-1; ML-1; MT-3; MV4-11; Me-F2; MiaPaca; Molm 14; N06BJ505(2); N06BJ573(9); N06BJ591(11); N06BJ593(13); N06BJ606(19); N06CS02; N06CS06; N06CS103; N06CS106; N06CS107; N06CS16; N06CS17; N06CS22(2)-R; N06CS22-1; N06CS22-2; N06CS23; N06CS39; N06CS40; N06CS75; N06CS77; N06CS87; N06CS90; N06CS91; N06CS93-2; N06CS94; N06CS97; N06CS98; N06CS98-2; N06CS98-R; N06N101; N06N102; N06N103; N06N106; N06N121; N06N127; N06N128; N06N131; N06N80; N06N90; N06N93; N06bj523(3); N06bj567(7); N06bj594(14); N06bj595(15); N06bj638(26); N06bj639(27); N06bj667(29); N06c144; N06c78; N06cs108; N06cs109; N06cs110; N06cs110-R; N06cs112; N06cs113; N06cs117; N06cs121; N06cs122; N06cs123; N06cs123(2); N06cs126; N06cs128; N06cs132; N06cs132-1; N06cs59; N06cs63; N06cs72; N06cs76; N06cs88; N06cs92; NALM-19; NCI-H716; OPM-1; OV90; PA-1; RSK2-3; RSK2-4; S 2; SCLC T1; SCLC T4; SEM; SK-ES-1; SK-N-AS; SK-N-BE(2); SK-N-DZ; SK-N-FI; SK-OV-3; SNB-19; SNU-1; SNU-16; SNU-5; SNU-C2B; SUP-T13; SW1088; SW1710; SW480; SW620; Scaber; T17; T98G; TOV112D; TOV21G; U118 MG; UM-UC-1; UT-7; ZR-75-30; brain; cs002; cs005; cs018; cs009; cs024; cs025; cs026; cs037; cs041; cs042; cs057; cs068; cs069; cs070; cs103; cs104; cs105; cs106; cs107; cs110; cs114; cs133; cs136; csC44; csC45; csC50; csC52; csC56; csC60; csC66; csC71; gz21; gz30; gz33; gz41; gz42; gz7; gz73; gz74; gz75; gzB1; h2073; sw48.

Tryptic phosphotyrosine-containing peptides were purified and analyzed from extracts of each of the cell lines mentioned above, as follows. Cells were cultured in DMEM medium or RPMI 1640 medium supplemented with 10% fetal bovine serum and penicillin/streptomycin.

Suspension cells were harvested by low speed centrifugation. After complete aspiration of medium, cells were resuspended in 1 mL lysis buffer per $1.25 \times 10^8$ cells (20 mM HEPES pH 8.0, 9 M urea, 1 mM sodium vanadate, supplemented or not with 2.5 mM sodium pyro-phosphate, 1 mM β-glycerol-phosphate) and sonicated.

Adherent cells at about 70-80% confluency were starved in medium without serum overnight and stimulated, with ligand depending on the cell type or not stimulated. After complete aspiration of medium from the plates, cells were scraped off the plate in 10 ml lysis buffer per $2 \times 10^8$ cells (20 mM HEPES pH 8.0, 9 M urea, 1 mM sodium vanadate, supplemented with 2.5 mM sodium pyrophosphate, 1 mM β-glycerol-phosphate) and sonicated.

Frozen tissue samples were cut to small pieces, homogenize in lysis buffer (20 mM HEPES pH 8.0, 9 M Urea, 1 mM sodium vanadate, supplemented with 2.5 mM sodium pyrophosphate, 1 mM β-glycerol-phosphate, 1 ml lysis buffer for 100 mg of frozen tissue) using a polytron for 2 times of 20 sec. each time. Homogenate is then briefly sonicated.

Sonicated cell lysates were cleared by centrifugation at 20,000×g, and proteins were reduced with DTT at a final concentration of 4.1 mM and alkylated with iodoacetamide at 8.3 mM. For digestion with trypsin, protein extracts were diluted in 20 mM HEPES pH 8.0 to a final concentration of 2 M urea and soluble TLCK-trypsin (Worthington) was added at 10-20 μg/mL. Digestion was performed for 1 day at room temperature.

Trifluoroacetic acid (TFA) was added to protein digests to a final concentration of 1%, precipitate was removed by centrifugation, and digests were loaded onto Sep-Pak $C_{18}$ columns (Waters) equilibrated with 0.1% TFA. A column volume of 0.7-1.0 ml was used per $2 \times 10^8$ cells. Columns were washed with 15 volumes of 0.1% TFA, followed by 4 volumes of 5% acetonitrile (MeCN) in 0.1% TFA. Peptide fraction I was obtained by eluting columns with 2 volumes each of 8, 12, and 15% MeCN in 0.1% TFA and combining the eluates. Fractions II and III were a combination of eluates after eluting columns with 18, 22, 25% MeCN in 0.1% TFA and with 30, 35, 40% MeCN in 0.1% TFA, respectively. All peptide fractions were lyophilized.

Peptides from each fraction corresponding to $2 \times 10^8$ cells were dissolved in 1 ml of IAP buffer (20 mM Tris/HCl or 50 mM MOPS pH 7.2, 10 mM sodium phosphate, 50 mM NaCl) and insoluble matter (mainly in peptide fractions III) was removed by centrifugation. IAP was performed on each peptide fraction separately. The phosphotyrosine monoclonal antibody P-Tyr-100 (Cell Signaling Technology, Inc., catalog number 9411) was coupled at 4 mg/ml beads to protein G (Roche), respectively. Immobilized antibody (15 μl, 60 μg) was added as 1:1 slurry in IAP buffer to 1 ml of each peptide fraction, and the mixture was incubated overnight at 4° C. with gentle rotation. The immobilized antibody beads were washed three times with 1 ml IAP buffer and twice with 1 ml water, all at 4° C. Peptides were eluted from beads by incubation with 75 μl of 0.1% TFA at room temperature for 10 minutes.

Alternatively, one single peptide fraction was obtained from Sep-Pak C18 columns by elution with 2 volumes each of 10%, 15%, 20%, 25%, 30%, 35% and 40% acetonitrile in 0.1% TFA and combination of all eluates. IAP on this peptide fraction was performed as follows: After lyophilization, peptide was dissolved in 1.4 ml IAP buffer (MOPS pH 7.2, 10 mM sodium phosphate, 50 mM NaCl) and insoluble matter was removed by centrifugation. Immobilized antibody (40 μl, 160 μg) was added as 1:1 slurry in IAP buffer, and the mixture was incubated overnight at 4° C. with gentle shaking. The immobilized antibody beads were washed three times with 1 ml IAP buffer and twice with 1 ml water, all at 4° C. Peptides were eluted from beads by incubation with 55 μl of 0.15% TFA at room temperature for 10 min (eluate 1), followed by a wash of the beads (eluate 2) with 45 μl of 0.15% TFA. Both eluates were combined.

Analysis by LC-MS/MS Mass Spectrometry.

40 μl or more of IAP eluate were purified by 0.2 μl C18 microtips (StageTips or ZipTips). Peptides were eluted from the microcolumns with 1 μl of 40% MeCN, 0.1% TFA (fractions I and II) or 1 μl of 60% MeCN, 0.1% TFA (fraction III) into 7.6-9.0 μl of 0.4% acetic acid/0.005% heptafluorobutyric acid. For single fraction analysis, 1 μl of 60% MeCN, 0.1% TFA, was used for elution from the microcolumns. This sample was loaded onto a 10 cm×75 μm PicoFrit capillary column (New Objective) packed with Magic C18 AQ reversed-phase resin (Michrom Bioresources) using a Famos autosampler with an inert sample injection valve (Dionex). The column was then developed with a 45-min linear gradient of acetonitrile delivered at 200 nl/min (Ultimate, Dionex), and tandem mass spectra were collected in a data-dependent manner with an LTQ ion trap mass spectrometer essentially as described by Gygi et al., supra.

Database Analysis & Assignments.

MS/MS spectra were evaluated using TurboSequest in the Sequest Browser package (v. 27, rev. 12) supplied as part of BioWorks 3.0 (ThermoFinnigan). Individual MS/MS spectra were extracted from the raw data file using the Sequest Browser program CreateDta, with the following settings: bottom MW, 700; top MW, 4,500; minimum number of ions, 40; minimum TIC, 2×10³; and precursor charge state, unspecified. Spectra were extracted from the beginning of the raw data file before sample injection to the end of the eluting gradient. The IonQuest and VuDta programs were not used to further select MS/MS spectra for Sequest analysis. MS/MS spectra were evaluated with the following TurboSequest parameters: peptide mass tolerance, 2.5; fragment ion tolerance, 1.0; maximum number of differential amino acids per modification, 4; mass type parent, average; mass type fragment, average; maximum number of internal cleavage sites, 10; neutral losses of water and ammonia from b and y ions were considered in the correlation analysis. Proteolytic enzyme was specified except for spectra collected from elastase digests.

Searches were performed against the then current NCBI human protein database. Cysteine carboxamidomethylation was specified as a static modification, and phosphorylation was allowed as a variable modification on serine, threonine, and tyrosine residues or on tyrosine residues alone. It was determined that restricting phosphorylation to tyrosine residues had little effect on the number of phosphorylation sites assigned.

In proteomics research, it is desirable to validate protein identifications based solely on the observation of a single peptide in one experimental result, in order to indicate that the protein is, in fact, present in a sample. This has led to the development of statistical methods for validating peptide assignments, which are not yet universally accepted, and guidelines for the publication of protein and peptide identification results (see Carr et al., *Mol. Cell Proteomics* 3: 531-533 (2004)), which were followed in this Example. However, because the immunoaffinity strategy separates phosphorylated peptides from unphosphorylated peptides, observing just one phosphopeptide from a protein is a common result, since many phosphorylated proteins have only one tyrosine-phosphorylated site. For this reason, it is appropriate to use additional criteria to validate phosphopeptide assignments. Assignments are likely to be correct if any of these additional criteria are met: (i) the same phosphopeptide sequence is assigned to co-eluting ions with different charge states, since the MS/MS spectrum changes markedly with charge state; (ii) the phosphorylation site is found in more than one peptide sequence context due to sequence overlaps from incomplete proteolysis or use of proteases other than trypsin; (iii) the phosphorylation site is found in more than one peptide sequence context due to homologous but not identical protein isoforms; (iv) the phosphorylation site is found in more than one peptide sequence context due to homologous but not identical proteins among species; and (v) phosphorylation sites validated by MS/MS analysis of synthetic phosphopeptides corresponding to assigned sequences, since the ion trap mass spectrometer produces highly reproducible MS/MS spectra. The last criterion is routinely used to confirm novel site assignments of particular interest.

All spectra and all sequence assignments made by Sequest were imported into a relational database. The following Sequest scoring thresholds were used to select phosphopeptide assignments that are likely to be correct: RSp<6, XCorr≧2.2, and DeltaCN>0.099. Further, the sequence assignments could be accepted or rejected with respect to accuracy by using the following conservative, two-step process.

In the first step, a subset of high-scoring sequence assignments should be selected by filtering for XCorr values of at least 1.5 for a charge state of +1, 2.2 for +2, and 3.3 for +3, allowing a maximum RSp value of 10. Assignments in this subset should be rejected if any of the following criteria are satisfied: (i) the spectrum contains at least one major peak (at least 10% as intense as the most intense ion in the spectrum) that can not be mapped to the assigned sequence as an a, b, or y ion, as an ion arising from neutral-loss of water or ammonia from a b or y ion, or as a multiply protonated ion; (ii) the spectrum does not contain a series of b or y ions equivalent to at least six uninterrupted residues; or (iii) the sequence is not observed at least five times in all the studies conducted (except for overlapping sequences due to incomplete proteolysis or use of proteases other than trypsin).

In the second step, assignments with below-threshold scores should be accepted if the low-scoring spectrum shows a high degree of similarity to a high-scoring spectrum collected in another study, which simulates a true reference library-searching strategy.

Example 2

Production of Phosphorylation Site-Specific Polyclonal Antibodies

Polyclonal antibodies that specifically bind a novel phosphorylation site of the invention (Table 1/FIG. 2) only when the tyrosine residue is phosphorylated (and does not bind to the same sequence when the tyrosine is not phosphorylated), and vice versa, are produced according to standard methods by first constructing a synthetic peptide antigen comprising the phosphorylation site and then immunizing an animal to raise antibodies against the antigen, as further described below. Production of exemplary polyclonal antibodies is provided below.

A. PSD-95 (tyrosine 576).

A 28 amino acid phospho-peptide antigen, EDSVLSYETVTQMEVHy*ARPIIILGPTK (SEQ NO: 35; y*=phosphotyrosine), which comprises the phosphorylation site derived from human PSD-95 (an adaptor/scaffold protein, Tyr 576 being the phosphorylatable residue), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra., Merrifield, supra. This peptide is then coupled to KLH and used to immunize animals to produce (and subsequently screen) phosphorylation site-specific polyclonal antibodies as described in Immunization/Screening below.

B. PIP5K (Tyrosine 154).

An 20 amino acid phospho-peptide antigen, GKSQDSDLKQy*WMPDSQCKE (SEQ ID NO: 200; y*=phosphotyrosine), which comprises the phosphorylation site derived from human PIP5K (a cytoskeletal protein, Tyr 154 being the phosphorylatable residue), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra., Merrifield, supra. This peptide is then coupled to KLH and used to immunize animals to produce (and subsequently screen) phosphorylation site-specific polyclonal antibodies as described in Immunization/Screening below.

C. FGFR1 (Tyrosine 522).

A 9 amino acid phospho-peptide antigen, GMEy*LASKK (SEQ ID NO: 266; y*=phosphotyrosine, which comprises the phosphorylation site derived from human FGFR1 (a protein kinase, Tyr 522 being the phosphorylatable residue), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra., Merrifield, supra. This peptide is then coupled to KLH and used to immunize animals to produce (and subsequently screen) phosphorylation site-specific polyclonal antibodies as described in Immunization/Screening below.

Immunization/Screening.

A synthetic phospho-peptide antigen as described in A-C above is coupled to KLH, and rabbits are injected intradermally (ID) on the back with antigen in complete Freunds adjuvant (500 µg antigen per rabbit). The rabbits are boosted with same antigen in incomplete Freund adjuvant (250 µg antigen per rabbit) every three weeks. After the fifth boost, bleeds are collected. The sera are purified by Protein A-affinity chromatography by standard methods (see ANTIBODIES: A LABORATORY MANUAL, Cold Spring Harbor, supra.). The eluted immunoglobulins are further loaded onto an unphosphorylated synthetic peptide antigen-resin Knotes column to pull out antibodies that bind the unphosphorylated form of the phosphorylation sites. The flow through fraction is collected and applied onto a phospho-synthetic peptide antigen-resin column to isolate antibodies that bind the phosphorylated form of the phosphorylation sites. After washing the column extensively, the bound antibodies (i.e. antibodies that bind the phosphorylated peptides described in A-C above, but do not bind the unphosphorylated form of the peptides) are eluted and kept in antibody storage buffer.

The isolated antibody is then tested for phospho-specificity using Western blot assay using an appropriate cell line that expresses (or overexpresses) target phospho-protein (i.e. phosphorylated PSD-95, PIP5K or FGFR1), for example, brain tissue, jurkat cells or colorectal cancer tissue. Cells are cultured in DMEM or RPMI supplemented with 10% FCS. Cell are collected, washed with PBS and directly lysed in cell lysis buffer. The protein concentration of cell lysates is then measured. The loading buffer is added into cell lysate and the mixture is boiled at 100° C. for 5 minutes. 20 µl (10 µg protein) of sample is then added onto 7.5% SDS-PAGE gel.

A standard Western blot may be performed according to the Immunoblotting Protocol set out in the CELL SIGNALING TECHNOLOGY, INC. 2003-04 Catalogue, p. 390. The isolated phosphorylation site-specific antibody is used at dilution 1:1000. Phospho-specificity of the antibody will be shown by binding of only the phosphorylated form of the target amino acid sequence. Isolated phosphorylation site-specific polyclonal antibody does not (substantially) recognize the same target sequence when not phosphorylated at the specified tyrosine position (e.g., the antibody does not bind to FGFR1 in the non-stimulated cells, when tyrosine 522 is not phosphorylated).

In order to confirm the specificity of the isolated antibody, different cell lysates containing various phosphorylated signaling proteins other than the target protein are prepared. The Western blot assay is performed again using these cell lysates. The phosphorylation site-specific polyclonal antibody isolated as described above is used (1:1000 dilution) to test reactivity with the different phosphorylated non-target proteins. The phosphorylation site-specific antibody does not significantly cross-react with other phosphorylated signaling proteins that do not have the described phosphorylation site, although occasionally slight binding to a highly homologous sequence on another protein may be observed. In such case the antibody may be further purified using affinity chromatography, or the specific immunoreactivity cloned by rabbit hybridoma technology.

Example 3

Production Of Phosphorylation Site-Specific Monoclonal Antibodies

Monoclonal antibodies that specifically bind a novel phosphorylation site of the invention (Table 1) only when the tyrosine residue is phosphorylated (and does not bind to the same sequence when the tyrosine is not phosphorylated) are produced according to standard methods by first constructing a synthetic peptide antigen comprising the phosphorylation site and then immunizing an animal to raise antibodies against the antigen, and harvesting spleen cells from such animals to produce fusion hybridomas, as further described below. Production of exemplary monoclonal antibodies is provided below.

A. PSD-95 (Tyrosine 576).

A 28 amino acid phospho-peptide antigen, EDSVLSYETVTQMEVHy*ARPIIILGPTK (SEQ ID NO: 35; y*=phosphotyrosine), which comprises the phosphorylation site derived from human PSD-95 (an adaptor/scaffold protein, Tyr 576 being the phosphorylatable residue), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phosphorylation site-specific monoclonal antibodies as described in Immunization/Fusion/Screening below.

B. PIP5K (Tyrosine 154).

A 20 amino acid phospho-peptide antigen, GKSQDSDLKQy*WMPDSQCKE (SEQ ID NO: 200; y*=phosphotyrosine), which comprises the phosphorylation site derived from human PIP5K (a non-protein kinase, Tyr 154 being the phosphorylatable residue), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phosphorylation site-specific monoclonal antibodies as described in Immunization/Fusion/Screening below.

C. FGFR1 (Tyrosine 522).

A 12 amino acid phospho-peptide antigen, GMEy*LASKK (SEQ ID NO: 266; y*=phosphotyrosines), which comprises the phosphorylation site derived from human FGFR1 (a protein kinase, Tyr 522 being the phosphorylatable residue), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phosphorylation site-specific monoclonal antibodies as described in Immunization/Fusion/Screening below.

Immunization/Fusion/Screening.

A synthetic phospho-peptide antigen as described in A-C above is coupled to KLH, and BALB/C mice are injected intradermally (ID) on the back with antigen in complete Freunds adjuvant (e.g., 50 µg antigen per mouse). The mice are boosted with same antigen in incomplete Freund adjuvant (e.g. 25 μg antigen per mouse) every three weeks. After the fifth boost, the animals are sacrificed and spleens are harvested.

Harvested spleen cells are fused to SP2/0 mouse myeloma fusion partner cells according to the standard protocol of Kohler and Milstein (1975). Colonies originating from the fusion are screened by ELISA for reactivity to the phospho-peptide and non-phospho-peptide forms of the antigen and by Western blot analysis (as described in Example 1 above). Colonies found to be positive by ELISA to the phospho-peptide while negative to the non-phospho-peptide are further characterized by Western blot analysis. Colonies found to be positive by Western blot analysis are subcloned by limited dilution. Mouse ascites are produced from a single clone obtained from subcloning, and tested for phospho-specificity (against the PSD-95, PIP5K and FGFR1) phospho-peptide antigen, as the case may be) on ELISA. Clones identified as positive on Western blot analysis using cell culture supernatant as having phospho-specificity, as indicated by a strong band in the induced lane and a weak band in the uninduced lane of the blot, are isolated and subcloned as clones producing monoclonal antibodies with the desired specificity.

Ascites fluid from isolated clones may be further tested by Western blot analysis. The ascites fluid should produce similar results on Western blot analysis as observed previously with the cell culture supernatant, indicating phospho-specificity against the phosphorylated target.

Example 4

Production and Use of AQUA Peptides for Detecting and Quantitating Phosphorylation at a Novel Phosphorylation Site Heavy-isotope labeled peptides (AQUA peptides (internal standards)) for the detecting and quantitating a novel phosphorylation site of the invention (Table 1) only when the tyrosine residue is phosphorylated are produced according to the standard AQUA methodology (see Gygi et al., Gerber et al., supra.) methods by first constructing a synthetic peptide standard corresponding to the phosphorylation site sequence and incorporating a heavy-isotope label. Subsequently, the MS" and LC-SRM signature of the peptide standard is validated, and the AQUA peptide is used to quantify native peptide in a biological sample, such as a digested cell extract. Production and use of exemplary AQUA peptides is provided below.

A. SKB1 (Tyrosine 283).

An AQUA peptide comprising the sequence, EFCSYLQy*LEYLSQNR (SEQ ID NO: 79; y*=phosphotyrosine; Leucine being $^{14}C/^{15}N$-labeled, as indicated in bold), which comprises the phosphorylation site derived from SKB1 (a cell cycle regulation protein, Tyr 283 being the phosphorylatable residue), is constructed according to standard synthesis techniques using, e.g., a Rainin/Protein Technologies, Inc., Symphony peptide synthesizer (see Merrifield, supra.) as further described below in Synthesis & MS/MS Signature. The SKB1 (tyr 283) AQUA peptide is then spiked into a biological sample to quantify the amount of phosphorylated SKB1 (tyr 283) in the sample, as further described below in Analysis & Quantification.

B. Cofilin 1 (Tyrosine 82).

An AQUA peptide comprising the sequence MLPDKDCRy*ALYDATYETKESK (SEQ ID NO: 103 y*=phosphotyrosine; Proline being $^{14}C/^{15}N$-labeled, as indicated in bold), which comprises the phosphorylation site derived from human Cofilin1 (Tyr 82) being the phosphorylatable residue), is constructed according to standard synthesis techniques using, e.g., a Rainin/Protein Technologies, Inc., Symphony peptide synthesizer (see Merrifield, supra.) as further described below in Synthesis & MS/MS Signature. The Cofilin 1 (Tyr 82) AQUA peptide is then spiked into a biological sample to quantify the amount of phosphorylated Cofilin 1 (Tyr 82) in the sample, as further described below in Analysis & Quantification.

C. CDK9 (Tyrosine 287).

An AQUA peptide comprising the sequence LKAYVRDPy*ALDLIDKLLVLDPAQR (SEQ ID NO: 239; y*=phosphotyrosine; Leucine being $^{14}C/^{15}N$-labeled, as indicated in bold), which comprises the phosphorylation site derived from human CDK9 (Tyr 287 being the phosphorylatable residue), is constructed according to standard synthesis techniques using, e.g., a Rainin/Protein Technologies, Inc., Symphony peptide synthesizer (see Merrifield, supra.) as further described below in Synthesis & MS/MS Signature. The CDK9 (Tyr 287) AQUA peptide is then spiked into a biological sample to quantify the amount of phosphorylated CDK9 (Tyr 287) in the sample, as further described below in Analysis & Quantification.

D. DNAJB6 (Tyrosine 53).

An AQUA peptide comprising the sequence QVAEAy*EVLSDAK (SEQ ID NO: 53; y*=phosphotyrosine; valine being $^{14}C/^{15}N$-labeled, as indicated in bold), which comprises the phosphorylation site derived from human DNAJB6 (Tyr 53 being the phosphorylatable residue), is constructed according to standard synthesis techniques using, e.g., a Rainin/Protein Technologies, Inc., Symphony peptide synthesizer (see Merrifield, supra.) as further described below in Synthesis & MS/MS Signature. The DNAJB6 (Tyr 53) AQUA peptide is then spiked into a biological sample to quantify the amount of phosphorylated DNAJB6 (Tyr 53) in the sample, as further described below in Analysis & Quantification.

Synthesis & MS/MS Spectra.

Fluorenylmethoxycarbonyl (Fmoc)-derivatized amino acid monomers may be obtained from AnaSpec (San Jose, Calif.). Fmoc-derivatized stable-isotope monomers containing one $^{15}N$ and five to nine $^{13}C$ atoms may be obtained from Cambridge Isotope Laboratories (Andover, Mass.). Pre-loaded Wang resins may be obtained from Applied Biosystems. Synthesis scales may vary from 5 to 25 μmol. Amino acids are activated in situ with 1-H-benzotriazolium, 1-bis (dimethylamino) methylene]-hexafluorophosphate (1-),3-oxide:1-hydroxybenzotriazole hydrate and coupled at a 5-fold molar excess over peptide. Each coupling cycle is followed by capping with acetic anhydride to avoid accumulation of one-residue deletion peptide by-products. After synthesis peptide-resins are treated with a standard scavenger-containing trifluoroacetic acid (TFA)-water cleavage solution, and the peptides are precipitated by addition to cold ether. Peptides (i.e. a desired AQUA peptide described in A-D above) are purified by reversed-phase C18 HPLC using standard TFA/acetonitrile gradients and characterized by matrix-assisted laser desorption ionization-time of flight (Biflex III, Bruker Daltonics, Billerica, Mass.) and ion-trap (ThermoFinnigan, LCQ DecaXP or LTQ) MS.

MS/MS spectra for each AQUA peptide should exhibit a strong y-type ion peak as the most intense fragment ion that is suitable for use in an SRM monitoring/analysis. Reverse-phase microcapillary columns (0.1 Å~150-220 mm) are prepared according to standard methods. An Agilent 1100 liquid chromatograph may be used to develop and deliver a solvent gradient [0.4% acetic acid/0.005% heptafluorobutyric acid (HFBA)/7% methanol and 0.4% acetic acid/0.005% HFBA/

65% methanol/35% acetonitrile] to the microcapillary column by means of a flow splitter. Samples are then directly loaded onto the microcapillary column by using a FAMOS inert capillary autosampler (LC Packings, San Francisco) after the flow split. Peptides are reconstituted in 6% acetic acid/0.01% TFA before injection.

Analysis & Quantification.

Target protein (e.g. a phosphorylated proteins of A-D above) in a biological sample is quantified using a validated AQUA peptide (as described above). The IAP method is then applied to the complex mixture of peptides derived from proteolytic cleavage of crude cell extracts to which the AQUA peptides have been spiked in.

LC-SRM of the entire sample is then carried out. MS/MS may be performed by using a ThermoFinnigan (San Jose, Calif.) mass spectrometer (LCQ DecaXP ion trap or TSQ Quantum triple quadrupole or LTQ). On the DecaXP, parent ions are isolated at 1.6 m/z width, the ion injection time being limited to 150 ms per microscan, with two microscans per peptide averaged, and with an AGC setting of $1 \times 10^8$; on the Quantum, Q1 is kept at 0.4 and Q3 at 0.8 m/z with a scan time of 200 ms per peptide. On both instruments, analyte and internal standard are analyzed in alternation within a previously known reverse-phase retention window; well-resolved pairs of internal standard and analyte are analyzed in separate retention segments to improve duty cycle. Data are processed by integrating the appropriate peaks in an extracted ion chromatogram (60.15 m/z from the fragment monitored) for the native and internal standard, followed by calculation of the ratio of peak areas multiplied by the absolute amount of internal standard (e.g., 500 fmol).

What is claimed is:

1. An isolated phosphorylation site-specific antibody that specifically binds a human DDEF2 only when phosphorylated at a tyrosine at position 724 comprised within the phosphorylatable peptide sequence set forth in SEQ ID NO: 172, wherein said antibody does not bind said protein when not phosphorylated at said tyrosine at position 724.

2. An isolated phosphorylation site-specific antibody that specifically binds a human DDEF2 only when not phosphorylated at a tyrosine at position 724 comprised within the phosphorylatable peptide sequence set forth in SEQ ID NO: 172, wherein said antibody does not bind said protein when phosphorylated at said tyrosine at position 724.

* * * * *